(12) United States Patent
Zhu et al.

(10) Patent No.: US 11,970,533 B2
(45) Date of Patent: *Apr. 30, 2024

(54) BISPECIFIC ANTIBODIES TARGETING HUMAN CLAUDIN 18.2 AND PROGRAMMED DEATH-LIGAND 1 (PD-L1)

(71) Applicant: SPARX BIOSCIENCE LIMITED, Tortola (VG)

(72) Inventors: Guidong Zhu, Gurnee, IL (US); Jingdong Ye, Vernon Hills, IL (US); Jichun Ma, Germantown, MD (US); Jingdong Qin, Woodridge, IL (US); Hongyu Zhao, Libertyville, IL (US)

(73) Assignee: SPARX BIOSCIENCE LIMITED, Tortola (VG)

( * ) Notice: Subject to any disclaimer, the term of this patent is extended or adjusted under 35 U.S.C. 154(b) by 0 days.

This patent is subject to a terminal disclaimer.

(21) Appl. No.: 17/350,525

(22) Filed: Jun. 17, 2021

(65) Prior Publication Data

US 2023/0002486 A1    Jan. 5, 2023

Related U.S. Application Data

(60) Provisional application No. 63/040,698, filed on Jun. 18, 2020.

(51) Int. Cl.
*C07K 16/28* (2006.01)

(52) U.S. Cl.
CPC ......... *C07K 16/28* (2013.01); *C07K 16/2827* (2013.01); *C07K 2317/24* (2013.01); *C07K 2317/31* (2013.01); *C07K 2317/622* (2013.01); *C07K 2317/732* (2013.01); *C07K 2317/734* (2013.01)

(58) Field of Classification Search
CPC . C07K 16/28; C07K 2317/31; C07K 2317/76
USPC ........................................... 424/133.1, 135.1
See application file for complete search history.

(56) References Cited

U.S. PATENT DOCUMENTS

| | | | |
|---|---|---|---|
| 11,447,551 B2 * | 9/2022 | Zhu | C07K 16/2827 |
| 2020/0207857 A1 * | 7/2020 | Zhu | C07K 16/2827 |

FOREIGN PATENT DOCUMENTS

| | | | |
|---|---|---|---|
| WO | WO 2018/222711 | * | 6/2018 |
| WO | WO 2018/134389 A1 | | 7/2018 |
| WO | WO 2019/173420 A1 | | 9/2019 |

OTHER PUBLICATIONS

Altshuler et al., "Generation of Recombinant Antibodies and Means for Increasing Their Affinity," Biochemistry (Moscow), 75(13): 1584-1605 (2010).*
Vajda et al., "Progress toward improved understanding of antibody maturation," Current Opinion in Structural Biology, 67 pp. 226-231 (2021).*
Akbar et al., Cell Reports 34, 108856, Mar. 16, 2021.*
Lo et al., "Conformational epitope matching and prediction based on protein surface spiral features," BMC Genomics vol. 22, Article No. 116.*
Clinicaltrials.gov (SparX Biotech(Jiangsu) Co., Ltd.; NCT05231733; filed Feb. 9, 2022).*
Zhu et al ( Cancer Research, (Aug. 2020) vol. 80, No. 16 SUPPL. Abstract No. 534. Meeting Info: American Association for Cancer Research Annual Meeting, AACR 2020. Philadelphia, PA, United States. Jun. 22-Jun. 24, 2020).*
Zhu et al (Cancer Research, (Aug. 2020) vol. 80, No. 16, Suppl. S, pp. 3361. Meeting Info.: AACR Annual Meeting. Jun. 22-24, 2020. Amer Assoc Canc Res).*

* cited by examiner

*Primary Examiner* — Lynn A Bristol
(74) *Attorney, Agent, or Firm* — Mintz, Levin, Cohn, Ferris, Glovsky and Popeo, P.C.

(57) ABSTRACT

Antibodies binding to human claudin 18.2 (CLDN 18.2) and bispecific antibodies binding to both human CLDN 18.2 and PD-L1, pharmaceutical compositions comprising such, and methods of using such for treating target diseases including cancer.

30 Claims, 18 Drawing Sheets

Specification includes a Sequence Listing.

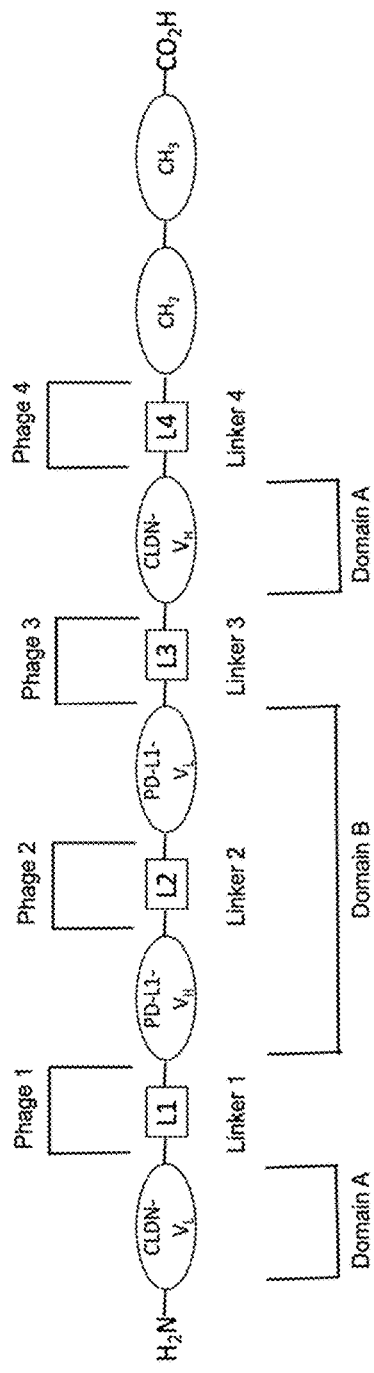
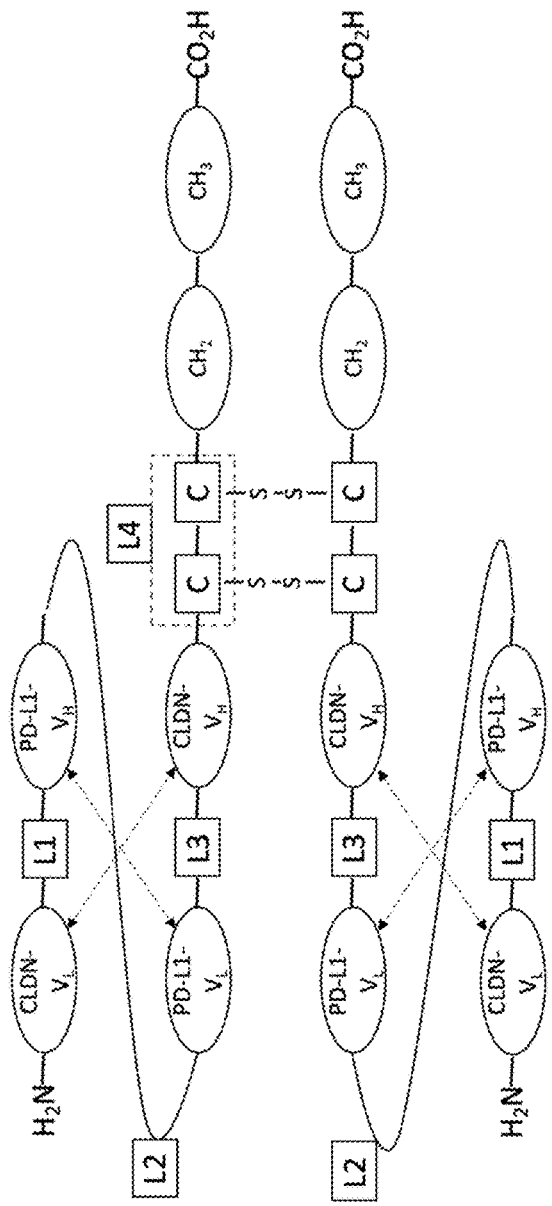

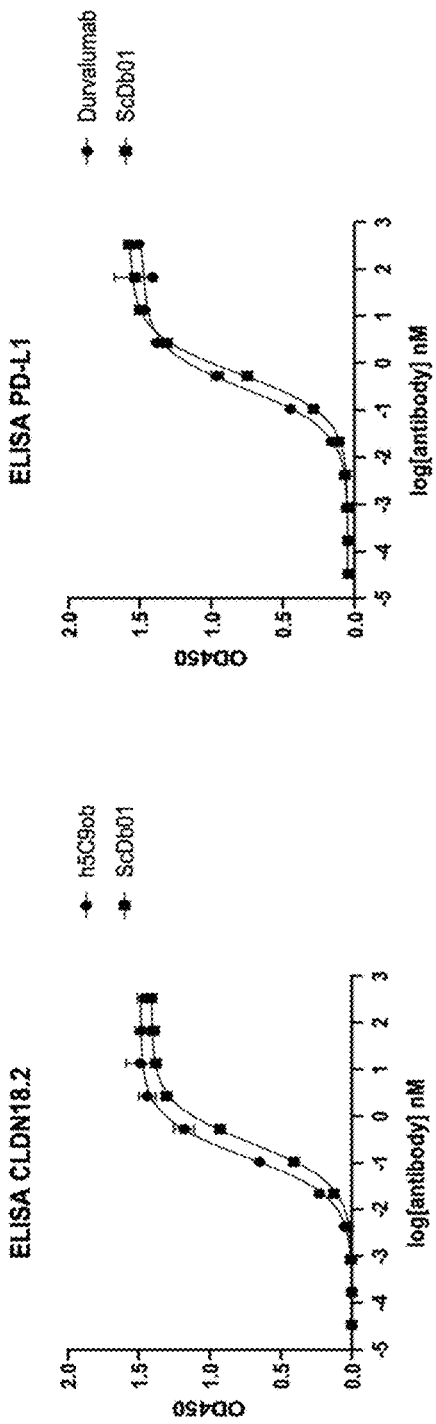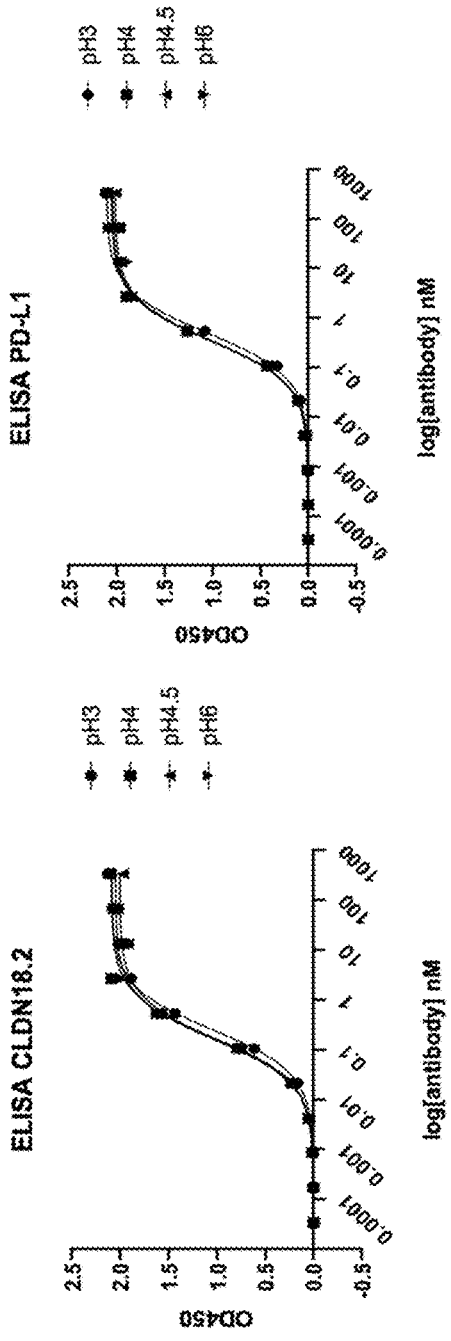

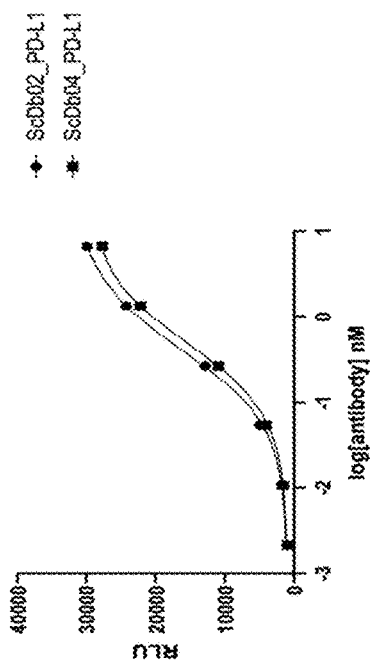
Figure 9A
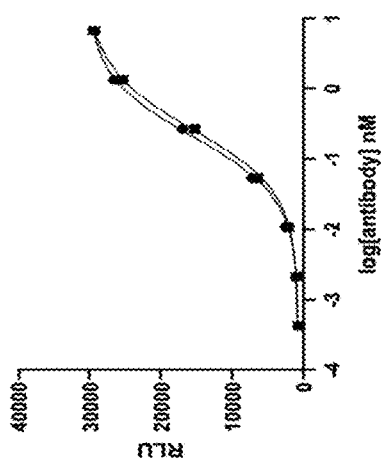
Figure 9B
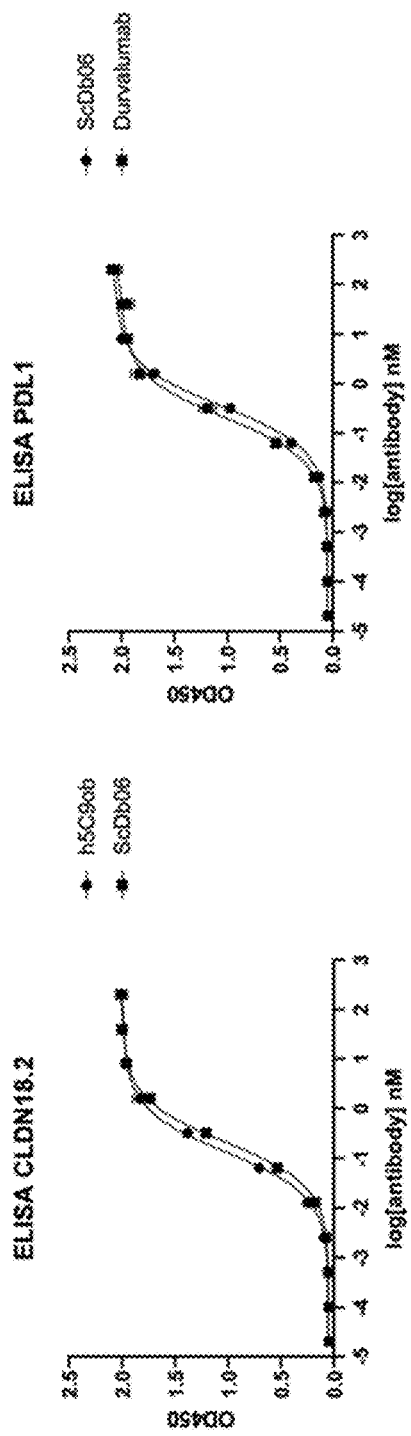
Figure 10A
Figure 10B

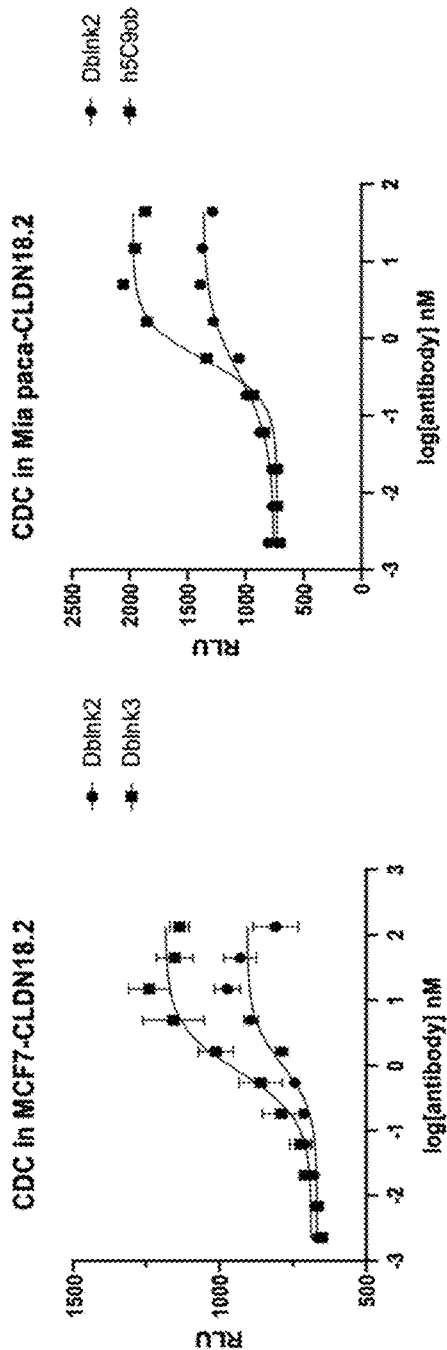
Figure 17A
Figure 17B
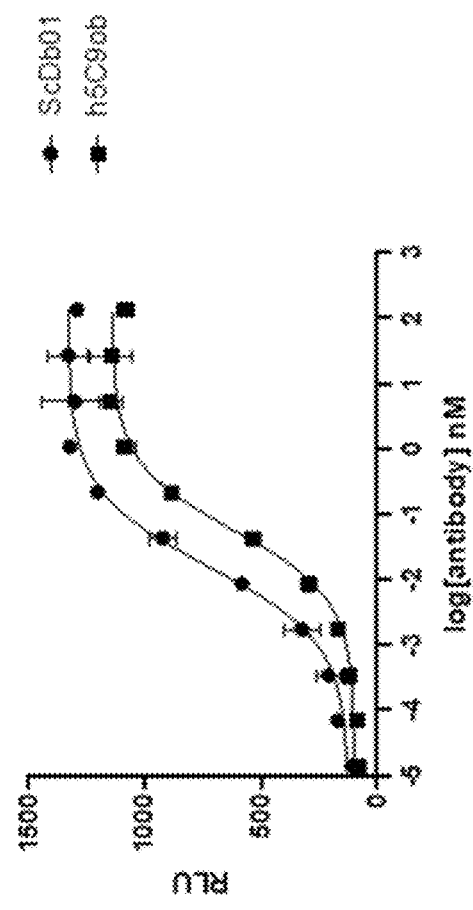
Figure 18

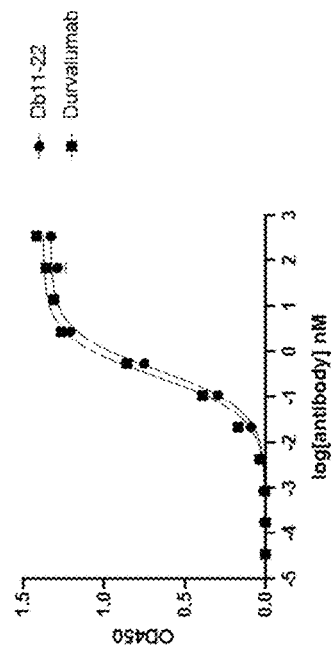
Figure 27
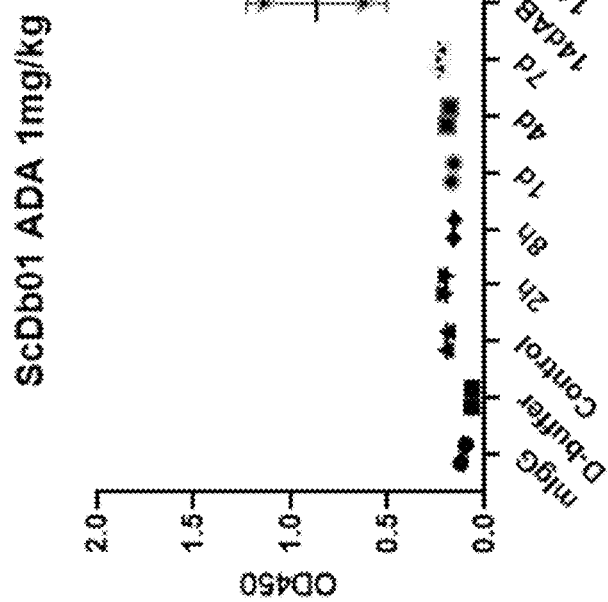
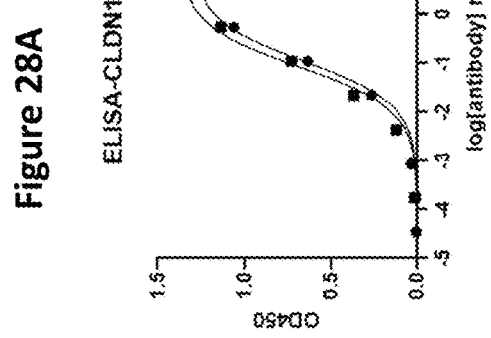
Figure 28A
Figure 28B

SEQUENCE LISTING

```
<160> NUMBER OF SEQ ID NOS: 331

<210> SEQ ID NO 1
<211> LENGTH: 130
<212> TYPE: PRT
<213> ORGANISM: Artificial Sequence
<220> FEATURE:
<223> OTHER INFORMATION: Synthetic

<400> SEQUENCE: 1

Val Lys Leu Gln Glu Ser Gly Pro Glu Leu Lys Lys Pro Gly Glu Thr
1               5                   10                  15

Val Lys Ile Ser Cys Lys Ala Ser Gly Tyr Thr Phe Thr Asn Tyr Gly
            20                  25                  30

Met Asn Trp Val Lys Gln Ala Pro Gly Lys Gly Leu Lys Trp Met Gly
        35                  40                  45

Trp Ile Asn Met Tyr Thr Gly Glu Pro Thr Tyr Ala Asp Asp Phe Lys
    50                  55                  60

Gly Arg Phe Ala Phe Ser Leu Glu Thr Ser Ala Ser Thr Ala Tyr Leu
65                  70                  75                  80

Gln Ile Asn Asn Leu Lys Asn Glu Asp Thr Ala Thr Tyr Phe Cys Ser
                85                  90                  95

Arg Leu Tyr Asn Gly Asn Ser Leu Asp Tyr Trp Gly Gln Gly Thr Ser
            100                 105                 110

Leu Thr Val Ser Ser Ala Lys Thr Thr Pro Lys Leu Val Tyr Pro Leu
        115                 120                 125

Ala Pro
    130

<210> SEQ ID NO 2
<211> LENGTH: 10
```

```
<212> TYPE: PRT
<213> ORGANISM: Artificial Sequence
<220> FEATURE:
<223> OTHER INFORMATION: Synthetic

<400> SEQUENCE: 2

Gly Tyr Thr Phe Thr Asn Tyr Gly Met Asn
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Synthetic

<400> SEQUENCE: 3

Trp Ile Asn Met Tyr Thr Gly Glu Pro Thr Tyr Ala Asp Asp Phe Lys
1               5                   10                  15

Gly

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4

Leu Tyr Asn Gly Asn Ser Leu Asp Tyr
1               5

<210> SEQ ID NO 5
<211> LENGTH: 125
<212> TYPE: PRT
<213> ORGANISM: Artificial Sequence
<220> FEATURE:
<223> OTHER INFORMATION: Synthetic

<400> SEQUENCE: 5

Gly Asp Ile Leu Leu Thr Gln Ser Pro Leu Ser Leu Thr Val Thr Ala
1               5                   10                  15

Gly Glu Lys Val Thr Met Ser Cys Lys Ser Ser Gln Ser Leu Leu Asn
                20                  25                  30

Ser Gly Asn Gln Lys Ser Tyr Leu Thr Trp Tyr Gln Gln Lys Pro Gly
        35                  40                  45

Gln Pro Pro Lys Leu Leu Leu Tyr Trp Ala Ser Thr Arg Glu Ser Gly
    50                  55                  60

Val Pro Ala Arg Phe Thr Gly Ser Gly Ser Gly Thr Asp Phe Ser Leu
65                  70                  75                  80

Thr Ile Ser Ser Val Gln Thr Glu Asp Leu Ala Val Tyr Tyr Cys Gln
                85                  90                  95

Asn Ala Tyr Ser Phe Pro Phe Thr Phe Gly Ser Gly Thr Lys Leu Glu
            100                 105                 110

Ile Asn Arg Ala Asp Ala Ala Pro Thr Gly Ser Ile Phe
        115                 120                 125

<210> SEQ ID NO 6
<211> LENGTH: 17
<212> TYPE: PRT
<213> ORGANISM: Artificial Sequence
<220> FEATURE:
<223> OTHER INFORMATION: Synthetic
```

<400> SEQUENCE: 6

Lys Ser Ser Gln Ser Leu Leu Asn Ser Gly Asn Gln Lys Ser Tyr Leu
1               5                   10                  15
Thr

<210> SEQ ID NO 7
<211> LENGTH: 7
<212> TYPE: PRT
<213> ORGANISM: Artificial Sequence
<220> FEATURE:
<223> OTHER INFORMATION: Synthetic

<400> SEQUENCE: 7

Trp Ala Ser Thr Arg Glu Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Gln Asn Ala Tyr Ser Phe Pro Phe Thr
1               5

<210> SEQ ID NO 9
<211> LENGTH: 115
<212> TYPE: PRT
<213> ORGANISM: Artificial Sequence
<220> FEATURE:
<223> OTHER INFORMATION: Synthetic

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser
        115

<210> SEQ ID NO 10
<211> LENGTH: 7
<212> TYPE: PRT
<213> ORGANISM: Artificial Sequence
<220> FEATURE:
<223> OTHER INFORMATION: Synthetic

<400> SEQUENCE: 10

Gly Tyr Thr Phe Ser Met Asn

<210> SEQ ID NO 11
<211> LENGTH: 114
<212> TYPE: PRT
<213> ORGANISM: Artificial Sequence
<220> FEATURE:
<223> OTHER INFORMATION: Synthetic

<400> SEQUENCE: 11

Asp Ile Gln Met Thr Gln Ser Pro Ser Ser Leu Ser Ala Ser Val Gly
1               5                   10                  15
Asp Arg Val Thr Ile Thr Cys Lys Ser Ser Gln Ser Leu Leu Asn Ser
            20                  25                  30
Gly Asn Gln Lys Ser Tyr Leu Thr Trp Tyr Gln Gln Lys Pro Gly Lys
        35                  40                  45
Ala Pro Lys Leu Leu Ile Tyr Trp Ala Ser Thr Leu Glu Ser Gly Val
    50                  55                  60
Pro Ser Arg Phe Ser Gly Ser Gly Ser Gly Thr Asp Tyr Thr Leu Thr
65                  70                  75                  80
Ile Ser Ser Leu Gln Pro Glu Asp Phe Ala Thr Tyr Tyr Cys Gln Asn
                85                  90                  95
Ala Tyr Ser Phe Pro Phe Thr Phe Gly Gln Gly Thr Lys Val Glu Ile
            100                 105                 110
Lys Arg

<210> SEQ ID NO 12
<211> LENGTH: 7
<212> TYPE: PRT
<213> ORGANISM: Artificial Sequence
<220> FEATURE:
<223> OTHER INFORMATION: Synthetic

<400> SEQUENCE: 12

Trp Ala Ser Thr Leu Glu Ser
1               5

<210> SEQ ID NO 13
<211> LENGTH: 113
<212> TYPE: PRT
<213> ORGANISM: Artificial Sequence
<220> FEATURE:
<223> OTHER INFORMATION: Synthetic

<400> SEQUENCE: 13

Asp Ile Gln Met Thr Gln Ser Pro Ser Ser Leu Ser Ala Ser Val Gly
1               5                   10                  15
Asp Arg Val Thr Ile Thr Cys Lys Ser Ser Gln Ser Leu Leu Asn Ser
            20                  25                  30
Gly Asn Gln Lys Ser Tyr Leu Thr Trp Tyr Gln Gln Lys Pro Gly Lys
        35                  40                  45
Ala Pro Lys Leu Leu Ile Tyr Trp Ala Ser Thr Leu Glu Ser Gly Val
    50                  55                  60
Pro Ser Arg Phe Ser Gly Ser Gly Ser Gly Thr Asp Tyr Thr Leu Thr
65                  70                  75                  80
Ile Ser Ser Leu Gln Pro Glu Asp Phe Ala Thr Tyr Tyr Cys Gln Asn
                85                  90                  95
Ala Tyr Phe Phe Pro Phe Thr Phe Gly Gln Gly Thr Lys Val Glu Ile
            100                 105                 110

Lys

<210> SEQ ID NO 14
<211> LENGTH: 9
<212> TYPE: PRT
<213> ORGANISM: Artificial Sequence
<220> FEATURE:
<223> OTHER INFORMATION: Synthetic

<400> SEQUENCE: 14

Gln Asn Ala Tyr Phe Phe Pro Phe Thr
1               5

<210> SEQ ID NO 15
<211> LENGTH: 445
<212> TYPE: PRT
<213> ORGANISM: Artificial Sequence
<220> FEATURE:
<223> OTHER INFORMATION: Synthetic

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 16
<211> LENGTH: 220
<212> TYPE: PRT
<213> ORGANISM: Artificial Sequence
<220> FEATURE:
<223> OTHER INFORMATION: Synthetic

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 17
<211> LENGTH: 115
<212> TYPE: PRT
<213> ORGANISM: Artificial Sequence
<220> FEATURE:
<223> OTHER INFORMATION: Synthetic

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Arg Gly Asn Ser Leu Asp Tyr Trp Gly Gln Gly Thr Leu Val Thr
            100                 105                 110

Val Ser Ser
        115

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Leu Tyr Arg Gly Asn Ser Leu Asp Tyr
1               5

<210> SEQ ID NO 19
<211> LENGTH: 114
<212> TYPE: PRT
<213> ORGANISM: Artificial Sequence
<220> FEATURE:
<223> OTHER INFORMATION: Synthetic

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Lys Pro Gly Lys
            35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile

Lys Arg

<210> SEQ ID NO 20
<211> LENGTH: 445
<212> TYPE: PRT
<213> ORGANISM: Artificial Sequence
<220> FEATURE:
<223> OTHER INFORMATION: Synthetic

<400> SEQUENCE: 20

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Arg Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350
```

```
Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445

<210> SEQ ID NO 21
<211> LENGTH: 115
<212> TYPE: PRT
<213> ORGANISM: Artificial Sequence
<220> FEATURE:
<223> OTHER INFORMATION: Synthetic

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Arg Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
                100                 105                 110

Val Ser Ser
        115

<210> SEQ ID NO 22
<211> LENGTH: 17
<212> TYPE: PRT
<213> ORGANISM: Artificial Sequence
<220> FEATURE:
<223> OTHER INFORMATION: Synthetic

<400> SEQUENCE: 22

Trp Ile Asn Met Tyr Thr Gly Glu Arg Thr Tyr Ala Asp Asp Phe Lys
1               5                   10                  15

Gly

<210> SEQ ID NO 23
<211> LENGTH: 114
<212> TYPE: PRT
<213> ORGANISM: Artificial Sequence
<220> FEATURE:
<223> OTHER INFORMATION: Synthetic

<400> SEQUENCE: 23

Asp Ile Gln Met Thr Gln Ser Pro Ser Ser Leu Ser Ala Ser Val Gly
```

```
               1               5                  10                 15
Asp Arg Val Thr Ile Thr Cys Lys Ser Ser Gln Ser Leu Leu Asn Trp
            20                  25              30

Gly Asn Gln Lys Ser Tyr Leu Thr Trp Tyr Gln Gln Lys Pro Gly Lys
          35              40                  45

Ala Pro Lys Leu Leu Ile Tyr Trp Ala Ser Thr Leu Gln Ser Gly Val
    50                  55              60

Pro Ser Arg Phe Ser Gly Ser Gly Ser Gly Thr Asp Tyr Thr Leu Thr
65              70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg
```

<210> SEQ ID NO 24
<211> LENGTH: 17
<212> TYPE: PRT
<213> ORGANISM: Artificial Sequence
<220> FEATURE:
<223> OTHER INFORMATION: Synthetic

<400> SEQUENCE: 24

```
Lys Ser Ser Gln Ser Leu Leu Asn Trp Gly Asn Gln Lys Ser Tyr Leu
1               5                   10                  15

Thr
```

<210> SEQ ID NO 25
<211> LENGTH: 7
<212> TYPE: PRT
<213> ORGANISM: Artificial Sequence
<220> FEATURE:
<223> OTHER INFORMATION: Synthetic

<400> SEQUENCE: 25

```
Trp Ala Ser Thr Leu Gln Ser
1               5
```

<210> SEQ ID NO 26
<211> LENGTH: 445
<212> TYPE: PRT
<213> ORGANISM: Artificial Sequence
<220> FEATURE:
<223> OTHER INFORMATION: Synthetic

<400> SEQUENCE: 26

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Arg Thr Tyr Ala Asp Asp Phe Lys Gly Arg
    50                  55                  60

Phe Thr Ile Ser Arg Asp Asp Ser Lys Asn Thr Leu Tyr Leu Gln Met
65              70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
```

```
                    100                 105                 110
Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 27
<211> LENGTH: 220
<212> TYPE: PRT
<213> ORGANISM: Artificial Sequence
<220> FEATURE:
<223> OTHER INFORMATION: Synthetic

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Trp
```

```
            20                  25                  30
Gly Asn Gln Lys Ser Tyr Leu Thr Trp Tyr Gln Gln Lys Pro Gly Lys
            35                  40                  45

Ala Pro Lys Leu Leu Ile Tyr Trp Ala Ser Thr Leu Gln Ser Gly Val
 50                  55                  60

Pro Ser Arg Phe Ser Gly Ser Gly Ser Gly Thr Asp Tyr Thr Leu Thr
 65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220
```

<210> SEQ ID NO 28
<211> LENGTH: 115
<212> TYPE: PRT
<213> ORGANISM: Artificial Sequence
<220> FEATURE:
<223> OTHER INFORMATION: Synthetic

<400> SEQUENCE: 28

```
Glu Val Gln Leu Val Glu Ser Gly Gly Gly Leu Val Gln Pro Gly Gly
 1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
            35                  40                  45

Asn Met Tyr Thr Gly Glu Lys Thr Tyr Ala Asp Asp Phe Lys Gly Arg
 50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser
        115
```

<210> SEQ ID NO 29
<211> LENGTH: 17
<212> TYPE: PRT
<213> ORGANISM: Artificial Sequence
<220> FEATURE:
<223> OTHER INFORMATION: Synthetic

<400> SEQUENCE: 29

Trp Ile Asn Met Tyr Thr Gly Glu Lys Thr Tyr Ala Asp Asp Phe Lys
1               5                   10                  15
Gly

<210> SEQ ID NO 30
<211> LENGTH: 113
<212> TYPE: PRT
<213> ORGANISM: Artificial Sequence
<220> FEATURE:
<223> OTHER INFORMATION: Synthetic

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Trp Lys Ser Tyr Leu Thr Trp Tyr Gln Gln Lys Pro Gly Lys
        35                  40                  45

Ala Pro Lys Leu Leu Ile Tyr Trp Ala Ser Thr Leu Val Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110
Lys

<210> SEQ ID NO 31
<211> LENGTH: 17
<212> TYPE: PRT
<213> ORGANISM: Artificial Sequence
<220> FEATURE:
<223> OTHER INFORMATION: Synthetic

<400> SEQUENCE: 31

Lys Ser Ser Gln Ser Leu Leu Asn Ser Gly Asn Trp Lys Ser Tyr Leu
1               5                   10                  15
Thr

<210> SEQ ID NO 32
<211> LENGTH: 7
<212> TYPE: PRT
<213> ORGANISM: Artificial Sequence
<220> FEATURE:
<223> OTHER INFORMATION: Synthetic

<400> SEQUENCE: 32

Trp Ala Ser Thr Leu Val Ser
1               5

<210> SEQ ID NO 33
<211> LENGTH: 445
<212> TYPE: PRT
<213> ORGANISM: Artificial Sequence
<220> FEATURE:
<223> OTHER INFORMATION: Synthetic

<400> SEQUENCE: 33

-continued

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
            35                  40                  45

Asn Met Tyr Thr Gly Glu Lys Thr Tyr Ala Asp Asp Phe Lys Gly Arg
50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Arg Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
```

His Tyr Thr Gln Lys Ser Leu Ser Leu Ser Pro Gly Lys
            435                 440                 445

<210> SEQ ID NO 34
<211> LENGTH: 220
<212> TYPE: PRT
<213> ORGANISM: Artificial Sequence
<220> FEATURE:
<223> OTHER INFORMATION: Synthetic

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Trp Lys Ser Tyr Leu Thr Trp Tyr Gln Gln Lys Pro Gly Lys
        35                  40                  45

Ala Pro Lys Leu Leu Ile Tyr Trp Ala Ser Thr Leu Val Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 35
<211> LENGTH: 113
<212> TYPE: PRT
<213> ORGANISM: Artificial Sequence
<220> FEATURE:
<223> OTHER INFORMATION: Synthetic

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Trp
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Met Ser Gly Val
    50                  55                  60

```
Pro Ser Arg Phe Ser Gly Ser Gly Ser Gly Thr Asp Tyr Thr Leu Thr
 65                  70                  75                  80

Ile Ser Ser Leu Gln Pro Glu Asp Phe Ala Thr Tyr Tyr Cys Gln Asn
                 85                  90                  95

Ala Tyr Ser Phe Pro Phe Thr Phe Gly Gln Gly Thr Lys Val Glu Ile
            100                 105                 110

Lys

<210> SEQ ID NO 36
<211> LENGTH: 7
<212> TYPE: PRT
<213> ORGANISM: Artificial Sequence
<220> FEATURE:
<223> OTHER INFORMATION: Synthetic

<400> SEQUENCE: 36

Trp Ala Ser Thr Leu Met Ser
 1               5

<210> SEQ ID NO 37
<211> LENGTH: 445
<212> TYPE: PRT
<213> ORGANISM: Artificial Sequence
<220> FEATURE:
<223> OTHER INFORMATION: Synthetic

<400> SEQUENCE: 37

Glu Val Gln Leu Val Glu Ser Gly Gly Gly Leu Val Gln Pro Gly Gly
 1               5                  10                  15

Ser Leu Arg Leu Ser Cys Ala Val Ser Gly Tyr Thr Phe Ser Met Asn
                 20                  25                  30

Trp Val Arg Gln Ala Pro Gly Lys Gly Leu Glu Trp Val Ala Trp Ile
             35                  40                  45

Asn Met Tyr Thr Gly Glu Pro Thr Tyr Ala Asp Asp Phe Lys Gly Arg
         50                  55                  60

Phe Thr Ile Ser Arg Asp Asp Ser Lys Asn Thr Leu Tyr Leu Gln Met
 65                  70                  75                  80

Asn Ser Leu Arg Ala Glu Asp Thr Ala Val Tyr Tyr Cys Ala Arg Leu
                 85                  90                  95

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240
```

```
Phe Pro Pro Lys Pro Lys Asp Thr Leu Met Ile Ser Arg Thr Pro Glu
                245                 250                 255

Val Thr Cys Val Val Asp Val Ser His Glu Asp Pro Glu Val Lys
        260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 38
<211> LENGTH: 220
<212> TYPE: PRT
<213> ORGANISM: Artificial Sequence
<220> FEATURE:
<223> OTHER INFORMATION: Synthetic

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Trp
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Met Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160
```

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 39
<211> LENGTH: 113
<212> TYPE: PRT
<213> ORGANISM: Artificial Sequence
<220> FEATURE:
<223> OTHER INFORMATION: Synthetic

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Ile Lys Ser Tyr Leu Thr Trp Tyr Gln Lys Pro Gly Lys
        35                  40                  45

Ala Pro Lys Leu Leu Ile Tyr Trp Ala Ser Thr Leu Arg Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys

<210> SEQ ID NO 40
<211> LENGTH: 17
<212> TYPE: PRT
<213> ORGANISM: Artificial Sequence
<220> FEATURE:
<223> OTHER INFORMATION: Synthetic

<400> SEQUENCE: 40

Lys Ser Ser Gln Ser Leu Leu Asn Ser Gly Asn Ile Lys Ser Tyr Leu
1               5                   10                  15

Thr

<210> SEQ ID NO 41
<211> LENGTH: 7
<212> TYPE: PRT
<213> ORGANISM: Artificial Sequence
<220> FEATURE:
<223> OTHER INFORMATION: Synthetic

<400> SEQUENCE: 41

Trp Ala Ser Thr Leu Arg Ser
1               5

<210> SEQ ID NO 42
<211> LENGTH: 445
<212> TYPE: PRT
<213> ORGANISM: Artificial Sequence
<220> FEATURE:

<223> OTHER INFORMATION: Synthetic

<400> SEQUENCE: 42

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Arg Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400
```

```
Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 43
<211> LENGTH: 220
<212> TYPE: PRT
<213> ORGANISM: Artificial Sequence
<220> FEATURE:
<223> OTHER INFORMATION: Synthetic

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Ile Lys Ser Tyr Leu Thr Trp Tyr Gln Gln Lys Pro Gly Lys
        35                  40                  45

Ala Pro Lys Leu Leu Ile Tyr Trp Ala Ser Thr Leu Arg Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 44
<211> LENGTH: 115
<212> TYPE: PRT
<213> ORGANISM: Artificial Sequence
<220> FEATURE:
<223> OTHER INFORMATION: Synthetic

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45
```

```
Asn Met Tyr Thr Gly Glu Thr Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser
        115

<210> SEQ ID NO 45
<211> LENGTH: 17
<212> TYPE: PRT
<213> ORGANISM: Artificial Sequence
<220> FEATURE:
<223> OTHER INFORMATION: Synthetic

<400> SEQUENCE: 45

Trp Ile Asn Met Tyr Thr Gly Glu Thr Thr Tyr Ala Asp Asp Phe Lys
1               5                   10                  15

Gly

<210> SEQ ID NO 46
<211> LENGTH: 113
<212> TYPE: PRT
<213> ORGANISM: Artificial Sequence
<220> FEATURE:
<223> OTHER INFORMATION: Synthetic

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Trp
                20                  25                  30

Gly Asn Gln Lys Ser Tyr Leu Thr Trp Tyr Gln Gln Lys Pro Gly Lys
            35                  40                  45

Ala Pro Lys Leu Leu Ile Tyr Trp Ala Ser Thr Leu Tyr Ser Gly Val
        50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys

<210> SEQ ID NO 47
<211> LENGTH: 7
<212> TYPE: PRT
<213> ORGANISM: Artificial Sequence
<220> FEATURE:
<223> OTHER INFORMATION: Synthetic

<400> SEQUENCE: 47

Trp Ala Ser Thr Leu Tyr Ser
1               5

<210> SEQ ID NO 48
```

```
<211> LENGTH: 445
<212> TYPE: PRT
<213> ORGANISM: Artificial Sequence
<220> FEATURE:
<223> OTHER INFORMATION: Synthetic

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Thr Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380
```

```
Pro Glu Asn Asn Tyr Lys Thr Thr Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

<210> SEQ ID NO 49
<211> LENGTH: 220
<212> TYPE: PRT
<213> ORGANISM: Artificial Sequence
<220> FEATURE:
<223> OTHER INFORMATION: Synthetic

<400> SEQUENCE: 49

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Trp
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Tyr Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 50
<211> LENGTH: 115
<212> TYPE: PRT
<213> ORGANISM: Artificial Sequence
<220> FEATURE:
<223> OTHER INFORMATION: Synthetic

<400> SEQUENCE: 50

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
```

```
                    20                  25                  30

Trp Val Arg Gln Ala Pro Gly Lys Gly Leu Glu Trp Val Ala Trp Ile
        35                  40                  45

Asn Met Tyr Thr Gly Glu Pro Ile Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser
        115

<210> SEQ ID NO 51
<211> LENGTH: 17
<212> TYPE: PRT
<213> ORGANISM: Artificial Sequence
<220> FEATURE:
<223> OTHER INFORMATION: Synthetic

<400> SEQUENCE: 51

Trp Ile Asn Met Tyr Thr Gly Glu Pro Ile Tyr Ala Asp Asp Phe Lys
1               5                   10                  15

Gly

<210> SEQ ID NO 52
<211> LENGTH: 113
<212> TYPE: PRT
<213> ORGANISM: Artificial Sequence
<220> FEATURE:
<223> OTHER INFORMATION: Synthetic

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Trp
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Phe Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys

<210> SEQ ID NO 53
<211> LENGTH: 7
<212> TYPE: PRT
<213> ORGANISM: Artificial Sequence
<220> FEATURE:
<223> OTHER INFORMATION: Synthetic

<400> SEQUENCE: 53

Trp Ala Ser Thr Leu Phe Ser
```

-continued

<210> SEQ ID NO 54
<211> LENGTH: 445
<212> TYPE: PRT
<213> ORGANISM: Artificial Sequence
<220> FEATURE:
<223> OTHER INFORMATION: Synthetic

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Ile Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys

```
                    355                 360                 365
Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 55
<211> LENGTH: 220
<212> TYPE: PRT
<213> ORGANISM: Artificial Sequence
<220> FEATURE:
<223> OTHER INFORMATION: Synthetic

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Trp
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Phe Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 56
<211> LENGTH: 115
<212> TYPE: PRT
<213> ORGANISM: Artificial Sequence
<220> FEATURE:
<223> OTHER INFORMATION: Synthetic

<400> SEQUENCE: 56
```

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Arg Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser
        115

<210> SEQ ID NO 57
<211> LENGTH: 17
<212> TYPE: PRT
<213> ORGANISM: Artificial Sequence
<220> FEATURE:
<223> OTHER INFORMATION: Synthetic

<400> SEQUENCE: 57

Trp Ile Asn Met Tyr Thr Gly Arg Pro Thr Tyr Ala Asp Asp Phe Lys
1               5                   10                  15

Gly

<210> SEQ ID NO 58
<211> LENGTH: 445
<212> TYPE: PRT
<213> ORGANISM: Artificial Sequence
<220> FEATURE:
<223> OTHER INFORMATION: Synthetic

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Arg Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

-continued

```
Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 59
<211> LENGTH: 113
<212> TYPE: PRT
<213> ORGANISM: Artificial Sequence
<220> FEATURE:
<223> OTHER INFORMATION: Synthetic

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Trp
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Gln Ser Gly Val
    50                  55                  60

Pro Ser Arg Phe Ser Gly Ser Gly Ser Gly Thr Asp Tyr Thr Leu Thr
65                  70                  75                  80
```

```
Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys

<210> SEQ ID NO 60
<211> LENGTH: 445
<212> TYPE: PRT
<213> ORGANISM: Artificial Sequence
<220> FEATURE:
<223> OTHER INFORMATION: Synthetic

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
            35                  40                  45

Asn Met Tyr Thr Gly Glu Arg Thr Tyr Ala Asp Asp Phe Lys Gly Arg
        50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Arg Val Glu Pro Lys Ser Cys Asp Lys Thr His Thr Cys
        210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
```

```
                            325                 330                 335
Ala Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 61
<211> LENGTH: 220
<212> TYPE: PRT
<213> ORGANISM: Artificial Sequence
<220> FEATURE:
<223> OTHER INFORMATION: Synthetic

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Trp
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Gln Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 62
<211> LENGTH: 113
<212> TYPE: PRT
```

<213> ORGANISM: Artificial Sequence
<220> FEATURE:
<223> OTHER INFORMATION: Synthetic

<400> SEQUENCE: 62

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Trp Lys Ser Tyr Leu Thr Trp Tyr Gln Gln Lys Pro Gly Lys
        35                  40                  45

Ala Pro Lys Leu Leu Ile Tyr Trp Ala Ser Thr Leu Val Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys
```

<210> SEQ ID NO 63
<211> LENGTH: 445
<212> TYPE: PRT
<213> ORGANISM: Artificial Sequence
<220> FEATURE:
<223> OTHER INFORMATION: Synthetic

<400> SEQUENCE: 63

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Lys Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
```

```
            210                 215                 220
Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
                275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
                435                 440                 445

<210> SEQ ID NO 64
<211> LENGTH: 220
<212> TYPE: PRT
<213> ORGANISM: Artificial Sequence
<220> FEATURE:
<223> OTHER INFORMATION: Synthetic

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
                20                  25                  30

Gly Asn Trp Lys Ser Tyr Leu Thr Trp Tyr Gln Gln Lys Pro Gly Lys
            35                  40                  45

Ala Pro Lys Leu Leu Ile Tyr Trp Ala Ser Thr Leu Val Ser Gly Val
        50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
```

```
                130                 135                 140
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
            210                 215                 220

<210> SEQ ID NO 65
<211> LENGTH: 113
<212> TYPE: PRT
<213> ORGANISM: Artificial Sequence
<220> FEATURE:
<223> OTHER INFORMATION: Synthetic

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Trp
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Phe Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys

<210> SEQ ID NO 66
<211> LENGTH: 8
<212> TYPE: PRT
<213> ORGANISM: Artificial Sequence
<220> FEATURE:
<223> OTHER INFORMATION: Synthetic

<400> SEQUENCE: 66

Tyr Trp Ala Ser Thr Leu Phe Ser
1               5

<210> SEQ ID NO 67
<211> LENGTH: 445
<212> TYPE: PRT
<213> ORGANISM: Artificial Sequence
<220> FEATURE:
<223> OTHER INFORMATION: Synthetic

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30
```

```
Trp Val Arg Gln Ala Pro Gly Lys Gly Leu Glu Trp Val Ala Trp Ile
         35                  40                  45

Asn Met Tyr Thr Gly Glu Pro Ile Tyr Ala Asp Asp Phe Lys Gly Arg
 50                  55                  60

Phe Thr Ile Ser Arg Asp Asp Ser Lys Asn Thr Leu Tyr Leu Gln Met
 65                  70                  75                  80

Asn Ser Leu Arg Ala Glu Asp Thr Ala Val Tyr Tyr Cys Ala Arg Leu
                 85                  90                  95

Tyr Asn Gly Asn Ser Leu Asp Tyr Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

-continued

```
<210> SEQ ID NO 68
<211> LENGTH: 220
<212> TYPE: PRT
<213> ORGANISM: Artificial Sequence
<220> FEATURE:
<223> OTHER INFORMATION: Synthetic

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Trp
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Phe Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 69
<211> LENGTH: 113
<212> TYPE: PRT
<213> ORGANISM: Artificial Sequence
<220> FEATURE:
<223> OTHER INFORMATION: Synthetic

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Trp
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Tyr Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95
```

```
Ala Tyr Phe Phe Pro Phe Thr Phe Gly Gln Gly Thr Lys Val Glu Ile
                100                 105                 110
Lys

<210> SEQ ID NO 70
<211> LENGTH: 445
<212> TYPE: PRT
<213> ORGANISM: Artificial Sequence
<220> FEATURE:
<223> OTHER INFORMATION: Synthetic

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Thr Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
```

-continued

```
                340                 345                 350
Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

<210> SEQ ID NO 71
<211> LENGTH: 220
<212> TYPE: PRT
<213> ORGANISM: Artificial Sequence
<220> FEATURE:
<223> OTHER INFORMATION: Synthetic

<400> SEQUENCE: 71

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Trp
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Tyr Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 72
<211> LENGTH: 113
<212> TYPE: PRT
<213> ORGANISM: Artificial Sequence
<220> FEATURE:
<223> OTHER INFORMATION: Synthetic

<400> SEQUENCE: 72

```
Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Trp
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Met Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys
```

<210> SEQ ID NO 73
<211> LENGTH: 445
<212> TYPE: PRT
<213> ORGANISM: Artificial Sequence
<220> FEATURE:
<223> OTHER INFORMATION: Synthetic

<400> SEQUENCE: 73

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
```

```
                225                 230                 235                 240
        Phe Pro Pro Lys Pro Lys Asp Thr Leu Met Ile Ser Arg Thr Pro Glu
                        245                 250                 255

Val Thr Cys Val Val Val Asp Val Ser His Glu Asp Pro Glu Val Lys
                        260                 265                 270

Phe Asn Trp Tyr Val Asp Gly Val Glu Val His Asn Ala Lys Thr Lys
                        275                 280                 285

Pro Arg Glu Glu Gln Tyr Asn Ser Thr Tyr Arg Val Val Ser Val Leu
                        290                 295                 300

Thr Val Leu His Gln Asp Trp Leu Asn Gly Lys Glu Tyr Lys Cys Lys
        305                 310                 315                 320

Val Ser Asn Lys Ala Leu Pro Ala Pro Ile Glu Lys Thr Ile Ser Lys
                        325                 330                 335

Ala Lys Gly Gln Pro Arg Glu Pro Gln Val Tyr Thr Leu Pro Pro Ser
                        340                 345                 350

Arg Glu Glu Met Thr Lys Asn Gln Val Ser Leu Thr Cys Leu Val Lys
                        355                 360                 365

Gly Phe Tyr Pro Ser Asp Ile Ala Val Glu Trp Glu Ser Asn Gly Gln
                        370                 375                 380

Pro Glu Asn Asn Tyr Lys Thr Thr Pro Pro Val Leu Asp Ser Asp Gly
        385                 390                 395                 400

Ser Phe Phe Leu Tyr Ser Lys Leu Thr Val Asp Lys Ser Arg Trp Gln
                        405                 410                 415

Gln Gly Asn Val Phe Ser Cys Ser Val Met His Glu Ala Leu His Asn
                        420                 425                 430

His Tyr Thr Gln Lys Ser Leu Ser Leu Ser Pro Gly Lys
                        435                 440                 445

<210> SEQ ID NO 74
<211> LENGTH: 220
<212> TYPE: PRT
<213> ORGANISM: Artificial Sequence
<220> FEATURE:
<223> OTHER INFORMATION: Synthetic

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Trp
                20                  25                  30

Gly Asn Gln Lys Ser Tyr Leu Thr Trp Tyr Gln Gln Lys Pro Gly Lys
            35                  40                  45

Ala Pro Lys Leu Leu Ile Tyr Trp Ala Ser Thr Leu Met Ser Gly Val
        50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
```

```
                145                 150                 155                 160
        Gln Ser Gly Asn Ser Gln Glu Ser Val Thr Glu Gln Asp Ser Lys Asp
                        165                 170                 175

Ser Thr Tyr Ser Leu Ser Ser Thr Leu Thr Leu Ser Lys Ala Asp Tyr
                        180                 185                 190

Glu Lys His Lys Val Tyr Ala Cys Glu Val Thr His Gln Gly Leu Ser
                        195                 200                 205

Ser Pro Val Thr Lys Ser Phe Asn Arg Gly Glu Cys
                        210                 215                 220

<210> SEQ ID NO 75
<211> LENGTH: 113
<212> TYPE: PRT
<213> ORGANISM: Artificial Sequence
<220> FEATURE:
<223> OTHER INFORMATION: Synthetic

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Ser
            20                  25                  30

Gly Asn Ile Lys Ser Tyr Leu Thr Trp Tyr Gln Gln Lys Pro Gly Lys
        35                  40                  45

Ala Pro Lys Leu Leu Ile Tyr Trp Ala Ser Thr Leu Arg Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys

<210> SEQ ID NO 76
<211> LENGTH: 445
<212> TYPE: PRT
<213> ORGANISM: Artificial Sequence
<220> FEATURE:
<223> OTHER INFORMATION: Synthetic

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Arg Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
```

```
            115                 120                 125
Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 77
<211> LENGTH: 220
<212> TYPE: PRT
<213> ORGANISM: Artificial Sequence
<220> FEATURE:
<223> OTHER INFORMATION: Synthetic

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Ile Lys Ser Tyr Leu Thr Trp Tyr Gln Gln Lys Pro Gly Lys
```

```
                35                  40                  45
Ala Pro Lys Leu Leu Ile Tyr Trp Ala Ser Thr Leu Arg Ser Gly Val
 50                  55                  60
Pro Ser Arg Phe Ser Gly Ser Gly Ser Gly Thr Asp Tyr Thr Leu Thr
 65                  70                  75                  80
Ile Ser Ser Leu Gln Pro Glu Asp Phe Ala Thr Tyr Tyr Cys Gln Asn
                 85                  90                  95
Ala Tyr Phe Phe Pro Phe Thr Phe Gly Gln Gly Thr Lys Val Glu Ile
                100                 105                 110
Lys Arg Thr Val Ala Ala Pro Ser Val Phe Ile Phe Pro Pro Ser Asp
            115                 120                 125
Glu Gln Leu Lys Ser Gly Thr Ala Ser Val Val Cys Leu Leu Asn Asn
130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
            180                 185                 190
Glu Lys His Lys Val Tyr Ala Cys Glu Val Thr His Gln Gly Leu Ser
            195                 200                 205
Ser Pro Val Thr Lys Ser Phe Asn Arg Gly Glu Cys
        210                 215                 220

<210> SEQ ID NO 78
<211> LENGTH: 115
<212> TYPE: PRT
<213> ORGANISM: Artificial Sequence
<220> FEATURE:
<223> OTHER INFORMATION: Synthetic

<400> SEQUENCE: 78

Glu Val Gln Leu Val Glu Ser Gly Gly Gly Leu Val Gln Pro Gly Gly
 1               5                  10                  15
Ser Leu Arg Leu Ser Cys Ala Val Ser Gly Tyr Thr Phe Ser Met Asn
             20                  25                  30
Trp Val Arg Gln Ala Pro Gly Lys Gly Leu Glu Trp Val Ala Trp Ile
         35                  40                  45
Asn Met Tyr Thr Gly Glu Arg Thr Tyr Ala Asp Asp Phe Lys Gly Arg
     50                  55                  60
Phe Thr Ile Ser Arg Asp Asp Ser Lys Asn Thr Leu Tyr Leu Gln Met
 65                  70                  75                  80
Asn Ser Leu Arg Ala Glu Asp Thr Ala Val Tyr Tyr Cys Ala Arg Leu
                 85                  90                  95
Tyr Arg Gly Asn Ser Leu Asp Tyr Trp Gly Gln Gly Thr Leu Val Thr
            100                 105                 110
Val Ser Ser
        115

<210> SEQ ID NO 79
<211> LENGTH: 445
<212> TYPE: PRT
<213> ORGANISM: Artificial Sequence
<220> FEATURE:
<223> OTHER INFORMATION: Synthetic

<400> SEQUENCE: 79
```

-continued

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
            35                  40                  45

Asn Met Tyr Thr Gly Glu Arg Thr Tyr Ala Asp Asp Phe Lys Gly Arg
50                      55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
            85                  90                  95

Tyr Arg Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Arg Val Glu Pro Lys Ser Cys Asp Lys Thr His Thr Cys
            210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
```

His Tyr Thr Gln Lys Ser Leu Ser Leu Ser Pro Gly Lys
        435                 440                 445

<210> SEQ ID NO 80
<211> LENGTH: 115
<212> TYPE: PRT
<213> ORGANISM: Artificial Sequence
<220> FEATURE:
<223> OTHER INFORMATION: Synthetic

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Lys Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Arg Gly Asn Ser Leu Asp Tyr Trp Gly Gln Gly Thr Leu Val Thr
            100                 105                 110

Val Ser Ser
        115

<210> SEQ ID NO 81
<211> LENGTH: 445
<212> TYPE: PRT
<213> ORGANISM: Artificial Sequence
<220> FEATURE:
<223> OTHER INFORMATION: Synthetic

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Lys Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Arg Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 82
<211> LENGTH: 115
<212> TYPE: PRT
<213> ORGANISM: Artificial Sequence
<220> FEATURE:
<223> OTHER INFORMATION: Synthetic

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Ile Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

```
Asn Ser Leu Arg Ala Glu Asp Thr Ala Val Tyr Tyr Cys Ala Arg Leu
                85                  90                  95

Tyr Arg Gly Asn Ser Leu Asp Tyr Trp Gly Gln Gly Thr Leu Val Thr
            100                 105                 110

Val Ser Ser
        115

<210> SEQ ID NO 83
<211> LENGTH: 445
<212> TYPE: PRT
<213> ORGANISM: Artificial Sequence
<220> FEATURE:
<223> OTHER INFORMATION: Synthetic

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Ile Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Arg Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320
```

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 84
<211> LENGTH: 115
<212> TYPE: PRT
<213> ORGANISM: Artificial Sequence
<220> FEATURE:
<223> OTHER INFORMATION: Synthetic

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Thr Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Arg Gly Asn Ser Leu Asp Tyr Trp Gly Gln Gly Thr Leu Val Thr
            100                 105                 110

Val Ser Ser
        115

<210> SEQ ID NO 85
<211> LENGTH: 445
<212> TYPE: PRT
<213> ORGANISM: Artificial Sequence
<220> FEATURE:
<223> OTHER INFORMATION: Synthetic

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Thr Thr Tyr Ala Asp Asp Phe Lys Gly Arg
    50                  55                  60

```
Phe Thr Ile Ser Arg Asp Asp Ser Lys Asn Thr Leu Tyr Leu Gln Met
 65                  70                  75                  80

Asn Ser Leu Arg Ala Glu Asp Thr Ala Val Tyr Tyr Cys Ala Arg Leu
                 85                  90                  95

Tyr Arg Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 86
<211> LENGTH: 445
<212> TYPE: PRT
<213> ORGANISM: Artificial Sequence
<220> FEATURE:
```

-continued

<223> OTHER INFORMATION: Synthetic

<400> SEQUENCE: 86

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Arg Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400
```

```
Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 87
<211> LENGTH: 445
<212> TYPE: PRT
<213> ORGANISM: Artificial Sequence
<220> FEATURE:
<223> OTHER INFORMATION: Synthetic

<400> SEQUENCE: 87

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Arg Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Arg Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320
```

-continued

```
Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

<210> SEQ ID NO 88
<211> LENGTH: 445
<212> TYPE: PRT
<213> ORGANISM: Artificial Sequence
<220> FEATURE:
<223> OTHER INFORMATION: Synthetic

<400> SEQUENCE: 88

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Ile Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Arg Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240
```

```
Phe Pro Pro Lys Pro Lys Asp Thr Leu Met Ile Ser Arg Thr Pro Glu
                245                 250                 255

Val Thr Cys Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 89
<211> LENGTH: 445
<212> TYPE: PRT
<213> ORGANISM: Artificial Sequence
<220> FEATURE:
<223> OTHER INFORMATION: Synthetic

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Arg Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Arg Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160
```

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 90
<211> LENGTH: 113
<212> TYPE: PRT
<213> ORGANISM: Artificial Sequence
<220> FEATURE:
<223> OTHER INFORMATION: Synthetic

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Trp
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
            85                  90                  95

Ala Tyr Ser Phe Pro Phe Thr Phe Gly Gln Gly Thr Lys Val Glu Ile
            100                 105                 110

Lys

<210> SEQ ID NO 91
<211> LENGTH: 445
<212> TYPE: PRT
<213> ORGANISM: Artificial Sequence
<220> FEATURE:
<223> OTHER INFORMATION: Synthetic

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
            35                  40                  45

Asn Met Tyr Thr Gly Glu Pro Ile Tyr Ala Asp Asp Phe Lys Gly Arg
        50                  55                  60

Phe Thr Ile Ser Arg Asp Asp Ser Lys Asn Thr Leu Tyr Leu Gln Met
65              70                  75                  80

Asn Ser Leu Arg Ala Glu Asp Thr Ala Val Tyr Tyr Cys Ala Arg Leu
            85                  90                  95

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Arg Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys

```
                    325                 330                 335
Ala Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445

<210> SEQ ID NO 92
<211> LENGTH: 220
<212> TYPE: PRT
<213> ORGANISM: Artificial Sequence
<220> FEATURE:
<223> OTHER INFORMATION: Synthetic

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Trp
                20                  25                  30

Gly Asn Gln Lys Ser Tyr Leu Thr Trp Tyr Gln Gln Lys Pro Gly Lys
                35                  40                  45

Ala Pro Lys Leu Leu Ile Tyr Trp Ala Ser Thr Leu Glu Ser Gly Val
                50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
                130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
                210                 215                 220

<210> SEQ ID NO 93
<211> LENGTH: 113
<212> TYPE: PRT
```

<213> ORGANISM: Artificial Sequence
<220> FEATURE:
<223> OTHER INFORMATION: Synthetic

<400> SEQUENCE: 93

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Trp
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys
```

<210> SEQ ID NO 94
<211> LENGTH: 445
<212> TYPE: PRT
<213> ORGANISM: Artificial Sequence
<220> FEATURE:
<223> OTHER INFORMATION: Synthetic

<400> SEQUENCE: 94

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Ile Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Arg Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
```

```
                210                 215                 220
Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 95
<211> LENGTH: 220
<212> TYPE: PRT
<213> ORGANISM: Artificial Sequence
<220> FEATURE:
<223> OTHER INFORMATION: Synthetic

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Trp
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
```

```
            130                 135                 140
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
            210                 215                 220

<210> SEQ ID NO 96
<211> LENGTH: 445
<212> TYPE: PRT
<213> ORGANISM: Artificial Sequence
<220> FEATURE:
<223> OTHER INFORMATION: Synthetic

<400> SEQUENCE: 96

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Arg Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Arg Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
```

```
                275                 280                 285
Pro Arg Glu Glu Gln Tyr Asn Ser Thr Tyr Arg Val Val Ser Val Leu
        290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Glu Glu Met Thr Lys Asn Gln Val Ser Leu Thr Cys Leu Val Lys
                355                 360                 365
Gly Phe Tyr Pro Ser Asp Ile Ala Val Glu Trp Glu Ser Asn Gly Gln
            370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
            435                 440                 445

<210> SEQ ID NO 97
<211> LENGTH: 121
<212> TYPE: PRT
<213> ORGANISM: Artificial Sequence
<220> FEATURE:
<223> OTHER INFORMATION: Synthetic

<400> SEQUENCE: 97

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Arg Tyr
                20                  25                  30
Trp Met Ser Trp Val Arg Gln Ala Pro Gly Lys Gly Leu Glu Trp Val
            35                  40                  45
Ala Asn Ile Lys Gln Asp Gly Ser Glu Lys Tyr Tyr Val Asp Ser Val
        50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Glu Gly Gly Trp Phe Gly Glu Leu Ala Phe Asp Tyr Trp Gly
            100                 105                 110
Gln Gly Thr Leu Val Thr Val Ser Ser
        115                 120

<210> SEQ ID NO 98
<211> LENGTH: 10
<212> TYPE: PRT
<213> ORGANISM: Artificial Sequence
<220> FEATURE:
<223> OTHER INFORMATION: Synthetic

<400> SEQUENCE: 98

Gly Phe Thr Phe Ser Arg Tyr Trp Met Ser
1               5                   10
```

<210> SEQ ID NO 99
<211> LENGTH: 17
<212> TYPE: PRT
<213> ORGANISM: Artificial Sequence
<220> FEATURE:
<223> OTHER INFORMATION: Synthetic

<400> SEQUENCE: 99

```
Asn Ile Lys Gln Asp Gly Ser Glu Lys Tyr Tyr Val Asp Ser Val Lys
1               5                   10                  15

Gly
```

<210> SEQ ID NO 100
<211> LENGTH: 12
<212> TYPE: PRT
<213> ORGANISM: Artificial Sequence
<220> FEATURE:
<223> OTHER INFORMATION: Synthetic

<400> SEQUENCE: 100

```
Glu Gly Gly Trp Phe Gly Glu Leu Ala Phe Asp Tyr
1               5                   10
```

<210> SEQ ID NO 101
<211> LENGTH: 108
<212> TYPE: PRT
<213> ORGANISM: Artificial Sequence
<220> FEATURE:
<223> OTHER INFORMATION: Synthetic

<400> SEQUENCE: 101

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105
```

<210> SEQ ID NO 102
<211> LENGTH: 12
<212> TYPE: PRT
<213> ORGANISM: Artificial Sequence
<220> FEATURE:
<223> OTHER INFORMATION: Synthetic

<400> SEQUENCE: 102

```
Arg Ala Ser Gln Arg Val Ser Ser Ser Tyr Leu Ala
1               5                   10
```

<210> SEQ ID NO 103
<211> LENGTH: 7
<212> TYPE: PRT
<213> ORGANISM: Artificial Sequence
<220> FEATURE:
<223> OTHER INFORMATION: Synthetic -continued

<400> SEQUENCE: 103

Asp Ala Ser Ser Arg Ala Thr
1               5

<210> SEQ ID NO 104
<211> LENGTH: 9
<212> TYPE: PRT
<213> ORGANISM: Artificial Sequence
<220> FEATURE:
<223> OTHER INFORMATION: Synthetic

<400> SEQUENCE: 104

Gln Gln Tyr Gly Ser Leu Pro Trp Thr
1               5

<210> SEQ ID NO 105
<211> LENGTH: 120
<212> TYPE: PRT
<213> ORGANISM: Artificial Sequence
<220> FEATURE:
<223> OTHER INFORMATION: Synthetic

<400> SEQUENCE: 105

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser
        115                 120

<210> SEQ ID NO 106
<211> LENGTH: 10
<212> TYPE: PRT
<213> ORGANISM: Artificial Sequence
<220> FEATURE:
<223> OTHER INFORMATION: Synthetic

<400> SEQUENCE: 106

Gly Phe Thr Phe Ser Ser Tyr Ile Met Met
1               5                   10

<210> SEQ ID NO 107
<211> LENGTH: 17
<212> TYPE: PRT
<213> ORGANISM: Artificial Sequence
<220> FEATURE:
<223> OTHER INFORMATION: Synthetic

<400> SEQUENCE: 107

Ser Ile Tyr Pro Ser Gly Gly Ile Thr Phe Tyr Ala Asp Thr Val Lys
1               5                   10                  15

Gly

<210> SEQ ID NO 108
<211> LENGTH: 11
<212> TYPE: PRT
<213> ORGANISM: Artificial Sequence
<220> FEATURE:
<223> OTHER INFORMATION: Synthetic

<400> SEQUENCE: 108

Ile Lys Leu Gly Thr Val Thr Thr Val Asp Tyr
1               5                   10

<210> SEQ ID NO 109
<211> LENGTH: 110
<212> TYPE: PRT
<213> ORGANISM: Artificial Sequence
<220> FEATURE:
<223> OTHER INFORMATION: Synthetic

<400> SEQUENCE: 109

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110

<210> SEQ ID NO 110
<211> LENGTH: 14
<212> TYPE: PRT
<213> ORGANISM: Artificial Sequence
<220> FEATURE:
<223> OTHER INFORMATION: Synthetic

<400> SEQUENCE: 110

Thr Gly Thr Ser Ser Asp Val Gly Gly Tyr Asn Tyr Val Ser
1               5                   10

<210> SEQ ID NO 111
<211> LENGTH: 7
<212> TYPE: PRT
<213> ORGANISM: Artificial Sequence
<220> FEATURE:
<223> OTHER INFORMATION: Synthetic

<400> SEQUENCE: 111

Asp Val Ser Asn Arg Pro Ser
1               5

<210> SEQ ID NO 112
<211> LENGTH: 10
<212> TYPE: PRT
<213> ORGANISM: Artificial Sequence
<220> FEATURE:
<223> OTHER INFORMATION: Synthetic

<400> SEQUENCE: 112

Ser Ser Tyr Thr Ser Ser Ser Thr Arg Val
1               5                   10

<210> SEQ ID NO 113
<211> LENGTH: 118
<212> TYPE: PRT
<213> ORGANISM: Artificial Sequence
<220> FEATURE:
<223> OTHER INFORMATION: Synthetic

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 114
<211> LENGTH: 10
<212> TYPE: PRT
<213> ORGANISM: Artificial Sequence
<220> FEATURE:
<223> OTHER INFORMATION: Synthetic

<400> SEQUENCE: 114

Gly Phe Thr Phe Ser Asp Ser Trp Ile His
1               5                   10

<210> SEQ ID NO 115
<211> LENGTH: 17
<212> TYPE: PRT
<213> ORGANISM: Artificial Sequence
<220> FEATURE:
<223> OTHER INFORMATION: Synthetic

<400> SEQUENCE: 115

Trp Ile Ser Pro Tyr Gly Gly Ser Thr Tyr Tyr Ala Asp Ser Val Lys
1               5                   10                  15

Gly

<210> SEQ ID NO 116
<211> LENGTH: 9
<212> TYPE: PRT
<213> ORGANISM: Artificial Sequence
<220> FEATURE:
<223> OTHER INFORMATION: Synthetic

<400> SEQUENCE: 116

Arg His Trp Pro Gly Gly Phe Asp Tyr

<210> SEQ ID NO 117
<211> LENGTH: 107
<212> TYPE: PRT
<213> ORGANISM: Artificial Sequence
<220> FEATURE:
<223> OTHER INFORMATION: Synthetic

<400> SEQUENCE: 117

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Ser Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Leu Tyr His Pro Ala
                85                  90                  95
Thr Phe Gly Gln Gly Thr Lys Val Glu Ile Lys
            100                 105

<210> SEQ ID NO 118
<211> LENGTH: 11
<212> TYPE: PRT
<213> ORGANISM: Artificial Sequence
<220> FEATURE:
<223> OTHER INFORMATION: Synthetic

<400> SEQUENCE: 118

Arg Ala Ser Gln Asp Val Ser Thr Ala Val Ala
1               5                   10

<210> SEQ ID NO 119
<211> LENGTH: 7
<212> TYPE: PRT
<213> ORGANISM: Artificial Sequence
<220> FEATURE:
<223> OTHER INFORMATION: Synthetic

<400> SEQUENCE: 119

Ser Ala Ser Phe Leu Tyr Ser
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic

<400> SEQUENCE: 120

Gln Gln Tyr Leu Tyr His Pro Ala Thr
1               5

<210> SEQ ID NO 121
<211> LENGTH: 5
<212> TYPE: PRT
<213> ORGANISM: Artificial Sequence
<220> FEATURE:
<223> OTHER INFORMATION: Synthetic

```
<400> SEQUENCE: 121

Ser Gly Gly Gly Gly
1               5

<210> SEQ ID NO 122
<211> LENGTH: 15
<212> TYPE: PRT
<213> ORGANISM: Artificial Sequence
<220> FEATURE:
<223> OTHER INFORMATION: Synthetic

<400> SEQUENCE: 122

Gly Gly Gly Gly Ser Gly Gly Gly Gly Ser Gly Gly Gly Gly Ser
1               5                   10                  15

<210> SEQ ID NO 123
<211> LENGTH: 20
<212> TYPE: PRT
<213> ORGANISM: Artificial Sequence
<220> FEATURE:
<223> OTHER INFORMATION: Synthetic

<400> SEQUENCE: 123

Gly Gly Gly Gly Ser Gly Gly Gly Gly Ser Gly Gly Gly Gly Ser Gly
1               5                   10                  15

Gly Gly Gly Ser
            20

<210> SEQ ID NO 124
<211> LENGTH: 6
<212> TYPE: PRT
<213> ORGANISM: Artificial Sequence
<220> FEATURE:
<223> OTHER INFORMATION: Synthetic

<400> SEQUENCE: 124

Gly Ser Ser Arg Ser Ser
1               5

<210> SEQ ID NO 125
<211> LENGTH: 17
<212> TYPE: PRT
<213> ORGANISM: Artificial Sequence
<220> FEATURE:
<223> OTHER INFORMATION: Synthetic

<400> SEQUENCE: 125

Gly Ser Gly Ser Ser Ser Ser Ser Arg Ser Ser Ser Gly Ser Gly Gly
1               5                   10                  15

Gly

<210> SEQ ID NO 126
<211> LENGTH: 6
<212> TYPE: PRT
<213> ORGANISM: Artificial Sequence
<220> FEATURE:
<223> OTHER INFORMATION: Synthetic

<400> SEQUENCE: 126

Ser Gly Gly Arg Gly Gly
1               5

<210> SEQ ID NO 127
<211> LENGTH: 15
```

<212> TYPE: PRT
<213> ORGANISM: Artificial Sequence
<220> FEATURE:
<223> OTHER INFORMATION: Synthetic

<400> SEQUENCE: 127

Gly Ser Ser Gly Ser Ser Ser Arg Gly Gly Ser Gly Ser Ser
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: Synthetic

<400> SEQUENCE: 128

Ser Ser Ser Gly Ser Gly Gly Gly Gly Ser Gly Gly Gly Gly Gly
1               5                   10                  15

<210> SEQ ID NO 129
<211> LENGTH: 5
<212> TYPE: PRT
<213> ORGANISM: Artificial Sequence
<220> FEATURE:
<223> OTHER INFORMATION: Synthetic

<400> SEQUENCE: 129

Gly Ser Ser Gly Ser
1               5

<210> SEQ ID NO 130
<211> LENGTH: 15
<212> TYPE: PRT
<213> ORGANISM: Artificial Sequence
<220> FEATURE:
<223> OTHER INFORMATION: Synthetic

<400> SEQUENCE: 130

Gly Gly Gly Gly Ser Gly Ser Gly Ser Ser Gly Ser Ser Ser Gly
1               5                   10                  15

<210> SEQ ID NO 131
<211> LENGTH: 6
<212> TYPE: PRT
<213> ORGANISM: Artificial Sequence
<220> FEATURE:
<223> OTHER INFORMATION: Synthetic

<400> SEQUENCE: 131

Gly Gly Gly Gly Ser Gly
1               5

<210> SEQ ID NO 132
<211> LENGTH: 16
<212> TYPE: PRT
<213> ORGANISM: Artificial Sequence
<220> FEATURE:
<223> OTHER INFORMATION: Synthetic

<400> SEQUENCE: 132

Gly Ser Ser Ser Gly Gly Gly Ser Gly Gly Ser Ser Ser Ser Ser
1               5                   10                  15

<210> SEQ ID NO 133
<211> LENGTH: 4
<212> TYPE: PRT

```
<213> ORGANISM: Artificial Sequence
<220> FEATURE:
<223> OTHER INFORMATION: Synthetic

<400> SEQUENCE: 133

Ser Gly Gly Ser
1

<210> SEQ ID NO 134
<211> LENGTH: 4
<212> TYPE: PRT
<213> ORGANISM: Artificial Sequence
<220> FEATURE:
<223> OTHER INFORMATION: Synthetic

<400> SEQUENCE: 134

Gly Gly Gly Ser
1

<210> SEQ ID NO 135
<211> LENGTH: 15
<212> TYPE: PRT
<213> ORGANISM: Artificial Sequence
<220> FEATURE:
<223> OTHER INFORMATION: Synthetic

<400> SEQUENCE: 135

Ser Ser Gly Ser Gly Gly Gly Ser Ser Ser Gly Ser Ser Gly Gly
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: Synthetic

<400> SEQUENCE: 136

Ser Gly Gly Arg Ser Gly Ser Gly Ser Gly Ser Asn Gly Gly Gly
1               5                   10                  15

<210> SEQ ID NO 137
<211> LENGTH: 6
<212> TYPE: PRT
<213> ORGANISM: Artificial Sequence
<220> FEATURE:
<223> OTHER INFORMATION: Synthetic

<400> SEQUENCE: 137

Gly Gly Ser Gly Gly Gly
1               5

<210> SEQ ID NO 138
<211> LENGTH: 16
<212> TYPE: PRT
<213> ORGANISM: Artificial Sequence
<220> FEATURE:
<223> OTHER INFORMATION: Synthetic

<400> SEQUENCE: 138

Gly Ser Ser Gly Arg Gly Ser Ser Gly Ser Gly Gly Ser Ser Gly
1               5                   10                  15

<210> SEQ ID NO 139
<211> LENGTH: 4
<212> TYPE: PRT
<213> ORGANISM: Artificial Sequence
```

```
<220> FEATURE:
<223> OTHER INFORMATION: Synthetic

<400> SEQUENCE: 139

Gly Gly Ser Gly
1

<210> SEQ ID NO 140
<211> LENGTH: 5
<212> TYPE: PRT
<213> ORGANISM: Artificial Sequence
<220> FEATURE:
<223> OTHER INFORMATION: Synthetic

<400> SEQUENCE: 140

Gly Gly Gly Ser Ser
1               5

<210> SEQ ID NO 141
<211> LENGTH: 6
<212> TYPE: PRT
<213> ORGANISM: Artificial Sequence
<220> FEATURE:
<223> OTHER INFORMATION: Synthetic

<400> SEQUENCE: 141

Gly Ser Gly Ser Gly Gly
1               5

<210> SEQ ID NO 142
<211> LENGTH: 15
<212> TYPE: PRT
<213> ORGANISM: Artificial Sequence
<220> FEATURE:
<223> OTHER INFORMATION: Synthetic

<400> SEQUENCE: 142

Ser Gly Ser Ser Gly Ser Ser Ser Ser Gly Ser Gly Ser Gly
1               5                   10                  15

<210> SEQ ID NO 143
<211> LENGTH: 6
<212> TYPE: PRT
<213> ORGANISM: Artificial Sequence
<220> FEATURE:
<223> OTHER INFORMATION: Synthetic

<400> SEQUENCE: 143

Ser Ser Gly Ser Gly Gly
1               5

<210> SEQ ID NO 144
<211> LENGTH: 14
<212> TYPE: PRT
<213> ORGANISM: Artificial Sequence
<220> FEATURE:
<223> OTHER INFORMATION: Synthetic

<400> SEQUENCE: 144

Ser Gly Ser Ser Gly Ser Ser Ser Ser Gly Ser Gly Ser Gly
1               5                   10

<210> SEQ ID NO 145
<211> LENGTH: 4
<212> TYPE: PRT
<213> ORGANISM: Artificial Sequence
<220> FEATURE:
```

```
<223> OTHER INFORMATION: Synthetic

<400> SEQUENCE: 145

Gly Ser Gly Ser
1

<210> SEQ ID NO 146
<211> LENGTH: 16
<212> TYPE: PRT
<213> ORGANISM: Artificial Sequence
<220> FEATURE:
<223> OTHER INFORMATION: Synthetic

<400> SEQUENCE: 146

Ser Ser Gly Gly Ser Ser Gly Ser Ser Gly Ser Gly Ser Ser Gly Gly
1               5                   10                  15

<210> SEQ ID NO 147
<211> LENGTH: 5
<212> TYPE: PRT
<213> ORGANISM: Artificial Sequence
<220> FEATURE:
<223> OTHER INFORMATION: Synthetic

<400> SEQUENCE: 147

Ser Gly Gly Gly Ser
1               5

<210> SEQ ID NO 148
<211> LENGTH: 16
<212> TYPE: PRT
<213> ORGANISM: Artificial Sequence
<220> FEATURE:
<223> OTHER INFORMATION: Synthetic

<400> SEQUENCE: 148

Ser Ser Ser Ser Ser Gly Gly Gly Gly Ser Gly Gly Ser Ser Ser Gly
1               5                   10                  15

<210> SEQ ID NO 149
<211> LENGTH: 6
<212> TYPE: PRT
<213> ORGANISM: Artificial Sequence
<220> FEATURE:
<223> OTHER INFORMATION: Synthetic

<400> SEQUENCE: 149

Ser Ser Ser Gly Gly Gly
1               5

<210> SEQ ID NO 150
<211> LENGTH: 5
<212> TYPE: PRT
<213> ORGANISM: Artificial Sequence
<220> FEATURE:
<223> OTHER INFORMATION: Synthetic

<400> SEQUENCE: 150

Gly Gly Gly Gly Gly
1               5

<210> SEQ ID NO 151
<211> LENGTH: 6
<212> TYPE: PRT
<213> ORGANISM: Artificial Sequence
<220> FEATURE:
<223> OTHER INFORMATION: Synthetic
```

```
<400> SEQUENCE: 151

Ser Gly Gly Ser Gly Gly
1               5

<210> SEQ ID NO 152
<211> LENGTH: 4
<212> TYPE: PRT
<213> ORGANISM: Artificial Sequence
<220> FEATURE:
<223> OTHER INFORMATION: Synthetic

<400> SEQUENCE: 152

Gly Ser Ser Gly
1

<210> SEQ ID NO 153
<211> LENGTH: 17
<212> TYPE: PRT
<213> ORGANISM: Artificial Sequence
<220> FEATURE:
<223> OTHER INFORMATION: Synthetic

<400> SEQUENCE: 153

Ser Ser Gly Ser Ser Ser Gly Ser Arg Ser Gly Ser Ser Ser Gly Gly
1               5                   10                  15

Ser

<210> SEQ ID NO 154
<211> LENGTH: 6
<212> TYPE: PRT
<213> ORGANISM: Artificial Sequence
<220> FEATURE:
<223> OTHER INFORMATION: Synthetic

<400> SEQUENCE: 154

Ser Gly Gly Gly Gly Gly
1               5

<210> SEQ ID NO 155
<211> LENGTH: 5
<212> TYPE: PRT
<213> ORGANISM: Artificial Sequence
<220> FEATURE:
<223> OTHER INFORMATION: Synthetic

<400> SEQUENCE: 155

Gly Gly Gly Ser Gly
1               5

<210> SEQ ID NO 156
<211> LENGTH: 17
<212> TYPE: PRT
<213> ORGANISM: Artificial Sequence
<220> FEATURE:
<223> OTHER INFORMATION: Synthetic

<400> SEQUENCE: 156

Gly Ser Ser Ser Gly Gly Ser Ser Gly Ser Gly Gly Gly Gly Gly
1               5                   10                  15

Gly

<210> SEQ ID NO 157
<211> LENGTH: 5
<212> TYPE: PRT
```

```
<213> ORGANISM: Artificial Sequence
<220> FEATURE:
<223> OTHER INFORMATION: Synthetic

<400> SEQUENCE: 157

Ser Ser Ser Gly Gly
1               5

<210> SEQ ID NO 158
<211> LENGTH: 15
<212> TYPE: PRT
<213> ORGANISM: Artificial Sequence
<220> FEATURE:
<223> OTHER INFORMATION: Synthetic

<400> SEQUENCE: 158

Ser Gly Gly Gly Ser Ser Gly Ser Gly Gly Arg Ser Gly Ser
1               5                   10                  15

<210> SEQ ID NO 159
<211> LENGTH: 6
<212> TYPE: PRT
<213> ORGANISM: Artificial Sequence
<220> FEATURE:
<223> OTHER INFORMATION: Synthetic

<400> SEQUENCE: 159

Ser Gly Ser Gly Gly Ser
1               5

<210> SEQ ID NO 160
<211> LENGTH: 17
<212> TYPE: PRT
<213> ORGANISM: Artificial Sequence
<220> FEATURE:
<223> OTHER INFORMATION: Synthetic

<400> SEQUENCE: 160

Gly Ser Gly Gly Gly Gly Ser Ser Gly Ser Ser Gly Ser Gly Gly Ser
1               5                   10                  15

Gly

<210> SEQ ID NO 161
<211> LENGTH: 6
<212> TYPE: PRT
<213> ORGANISM: Artificial Sequence
<220> FEATURE:
<223> OTHER INFORMATION: Synthetic

<400> SEQUENCE: 161

Ser Ser Ser Gly Ser Ser
1               5

<210> SEQ ID NO 162
<211> LENGTH: 17
<212> TYPE: PRT
<213> ORGANISM: Artificial Sequence
<220> FEATURE:
<223> OTHER INFORMATION: Synthetic

<400> SEQUENCE: 162

Gly Gly Gly Gly Ser Ser Gly Ser Gly Ser Ser Ser Arg Ser Ser Gly
1               5                   10                  15

Gly
```

```
<210> SEQ ID NO 163
<211> LENGTH: 5
<212> TYPE: PRT
<213> ORGANISM: Artificial Sequence
<220> FEATURE:
<223> OTHER INFORMATION: Synthetic

<400> SEQUENCE: 163

Gly Ser Gly Gly Gly
1               5

<210> SEQ ID NO 164
<211> LENGTH: 5
<212> TYPE: PRT
<213> ORGANISM: Artificial Sequence
<220> FEATURE:
<223> OTHER INFORMATION: Synthetic

<400> SEQUENCE: 164

Gly Gly Gly Gly Ser
1               5

<210> SEQ ID NO 165
<211> LENGTH: 232
<212> TYPE: PRT
<213> ORGANISM: Artificial Sequence
<220> FEATURE:
<223> OTHER INFORMATION: Synthetic

<400> SEQUENCE: 165

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 166
<211> LENGTH: 115
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (39)..(39)
<223> OTHER INFORMATION: Xaa is Gly or Cys
<220> FEATURE:
<221> NAME/KEY: MISC_FEATURE
<222> LOCATION: (41)..(41)
<223> OTHER INFORMATION: Xaa is Gly or Cys
<220> FEATURE:
<221> NAME/KEY: MISC_FEATURE
<222> LOCATION: (55)..(55)
<223> OTHER INFORMATION: Xaa is Pro or Arg
<220> FEATURE:
<221> NAME/KEY: MISC_FEATURE
<222> LOCATION: (107)..(107)
<223> OTHER INFORMATION: Xaa is Gln or Cys
<220> FEATURE:
<221> NAME/KEY: MISC_FEATURE
<222> LOCATION: (114)..(114)
<223> OTHER INFORMATION: Xaa is Ser or Cys

<400> SEQUENCE: 166

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Xaa Lys Xaa Leu Glu Trp Val Ala Trp Ile
        35                  40                  45

Asn Met Tyr Thr Gly Glu Xaa Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Xaa Gly Thr Leu Val Thr
            100                 105                 110

Val Xaa Ser
        115

<210> SEQ ID NO 167
<211> LENGTH: 113
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: Xaa is Ser or Trp
<220> FEATURE:
<221> NAME/KEY: MISC_FEATURE
<222> LOCATION: (49)..(49)
<223> OTHER INFORMATION: Xaa is Ala or Cys
<220> FEATURE:
<221> NAME/KEY: MISC_FEATURE
<222> LOCATION: (61)..(61)
<223> OTHER INFORMATION: Xaa is Glu or Gln
<220> FEATURE:
<221> NAME/KEY: MISC_FEATURE
<222> LOCATION: (106)..(106)
<223> OTHER INFORMATION: Xaa is Gln or Cys

<400> SEQUENCE: 167

Asp Ile Gln Met Thr Gln Ser Pro Ser Leu Ser Ala Ser Val Gly
1               5                   10                  15

Asp Arg Val Thr Ile Thr Cys Lys Ser Ser Gln Ser Leu Leu Asn Xaa
                20                  25                  30

Gly Asn Gln Lys Ser Tyr Leu Thr Trp Tyr Gln Gln Lys Pro Gly Lys
            35                  40                  45

Xaa Pro Lys Leu Leu Ile Tyr Trp Ala Ser Thr Leu Xaa Ser Gly Val
    50                  55                  60

Pro Ser Arg Phe Ser Gly Ser Gly Ser Gly Thr Asp Tyr Thr Leu Thr
65              70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Xaa Gly Thr Lys Val Glu Ile
                100                 105                 110

Lys

<210> SEQ ID NO 168
<211> LENGTH: 115
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (39)..(39)
<223> OTHER INFORMATION: Xaa is Gly or Cys
<220> FEATURE:
<221> NAME/KEY: MISC_FEATURE
<222> LOCATION: (41)..(41)
<223> OTHER INFORMATION: Xaa is Gly or Cys
<220> FEATURE:
<221> NAME/KEY: MISC_FEATURE
<222> LOCATION: (107)..(107)
<223> OTHER INFORMATION: Xaa is Gln or Cys
<220> FEATURE:
<221> NAME/KEY: MISC_FEATURE
<222> LOCATION: (114)..(114)
<223> OTHER INFORMATION: Xaa is Ser or Cys

<400> SEQUENCE: 168

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
                20                  25                  30

Trp Val Arg Gln Ala Pro Xaa Lys Xaa Leu Glu Trp Val Ala Trp Ile
            35                  40                  45

Asn Met Tyr Thr Gly Glu Pro Thr Tyr Ala Asp Asp Phe Lys Gly Arg
        50                  55                  60

Phe Thr Ile Ser Arg Asp Asp Ser Lys Asn Thr Leu Tyr Leu Gln Met
65              70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Xaa Gly Thr Leu Val Thr
                100                 105                 110

Val Xaa Ser
        115

<210> SEQ ID NO 169
<211> LENGTH: 113
<212> TYPE: PRT

<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (49)..(49)
<223> OTHER INFORMATION: Xaa is Ala or Cys
<220> FEATURE:
<221> NAME/KEY: MISC_FEATURE
<222> LOCATION: (106)..(106)
<223> OTHER INFORMATION: Xaa is Gln or Cys

<400> SEQUENCE: 169

Asp Ile Gln Met Thr Gln Ser Pro Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Lys Pro Gly Lys
        35                  40                  45

Xaa Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Xaa Gly Thr Lys Val Glu Ile
            100                 105                 110

Lys

<210> SEQ ID NO 170
<211> LENGTH: 121
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is Gln or Cys
<220> FEATURE:
<221> NAME/KEY: MISC_FEATURE
<222> LOCATION: (9)..(9)
<223> OTHER INFORMATION: Xaa is Gly or Cys
<220> FEATURE:
<221> NAME/KEY: MISC_FEATURE
<222> LOCATION: (44)..(44)
<223> OTHER INFORMATION: Xaa is Gly or Cys
<220> FEATURE:
<221> NAME/KEY: MISC_FEATURE
<222> LOCATION: (113)..(113)
<223> OTHER INFORMATION: Xaa is Gln or Cys

<400> SEQUENCE: 170

Glu Val Xaa Leu Val Glu Ser Gly Xaa Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Xaa Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys

```
                85                  90                  95

Ala Arg Glu Gly Gly Trp Phe Gly Glu Leu Ala Phe Asp Tyr Trp Gly
            100                 105                 110

Xaa Gly Thr Leu Val Thr Val Ser Ser
            115                 120

<210> SEQ ID NO 171
<211> LENGTH: 108
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (44)..(44)
<223> OTHER INFORMATION: Xaa is Ala or Cys
<220> FEATURE:
<221> NAME/KEY: MISC_FEATURE
<222> LOCATION: (101)..(101)
<223> OTHER INFORMATION: Xaa is Gln or Cys

<400> SEQUENCE: 171

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Xaa Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Xaa Gly Thr Lys Val Glu Ile Lys
            100                 105

<210> SEQ ID NO 172
<211> LENGTH: 719
<212> TYPE: PRT
<213> ORGANISM: Artificial Sequence
<220> FEATURE:
<223> OTHER INFORMATION: Synthetic

<400> SEQUENCE: 172

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Ser Gly Gly Gly Gly Glu Val Gln Leu Val Glu Ser Gly Gly Gly
```

-continued

```
            115                 120                 125
Leu Val Gln Pro Gly Gly Ser Leu Arg Leu Ser Cys Ala Ala Ser Gly
    130                 135                 140

Phe Thr Phe Ser Arg Tyr Trp Met Ser Trp Val Arg Gln Ala Pro Gly
145                 150                 155                 160

Lys Gly Leu Glu Trp Val Ala Asn Ile Lys Gln Asp Gly Ser Glu Lys
                165                 170                 175

Tyr Tyr Val Asp Ser Val Lys Gly Arg Phe Thr Ile Ser Arg Asp Asn
            180                 185                 190

Ala Lys Asn Ser Leu Tyr Leu Gln Met Asn Ser Leu Arg Ala Glu Asp
        195                 200                 205

Thr Ala Val Tyr Tyr Cys Ala Arg Glu Gly Gly Trp Phe Gly Glu Leu
    210                 215                 220

Ala Phe Asp Tyr Trp Gly Gln Gly Thr Leu Val Thr Val Ser Ser Gly
225                 230                 235                 240

Gly Gly Gly Ser Gly Gly Gly Ser Gly Gly Gly Ser Glu Ile
                245                 250                 255

Val Leu Thr Gln Ser Pro Gly Thr Leu Ser Leu Ser Pro Gly Glu Arg
            260                 265                 270

Ala Thr Leu Ser Cys Arg Ala Ser Gln Arg Val Ser Ser Ser Tyr Leu
        275                 280                 285

Ala Trp Tyr Gln Gln Lys Pro Gly Gln Ala Pro Arg Leu Leu Ile Tyr
    290                 295                 300

Asp Ala Ser Ser Arg Ala Thr Gly Ile Pro Asp Arg Phe Ser Gly Ser
305                 310                 315                 320

Gly Ser Gly Thr Asp Phe Thr Leu Thr Ile Ser Arg Leu Glu Pro Glu
                325                 330                 335

Asp Phe Ala Val Tyr Tyr Cys Gln Gln Tyr Gly Ser Leu Pro Trp Thr
            340                 345                 350

Phe Gly Gln Gly Thr Lys Val Glu Ile Lys Ser Gly Gly Gly Gly Glu
        355                 360                 365

Val Gln Leu Val Glu Ser Gly Gly Gly Leu Val Gln Pro Gly Gly Ser
    370                 375                 380

Leu Arg Leu Ser Cys Ala Val Ser Gly Tyr Thr Phe Ser Met Asn Trp
385                 390                 395                 400

Val Arg Gln Ala Pro Gly Lys Gly Leu Glu Trp Val Ala Trp Ile Asn
                405                 410                 415

Met Tyr Thr Gly Glu Pro Thr Tyr Ala Asp Asp Phe Lys Gly Arg Phe
            420                 425                 430

Thr Ile Ser Arg Asp Asp Ser Lys Asn Thr Leu Tyr Leu Gln Met Asn
        435                 440                 445

Ser Leu Arg Ala Glu Asp Thr Ala Val Tyr Tyr Cys Ala Arg Leu Tyr
    450                 455                 460

Asn Gly Asn Ser Leu Asp Tyr Trp Gly Gln Gly Thr Leu Val Thr Val
465                 470                 475                 480

Ser Ser Gly Gly Gly Gly Ser Glu Pro Lys Ser Ser Asp Lys Thr His
                485                 490                 495

Thr Cys Pro Pro Cys Pro Ala Pro Glu Leu Leu Gly Gly Pro Ser Val
            500                 505                 510

Phe Leu Phe Pro Pro Lys Pro Lys Asp Thr Leu Met Ile Ser Arg Thr
        515                 520                 525

Pro Glu Val Thr Cys Val Val Val Asp Val Ser His Glu Asp Pro Glu
    530                 535                 540
```

```
Val Lys Phe Asn Trp Tyr Val Asp Gly Val Glu Val His Asn Ala Lys
545                 550                 555                 560

Thr Lys Pro Arg Glu Glu Gln Tyr Asn Ser Thr Tyr Arg Val Val Ser
                565                 570                 575

Val Leu Thr Val Leu His Gln Asp Trp Leu Asn Gly Lys Glu Tyr Lys
            580                 585                 590

Cys Lys Val Ser Asn Lys Ala Leu Pro Ala Pro Ile Glu Lys Thr Ile
                595                 600                 605

Ser Lys Ala Lys Gly Gln Pro Arg Glu Pro Gln Val Tyr Thr Leu Pro
610                 615                 620

Pro Ser Arg Glu Glu Met Thr Lys Asn Gln Val Ser Leu Thr Cys Leu
625                 630                 635                 640

Val Lys Gly Phe Tyr Pro Ser Asp Ile Ala Val Glu Trp Glu Ser Asn
                645                 650                 655

Gly Gln Pro Glu Asn Asn Tyr Lys Thr Thr Pro Pro Val Leu Asp Ser
                660                 665                 670

Asp Gly Ser Phe Phe Leu Tyr Ser Lys Leu Thr Val Asp Lys Ser Arg
            675                 680                 685

Trp Gln Gln Gly Asn Val Phe Ser Cys Ser Val Met His Glu Ala Leu
            690                 695                 700

His Asn His Tyr Thr Gln Lys Ser Leu Ser Leu Ser Pro Gly Lys
705                 710                 715

<210> SEQ ID NO 173
<211> LENGTH: 719
<212> TYPE: PRT
<213> ORGANISM: Artificial Sequence
<220> FEATURE:
<223> OTHER INFORMATION: Synthetic

<400> SEQUENCE: 173

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Cys Gly Thr Lys Val Glu Ile
            100                 105                 110

Lys Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
130                 135                 140

Phe Thr Phe Ser Arg Tyr Trp Met Ser Trp Val Arg Gln Ala Pro Gly
145                 150                 155                 160

Lys Cys Leu Glu Trp Val Ala Asn Ile Lys Gln Asp Gly Ser Glu Lys
                165                 170                 175

Tyr Tyr Val Asp Ser Val Lys Gly Arg Phe Thr Ile Ser Arg Asp Asn
            180                 185                 190
```

```
Ala Lys Asn Ser Leu Tyr Leu Gln Met Asn Ser Leu Arg Ala Glu Asp
        195                 200                 205

Thr Ala Val Tyr Tyr Cys Ala Arg Glu Gly Gly Trp Phe Gly Glu Leu
    210                 215                 220

Ala Phe Asp Tyr Trp Gly Gln Gly Thr Leu Val Thr Val Ser Ser Gly
225                 230                 235                 240

Gly Gly Gly Ser Gly Gly Gly Ser Gly Gly Gly Ser Glu Ile
                245                 250                 255

Val Leu Thr Gln Ser Pro Gly Thr Leu Ser Leu Ser Pro Gly Glu Arg
            260                 265                 270

Ala Thr Leu Ser Cys Arg Ala Ser Gln Arg Val Ser Ser Tyr Leu
        275                 280                 285

Ala Trp Tyr Gln Gln Lys Pro Gly Gln Ala Pro Arg Leu Leu Ile Tyr
        290                 295                 300

Asp Ala Ser Ser Arg Ala Thr Gly Ile Pro Asp Arg Phe Ser Gly Ser
305                 310                 315                 320

Gly Ser Gly Thr Asp Phe Thr Leu Thr Ile Ser Arg Leu Glu Pro Glu
                325                 330                 335

Asp Phe Ala Val Tyr Tyr Cys Gln Gln Tyr Gly Ser Leu Pro Trp Thr
            340                 345                 350

Phe Gly Cys Gly Thr Lys Val Glu Ile Lys Ser Gly Gly Gly Gly Glu
        355                 360                 365

Val Gln Leu Val Glu Ser Gly Gly Gly Leu Val Gln Pro Gly Gly Ser
    370                 375                 380

Leu Arg Leu Ser Cys Ala Val Ser Gly Tyr Thr Phe Ser Met Asn Trp
385                 390                 395                 400

Val Arg Gln Ala Pro Gly Lys Cys Leu Glu Trp Val Ala Trp Ile Asn
                405                 410                 415

Met Tyr Thr Gly Glu Pro Thr Tyr Ala Asp Asp Phe Lys Gly Arg Phe
            420                 425                 430

Thr Ile Ser Arg Asp Asp Ser Lys Asn Thr Leu Tyr Leu Gln Met Asn
        435                 440                 445

Ser Leu Arg Ala Glu Asp Thr Ala Val Tyr Tyr Cys Ala Arg Leu Tyr
    450                 455                 460

Asn Gly Asn Ser Leu Asp Tyr Trp Gly Gln Gly Thr Leu Val Thr Val
465                 470                 475                 480

Ser Ser Gly Gly Gly Gly Ser Glu Pro Lys Ser Ser Asp Lys Thr His
                485                 490                 495

Thr Cys Pro Pro Cys Pro Ala Pro Glu Leu Leu Gly Gly Pro Ser Val
            500                 505                 510

Phe Leu Phe Pro Pro Lys Pro Lys Asp Thr Leu Met Ile Ser Arg Thr
        515                 520                 525

Pro Glu Val Thr Cys Val Val Val Asp Val Ser His Glu Asp Pro Glu
    530                 535                 540

Val Lys Phe Asn Trp Tyr Val Asp Gly Val Glu Val His Asn Ala Lys
545                 550                 555                 560

Thr Lys Pro Arg Glu Glu Gln Tyr Asn Ser Thr Tyr Arg Val Val Ser
                565                 570                 575

Val Leu Thr Val Leu His Gln Asp Trp Leu Asn Gly Lys Glu Tyr Lys
            580                 585                 590

Cys Lys Val Ser Asn Lys Ala Leu Pro Ala Pro Ile Glu Lys Thr Ile
        595                 600                 605
```

```
Ser Lys Ala Lys Gly Gln Pro Arg Glu Pro Gln Val Tyr Thr Leu Pro
        610                 615                 620

Pro Ser Arg Glu Glu Met Thr Lys Asn Gln Val Ser Leu Thr Cys Leu
625                 630                 635                 640

Val Lys Gly Phe Tyr Pro Ser Asp Ile Ala Val Glu Trp Glu Ser Asn
            645                 650                 655

Gly Gln Pro Glu Asn Asn Tyr Lys Thr Thr Pro Pro Val Leu Asp Ser
        660                 665                 670

Asp Gly Ser Phe Phe Leu Tyr Ser Lys Leu Thr Val Asp Lys Ser Arg
    675                 680                 685

Trp Gln Gln Gly Asn Val Phe Ser Cys Ser Val Met His Glu Ala Leu
690                 695                 700

His Asn His Tyr Thr Gln Lys Ser Leu Ser Leu Ser Pro Gly Lys
705                 710                 715

<210> SEQ ID NO 174
<211> LENGTH: 719
<212> TYPE: PRT
<213> ORGANISM: Artificial Sequence
<220> FEATURE:
<223> OTHER INFORMATION: Synthetic

<400> SEQUENCE: 174

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Cys Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Thr Phe Ser Arg Tyr Trp Met Ser Trp Val Arg Gln Ala Pro Gly
145                 150                 155                 160

Lys Gly Leu Glu Trp Val Ala Asn Ile Lys Gln Asp Gly Ser Glu Lys
                165                 170                 175

Tyr Tyr Val Asp Ser Val Lys Gly Arg Phe Thr Ile Ser Arg Asp Asn
            180                 185                 190

Ala Lys Asn Ser Leu Tyr Leu Gln Met Asn Ser Leu Arg Ala Glu Asp
        195                 200                 205

Thr Ala Val Tyr Tyr Cys Ala Arg Glu Gly Gly Trp Phe Gly Glu Leu
    210                 215                 220

Ala Phe Asp Tyr Trp Gly Cys Gly Thr Leu Val Thr Val Ser Ser Gly
225                 230                 235                 240

Gly Gly Gly Ser Gly Gly Gly Ser Gly Gly Gly Ser Glu Ile
                245                 250                 255
```

```
Val Leu Thr Gln Ser Pro Gly Thr Leu Ser Leu Ser Pro Gly Glu Arg
            260                 265                 270

Ala Thr Leu Ser Cys Arg Ala Ser Gln Arg Val Ser Ser Ser Tyr Leu
        275                 280                 285

Ala Trp Tyr Gln Gln Lys Pro Gly Gln Cys Pro Arg Leu Leu Ile Tyr
    290                 295                 300

Asp Ala Ser Ser Arg Ala Thr Gly Ile Pro Asp Arg Phe Ser Gly Ser
305                 310                 315                 320

Gly Ser Gly Thr Asp Phe Thr Leu Thr Ile Ser Arg Leu Glu Pro Glu
                325                 330                 335

Asp Phe Ala Val Tyr Tyr Cys Gln Gln Tyr Gly Ser Leu Pro Trp Thr
            340                 345                 350

Phe Gly Gln Gly Thr Lys Val Glu Ile Lys Ser Gly Gly Gly Gly Glu
        355                 360                 365

Val Gln Leu Val Glu Ser Gly Gly Leu Val Gln Pro Gly Gly Ser
    370                 375                 380

Leu Arg Leu Ser Cys Ala Val Ser Gly Tyr Thr Phe Ser Met Asn Trp
385                 390                 395                 400

Val Arg Gln Ala Pro Gly Lys Gly Leu Glu Trp Val Ala Trp Ile Asn
                405                 410                 415

Met Tyr Thr Gly Glu Pro Thr Tyr Ala Asp Asp Phe Lys Gly Arg Phe
            420                 425                 430

Thr Ile Ser Arg Asp Asp Ser Lys Asn Thr Leu Tyr Leu Gln Met Asn
        435                 440                 445

Ser Leu Arg Ala Glu Asp Thr Ala Val Tyr Tyr Cys Ala Arg Leu Tyr
450                 455                 460

Asn Gly Asn Ser Leu Asp Tyr Trp Gly Cys Gly Thr Leu Val Thr Val
465                 470                 475                 480

Ser Ser Gly Gly Gly Gly Ser Glu Pro Lys Ser Ser Asp Lys Thr His
                485                 490                 495

Thr Cys Pro Pro Cys Pro Ala Pro Glu Leu Leu Gly Gly Pro Ser Val
            500                 505                 510

Phe Leu Phe Pro Pro Lys Pro Lys Asp Thr Leu Met Ile Ser Arg Thr
        515                 520                 525

Pro Glu Val Thr Cys Val Val Val Asp Val Ser His Glu Asp Pro Glu
    530                 535                 540

Val Lys Phe Asn Trp Tyr Val Asp Gly Val Glu Val His Asn Ala Lys
545                 550                 555                 560

Thr Lys Pro Arg Glu Glu Gln Tyr Asn Ser Thr Tyr Arg Val Val Ser
                565                 570                 575

Val Leu Thr Val Leu His Gln Asp Trp Leu Asn Gly Lys Glu Tyr Lys
            580                 585                 590

Cys Lys Val Ser Asn Lys Ala Leu Pro Ala Pro Ile Glu Lys Thr Ile
        595                 600                 605

Ser Lys Ala Lys Gly Gln Pro Arg Glu Pro Gln Val Tyr Thr Leu Pro
    610                 615                 620

Pro Ser Arg Glu Glu Met Thr Lys Asn Gln Val Ser Leu Thr Cys Leu
625                 630                 635                 640

Val Lys Gly Phe Tyr Pro Ser Asp Ile Ala Val Glu Trp Glu Ser Asn
                645                 650                 655

Gly Gln Pro Glu Asn Asn Tyr Lys Thr Thr Pro Pro Val Leu Asp Ser
            660                 665                 670

Asp Gly Ser Phe Phe Leu Tyr Ser Lys Leu Thr Val Asp Lys Ser Arg
```

```
                675                 680                 685
Trp Gln Gln Gly Asn Val Phe Ser Cys Ser Val Met His Glu Ala Leu
        690                 695                 700

His Asn His Tyr Thr Gln Lys Ser Leu Ser Leu Ser Pro Gly Lys
705                 710                 715

<210> SEQ ID NO 175
<211> LENGTH: 719
<212> TYPE: PRT
<213> ORGANISM: Artificial Sequence
<220> FEATURE:
<223> OTHER INFORMATION: Synthetic

<400> SEQUENCE: 175

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Ser Gly Gly Gly Gly Glu Val Cys Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Thr Phe Ser Arg Tyr Trp Met Ser Trp Val Arg Gln Ala Pro Gly
145                 150                 155                 160

Lys Gly Leu Glu Trp Val Ala Asn Ile Lys Gln Asp Gly Ser Glu Lys
                165                 170                 175

Tyr Tyr Val Asp Ser Val Lys Gly Arg Phe Thr Ile Ser Arg Asp Asn
            180                 185                 190

Ala Lys Asn Ser Leu Tyr Leu Gln Met Asn Ser Leu Arg Ala Glu Asp
        195                 200                 205

Thr Ala Val Tyr Tyr Cys Ala Arg Glu Gly Gly Trp Phe Gly Glu Leu
    210                 215                 220

Ala Phe Asp Tyr Trp Gly Gln Gly Thr Leu Val Thr Val Ser Ser Gly
225                 230                 235                 240

Gly Gly Gly Ser Gly Gly Gly Gly Ser Gly Gly Gly Gly Ser Glu Ile
                245                 250                 255

Val Leu Thr Gln Ser Pro Gly Thr Leu Ser Leu Ser Pro Gly Glu Arg
            260                 265                 270

Ala Thr Leu Ser Cys Arg Ala Ser Gln Arg Val Ser Ser Ser Tyr Leu
        275                 280                 285

Ala Trp Tyr Gln Gln Lys Pro Gly Gln Ala Pro Arg Leu Leu Ile Tyr
    290                 295                 300

Asp Ala Ser Ser Arg Ala Thr Gly Ile Pro Asp Arg Phe Ser Gly Ser
305                 310                 315                 320

Gly Ser Gly Thr Asp Phe Thr Leu Thr Ile Ser Arg Leu Glu Pro Glu
```

```
                        325                 330                 335
Asp Phe Ala Val Tyr Tyr Cys Gln Gln Tyr Gly Ser Leu Pro Trp Thr
                    340                 345                 350
Phe Gly Gln Gly Thr Lys Val Glu Ile Lys Ser Gly Gly Gly Gly Glu
                355                 360                 365
Val Gln Leu Val Glu Ser Gly Gly Leu Val Gln Pro Gly Gly Ser
            370                 375                 380
Leu Arg Leu Ser Cys Ala Val Ser Gly Tyr Thr Phe Ser Met Asn Trp
385                 390                 395                 400
Val Arg Gln Ala Pro Cys Lys Gly Leu Glu Trp Val Ala Trp Ile Asn
                405                 410                 415
Met Tyr Thr Gly Glu Pro Thr Tyr Ala Asp Asp Phe Lys Gly Arg Phe
            420                 425                 430
Thr Ile Ser Arg Asp Asp Ser Lys Asn Thr Leu Tyr Leu Gln Met Asn
        435                 440                 445
Ser Leu Arg Ala Glu Asp Thr Ala Val Tyr Tyr Cys Ala Arg Leu Tyr
    450                 455                 460
Asn Gly Asn Ser Leu Asp Tyr Trp Gly Gln Gly Thr Leu Val Thr Val
465                 470                 475                 480
Ser Ser Gly Gly Gly Gly Ser Glu Pro Lys Ser Ser Asp Lys Thr His
                485                 490                 495
Thr Cys Pro Pro Cys Pro Ala Pro Glu Leu Leu Gly Gly Pro Ser Val
            500                 505                 510
Phe Leu Phe Pro Pro Lys Pro Lys Asp Thr Leu Met Ile Ser Arg Thr
        515                 520                 525
Pro Glu Val Thr Cys Val Val Val Asp Val Ser His Glu Asp Pro Glu
    530                 535                 540
Val Lys Phe Asn Trp Tyr Val Asp Gly Val Glu Val His Asn Ala Lys
545                 550                 555                 560
Thr Lys Pro Arg Glu Glu Gln Tyr Asn Ser Thr Tyr Arg Val Val Ser
                565                 570                 575
Val Leu Thr Val Leu His Gln Asp Trp Leu Asn Gly Lys Glu Tyr Lys
            580                 585                 590
Cys Lys Val Ser Asn Lys Ala Leu Pro Ala Pro Ile Glu Lys Thr Ile
        595                 600                 605
Ser Lys Ala Lys Gly Gln Pro Arg Glu Pro Gln Val Tyr Thr Leu Pro
    610                 615                 620
Pro Ser Arg Glu Glu Met Thr Lys Asn Gln Val Ser Leu Thr Cys Leu
625                 630                 635                 640
Val Lys Gly Phe Tyr Pro Ser Asp Ile Ala Val Glu Trp Glu Ser Asn
                645                 650                 655
Gly Gln Pro Glu Asn Asn Tyr Lys Thr Thr Pro Pro Val Leu Asp Ser
            660                 665                 670
Asp Gly Ser Phe Phe Leu Tyr Ser Lys Leu Thr Val Asp Lys Ser Arg
        675                 680                 685
Trp Gln Gln Gly Asn Val Phe Ser Cys Ser Val Met His Glu Ala Leu
    690                 695                 700
His Asn His Tyr Thr Gln Lys Ser Leu Ser Leu Ser Pro Gly Lys
705                 710                 715

<210> SEQ ID NO 176
<211> LENGTH: 719
<212> TYPE: PRT
<213> ORGANISM: Artificial Sequence
```

```
<220> FEATURE:
<223> OTHER INFORMATION: Synthetic

<400> SEQUENCE: 176

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Ser Gly Gly Gly Gly Glu Val Gln Leu Val Glu Ser Gly Cys Gly
        115                 120                 125

Leu Val Gln Pro Gly Gly Ser Leu Arg Leu Ser Cys Ala Ala Ser Gly
    130                 135                 140

Phe Thr Phe Ser Arg Tyr Trp Met Ser Trp Val Arg Gln Ala Pro Gly
145                 150                 155                 160

Lys Gly Leu Glu Trp Val Ala Asn Ile Lys Gln Asp Gly Ser Glu Lys
                165                 170                 175

Tyr Tyr Val Asp Ser Val Lys Gly Arg Phe Thr Ile Ser Arg Asp Asn
            180                 185                 190

Ala Lys Asn Ser Leu Tyr Leu Gln Met Asn Ser Leu Arg Ala Glu Asp
        195                 200                 205

Thr Ala Val Tyr Tyr Cys Ala Arg Glu Gly Gly Trp Phe Gly Glu Leu
    210                 215                 220

Ala Phe Asp Tyr Trp Gly Gln Gly Thr Leu Val Thr Val Ser Ser Gly
225                 230                 235                 240

Gly Gly Gly Ser Gly Gly Gly Ser Gly Gly Gly Ser Glu Ile
                245                 250                 255

Val Leu Thr Gln Ser Pro Gly Thr Leu Ser Leu Ser Pro Gly Glu Arg
            260                 265                 270

Ala Thr Leu Ser Cys Arg Ala Ser Gln Arg Val Ser Ser Ser Tyr Leu
        275                 280                 285

Ala Trp Tyr Gln Gln Lys Pro Gly Gln Ala Pro Arg Leu Leu Ile Tyr
    290                 295                 300

Asp Ala Ser Ser Arg Ala Thr Gly Ile Pro Asp Arg Phe Ser Gly Ser
305                 310                 315                 320

Gly Ser Gly Thr Asp Phe Thr Leu Thr Ile Ser Arg Leu Glu Pro Glu
                325                 330                 335

Asp Phe Ala Val Tyr Tyr Cys Gln Gln Tyr Gly Ser Leu Pro Trp Thr
            340                 345                 350

Phe Gly Gln Gly Thr Lys Val Glu Ile Lys Ser Gly Gly Gly Gly Glu
        355                 360                 365

Val Gln Leu Val Glu Ser Gly Gly Gly Leu Val Gln Pro Gly Gly Ser
    370                 375                 380

Leu Arg Leu Ser Cys Ala Val Ser Gly Tyr Thr Phe Ser Met Asn Trp
385                 390                 395                 400
```

Val Arg Gln Ala Pro Gly Lys Gly Leu Glu Trp Val Ala Trp Ile Asn
            405                 410                 415

Met Tyr Thr Gly Glu Pro Thr Tyr Ala Asp Asp Phe Lys Gly Arg Phe
        420                 425                 430

Thr Ile Ser Arg Asp Asp Ser Lys Asn Thr Leu Tyr Leu Gln Met Asn
            435                 440                 445

Ser Leu Arg Ala Glu Asp Thr Ala Val Tyr Tyr Cys Ala Arg Leu Tyr
450                 455                 460

Asn Gly Asn Ser Leu Asp Tyr Trp Gly Gln Gly Thr Leu Val Thr Val
465                 470                 475                 480

Cys Ser Gly Gly Gly Ser Glu Pro Lys Ser Ser Asp Lys Thr His
                485                 490                 495

Thr Cys Pro Pro Cys Pro Ala Pro Glu Leu Leu Gly Gly Pro Ser Val
            500                 505                 510

Phe Leu Phe Pro Pro Lys Pro Lys Asp Thr Leu Met Ile Ser Arg Thr
        515                 520                 525

Pro Glu Val Thr Cys Val Val Val Asp Val Ser His Glu Asp Pro Glu
        530                 535                 540

Val Lys Phe Asn Trp Tyr Val Asp Gly Val Glu Val His Asn Ala Lys
545                 550                 555                 560

Thr Lys Pro Arg Glu Glu Gln Tyr Asn Ser Thr Tyr Arg Val Val Ser
                565                 570                 575

Val Leu Thr Val Leu His Gln Asp Trp Leu Asn Gly Lys Glu Tyr Lys
            580                 585                 590

Cys Lys Val Ser Asn Lys Ala Leu Pro Ala Pro Ile Glu Lys Thr Ile
        595                 600                 605

Ser Lys Ala Lys Gly Gln Pro Arg Glu Pro Gln Val Tyr Thr Leu Pro
    610                 615                 620

Pro Ser Arg Glu Glu Met Thr Lys Asn Gln Val Ser Leu Thr Cys Leu
625                 630                 635                 640

Val Lys Gly Phe Tyr Pro Ser Asp Ile Ala Val Glu Trp Glu Ser Asn
                645                 650                 655

Gly Gln Pro Glu Asn Asn Tyr Lys Thr Thr Pro Pro Val Leu Asp Ser
            660                 665                 670

Asp Gly Ser Phe Phe Leu Tyr Ser Lys Leu Thr Val Asp Lys Ser Arg
        675                 680                 685

Trp Gln Gln Gly Asn Val Phe Ser Cys Ser Val Met His Glu Ala Leu
    690                 695                 700

His Asn His Tyr Thr Gln Lys Ser Leu Ser Leu Ser Pro Gly Lys
705                 710                 715

<210> SEQ ID NO 177
<211> LENGTH: 724
<212> TYPE: PRT
<213> ORGANISM: Artificial Sequence
<220> FEATURE:
<223> OTHER INFORMATION: Synthetic

<400> SEQUENCE: 177

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
 50                 55                  60

Pro Ser Arg Phe Ser Gly Ser Gly Ser Gly Thr Asp Tyr Thr Leu Thr
 65                  70                  75                  80

Ile Ser Ser Leu Gln Pro Glu Asp Phe Ala Thr Tyr Tyr Cys Gln Asn
                 85                  90                  95

Ala Tyr Phe Phe Pro Phe Thr Phe Gly Cys Gly Thr Lys Val Glu Ile
            100                 105                 110

Lys Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
130                 135                 140

Phe Thr Phe Ser Arg Tyr Trp Met Ser Trp Val Arg Gln Ala Pro Gly
145                 150                 155                 160

Lys Cys Leu Glu Trp Val Ala Asn Ile Lys Gln Asp Gly Ser Glu Lys
                165                 170                 175

Tyr Tyr Val Asp Ser Val Lys Gly Arg Phe Thr Ile Ser Arg Asp Asn
            180                 185                 190

Ala Lys Asn Ser Leu Tyr Leu Gln Met Asn Ser Leu Arg Ala Glu Asp
        195                 200                 205

Thr Ala Val Tyr Tyr Cys Ala Arg Glu Gly Gly Trp Phe Gly Glu Leu
210                 215                 220

Ala Phe Asp Tyr Trp Gly Gln Gly Thr Leu Val Thr Val Ser Ser Gly
225                 230                 235                 240

Gly Gly Gly Ser Gly Gly Gly Ser Gly Gly Gly Ser Gly
                245                 250                 255

Gly Gly Ser Glu Ile Val Leu Thr Gln Ser Pro Gly Thr Leu Ser Leu
        260                 265                 270

Ser Pro Gly Glu Arg Ala Thr Leu Ser Cys Arg Ala Ser Gln Arg Val
275                 280                 285

Ser Ser Ser Tyr Leu Ala Trp Tyr Gln Gln Lys Pro Gly Gln Ala Pro
290                 295                 300

Arg Leu Leu Ile Tyr Asp Ala Ser Ser Arg Ala Thr Gly Ile Pro Asp
305                 310                 315                 320

Arg Phe Ser Gly Ser Gly Ser Gly Thr Asp Phe Thr Leu Thr Ile Ser
            325                 330                 335

Arg Leu Glu Pro Glu Asp Phe Ala Val Tyr Tyr Cys Gln Gln Tyr Gly
            340                 345                 350

Ser Leu Pro Trp Thr Phe Gly Cys Gly Thr Lys Val Glu Ile Lys Ser
        355                 360                 365

Gly Gly Gly Gly Glu Val Gln Leu Val Glu Ser Gly Gly Gly Leu Val
        370                 375                 380

Gln Pro Gly Gly Ser Leu Arg Leu Ser Cys Ala Val Ser Gly Tyr Thr
385                 390                 395                 400

Phe Ser Met Asn Trp Val Arg Gln Ala Pro Gly Lys Cys Leu Glu Trp
                405                 410                 415

Val Ala Trp Ile Asn Met Tyr Thr Gly Glu Pro Thr Tyr Ala Asp Asp
            420                 425                 430

Phe Lys Gly Arg Phe Thr Ile Ser Arg Asp Asp Ser Lys Asn Thr Leu
        435                 440                 445

Tyr Leu Gln Met Asn Ser Leu Arg Ala Glu Asp Thr Ala Val Tyr Tyr
450                 455                 460

Cys Ala Arg Leu Tyr Asn Gly Asn Ser Leu Asp Tyr Trp Gly Gln Gly
465                 470                 475                 480

Thr Leu Val Thr Val Ser Ser Gly Gly Gly Gly Ser Glu Pro Lys Ser
            485                 490                 495

Ser Asp Lys Thr His Thr Cys Pro Pro Cys Pro Ala Pro Glu Leu Leu
            500                 505                 510

Gly Gly Pro Ser Val Phe Leu Phe Pro Pro Lys Pro Lys Asp Thr Leu
            515                 520                 525

Met Ile Ser Arg Thr Pro Glu Val Thr Cys Val Val Val Asp Val Ser
            530                 535                 540

His Glu Asp Pro Glu Val Lys Phe Asn Trp Tyr Val Asp Gly Val Glu
545                 550                 555                 560

Val His Asn Ala Lys Thr Lys Pro Arg Glu Glu Gln Tyr Asn Ser Thr
            565                 570                 575

Tyr Arg Val Val Ser Val Leu Thr Val Leu His Gln Asp Trp Leu Asn
            580                 585                 590

Gly Lys Glu Tyr Lys Cys Lys Val Ser Asn Lys Ala Leu Pro Ala Pro
            595                 600                 605

Ile Glu Lys Thr Ile Ser Lys Ala Lys Gly Gln Pro Arg Glu Pro Gln
            610                 615                 620

Val Tyr Thr Leu Pro Pro Ser Arg Glu Glu Met Thr Lys Asn Gln Val
625                 630                 635                 640

Ser Leu Thr Cys Leu Val Lys Gly Phe Tyr Pro Ser Asp Ile Ala Val
            645                 650                 655

Glu Trp Glu Ser Asn Gly Gln Pro Glu Asn Asn Tyr Lys Thr Thr Pro
            660                 665                 670

Pro Val Leu Asp Ser Asp Gly Ser Phe Phe Leu Tyr Ser Lys Leu Thr
            675                 680                 685

Val Asp Lys Ser Arg Trp Gln Gln Gly Asn Val Phe Ser Cys Ser Val
            690                 695                 700

Met His Glu Ala Leu His Asn His Tyr Thr Gln Lys Ser Leu Ser Leu
705                 710                 715                 720

Ser Pro Gly Lys

<210> SEQ ID NO 178
<211> LENGTH: 719
<212> TYPE: PRT
<213> ORGANISM: Artificial Sequence
<220> FEATURE:
<223> OTHER INFORMATION: Synthetic

<400> SEQUENCE: 178

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Trp
            20                  25                  30

Gly Asn Gln Lys Ser Tyr Leu Thr Trp Tyr Gln Lys Pro Gly Lys
            35                  40                  45

Ala Pro Lys Leu Leu Ile Tyr Trp Ala Ser Thr Leu Gln Ser Gly Val
            50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
            85                  90                  95

Ala Tyr Phe Phe Pro Phe Thr Phe Gly Gln Gly Thr Lys Val Glu Ile

```
                100                 105                 110
Lys Ser Gly Gly Gly Glu Val Gln Leu Val Glu Ser Gly Gly Gly
            115                 120                 125
Leu Val Gln Pro Gly Gly Ser Leu Arg Leu Ser Cys Ala Ala Ser Gly
130                 135                 140
Phe Thr Phe Ser Arg Tyr Trp Met Ser Trp Val Arg Gln Ala Pro Gly
145                 150                 155                 160
Lys Gly Leu Glu Trp Val Ala Asn Ile Lys Gln Asp Gly Ser Glu Lys
                165                 170                 175
Tyr Tyr Val Asp Ser Val Lys Gly Arg Phe Thr Ile Ser Arg Asp Asn
            180                 185                 190
Ala Lys Asn Ser Leu Tyr Leu Gln Met Asn Ser Leu Arg Ala Glu Asp
        195                 200                 205
Thr Ala Val Tyr Tyr Cys Ala Arg Glu Gly Gly Trp Phe Gly Glu Leu
    210                 215                 220
Ala Phe Asp Tyr Trp Gly Gln Gly Thr Leu Val Thr Val Ser Ser Gly
225                 230                 235                 240
Gly Gly Gly Ser Gly Gly Gly Ser Gly Gly Gly Ser Glu Ile
                245                 250                 255
Val Leu Thr Gln Ser Pro Gly Thr Leu Ser Leu Ser Pro Gly Glu Arg
            260                 265                 270
Ala Thr Leu Ser Cys Arg Ala Ser Gln Arg Val Ser Ser Ser Tyr Leu
        275                 280                 285
Ala Trp Tyr Gln Gln Lys Pro Gly Gln Ala Pro Arg Leu Leu Ile Tyr
    290                 295                 300
Asp Ala Ser Ser Arg Ala Thr Gly Ile Pro Asp Arg Phe Ser Gly Ser
305                 310                 315                 320
Gly Ser Gly Thr Asp Phe Thr Leu Thr Ile Ser Arg Leu Glu Pro Glu
                325                 330                 335
Asp Phe Ala Val Tyr Tyr Cys Gln Gln Tyr Gly Ser Leu Pro Trp Thr
            340                 345                 350
Phe Gly Gln Gly Thr Lys Val Glu Ile Lys Ser Gly Gly Gly Gly Glu
        355                 360                 365
Val Gln Leu Val Glu Ser Gly Gly Leu Val Gln Pro Gly Gly Ser
    370                 375                 380
Leu Arg Leu Ser Cys Ala Val Ser Gly Tyr Thr Phe Ser Met Asn Trp
385                 390                 395                 400
Val Arg Gln Ala Pro Gly Lys Gly Leu Glu Trp Val Ala Trp Ile Asn
                405                 410                 415
Met Tyr Thr Gly Glu Arg Thr Tyr Ala Asp Asp Phe Lys Gly Arg Phe
            420                 425                 430
Thr Ile Ser Arg Asp Asp Ser Lys Asn Thr Leu Tyr Leu Gln Met Asn
        435                 440                 445
Ser Leu Arg Ala Glu Asp Thr Ala Val Tyr Tyr Cys Ala Arg Leu Tyr
    450                 455                 460
Asn Gly Asn Ser Leu Asp Tyr Trp Gly Gln Gly Thr Leu Val Thr Val
465                 470                 475                 480
Ser Ser Gly Gly Gly Gly Ser Glu Pro Lys Ser Asp Lys Thr His
                485                 490                 495
Thr Cys Pro Pro Cys Pro Ala Pro Glu Leu Leu Gly Gly Pro Ser Val
            500                 505                 510
Phe Leu Phe Pro Pro Lys Pro Lys Asp Thr Leu Met Ile Ser Arg Thr
        515                 520                 525
```

```
Pro Glu Val Thr Cys Val Val Asp Val Ser His Glu Asp Pro Glu
            530                 535                 540

Val Lys Phe Asn Trp Tyr Val Asp Gly Val Glu Val His Asn Ala Lys
545                 550                 555                 560

Thr Lys Pro Arg Glu Glu Gln Tyr Asn Ser Thr Tyr Arg Val Val Ser
            565                 570                 575

Val Leu Thr Val Leu His Gln Asp Trp Leu Asn Gly Lys Glu Tyr Lys
            580                 585                 590

Cys Lys Val Ser Asn Lys Ala Leu Pro Ala Pro Ile Glu Lys Thr Ile
            595                 600                 605

Ser Lys Ala Lys Gly Gln Pro Arg Glu Pro Gln Val Tyr Thr Leu Pro
            610                 615                 620

Pro Ser Arg Glu Glu Met Thr Lys Asn Gln Val Ser Leu Thr Cys Leu
625                 630                 635                 640

Val Lys Gly Phe Tyr Pro Ser Asp Ile Ala Val Glu Trp Glu Ser Asn
            645                 650                 655

Gly Gln Pro Glu Asn Asn Tyr Lys Thr Thr Pro Pro Val Leu Asp Ser
            660                 665                 670

Asp Gly Ser Phe Phe Leu Tyr Ser Lys Leu Thr Val Asp Lys Ser Arg
            675                 680                 685

Trp Gln Gln Gly Asn Val Phe Ser Cys Ser Val Met His Glu Ala Leu
690                 695                 700

His Asn His Tyr Thr Gln Lys Ser Leu Ser Leu Ser Pro Gly Lys
            710                 715

<210> SEQ ID NO 179
<211> LENGTH: 723
<212> TYPE: PRT
<213> ORGANISM: Artificial Sequence
<220> FEATURE:
<223> OTHER INFORMATION: Synthetic

<400> SEQUENCE: 179

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
            85                  90                  95

Ala Tyr Phe Phe Pro Phe Thr Phe Gly Gln Gly Thr Lys Val Glu Ile
            100                 105                 110

Lys Gly Ser Ser Arg Ser Ser Glu Val Gln Leu Val Glu Ser Gly Gly
        115                 120                 125

Gly Leu Val Gln Pro Gly Gly Ser Leu Arg Leu Ser Cys Ala Ala Ser
    130                 135                 140

Gly Phe Thr Phe Ser Arg Tyr Trp Met Ser Trp Val Arg Gln Ala Pro
145                 150                 155                 160

Gly Lys Gly Leu Glu Trp Val Ala Asn Ile Lys Gln Asp Gly Ser Glu
            165                 170                 175
```

```
Lys Tyr Tyr Val Asp Ser Val Lys Gly Arg Phe Thr Ile Ser Arg Asp
                180                 185                 190

Asn Ala Lys Asn Ser Leu Tyr Leu Gln Met Asn Ser Leu Arg Ala Glu
            195                 200                 205

Asp Thr Ala Val Tyr Tyr Cys Ala Arg Glu Gly Gly Trp Phe Gly Glu
210                 215                 220

Leu Ala Phe Asp Tyr Trp Gly Gln Gly Thr Leu Val Thr Val Ser Ser
225                 230                 235                 240

Gly Ser Gly Ser Ser Ser Ser Arg Ser Ser Gly Ser Gly Gly
                245                 250                 255

Gly Glu Ile Val Leu Thr Gln Ser Pro Gly Thr Leu Ser Leu Ser Pro
                260                 265                 270

Gly Glu Arg Ala Thr Leu Ser Cys Arg Ala Ser Gln Arg Val Ser Ser
            275                 280                 285

Ser Tyr Leu Ala Trp Tyr Gln Gln Lys Pro Gly Gln Ala Pro Arg Leu
        290                 295                 300

Leu Ile Tyr Asp Ala Ser Ser Arg Ala Thr Gly Ile Pro Asp Arg Phe
305                 310                 315                 320

Ser Gly Ser Gly Ser Gly Thr Asp Phe Thr Leu Thr Ile Ser Arg Leu
                325                 330                 335

Glu Pro Glu Asp Phe Ala Val Tyr Tyr Cys Gln Gln Tyr Gly Ser Leu
            340                 345                 350

Pro Trp Thr Phe Gly Gln Gly Thr Lys Val Glu Ile Lys Ser Gly Gly
        355                 360                 365

Arg Gly Gly Glu Val Gln Leu Val Glu Ser Gly Gly Gly Leu Val Gln
    370                 375                 380

Pro Gly Gly Ser Leu Arg Leu Ser Cys Ala Val Ser Gly Tyr Thr Phe
385                 390                 395                 400

Ser Met Asn Trp Val Arg Gln Ala Pro Gly Lys Gly Leu Glu Trp Val
                405                 410                 415

Ala Trp Ile Asn Met Tyr Thr Gly Glu Pro Thr Tyr Ala Asp Asp Phe
            420                 425                 430

Lys Gly Arg Phe Thr Ile Ser Arg Asp Asp Ser Lys Asn Thr Leu Tyr
        435                 440                 445

Leu Gln Met Asn Ser Leu Arg Ala Glu Asp Thr Ala Val Tyr Tyr Cys
450                 455                 460

Ala Arg Leu Tyr Asn Gly Asn Ser Leu Asp Tyr Trp Gly Gln Gly Thr
465                 470                 475                 480

Leu Val Thr Val Ser Ser Gly Gly Gly Gly Ser Glu Pro Lys Ser Ser
                485                 490                 495

Asp Lys Thr His Thr Cys Pro Pro Cys Pro Ala Pro Glu Leu Leu Gly
            500                 505                 510

Gly Pro Ser Val Phe Leu Phe Pro Pro Lys Pro Lys Asp Thr Leu Met
        515                 520                 525

Ile Ser Arg Thr Pro Glu Val Thr Cys Val Val Val Asp Val Ser His
        530                 535                 540

Glu Asp Pro Glu Val Lys Phe Asn Trp Tyr Val Asp Gly Val Glu Val
545                 550                 555                 560

His Asn Ala Lys Thr Lys Pro Arg Glu Glu Gln Tyr Asn Ser Thr Tyr
                565                 570                 575

Arg Val Val Ser Val Leu Thr Val Leu His Gln Asp Trp Leu Asn Gly
                580                 585                 590
```

```
Lys Glu Tyr Lys Cys Lys Val Ser Asn Lys Ala Leu Pro Ala Pro Ile
                595                 600                 605

Glu Lys Thr Ile Ser Lys Ala Lys Gly Gln Pro Arg Glu Pro Gln Val
    610                 615                 620

Tyr Thr Leu Pro Pro Ser Arg Glu Glu Met Thr Lys Asn Gln Val Ser
625                 630                 635                 640

Leu Thr Cys Leu Val Lys Gly Phe Tyr Pro Ser Asp Ile Ala Val Glu
                645                 650                 655

Trp Glu Ser Asn Gly Gln Pro Glu Asn Asn Tyr Lys Thr Thr Pro Pro
                660                 665                 670

Val Leu Asp Ser Asp Gly Ser Phe Phe Leu Tyr Ser Lys Leu Thr Val
                675                 680                 685

Asp Lys Ser Arg Trp Gln Gln Gly Asn Val Phe Ser Cys Ser Val Met
    690                 695                 700

His Glu Ala Leu His Asn His Tyr Thr Gln Lys Ser Leu Ser Leu Ser
705                 710                 715                 720

Pro Gly Lys

<210> SEQ ID NO 180
<211> LENGTH: 723
<212> TYPE: PRT
<213> ORGANISM: Artificial Sequence
<220> FEATURE:
<223> OTHER INFORMATION: Synthetic

<400> SEQUENCE: 180

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Trp
                20                  25                  30

Gly Asn Gln Lys Ser Tyr Leu Thr Trp Tyr Gln Gln Lys Pro Gly Lys
            35                  40                  45

Ala Pro Lys Leu Leu Ile Tyr Trp Ala Ser Thr Leu Gln Ser Gly Val
        50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Gly Ser Ser Arg Ser Ser Glu Val Gln Leu Val Glu Ser Gly Gly
        115                 120                 125

Gly Leu Val Gln Pro Gly Gly Ser Leu Arg Leu Ser Cys Ala Ala Ser
130                 135                 140

Gly Phe Thr Phe Ser Arg Tyr Trp Met Ser Trp Val Arg Gln Ala Pro
145                 150                 155                 160

Gly Lys Gly Leu Glu Trp Val Ala Asn Ile Lys Gln Asp Gly Ser Glu
                165                 170                 175

Lys Tyr Tyr Val Asp Ser Val Lys Gly Arg Phe Thr Ile Ser Arg Asp
            180                 185                 190

Asn Ala Lys Asn Ser Leu Tyr Leu Gln Met Asn Ser Leu Arg Ala Glu
        195                 200                 205

Asp Thr Ala Val Tyr Tyr Cys Ala Arg Glu Gly Gly Trp Phe Gly Glu
    210                 215                 220

Leu Ala Phe Asp Tyr Trp Gly Gln Gly Thr Leu Val Thr Val Ser Ser
```

```
            225                 230                 235                 240
Gly Ser Gly Ser Ser Ser Ser Arg Ser Ser Gly Ser Gly Gly
                245                 250                 255
Gly Glu Ile Val Leu Thr Gln Ser Pro Gly Thr Leu Ser Leu Ser Pro
            260                 265                 270
Gly Glu Arg Ala Thr Leu Ser Cys Arg Ala Ser Gln Arg Val Ser Ser
            275                 280                 285
Ser Tyr Leu Ala Trp Tyr Gln Gln Lys Pro Gly Gln Ala Pro Arg Leu
        290                 295                 300
Leu Ile Tyr Asp Ala Ser Ser Arg Ala Thr Gly Ile Pro Asp Arg Phe
305                 310                 315                 320
Ser Gly Ser Gly Ser Gly Thr Asp Phe Thr Leu Thr Ile Ser Arg Leu
            325                 330                 335
Glu Pro Glu Asp Phe Ala Val Tyr Tyr Cys Gln Gln Tyr Gly Ser Leu
            340                 345                 350
Pro Trp Thr Phe Gly Gln Gly Thr Lys Val Glu Ile Lys Ser Gly Gly
            355                 360                 365
Arg Gly Gly Glu Val Gln Leu Val Glu Ser Gly Gly Leu Val Gln
        370                 375                 380
Pro Gly Gly Ser Leu Arg Leu Ser Cys Ala Val Ser Gly Tyr Thr Phe
385                 390                 395                 400
Ser Met Asn Trp Val Arg Gln Ala Pro Gly Lys Gly Leu Glu Trp Val
            405                 410                 415
Ala Trp Ile Asn Met Tyr Thr Gly Glu Arg Thr Tyr Ala Asp Asp Phe
            420                 425                 430
Lys Gly Arg Phe Thr Ile Ser Arg Asp Asp Ser Lys Asn Thr Leu Tyr
            435                 440                 445
Leu Gln Met Asn Ser Leu Arg Ala Glu Asp Thr Ala Val Tyr Tyr Cys
        450                 455                 460
Ala Arg Leu Tyr Asn Gly Asn Ser Leu Asp Tyr Trp Gly Gln Gly Thr
465                 470                 475                 480
Leu Val Thr Val Ser Ser Gly Gly Gly Ser Glu Pro Lys Ser Ser
            485                 490                 495
Asp Lys Thr His Thr Cys Pro Pro Cys Pro Ala Pro Glu Leu Leu Gly
            500                 505                 510
Gly Pro Ser Val Phe Leu Phe Pro Pro Lys Pro Lys Asp Thr Leu Met
            515                 520                 525
Ile Ser Arg Thr Pro Glu Val Thr Cys Val Val Val Asp Val Ser His
            530                 535                 540
Glu Asp Pro Glu Val Lys Phe Asn Trp Tyr Val Asp Gly Val Glu Val
545                 550                 555                 560
His Asn Ala Lys Thr Lys Pro Arg Glu Glu Gln Tyr Asn Ser Thr Tyr
                565                 570                 575
Arg Val Val Ser Val Leu Thr Val Leu His Gln Asp Trp Leu Asn Gly
                580                 585                 590
Lys Glu Tyr Lys Cys Lys Val Ser Asn Lys Ala Leu Pro Ala Pro Ile
        595                 600                 605
Glu Lys Thr Ile Ser Lys Ala Lys Gly Gln Pro Arg Glu Pro Gln Val
        610                 615                 620
Tyr Thr Leu Pro Pro Ser Arg Glu Glu Met Thr Lys Asn Gln Val Ser
625                 630                 635                 640
Leu Thr Cys Leu Val Lys Gly Phe Tyr Pro Ser Asp Ile Ala Val Glu
            645                 650                 655
```

```
Trp Glu Ser Asn Gly Gln Pro Glu Asn Asn Tyr Lys Thr Thr Pro Pro
            660                 665                 670

Val Leu Asp Ser Asp Gly Ser Phe Phe Leu Tyr Ser Lys Leu Thr Val
        675                 680                 685

Asp Lys Ser Arg Trp Gln Gln Gly Asn Val Phe Ser Cys Ser Val Met
    690                 695                 700

His Glu Ala Leu His Asn His Tyr Thr Gln Lys Ser Leu Ser Leu Ser
705                 710                 715                 720

Pro Gly Lys

<210> SEQ ID NO 181
<211> LENGTH: 719
<212> TYPE: PRT
<213> ORGANISM: Artificial Sequence
<220> FEATURE:
<223> OTHER INFORMATION: Synthetic

<400> SEQUENCE: 181

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Thr Phe Ser Arg Tyr Trp Met Ser Trp Val Arg Gln Ala Pro Gly
145                 150                 155                 160

Lys Gly Leu Glu Trp Val Ala Asn Ile Lys Gln Asp Gly Ser Glu Lys
                165                 170                 175

Tyr Tyr Val Asp Ser Val Lys Gly Arg Phe Thr Ile Ser Arg Asp Asn
            180                 185                 190

Ala Lys Asn Ser Leu Tyr Leu Gln Met Asn Ser Leu Arg Ala Glu Asp
        195                 200                 205

Thr Ala Val Tyr Tyr Cys Ala Arg Glu Gly Gly Trp Phe Gly Glu Leu
    210                 215                 220

Ala Phe Asp Tyr Trp Gly Gln Gly Thr Leu Val Thr Val Ser Ser Gly
225                 230                 235                 240

Ser Ser Gly Ser Ser Ser Arg Gly Gly Ser Gly Ser Ser Glu Ile
                245                 250                 255

Val Leu Thr Gln Ser Pro Gly Thr Leu Ser Leu Ser Pro Gly Glu Arg
            260                 265                 270

Ala Thr Leu Ser Cys Arg Ala Ser Gln Arg Val Ser Ser Ser Tyr Leu
        275                 280                 285
```

```
Ala Trp Tyr Gln Gln Lys Pro Gly Gln Ala Pro Arg Leu Leu Ile Tyr
290                 295                 300

Asp Ala Ser Ser Arg Ala Thr Gly Ile Pro Asp Arg Phe Ser Gly Ser
305                 310                 315                 320

Gly Ser Gly Thr Asp Phe Thr Leu Thr Ile Ser Arg Leu Glu Pro Glu
                325                 330                 335

Asp Phe Ala Val Tyr Tyr Cys Gln Gln Tyr Gly Ser Leu Pro Trp Thr
            340                 345                 350

Phe Gly Gln Gly Thr Lys Val Glu Ile Lys Ser Gly Gly Gly Gly Glu
        355                 360                 365

Val Gln Leu Val Glu Ser Gly Gly Gly Leu Val Gln Pro Gly Gly Ser
370                 375                 380

Leu Arg Leu Ser Cys Ala Val Ser Gly Tyr Thr Phe Ser Met Asn Trp
385                 390                 395                 400

Val Arg Gln Ala Pro Gly Lys Gly Leu Glu Trp Val Ala Trp Ile Asn
                405                 410                 415

Met Tyr Thr Gly Glu Pro Thr Tyr Ala Asp Asp Phe Lys Gly Arg Phe
            420                 425                 430

Thr Ile Ser Arg Asp Asp Ser Lys Asn Thr Leu Tyr Leu Gln Met Asn
        435                 440                 445

Ser Leu Arg Ala Glu Asp Thr Ala Val Tyr Tyr Cys Ala Arg Leu Tyr
450                 455                 460

Asn Gly Asn Ser Leu Asp Tyr Trp Gly Gln Gly Thr Leu Val Thr Val
465                 470                 475                 480

Ser Ser Gly Gly Gly Gly Ser Glu Pro Lys Ser Ser Asp Lys Thr His
                485                 490                 495

Thr Cys Pro Pro Cys Pro Ala Pro Glu Leu Leu Gly Gly Pro Ser Val
            500                 505                 510

Phe Leu Phe Pro Pro Lys Pro Lys Asp Thr Leu Met Ile Ser Arg Thr
        515                 520                 525

Pro Glu Val Thr Cys Val Val Val Asp Val Ser His Glu Asp Pro Glu
530                 535                 540

Val Lys Phe Asn Trp Tyr Val Asp Gly Val Glu Val His Asn Ala Lys
545                 550                 555                 560

Thr Lys Pro Arg Glu Glu Gln Tyr Asn Ser Thr Tyr Arg Val Val Ser
                565                 570                 575

Val Leu Thr Val Leu His Gln Asp Trp Leu Asn Gly Lys Glu Tyr Lys
            580                 585                 590

Cys Lys Val Ser Asn Lys Ala Leu Pro Ala Pro Ile Glu Lys Thr Ile
        595                 600                 605

Ser Lys Ala Lys Gly Gln Pro Arg Glu Pro Gln Val Tyr Thr Leu Pro
610                 615                 620

Pro Ser Arg Glu Glu Met Thr Lys Asn Gln Val Ser Leu Thr Cys Leu
625                 630                 635                 640

Val Lys Gly Phe Tyr Pro Ser Asp Ile Ala Val Glu Trp Glu Ser Asn
                645                 650                 655

Gly Gln Pro Glu Asn Asn Tyr Lys Thr Thr Pro Pro Val Leu Asp Ser
            660                 665                 670

Asp Gly Ser Phe Phe Leu Tyr Ser Lys Leu Thr Val Asp Lys Ser Arg
        675                 680                 685

Trp Gln Gln Gly Asn Val Phe Ser Cys Ser Val Met His Glu Ala Leu
690                 695                 700

His Asn His Tyr Thr Gln Lys Ser Leu Ser Leu Ser Pro Gly Lys
```

705                 710                 715

<210> SEQ ID NO 182
<211> LENGTH: 720
<212> TYPE: PRT
<213> ORGANISM: Artificial Sequence
<220> FEATURE:
<223> OTHER INFORMATION: Synthetic

<400> SEQUENCE: 182

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
130                 135                 140

Phe Thr Phe Ser Arg Tyr Trp Met Ser Trp Val Arg Gln Ala Pro Gly
145                 150                 155                 160

Lys Gly Leu Glu Trp Val Ala Asn Ile Lys Gln Asp Gly Ser Glu Lys
                165                 170                 175

Tyr Tyr Val Asp Ser Val Lys Gly Arg Phe Thr Ile Ser Arg Asp Asn
            180                 185                 190

Ala Lys Asn Ser Leu Tyr Leu Gln Met Asn Ser Leu Arg Ala Glu Asp
        195                 200                 205

Thr Ala Val Tyr Tyr Cys Ala Arg Glu Gly Gly Trp Phe Gly Glu Leu
    210                 215                 220

Ala Phe Asp Tyr Trp Gly Gln Gly Thr Leu Val Thr Val Ser Ser Ser
225                 230                 235                 240

Ser Ser Gly Ser Gly Gly Gly Ser Gly Gly Gly Gly Gly Gly Gly Glu
                245                 250                 255

Ile Val Leu Thr Gln Ser Pro Gly Thr Leu Ser Leu Ser Pro Gly Glu
            260                 265                 270

Arg Ala Thr Leu Ser Cys Arg Ala Ser Gln Arg Val Ser Ser Ser Tyr
        275                 280                 285

Leu Ala Trp Tyr Gln Gln Lys Pro Gly Gln Ala Pro Arg Leu Leu Ile
    290                 295                 300

Tyr Asp Ala Ser Ser Arg Ala Thr Gly Ile Pro Asp Arg Phe Ser Gly
305                 310                 315                 320

Ser Gly Ser Gly Thr Asp Phe Thr Leu Thr Ile Ser Arg Leu Glu Pro
                325                 330                 335

Glu Asp Phe Ala Val Tyr Tyr Cys Gln Gln Tyr Gly Ser Leu Pro Trp
            340                 345                 350

Thr Phe Gly Gln Gly Thr Lys Val Glu Ile Lys Gly Ser Ser Gly Ser

```
                355                 360                 365
Glu Val Gln Leu Val Glu Ser Gly Gly Gly Leu Val Gln Pro Gly Gly
            370                 375                 380
Ser Leu Arg Leu Ser Cys Ala Val Ser Gly Tyr Thr Phe Ser Met Asn
385                 390                 395                 400
Trp Val Arg Gln Ala Pro Gly Lys Gly Leu Glu Trp Val Ala Trp Ile
                405                 410                 415
Asn Met Tyr Thr Gly Glu Pro Thr Tyr Ala Asp Asp Phe Lys Gly Arg
            420                 425                 430
Phe Thr Ile Ser Arg Asp Asp Ser Lys Asn Thr Leu Tyr Leu Gln Met
                435                 440                 445
Asn Ser Leu Arg Ala Glu Asp Thr Ala Val Tyr Tyr Cys Ala Arg Leu
450                 455                 460
Tyr Asn Gly Asn Ser Leu Asp Tyr Trp Gly Gln Gly Thr Leu Val Thr
465                 470                 475                 480
Val Ser Ser Gly Gly Gly Gly Ser Glu Pro Lys Ser Ser Asp Lys Thr
                485                 490                 495
His Thr Cys Pro Pro Cys Pro Ala Pro Glu Leu Leu Gly Gly Pro Ser
            500                 505                 510
Val Phe Leu Phe Pro Pro Lys Pro Lys Asp Thr Leu Met Ile Ser Arg
            515                 520                 525
Thr Pro Glu Val Thr Cys Val Val Val Asp Val Ser His Glu Asp Pro
530                 535                 540
Glu Val Lys Phe Asn Trp Tyr Val Asp Gly Val Glu Val His Asn Ala
545                 550                 555                 560
Lys Thr Lys Pro Arg Glu Glu Gln Tyr Asn Ser Thr Tyr Arg Val Val
                565                 570                 575
Ser Val Leu Thr Val Leu His Gln Asp Trp Leu Asn Gly Lys Glu Tyr
            580                 585                 590
Lys Cys Lys Val Ser Asn Lys Ala Leu Pro Ala Pro Ile Glu Lys Thr
            595                 600                 605
Ile Ser Lys Ala Lys Gly Gln Pro Arg Glu Pro Gln Val Tyr Thr Leu
610                 615                 620
Pro Pro Ser Arg Glu Glu Met Thr Lys Asn Gln Val Ser Leu Thr Cys
625                 630                 635                 640
Leu Val Lys Gly Phe Tyr Pro Ser Asp Ile Ala Val Glu Trp Glu Ser
                645                 650                 655
Asn Gly Gln Pro Glu Asn Asn Tyr Lys Thr Thr Pro Pro Val Leu Asp
            660                 665                 670
Ser Asp Gly Ser Phe Phe Leu Tyr Ser Lys Leu Thr Val Asp Lys Ser
            675                 680                 685
Arg Trp Gln Gln Gly Asn Val Phe Ser Cys Ser Val Met His Glu Ala
                690                 695                 700
Leu His Asn His Tyr Thr Gln Lys Ser Leu Ser Leu Ser Pro Gly Lys
705                 710                 715                 720

<210> SEQ ID NO 183
<211> LENGTH: 719
<212> TYPE: PRT
<213> ORGANISM: Artificial Sequence
<220> FEATURE:
<223> OTHER INFORMATION: Synthetic

<400> SEQUENCE: 183

Asp Ile Gln Met Thr Gln Ser Pro Ser Ser Leu Ser Ala Ser Val Gly
```

-continued

```
1               5                   10                  15
Asp Arg Val Thr Ile Thr Cys Lys Ser Ser Gln Ser Leu Leu Asn Ser
                20                  25                  30

Gly Asn Gln Lys Ser Tyr Leu Thr Trp Tyr Gln Gln Lys Pro Gly Lys
                35                  40                  45

Ala Pro Lys Leu Leu Ile Tyr Trp Ala Ser Thr Leu Glu Ser Gly Val
50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
                100                 105                 110

Lys Ser Gly Gly Gly Gly Glu Val Gln Leu Val Glu Ser Gly Gly Gly
                115                 120                 125

Leu Val Gln Pro Gly Gly Ser Leu Arg Leu Ser Cys Ala Ala Ser Gly
                130                 135                 140

Phe Thr Phe Ser Arg Tyr Trp Met Ser Trp Val Arg Gln Ala Pro Gly
145                 150                 155                 160

Lys Gly Leu Glu Trp Val Ala Asn Ile Lys Gln Asp Gly Ser Glu Lys
                165                 170                 175

Tyr Tyr Val Asp Ser Val Lys Gly Arg Phe Thr Ile Ser Arg Asp Asn
                180                 185                 190

Ala Lys Asn Ser Leu Tyr Leu Gln Met Asn Ser Leu Arg Ala Glu Asp
                195                 200                 205

Thr Ala Val Tyr Tyr Cys Ala Arg Glu Gly Gly Trp Phe Gly Glu Leu
210                 215                 220

Ala Phe Asp Tyr Trp Gly Gln Gly Thr Leu Val Thr Val Ser Ser Gly
225                 230                 235                 240

Gly Gly Gly Ser Gly Ser Gly Ser Ser Gly Ser Ser Ser Gly Glu Ile
                245                 250                 255

Val Leu Thr Gln Ser Pro Gly Thr Leu Ser Leu Ser Pro Gly Glu Arg
                260                 265                 270

Ala Thr Leu Ser Cys Arg Ala Ser Gln Arg Val Ser Ser Ser Tyr Leu
                275                 280                 285

Ala Trp Tyr Gln Gln Lys Pro Gly Gln Ala Pro Arg Leu Leu Ile Tyr
                290                 295                 300

Asp Ala Ser Ser Arg Ala Thr Gly Ile Pro Asp Arg Phe Ser Gly Ser
305                 310                 315                 320

Gly Ser Gly Thr Asp Phe Thr Leu Thr Ile Ser Arg Leu Glu Pro Glu
                325                 330                 335

Asp Phe Ala Val Tyr Tyr Cys Gln Gln Tyr Gly Ser Leu Pro Trp Thr
                340                 345                 350

Phe Gly Gln Gly Thr Lys Val Glu Ile Lys Ser Gly Gly Gly Gly Glu
                355                 360                 365

Val Gln Leu Val Glu Ser Gly Gly Gly Leu Val Gln Pro Gly Gly Ser
                370                 375                 380

Leu Arg Leu Ser Cys Ala Val Ser Gly Tyr Thr Phe Ser Met Asn Trp
385                 390                 395                 400

Val Arg Gln Ala Pro Gly Lys Gly Leu Glu Trp Val Ala Trp Ile Asn
                405                 410                 415

Met Tyr Thr Gly Glu Pro Thr Tyr Ala Asp Asp Phe Lys Gly Arg Phe
                420                 425                 430
```

```
Thr Ile Ser Arg Asp Asp Ser Lys Asn Thr Leu Tyr Leu Gln Met Asn
            435                 440                 445

Ser Leu Arg Ala Glu Asp Thr Ala Val Tyr Tyr Cys Ala Arg Leu Tyr
    450                 455                 460

Asn Gly Asn Ser Leu Asp Tyr Trp Gly Gln Gly Thr Leu Val Thr Val
465                 470                 475                 480

Ser Ser Gly Gly Gly Gly Ser Glu Pro Lys Ser Ser Asp Lys Thr His
                485                 490                 495

Thr Cys Pro Pro Cys Pro Ala Pro Glu Leu Leu Gly Gly Pro Ser Val
            500                 505                 510

Phe Leu Phe Pro Pro Lys Pro Lys Asp Thr Leu Met Ile Ser Arg Thr
            515                 520                 525

Pro Glu Val Thr Cys Val Val Val Asp Val Ser His Glu Asp Pro Glu
            530                 535                 540

Val Lys Phe Asn Trp Tyr Val Asp Gly Val Glu Val His Asn Ala Lys
545                 550                 555                 560

Thr Lys Pro Arg Glu Glu Gln Tyr Asn Ser Thr Tyr Arg Val Val Ser
                565                 570                 575

Val Leu Thr Val Leu His Gln Asp Trp Leu Asn Gly Lys Glu Tyr Lys
            580                 585                 590

Cys Lys Val Ser Asn Lys Ala Leu Pro Ala Pro Ile Glu Lys Thr Ile
                595                 600                 605

Ser Lys Ala Lys Gly Gln Pro Arg Glu Pro Gln Val Tyr Thr Leu Pro
            610                 615                 620

Pro Ser Arg Glu Glu Met Thr Lys Asn Gln Val Ser Leu Thr Cys Leu
625                 630                 635                 640

Val Lys Gly Phe Tyr Pro Ser Asp Ile Ala Val Glu Trp Glu Ser Asn
                645                 650                 655

Gly Gln Pro Glu Asn Asn Tyr Lys Thr Thr Pro Pro Val Leu Asp Ser
            660                 665                 670

Asp Gly Ser Phe Phe Leu Tyr Ser Lys Leu Thr Val Asp Lys Ser Arg
            675                 680                 685

Trp Gln Gln Gly Asn Val Phe Ser Cys Ser Val Met His Glu Ala Leu
            690                 695                 700

His Asn His Tyr Thr Gln Lys Ser Leu Ser Leu Ser Pro Gly Lys
705                 710                 715

<210> SEQ ID NO 184
<211> LENGTH: 720
<212> TYPE: PRT
<213> ORGANISM: Artificial Sequence
<220> FEATURE:
<223> OTHER INFORMATION: Synthetic

<400> SEQUENCE: 184

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80
```

```
Ile Ser Ser Leu Gln Pro Glu Asp Phe Ala Thr Tyr Cys Gln Asn
                85                  90                  95

Ala Tyr Phe Phe Pro Phe Thr Phe Gly Gln Gly Thr Lys Val Glu Ile
            100                 105                 110

Lys Gly Gly Gly Gly Ser Gly Glu Val Gln Leu Val Glu Ser Gly Gly
        115                 120                 125

Gly Leu Val Gln Pro Gly Gly Ser Leu Arg Leu Ser Cys Ala Ala Ser
    130                 135                 140

Gly Phe Thr Phe Ser Arg Tyr Trp Met Ser Trp Val Arg Gln Ala Pro
145                 150                 155                 160

Gly Lys Gly Leu Glu Trp Val Ala Asn Ile Lys Gln Asp Gly Ser Glu
                165                 170                 175

Lys Tyr Tyr Val Asp Ser Val Lys Gly Arg Phe Thr Ile Ser Arg Asp
                180                 185                 190

Asn Ala Lys Asn Ser Leu Tyr Leu Gln Met Asn Ser Leu Arg Ala Glu
            195                 200                 205

Asp Thr Ala Val Tyr Tyr Cys Ala Arg Glu Gly Gly Trp Phe Gly Glu
    210                 215                 220

Leu Ala Phe Asp Tyr Trp Gly Gln Gly Thr Leu Val Thr Val Ser Ser
225                 230                 235                 240

Gly Ser Ser Ser Gly Gly Gly Ser Gly Ser Ser Ser Ser Ser Ser Ser
                245                 250                 255

Glu Ile Val Leu Thr Gln Ser Pro Gly Thr Leu Ser Leu Ser Pro Gly
            260                 265                 270

Glu Arg Ala Thr Leu Ser Cys Arg Ala Ser Gln Arg Val Ser Ser Ser
    275                 280                 285

Tyr Leu Ala Trp Tyr Gln Gln Lys Pro Gly Gln Ala Pro Arg Leu Leu
290                 295                 300

Ile Tyr Asp Ala Ser Ser Arg Ala Thr Gly Ile Pro Asp Arg Phe Ser
305                 310                 315                 320

Gly Ser Gly Ser Gly Thr Asp Phe Thr Leu Thr Ile Ser Arg Leu Glu
                325                 330                 335

Pro Glu Asp Phe Ala Val Tyr Tyr Cys Gln Gln Tyr Gly Ser Leu Pro
            340                 345                 350

Trp Thr Phe Gly Gln Gly Thr Lys Val Glu Ile Lys Ser Gly Gly Ser
    355                 360                 365

Glu Val Gln Leu Val Glu Ser Gly Gly Gly Leu Val Gln Pro Gly Gly
    370                 375                 380

Ser Leu Arg Leu Ser Cys Ala Val Ser Gly Tyr Thr Phe Ser Met Asn
385                 390                 395                 400

Trp Val Arg Gln Ala Pro Gly Lys Gly Leu Glu Trp Val Ala Trp Ile
                405                 410                 415

Asn Met Tyr Thr Gly Glu Pro Thr Tyr Ala Asp Asp Phe Lys Gly Arg
            420                 425                 430

Phe Thr Ile Ser Arg Asp Asp Ser Lys Asn Thr Leu Tyr Leu Gln Met
        435                 440                 445

Asn Ser Leu Arg Ala Glu Asp Thr Ala Val Tyr Tyr Cys Ala Arg Leu
    450                 455                 460

Tyr Asn Gly Asn Ser Leu Asp Tyr Trp Gly Gln Gly Thr Leu Val Thr
465                 470                 475                 480

Val Ser Ser Gly Gly Gly Gly Ser Glu Pro Lys Ser Ser Asp Lys Thr
                485                 490                 495
```

```
His Thr Cys Pro Pro Cys Pro Ala Pro Glu Leu Leu Gly Gly Pro Ser
                500                 505                 510

Val Phe Leu Phe Pro Pro Lys Pro Lys Asp Thr Leu Met Ile Ser Arg
            515                 520                 525

Thr Pro Glu Val Thr Cys Val Val Val Asp Val Ser His Glu Asp Pro
        530                 535                 540

Glu Val Lys Phe Asn Trp Tyr Val Asp Gly Val Glu Val His Asn Ala
545                 550                 555                 560

Lys Thr Lys Pro Arg Glu Glu Gln Tyr Asn Ser Thr Tyr Arg Val Val
                565                 570                 575

Ser Val Leu Thr Val Leu His Gln Asp Trp Leu Asn Gly Lys Glu Tyr
            580                 585                 590

Lys Cys Lys Val Ser Asn Lys Ala Leu Pro Ala Pro Ile Glu Lys Thr
        595                 600                 605

Ile Ser Lys Ala Lys Gly Gln Pro Arg Glu Pro Gln Val Tyr Thr Leu
    610                 615                 620

Pro Pro Ser Arg Glu Glu Met Thr Lys Asn Gln Val Ser Leu Thr Cys
625                 630                 635                 640

Leu Val Lys Gly Phe Tyr Pro Ser Asp Ile Ala Val Glu Trp Glu Ser
                645                 650                 655

Asn Gly Gln Pro Glu Asn Asn Tyr Lys Thr Thr Pro Pro Val Leu Asp
            660                 665                 670

Ser Asp Gly Ser Phe Phe Leu Tyr Ser Lys Leu Thr Val Asp Lys Ser
        675                 680                 685

Arg Trp Gln Gln Gly Asn Val Phe Ser Cys Ser Val Met His Glu Ala
    690                 695                 700

Leu His Asn His Tyr Thr Gln Lys Ser Leu Ser Leu Ser Pro Gly Lys
705                 710                 715                 720

<210> SEQ ID NO 185
<211> LENGTH: 719
<212> TYPE: PRT
<213> ORGANISM: Artificial Sequence
<220> FEATURE:
<223> OTHER INFORMATION: Synthetic

<400> SEQUENCE: 185

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Gly Gly Gly Ser Glu Val Gln Leu Val Glu Ser Gly Gly Gly Leu
        115                 120                 125

Val Gln Pro Gly Gly Ser Leu Arg Leu Ser Cys Ala Ala Ser Gly Phe
    130                 135                 140
```

-continued

```
Thr Phe Ser Arg Tyr Trp Met Ser Trp Val Arg Gln Ala Pro Gly Lys
145                 150                 155                 160

Gly Leu Glu Trp Val Ala Asn Ile Lys Gln Asp Gly Ser Glu Lys Tyr
                165                 170                 175

Tyr Val Asp Ser Val Lys Gly Arg Phe Thr Ile Ser Arg Asp Asn Ala
                180                 185                 190

Lys Asn Ser Leu Tyr Leu Gln Met Asn Ser Leu Arg Ala Glu Asp Thr
                195                 200                 205

Ala Val Tyr Tyr Cys Ala Arg Glu Gly Gly Trp Phe Gly Glu Leu Ala
                210                 215                 220

Phe Asp Tyr Trp Gly Gln Gly Thr Leu Val Thr Val Ser Ser Ser Ser
225                 230                 235                 240

Gly Ser Gly Gly Gly Ser Ser Gly Ser Ser Gly Gly Glu Ile Val
                245                 250                 255

Leu Thr Gln Ser Pro Gly Thr Leu Ser Leu Ser Pro Gly Glu Arg Ala
                260                 265                 270

Thr Leu Ser Cys Arg Ala Ser Gln Arg Val Ser Ser Tyr Leu Ala
                275                 280                 285

Trp Tyr Gln Gln Lys Pro Gly Gln Ala Pro Arg Leu Leu Ile Tyr Asp
290                 295                 300

Ala Ser Ser Arg Ala Thr Gly Ile Pro Asp Arg Phe Ser Gly Ser Gly
305                 310                 315                 320

Ser Gly Thr Asp Phe Thr Leu Thr Ile Ser Arg Leu Glu Pro Glu Asp
                325                 330                 335

Phe Ala Val Tyr Tyr Cys Gln Gln Tyr Gly Ser Leu Pro Trp Thr Phe
                340                 345                 350

Gly Gln Gly Thr Lys Val Glu Ile Lys Ser Gly Gly Arg Gly Gly Glu
                355                 360                 365

Val Gln Leu Val Glu Ser Gly Gly Gly Leu Val Gln Pro Gly Gly Ser
                370                 375                 380

Leu Arg Leu Ser Cys Ala Val Ser Gly Tyr Thr Phe Ser Met Asn Trp
385                 390                 395                 400

Val Arg Gln Ala Pro Gly Lys Gly Leu Glu Trp Val Ala Trp Ile Asn
                405                 410                 415

Met Tyr Thr Gly Glu Pro Thr Tyr Ala Asp Asp Phe Lys Gly Arg Phe
                420                 425                 430

Thr Ile Ser Arg Asp Asp Ser Lys Asn Thr Leu Tyr Leu Gln Met Asn
                435                 440                 445

Ser Leu Arg Ala Glu Asp Thr Ala Val Tyr Tyr Cys Ala Arg Leu Tyr
450                 455                 460

Asn Gly Asn Ser Leu Asp Tyr Trp Gly Gln Gly Thr Leu Val Thr Val
465                 470                 475                 480

Ser Ser Gly Gly Gly Gly Ser Glu Pro Lys Ser Ser Asp Lys Thr His
                485                 490                 495

Thr Cys Pro Pro Cys Pro Ala Pro Glu Leu Leu Gly Gly Pro Ser Val
                500                 505                 510

Phe Leu Phe Pro Pro Lys Pro Lys Asp Thr Leu Met Ile Ser Arg Thr
                515                 520                 525

Pro Glu Val Thr Cys Val Val Val Asp Val Ser His Glu Asp Pro Glu
                530                 535                 540

Val Lys Phe Asn Trp Tyr Val Asp Gly Val Glu Val His Asn Ala Lys
545                 550                 555                 560

Thr Lys Pro Arg Glu Glu Gln Tyr Asn Ser Thr Tyr Arg Val Val Ser
```

```
                565                 570                 575
Val Leu Thr Val Leu His Gln Asp Trp Leu Asn Gly Lys Glu Tyr Lys
            580                 585                 590

Cys Lys Val Ser Asn Lys Ala Leu Pro Ala Pro Ile Glu Lys Thr Ile
            595                 600                 605

Ser Lys Ala Lys Gly Gln Pro Arg Glu Pro Gln Val Tyr Thr Leu Pro
610                 615                 620

Pro Ser Arg Glu Glu Met Thr Lys Asn Gln Val Ser Leu Thr Cys Leu
625                 630                 635                 640

Val Lys Gly Phe Tyr Pro Ser Asp Ile Ala Val Glu Trp Glu Ser Asn
            645                 650                 655

Gly Gln Pro Glu Asn Asn Tyr Lys Thr Thr Pro Pro Val Leu Asp Ser
            660                 665                 670

Asp Gly Ser Phe Phe Leu Tyr Ser Lys Leu Thr Val Asp Lys Ser Arg
            675                 680                 685

Trp Gln Gln Gly Asn Val Phe Ser Cys Ser Val Met His Glu Ala Leu
690                 695                 700

His Asn His Tyr Thr Gln Lys Ser Leu Ser Leu Ser Pro Gly Lys
705                 710                 715

<210> SEQ ID NO 186
<211> LENGTH: 719
<212> TYPE: PRT
<213> ORGANISM: Artificial Sequence
<220> FEATURE:
<223> OTHER INFORMATION: Synthetic

<400> SEQUENCE: 186

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Gly Gly Gly Ser Glu Val Gln Leu Val Glu Ser Gly Gly Gly Leu
        115                 120                 125

Val Gln Pro Gly Gly Ser Leu Arg Leu Ser Cys Ala Ala Ser Gly Phe
    130                 135                 140

Thr Phe Ser Arg Tyr Trp Met Ser Trp Val Arg Gln Ala Pro Gly Lys
145                 150                 155                 160

Gly Leu Glu Trp Val Ala Asn Ile Lys Gln Asp Gly Ser Glu Lys Tyr
                165                 170                 175

Tyr Val Asp Ser Val Lys Gly Arg Phe Thr Ile Ser Arg Asp Asn Ala
            180                 185                 190

Lys Asn Ser Leu Tyr Leu Gln Met Asn Ser Leu Arg Ala Glu Asp Thr
        195                 200                 205

Ala Val Tyr Tyr Cys Ala Arg Glu Gly Gly Trp Phe Gly Glu Leu Ala
```

-continued

```
                210                 215                 220
Phe Asp Tyr Trp Gly Gln Gly Thr Leu Val Thr Val Ser Ser Ser Gly
225                 230                 235                 240

Gly Arg Ser Gly Ser Gly Ser Asn Gly Gly Glu Ile Val
                245                 250                 255

Leu Thr Gln Ser Pro Gly Thr Leu Ser Leu Ser Pro Gly Glu Arg Ala
                260                 265                 270

Thr Leu Ser Cys Arg Ala Ser Gln Arg Val Ser Ser Ser Tyr Leu Ala
                275                 280                 285

Trp Tyr Gln Gln Lys Pro Gly Gln Ala Pro Arg Leu Leu Ile Tyr Asp
                290                 295                 300

Ala Ser Ser Arg Ala Thr Gly Ile Pro Asp Arg Phe Ser Gly Ser Gly
305                 310                 315                 320

Ser Gly Thr Asp Phe Thr Leu Thr Ile Ser Arg Leu Glu Pro Glu Asp
                325                 330                 335

Phe Ala Val Tyr Tyr Cys Gln Gln Tyr Gly Ser Leu Pro Trp Thr Phe
                340                 345                 350

Gly Gln Gly Thr Lys Val Glu Ile Lys Gly Ser Gly Gly Gly Glu
                355                 360                 365

Val Gln Leu Val Glu Ser Gly Gly Gly Leu Val Gln Pro Gly Gly Ser
370                 375                 380

Leu Arg Leu Ser Cys Ala Val Ser Gly Tyr Thr Phe Ser Met Asn Trp
385                 390                 395                 400

Val Arg Gln Ala Pro Gly Lys Gly Leu Glu Trp Val Ala Trp Ile Asn
                405                 410                 415

Met Tyr Thr Gly Glu Pro Thr Tyr Ala Asp Asp Phe Lys Gly Arg Phe
                420                 425                 430

Thr Ile Ser Arg Asp Asp Ser Lys Asn Thr Leu Tyr Leu Gln Met Asn
                435                 440                 445

Ser Leu Arg Ala Glu Asp Thr Ala Val Tyr Tyr Cys Ala Arg Leu Tyr
450                 455                 460

Asn Gly Asn Ser Leu Asp Tyr Trp Gly Gln Gly Thr Leu Val Thr Val
465                 470                 475                 480

Ser Ser Gly Gly Gly Gly Ser Glu Pro Lys Ser Ser Asp Lys Thr His
                485                 490                 495

Thr Cys Pro Pro Cys Pro Ala Pro Glu Leu Leu Gly Gly Pro Ser Val
                500                 505                 510

Phe Leu Phe Pro Pro Lys Pro Lys Asp Thr Leu Met Ile Ser Arg Thr
                515                 520                 525

Pro Glu Val Thr Cys Val Val Val Asp Val Ser His Glu Asp Pro Glu
530                 535                 540

Val Lys Phe Asn Trp Tyr Val Asp Gly Val Glu Val His Asn Ala Lys
545                 550                 555                 560

Thr Lys Pro Arg Glu Glu Gln Tyr Asn Ser Thr Tyr Arg Val Val Ser
                565                 570                 575

Val Leu Thr Val Leu His Gln Asp Trp Leu Asn Gly Lys Glu Tyr Lys
                580                 585                 590

Cys Lys Val Ser Asn Lys Ala Leu Pro Ala Pro Ile Glu Lys Thr Ile
                595                 600                 605

Ser Lys Ala Lys Gly Gln Pro Arg Glu Pro Gln Val Tyr Thr Leu Pro
                610                 615                 620

Pro Ser Arg Glu Glu Met Thr Lys Asn Gln Val Ser Leu Thr Cys Leu
625                 630                 635                 640
```

Val Lys Gly Phe Tyr Pro Ser Asp Ile Ala Val Glu Trp Glu Ser Asn
            645                 650                 655
Gly Gln Pro Glu Asn Asn Tyr Lys Thr Thr Pro Pro Val Leu Asp Ser
        660                 665                 670
Asp Gly Ser Phe Phe Leu Tyr Ser Lys Leu Thr Val Asp Lys Ser Arg
    675                 680                 685
Trp Gln Gln Gly Asn Val Phe Ser Cys Ser Val Met His Glu Ala Leu
690                 695                 700
His Asn His Tyr Thr Gln Lys Ser Leu Ser Leu Ser Pro Gly Lys
705                 710                 715

<210> SEQ ID NO 187
<211> LENGTH: 718
<212> TYPE: PRT
<213> ORGANISM: Artificial Sequence
<220> FEATURE:
<223> OTHER INFORMATION: Synthetic

<400> SEQUENCE: 187

Asp Ile Gln Met Thr Gln Ser Pro Ser Ser Leu Ser Ala Ser Val Gly
1               5                   10                  15
Asp Arg Val Thr Ile Thr Cys Lys Ser Ser Gln Ser Leu Leu Asn Ser
            20                  25                  30
Gly Asn Gln Lys Ser Tyr Leu Thr Trp Tyr Gln Gln Lys Pro Gly Lys
        35                  40                  45
Ala Pro Lys Leu Leu Ile Tyr Trp Ala Ser Thr Leu Glu Ser Gly Val
    50                  55                  60
Pro Ser Arg Phe Ser Gly Ser Gly Ser Gly Thr Asp Tyr Thr Leu Thr
65                  70                  75                  80
Ile Ser Ser Leu Gln Pro Glu Asp Phe Ala Thr Tyr Tyr Cys Gln Asn
                85                  90                  95
Ala Tyr Phe Phe Pro Phe Thr Phe Gly Gln Gly Thr Lys Val Glu Ile
            100                 105                 110
Lys Gly Gly Gly Ser Glu Val Gln Leu Val Glu Ser Gly Gly Gly Leu
        115                 120                 125
Val Gln Pro Gly Gly Ser Leu Arg Leu Ser Cys Ala Ala Ser Gly Phe
    130                 135                 140
Thr Phe Ser Arg Tyr Trp Met Ser Trp Val Arg Gln Ala Pro Gly Lys
145                 150                 155                 160
Gly Leu Glu Trp Val Ala Asn Ile Lys Gln Asp Gly Ser Glu Lys Tyr
                165                 170                 175
Tyr Val Asp Ser Val Lys Gly Arg Phe Thr Ile Ser Arg Asp Asn Ala
            180                 185                 190
Lys Asn Ser Leu Tyr Leu Gln Met Asn Ser Leu Arg Ala Glu Asp Thr
        195                 200                 205
Ala Val Tyr Tyr Cys Ala Arg Glu Gly Gly Trp Phe Gly Glu Leu Ala
    210                 215                 220
Phe Asp Tyr Trp Gly Gln Gly Thr Leu Val Thr Val Ser Ser Gly Ser
225                 230                 235                 240
Ser Gly Arg Gly Ser Ser Gly Ser Gly Ser Ser Gly Glu Ile
                245                 250                 255
Val Leu Thr Gln Ser Pro Gly Thr Leu Ser Leu Ser Pro Gly Glu Arg
            260                 265                 270
Ala Thr Leu Ser Cys Arg Ala Ser Gln Arg Val Ser Ser Ser Tyr Leu
        275                 280                 285

```
Ala Trp Tyr Gln Gln Lys Pro Gly Gln Ala Pro Arg Leu Leu Ile Tyr
            290                 295                 300

Asp Ala Ser Ser Arg Ala Thr Gly Ile Pro Asp Arg Phe Ser Gly Ser
305                 310                 315                 320

Gly Ser Gly Thr Asp Phe Thr Leu Thr Ile Ser Arg Leu Glu Pro Glu
                325                 330                 335

Asp Phe Ala Val Tyr Tyr Cys Gln Gln Tyr Gly Ser Leu Pro Trp Thr
            340                 345                 350

Phe Gly Gln Gly Thr Lys Val Glu Ile Lys Gly Gly Ser Gly Glu Val
            355                 360                 365

Gln Leu Val Glu Ser Gly Gly Leu Val Gln Pro Gly Gly Ser Leu
370                 375                 380

Arg Leu Ser Cys Ala Val Ser Gly Tyr Thr Phe Ser Met Asn Trp Val
385                 390                 395                 400

Arg Gln Ala Pro Gly Lys Gly Leu Glu Trp Val Ala Trp Ile Asn Met
                405                 410                 415

Tyr Thr Gly Glu Pro Thr Tyr Ala Asp Asp Phe Lys Gly Arg Phe Thr
            420                 425                 430

Ile Ser Arg Asp Asp Ser Lys Asn Thr Leu Tyr Leu Gln Met Asn Ser
            435                 440                 445

Leu Arg Ala Glu Asp Thr Ala Val Tyr Tyr Cys Ala Arg Leu Tyr Asn
450                 455                 460

Gly Asn Ser Leu Asp Tyr Trp Gly Gln Gly Thr Leu Val Thr Val Ser
465                 470                 475                 480

Ser Gly Gly Gly Gly Ser Glu Pro Lys Ser Ser Asp Lys Thr His Thr
                485                 490                 495

Cys Pro Pro Cys Pro Ala Pro Glu Leu Leu Gly Gly Pro Ser Val Phe
            500                 505                 510

Leu Phe Pro Pro Lys Pro Lys Asp Thr Leu Met Ile Ser Arg Thr Pro
            515                 520                 525

Glu Val Thr Cys Val Val Val Asp Val Ser His Glu Asp Pro Glu Val
            530                 535                 540

Lys Phe Asn Trp Tyr Val Asp Gly Val Glu Val His Asn Ala Lys Thr
545                 550                 555                 560

Lys Pro Arg Glu Glu Gln Tyr Asn Ser Thr Tyr Arg Val Val Ser Val
                565                 570                 575

Leu Thr Val Leu His Gln Asp Trp Leu Asn Gly Lys Glu Tyr Lys Cys
            580                 585                 590

Lys Val Ser Asn Lys Ala Leu Pro Ala Pro Ile Glu Lys Thr Ile Ser
            595                 600                 605

Lys Ala Lys Gly Gln Pro Arg Glu Pro Gln Val Tyr Thr Leu Pro Pro
610                 615                 620

Ser Arg Glu Glu Met Thr Lys Asn Gln Val Ser Leu Thr Cys Leu Val
625                 630                 635                 640

Lys Gly Phe Tyr Pro Ser Asp Ile Ala Val Glu Trp Glu Ser Asn Gly
                645                 650                 655

Gln Pro Glu Asn Asn Tyr Lys Thr Thr Pro Pro Val Leu Asp Ser Asp
            660                 665                 670

Gly Ser Phe Phe Leu Tyr Ser Lys Leu Thr Val Asp Lys Ser Arg Trp
            675                 680                 685

Gln Gln Gly Asn Val Phe Ser Cys Ser Val Met His Glu Ala Leu His
            690                 695                 700
```

Asn His Tyr Thr Gln Lys Ser Leu Ser Leu Ser Pro Gly Lys
705                 710                 715

<210> SEQ ID NO 188
<211> LENGTH: 720
<212> TYPE: PRT
<213> ORGANISM: Artificial Sequence
<220> FEATURE:
<223> OTHER INFORMATION: Synthetic

<400> SEQUENCE: 188

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Gly Gly Gly Ser Ser Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Thr Phe Ser Arg Tyr Trp Met Ser Trp Val Arg Gln Ala Pro Gly
145                 150                 155                 160

Lys Gly Leu Glu Trp Val Ala Asn Ile Lys Gln Asp Gly Ser Glu Lys
                165                 170                 175

Tyr Tyr Val Asp Ser Val Lys Gly Arg Phe Thr Ile Ser Arg Asp Asn
            180                 185                 190

Ala Lys Asn Ser Leu Tyr Leu Gln Met Asn Ser Leu Arg Ala Glu Asp
        195                 200                 205

Thr Ala Val Tyr Tyr Cys Ala Arg Glu Gly Gly Trp Phe Gly Glu Leu
    210                 215                 220

Ala Phe Asp Tyr Trp Gly Gln Gly Thr Leu Val Thr Val Ser Ser Gly
225                 230                 235                 240

Gly Gly Gly Ser Gly Gly Gly Gly Ser Gly Gly Gly Gly Ser Glu Ile
                245                 250                 255

Val Leu Thr Gln Ser Pro Gly Thr Leu Ser Leu Ser Pro Gly Glu Arg
            260                 265                 270

Ala Thr Leu Ser Cys Arg Ala Ser Gln Arg Val Ser Ser Ser Tyr Leu
        275                 280                 285

Ala Trp Tyr Gln Gln Lys Pro Gly Gln Ala Pro Arg Leu Leu Ile Tyr
    290                 295                 300

Asp Ala Ser Ser Arg Ala Thr Gly Ile Pro Asp Arg Phe Ser Gly Ser
305                 310                 315                 320

Gly Ser Gly Thr Asp Phe Thr Leu Thr Ile Ser Arg Leu Glu Pro Glu
                325                 330                 335

Asp Phe Ala Val Tyr Tyr Cys Gln Gln Tyr Gly Ser Leu Pro Trp Thr
            340                 345                 350

Phe Gly Gln Gly Thr Lys Val Glu Ile Lys Gly Ser Gly Gly
            355                 360                 365

Glu Val Gln Leu Val Glu Ser Gly Gly Gly Leu Val Gln Pro Gly Gly
370                 375                 380

Ser Leu Arg Leu Ser Cys Ala Val Ser Gly Tyr Thr Phe Ser Met Asn
385                 390                 395                 400

Trp Val Arg Gln Ala Pro Gly Lys Gly Leu Glu Trp Val Ala Trp Ile
                405                 410                 415

Asn Met Tyr Thr Gly Glu Pro Thr Tyr Ala Asp Asp Phe Lys Gly Arg
            420                 425                 430

Phe Thr Ile Ser Arg Asp Asp Ser Lys Asn Thr Leu Tyr Leu Gln Met
            435                 440                 445

Asn Ser Leu Arg Ala Glu Asp Thr Ala Val Tyr Tyr Cys Ala Arg Leu
450                 455                 460

Tyr Asn Gly Asn Ser Leu Asp Tyr Trp Gly Gln Gly Thr Leu Val Thr
465                 470                 475                 480

Val Ser Ser Gly Gly Gly Gly Ser Glu Pro Lys Ser Ser Asp Lys Thr
                485                 490                 495

His Thr Cys Pro Pro Cys Pro Ala Pro Glu Leu Leu Gly Gly Pro Ser
            500                 505                 510

Val Phe Leu Phe Pro Pro Lys Pro Lys Asp Thr Leu Met Ile Ser Arg
            515                 520                 525

Thr Pro Glu Val Thr Cys Val Val Asp Val Ser His Glu Asp Pro
530                 535                 540

Glu Val Lys Phe Asn Trp Tyr Val Asp Gly Val Glu Val His Asn Ala
545                 550                 555                 560

Lys Thr Lys Pro Arg Glu Glu Gln Tyr Asn Ser Thr Tyr Arg Val Val
                565                 570                 575

Ser Val Leu Thr Val Leu His Gln Asp Trp Leu Asn Gly Lys Glu Tyr
            580                 585                 590

Lys Cys Lys Val Ser Asn Lys Ala Leu Pro Ala Pro Ile Glu Lys Thr
            595                 600                 605

Ile Ser Lys Ala Lys Gly Gln Pro Arg Glu Pro Gln Val Tyr Thr Leu
610                 615                 620

Pro Pro Ser Arg Glu Glu Met Thr Lys Asn Gln Val Ser Leu Thr Cys
625                 630                 635                 640

Leu Val Lys Gly Phe Tyr Pro Ser Asp Ile Ala Val Glu Trp Glu Ser
                645                 650                 655

Asn Gly Gln Pro Glu Asn Asn Tyr Lys Thr Thr Pro Pro Val Leu Asp
            660                 665                 670

Ser Asp Gly Ser Phe Phe Leu Tyr Ser Lys Leu Thr Val Asp Lys Ser
            675                 680                 685

Arg Trp Gln Gln Gly Asn Val Phe Ser Cys Ser Val Met His Glu Ala
690                 695                 700

Leu His Asn His Tyr Thr Gln Lys Ser Leu Ser Leu Ser Pro Gly Lys
705                 710                 715                 720

<210> SEQ ID NO 189
<211> LENGTH: 721
<212> TYPE: PRT
<213> ORGANISM: Artificial Sequence
<220> FEATURE:
<223> OTHER INFORMATION: Synthetic

<400> SEQUENCE: 189

-continued

```
Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Gly Ser Ser Arg Ser Ser Glu Val Gln Leu Val Glu Ser Gly Gly
        115                 120                 125

Gly Leu Val Gln Pro Gly Gly Ser Leu Arg Leu Ser Cys Ala Ala Ser
130                 135                 140

Gly Phe Thr Phe Ser Arg Tyr Trp Met Ser Trp Val Arg Gln Ala Pro
145                 150                 155                 160

Gly Lys Gly Leu Glu Trp Val Ala Asn Ile Lys Gln Asp Gly Ser Glu
            165                 170                 175

Lys Tyr Tyr Val Asp Ser Val Lys Gly Arg Phe Thr Ile Ser Arg Asp
            180                 185                 190

Asn Ala Lys Asn Ser Leu Tyr Leu Gln Met Asn Ser Leu Arg Ala Glu
        195                 200                 205

Asp Thr Ala Val Tyr Tyr Cys Ala Arg Glu Gly Gly Trp Phe Gly Glu
    210                 215                 220

Leu Ala Phe Asp Tyr Trp Gly Gln Gly Thr Leu Val Thr Val Ser Ser
225                 230                 235                 240

Ser Gly Ser Ser Gly Ser Ser Ser Gly Ser Gly Ser Gly Glu
            245                 250                 255

Ile Val Leu Thr Gln Ser Pro Gly Thr Leu Ser Leu Ser Pro Gly Glu
            260                 265                 270

Arg Ala Thr Leu Ser Cys Arg Ala Ser Gln Arg Val Ser Ser Ser Tyr
        275                 280                 285

Leu Ala Trp Tyr Gln Gln Lys Pro Gly Gln Ala Pro Arg Leu Leu Ile
290                 295                 300

Tyr Asp Ala Ser Ser Arg Ala Thr Gly Ile Pro Asp Arg Phe Ser Gly
305                 310                 315                 320

Ser Gly Ser Gly Thr Asp Phe Thr Leu Thr Ile Ser Arg Leu Glu Pro
            325                 330                 335

Glu Asp Phe Ala Val Tyr Tyr Cys Gln Gln Tyr Gly Ser Leu Pro Trp
            340                 345                 350

Thr Phe Gly Gln Gly Thr Lys Val Glu Ile Lys Ser Ser Gly Ser Gly
        355                 360                 365

Gly Glu Val Gln Leu Val Glu Ser Gly Gly Gly Leu Val Gln Pro Gly
    370                 375                 380

Gly Ser Leu Arg Leu Ser Cys Ala Val Ser Gly Tyr Thr Phe Ser Met
385                 390                 395                 400

Asn Trp Val Arg Gln Ala Pro Gly Lys Gly Leu Glu Trp Val Ala Trp
            405                 410                 415

Ile Asn Met Tyr Thr Gly Glu Pro Thr Tyr Ala Asp Asp Phe Lys Gly
```

-continued

```
                420                 425                 430
Arg Phe Thr Ile Ser Arg Asp Asp Ser Lys Asn Thr Leu Tyr Leu Gln
            435                 440                 445
Met Asn Ser Leu Arg Ala Glu Asp Thr Ala Val Tyr Tyr Cys Ala Arg
        450                 455                 460
Leu Tyr Asn Gly Asn Ser Leu Asp Tyr Trp Gly Gln Gly Thr Leu Val
465                 470                 475                 480
Thr Val Ser Ser Gly Gly Gly Ser Glu Pro Lys Ser Ser Asp Lys
                485                 490                 495
Thr His Thr Cys Pro Pro Cys Pro Ala Pro Glu Leu Leu Gly Gly Pro
            500                 505                 510
Ser Val Phe Leu Phe Pro Pro Lys Pro Lys Asp Thr Leu Met Ile Ser
        515                 520                 525
Arg Thr Pro Glu Val Thr Cys Val Val Val Asp Val Ser His Glu Asp
    530                 535                 540
Pro Glu Val Lys Phe Asn Trp Tyr Val Asp Gly Val Glu Val His Asn
545                 550                 555                 560
Ala Lys Thr Lys Pro Arg Glu Glu Gln Tyr Asn Ser Thr Tyr Arg Val
                565                 570                 575
Val Ser Val Leu Thr Val Leu His Gln Asp Trp Leu Asn Gly Lys Glu
            580                 585                 590
Tyr Lys Cys Lys Val Ser Asn Lys Ala Leu Pro Ala Pro Ile Glu Lys
        595                 600                 605
Thr Ile Ser Lys Ala Lys Gly Gln Pro Arg Glu Pro Gln Val Tyr Thr
    610                 615                 620
Leu Pro Pro Ser Arg Glu Glu Met Thr Lys Asn Gln Val Ser Leu Thr
625                 630                 635                 640
Cys Leu Val Lys Gly Phe Tyr Pro Ser Asp Ile Ala Val Glu Trp Glu
                645                 650                 655
Ser Asn Gly Gln Pro Glu Asn Asn Tyr Lys Thr Thr Pro Pro Val Leu
            660                 665                 670
Asp Ser Asp Gly Ser Phe Phe Leu Tyr Ser Lys Leu Thr Val Asp Lys
        675                 680                 685
Ser Arg Trp Gln Gln Gly Asn Val Phe Ser Cys Ser Val Met His Glu
    690                 695                 700
Ala Leu His Asn His Tyr Thr Gln Lys Ser Leu Ser Leu Ser Pro Gly
705                 710                 715                 720
Lys
```

<210> SEQ ID NO 190
<211> LENGTH: 721
<212> TYPE: PRT
<213> ORGANISM: Artificial Sequence
<220> FEATURE:
<223> OTHER INFORMATION: Synthetic

<400> SEQUENCE: 190

```
Asp Ile Gln Met Thr Gln Ser Pro Ser Ser Leu Ser Ala Ser Val Gly
1               5                   10                  15
Asp Arg Val Thr Ile Thr Cys Lys Ser Ser Gln Ser Leu Leu Asn Ser
            20                  25                  30
Gly Asn Gln Lys Ser Tyr Leu Thr Trp Tyr Gln Gln Lys Pro Gly Lys
        35                  40                  45
Ala Pro Lys Leu Leu Ile Tyr Trp Ala Ser Thr Leu Glu Ser Gly Val
    50                  55                  60
```

```
Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Gly Ser Ser Arg Ser Ser Glu Val Gln Leu Val Glu Ser Gly Gly
                115                 120                 125

Gly Leu Val Gln Pro Gly Gly Ser Leu Arg Leu Ser Cys Ala Ala Ser
    130                 135                 140

Gly Phe Thr Phe Ser Arg Tyr Trp Met Ser Trp Val Arg Gln Ala Pro
145                 150                 155                 160

Gly Lys Gly Leu Glu Trp Val Ala Asn Ile Lys Gln Asp Gly Ser Glu
                165                 170                 175

Lys Tyr Tyr Val Asp Ser Val Lys Gly Arg Phe Thr Ile Ser Arg Asp
                180                 185                 190

Asn Ala Lys Asn Ser Leu Tyr Leu Gln Met Asn Ser Leu Arg Ala Glu
            195                 200                 205

Asp Thr Ala Val Tyr Tyr Cys Ala Arg Glu Gly Trp Phe Gly Glu
    210                 215                 220

Leu Ala Phe Asp Tyr Trp Gly Gln Gly Thr Leu Val Thr Val Ser Ser
225                 230                 235                 240

Ser Gly Ser Ser Gly Ser Ser Ser Ser Gly Ser Gly Ser Gly Glu
                245                 250                 255

Ile Val Leu Thr Gln Ser Pro Gly Thr Leu Ser Leu Ser Pro Gly Glu
                260                 265                 270

Arg Ala Thr Leu Ser Cys Arg Ala Ser Gln Arg Val Ser Ser Ser Tyr
                275                 280                 285

Leu Ala Trp Tyr Gln Gln Lys Pro Gly Gln Ala Pro Arg Leu Leu Ile
    290                 295                 300

Tyr Asp Ala Ser Ser Arg Ala Thr Gly Ile Pro Asp Arg Phe Ser Gly
305                 310                 315                 320

Ser Gly Ser Gly Thr Asp Phe Thr Leu Thr Ile Ser Arg Leu Glu Pro
                325                 330                 335

Glu Asp Phe Ala Val Tyr Tyr Cys Gln Gln Tyr Gly Ser Leu Pro Trp
            340                 345                 350

Thr Phe Gly Gln Gly Thr Lys Val Glu Ile Lys Ser Ser Gly Ser Gly
            355                 360                 365

Gly Glu Val Gln Leu Val Glu Ser Gly Gly Gly Leu Val Gln Pro Gly
    370                 375                 380

Gly Ser Leu Arg Leu Ser Cys Ala Val Ser Gly Tyr Thr Phe Ser Met
385                 390                 395                 400

Asn Trp Val Arg Gln Ala Pro Gly Lys Gly Leu Glu Trp Val Ala Trp
                405                 410                 415

Ile Asn Met Tyr Thr Gly Glu Pro Thr Tyr Ala Asp Asp Phe Lys Gly
            420                 425                 430

Arg Phe Thr Ile Ser Arg Asp Asp Ser Lys Asn Thr Leu Tyr Leu Gln
            435                 440                 445

Met Asn Ser Leu Arg Ala Glu Asp Thr Ala Val Tyr Tyr Cys Ala Arg
    450                 455                 460

Leu Tyr Asn Gly Asn Ser Leu Asp Tyr Trp Gly Gln Gly Thr Leu Val
465                 470                 475                 480
```

```
Thr Val Ser Ser Gly Gly Gly Ser Glu Pro Lys Ser Ser Asp Lys
                485             490             495

Thr His Thr Cys Pro Cys Pro Ala Pro Glu Leu Leu Gly Gly Pro
            500             505             510

Ser Val Phe Leu Phe Pro Pro Lys Pro Lys Asp Thr Leu Met Ile Ser
            515             520             525

Arg Thr Pro Glu Val Thr Cys Val Val Val Asp Val Ser His Glu Asp
530             535             540

Pro Glu Val Lys Phe Asn Trp Tyr Val Asp Gly Val Glu Val His Asn
545             550             555             560

Ala Lys Thr Lys Pro Arg Glu Glu Gln Tyr Asn Ser Thr Tyr Arg Val
            565             570             575

Val Ser Val Leu Thr Val Leu His Gln Asp Trp Leu Asn Gly Lys Glu
            580             585             590

Tyr Lys Cys Lys Val Ser Asn Lys Ala Leu Pro Ala Pro Ile Glu Lys
            595             600             605

Thr Ile Ser Lys Ala Lys Gly Gln Pro Arg Glu Pro Gln Val Tyr Thr
    610             615             620

Leu Pro Pro Ser Arg Glu Glu Met Thr Lys Asn Gln Val Ser Leu Thr
625             630             635             640

Cys Leu Val Lys Gly Phe Tyr Pro Ser Asp Ile Ala Val Glu Trp Glu
            645             650             655

Ser Asn Gly Gln Pro Glu Asn Asn Tyr Lys Thr Thr Pro Pro Val Leu
            660             665             670

Asp Ser Asp Gly Ser Phe Phe Leu Tyr Ser Lys Leu Thr Val Asp Lys
            675             680             685

Ser Arg Trp Gln Gln Gly Asn Val Phe Ser Cys Ser Val Met His Glu
            690             695             700

Ala Leu His Asn His Tyr Thr Gln Lys Ser Leu Ser Leu Ser Pro Gly
705             710             715             720

Lys

<210> SEQ ID NO 191
<211> LENGTH: 719
<212> TYPE: PRT
<213> ORGANISM: Artificial Sequence
<220> FEATURE:
<223> OTHER INFORMATION: Synthetic

<400> SEQUENCE: 191

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65              70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Gly Ser Gly Ser Glu Val Gln Leu Val Glu Ser Gly Gly Gly Leu
```

-continued

```
            115                 120                 125
Val Gln Pro Gly Gly Ser Leu Arg Leu Ser Cys Ala Ala Ser Gly Phe
130                 135                 140

Thr Phe Ser Arg Tyr Trp Met Ser Trp Val Arg Gln Ala Pro Gly Lys
145                 150                 155                 160

Gly Leu Glu Trp Val Ala Asn Ile Lys Gln Asp Gly Ser Glu Lys Tyr
                165                 170                 175

Tyr Val Asp Ser Val Lys Gly Arg Phe Thr Ile Ser Arg Asp Asn Ala
                180                 185                 190

Lys Asn Ser Leu Tyr Leu Gln Met Asn Ser Leu Arg Ala Glu Asp Thr
            195                 200                 205

Ala Val Tyr Tyr Cys Ala Arg Glu Gly Gly Trp Phe Gly Glu Leu Ala
210                 215                 220

Phe Asp Tyr Trp Gly Gln Gly Thr Leu Val Thr Val Ser Ser Ser Ser
225                 230                 235                 240

Gly Gly Ser Ser Gly Ser Ser Gly Ser Ser Gly Gly Glu Ile
                245                 250                 255

Val Leu Thr Gln Ser Pro Gly Thr Leu Ser Leu Ser Pro Gly Glu Arg
            260                 265                 270

Ala Thr Leu Ser Cys Arg Ala Ser Gln Arg Val Ser Ser Ser Tyr Leu
            275                 280                 285

Ala Trp Tyr Gln Gln Lys Pro Gly Gln Ala Pro Arg Leu Leu Ile Tyr
290                 295                 300

Asp Ala Ser Ser Arg Ala Thr Gly Ile Pro Asp Arg Phe Ser Gly Ser
305                 310                 315                 320

Gly Ser Gly Thr Asp Phe Thr Leu Thr Ile Ser Arg Leu Glu Pro Glu
                325                 330                 335

Asp Phe Ala Val Tyr Tyr Cys Gln Gln Tyr Gly Ser Leu Pro Trp Thr
                340                 345                 350

Phe Gly Gln Gly Thr Lys Val Glu Ile Lys Ser Gly Gly Gly Ser Glu
            355                 360                 365

Val Gln Leu Val Glu Ser Gly Gly Gly Leu Val Gln Pro Gly Gly Ser
            370                 375                 380

Leu Arg Leu Ser Cys Ala Val Ser Gly Tyr Thr Phe Ser Met Asn Trp
385                 390                 395                 400

Val Arg Gln Ala Pro Gly Lys Gly Leu Glu Trp Val Ala Trp Ile Asn
                405                 410                 415

Met Tyr Thr Gly Glu Pro Thr Tyr Ala Asp Asp Phe Lys Gly Arg Phe
                420                 425                 430

Thr Ile Ser Arg Asp Asp Ser Lys Asn Thr Leu Tyr Leu Gln Met Asn
            435                 440                 445

Ser Leu Arg Ala Glu Asp Thr Ala Val Tyr Tyr Cys Ala Arg Leu Tyr
            450                 455                 460

Asn Gly Asn Ser Leu Asp Tyr Trp Gly Gln Gly Thr Leu Val Thr Val
465                 470                 475                 480

Ser Ser Gly Gly Gly Gly Ser Glu Pro Lys Ser Ser Asp Lys Thr His
                485                 490                 495

Thr Cys Pro Pro Cys Pro Ala Pro Glu Leu Leu Gly Gly Pro Ser Val
                500                 505                 510

Phe Leu Phe Pro Pro Lys Pro Lys Asp Thr Leu Met Ile Ser Arg Thr
            515                 520                 525

Pro Glu Val Thr Cys Val Val Val Asp Val Ser His Glu Asp Pro Glu
            530                 535                 540
```

```
Val Lys Phe Asn Trp Tyr Val Asp Gly Val Glu Val His Asn Ala Lys
545                 550                 555                 560

Thr Lys Pro Arg Glu Glu Gln Tyr Asn Ser Thr Tyr Arg Val Val Ser
                565                 570                 575

Val Leu Thr Val Leu His Gln Asp Trp Leu Asn Gly Lys Glu Tyr Lys
            580                 585                 590

Cys Lys Val Ser Asn Lys Ala Leu Pro Ala Pro Ile Glu Lys Thr Ile
        595                 600                 605

Ser Lys Ala Lys Gly Gln Pro Arg Glu Pro Gln Val Tyr Thr Leu Pro
    610                 615                 620

Pro Ser Arg Glu Glu Met Thr Lys Asn Gln Val Ser Leu Thr Cys Leu
625                 630                 635                 640

Val Lys Gly Phe Tyr Pro Ser Asp Ile Ala Val Glu Trp Glu Ser Asn
                645                 650                 655

Gly Gln Pro Glu Asn Asn Tyr Lys Thr Thr Pro Pro Val Leu Asp Ser
                660                 665                 670

Asp Gly Ser Phe Phe Leu Tyr Ser Lys Leu Thr Val Asp Lys Ser Arg
            675                 680                 685

Trp Gln Gln Gly Asn Val Phe Ser Cys Ser Val Met His Glu Ala Leu
        690                 695                 700

His Asn His Tyr Thr Gln Lys Ser Leu Ser Leu Ser Pro Gly Lys
705                 710                 715

<210> SEQ ID NO 192
<211> LENGTH: 720
<212> TYPE: PRT
<213> ORGANISM: Artificial Sequence
<220> FEATURE:
<223> OTHER INFORMATION: Synthetic

<400> SEQUENCE: 192

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Gly Ser Gly Ser Glu Val Gln Leu Val Glu Ser Gly Gly Gly Leu
        115                 120                 125

Val Gln Pro Gly Gly Ser Leu Arg Leu Ser Cys Ala Ala Ser Gly Phe
    130                 135                 140

Thr Phe Ser Arg Tyr Trp Met Ser Trp Val Arg Gln Ala Pro Gly Lys
145                 150                 155                 160

Gly Leu Glu Trp Val Ala Asn Ile Lys Gln Asp Gly Ser Glu Lys Tyr
                165                 170                 175

Tyr Val Asp Ser Val Lys Gly Arg Phe Thr Ile Ser Arg Asp Asn Ala
            180                 185                 190
```

-continued

```
Lys Asn Ser Leu Tyr Leu Gln Met Asn Ser Leu Arg Ala Glu Asp Thr
            195                 200                 205

Ala Val Tyr Tyr Cys Ala Arg Glu Gly Gly Trp Phe Gly Glu Leu Ala
    210                 215                 220

Phe Asp Tyr Trp Gly Gln Gly Thr Leu Val Thr Val Ser Ser Ser Ser
225                 230                 235                 240

Ser Ser Ser Gly Gly Gly Ser Gly Gly Ser Ser Ser Gly Glu Ile
                245                 250                 255

Val Leu Thr Gln Ser Pro Gly Thr Leu Ser Leu Ser Pro Gly Glu Arg
            260                 265                 270

Ala Thr Leu Ser Cys Arg Ala Ser Gln Arg Val Ser Ser Ser Tyr Leu
            275                 280                 285

Ala Trp Tyr Gln Gln Lys Pro Gly Gln Ala Pro Arg Leu Leu Ile Tyr
            290                 295                 300

Asp Ala Ser Ser Arg Ala Thr Gly Ile Pro Asp Arg Phe Ser Gly Ser
305                 310                 315                 320

Gly Ser Gly Thr Asp Phe Thr Leu Thr Ile Ser Arg Leu Glu Pro Glu
                325                 330                 335

Asp Phe Ala Val Tyr Tyr Cys Gln Gln Tyr Gly Ser Leu Pro Trp Thr
            340                 345                 350

Phe Gly Gln Gly Thr Lys Val Glu Ile Lys Ser Ser Ser Gly Gly Gly
            355                 360                 365

Glu Val Gln Leu Val Glu Ser Gly Gly Gly Leu Val Gln Pro Gly Gly
            370                 375                 380

Ser Leu Arg Leu Ser Cys Ala Val Ser Gly Tyr Thr Phe Ser Met Asn
385                 390                 395                 400

Trp Val Arg Gln Ala Pro Gly Lys Gly Leu Glu Trp Val Ala Trp Ile
                405                 410                 415

Asn Met Tyr Thr Gly Glu Pro Thr Tyr Ala Asp Asp Phe Lys Gly Arg
            420                 425                 430

Phe Thr Ile Ser Arg Asp Asp Ser Lys Asn Thr Leu Tyr Leu Gln Met
            435                 440                 445

Asn Ser Leu Arg Ala Glu Asp Thr Ala Val Tyr Tyr Cys Ala Arg Leu
            450                 455                 460

Tyr Asn Gly Asn Ser Leu Asp Tyr Trp Gly Gln Gly Thr Leu Val Thr
465                 470                 475                 480

Val Ser Ser Gly Gly Gly Gly Ser Glu Pro Lys Ser Ser Asp Lys Thr
                485                 490                 495

His Thr Cys Pro Pro Cys Pro Ala Pro Glu Leu Leu Gly Gly Pro Ser
            500                 505                 510

Val Phe Leu Phe Pro Pro Lys Pro Lys Asp Thr Leu Met Ile Ser Arg
            515                 520                 525

Thr Pro Glu Val Thr Cys Val Val Val Asp Val Ser His Glu Asp Pro
            530                 535                 540

Glu Val Lys Phe Asn Trp Tyr Val Asp Gly Val Glu Val His Asn Ala
545                 550                 555                 560

Lys Thr Lys Pro Arg Glu Glu Gln Tyr Asn Ser Thr Tyr Arg Val Val
                565                 570                 575

Ser Val Leu Thr Val Leu His Gln Asp Trp Leu Asn Gly Lys Glu Tyr
            580                 585                 590

Lys Cys Lys Val Ser Asn Lys Ala Leu Pro Ala Pro Ile Glu Lys Thr
            595                 600                 605
```

```
Ile Ser Lys Ala Lys Gly Gln Pro Arg Glu Pro Gln Val Tyr Thr Leu
            610                 615                 620

Pro Pro Ser Arg Glu Glu Met Thr Lys Asn Gln Val Ser Leu Thr Cys
625                 630                 635                 640

Leu Val Lys Gly Phe Tyr Pro Ser Asp Ile Ala Val Glu Trp Glu Ser
            645                 650                 655

Asn Gly Gln Pro Glu Asn Asn Tyr Lys Thr Thr Pro Pro Val Leu Asp
            660                 665                 670

Ser Asp Gly Ser Phe Phe Leu Tyr Ser Lys Leu Thr Val Asp Lys Ser
            675                 680                 685

Arg Trp Gln Gln Gly Asn Val Phe Ser Cys Ser Val Met His Glu Ala
690                 695                 700

Leu His Asn His Tyr Thr Gln Lys Ser Leu Ser Leu Ser Pro Gly Lys
705                 710                 715                 720

<210> SEQ ID NO 193
<211> LENGTH: 722
<212> TYPE: PRT
<213> ORGANISM: Artificial Sequence
<220> FEATURE:
<223> OTHER INFORMATION: Synthetic

<400> SEQUENCE: 193

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Thr Phe Ser Arg Tyr Trp Met Ser Trp Val Arg Gln Ala Pro Gly
145                 150                 155                 160

Lys Gly Leu Glu Trp Val Ala Asn Ile Lys Gln Asp Gly Ser Glu Lys
                165                 170                 175

Tyr Tyr Val Asp Ser Val Lys Gly Arg Phe Thr Ile Ser Arg Asp Asn
            180                 185                 190

Ala Lys Asn Ser Leu Tyr Leu Gln Met Asn Ser Leu Arg Ala Glu Asp
        195                 200                 205

Thr Ala Val Tyr Tyr Cys Ala Arg Glu Gly Gly Trp Phe Gly Glu Leu
    210                 215                 220

Ala Phe Asp Tyr Trp Gly Gln Gly Thr Leu Val Thr Val Ser Ser Gly
225                 230                 235                 240

Ser Gly Ser Ser Ser Ser Ser Arg Ser Ser Ser Gly Gly Gly Gly
                245                 250                 255
```

-continued

```
Glu Ile Val Leu Thr Gln Ser Pro Gly Thr Leu Ser Leu Ser Pro Gly
            260                 265                 270

Glu Arg Ala Thr Leu Ser Cys Arg Ala Ser Gln Arg Val Ser Ser Ser
        275                 280                 285

Tyr Leu Ala Trp Tyr Gln Gln Lys Pro Gly Gln Ala Pro Arg Leu Leu
    290                 295                 300

Ile Tyr Asp Ala Ser Ser Arg Ala Thr Gly Ile Pro Asp Arg Phe Ser
305                 310                 315                 320

Gly Ser Gly Ser Gly Thr Asp Phe Thr Leu Thr Ile Ser Arg Leu Glu
                325                 330                 335

Pro Glu Asp Phe Ala Val Tyr Tyr Cys Gln Gln Tyr Gly Ser Leu Pro
            340                 345                 350

Trp Thr Phe Gly Gln Gly Thr Lys Val Glu Ile Lys Ser Gly Gly Ser
        355                 360                 365

Gly Gly Glu Val Gln Leu Val Glu Ser Gly Gly Leu Val Gln Pro
    370                 375                 380

Gly Gly Ser Leu Arg Leu Ser Cys Ala Val Ser Gly Tyr Thr Phe Ser
385                 390                 395                 400

Met Asn Trp Val Arg Gln Ala Pro Gly Lys Gly Leu Glu Trp Val Ala
                405                 410                 415

Trp Ile Asn Met Tyr Thr Gly Glu Pro Thr Tyr Ala Asp Asp Phe Lys
            420                 425                 430

Gly Arg Phe Thr Ile Ser Arg Asp Asp Ser Lys Asn Thr Leu Tyr Leu
        435                 440                 445

Gln Met Asn Ser Leu Arg Ala Glu Asp Thr Ala Val Tyr Tyr Cys Ala
    450                 455                 460

Arg Leu Tyr Asn Gly Asn Ser Leu Asp Tyr Trp Gly Gln Gly Thr Leu
465                 470                 475                 480

Val Thr Val Ser Ser Gly Gly Gly Ser Glu Pro Lys Ser Ser Asp
                485                 490                 495

Lys Thr His Thr Cys Pro Pro Cys Pro Ala Pro Glu Leu Leu Gly Gly
            500                 505                 510

Pro Ser Val Phe Leu Phe Pro Pro Lys Pro Lys Asp Thr Leu Met Ile
        515                 520                 525

Ser Arg Thr Pro Glu Val Thr Cys Val Val Val Asp Val Ser His Glu
    530                 535                 540

Asp Pro Glu Val Lys Phe Asn Trp Tyr Val Asp Gly Val Glu Val His
545                 550                 555                 560

Asn Ala Lys Thr Lys Pro Arg Glu Glu Gln Tyr Asn Ser Thr Tyr Arg
                565                 570                 575

Val Val Ser Val Leu Thr Val Leu His Gln Asp Trp Leu Asn Gly Lys
            580                 585                 590

Glu Tyr Lys Cys Lys Val Ser Asn Lys Ala Leu Pro Ala Pro Ile Glu
        595                 600                 605

Lys Thr Ile Ser Lys Ala Lys Gly Gln Pro Arg Glu Pro Gln Val Tyr
    610                 615                 620

Thr Leu Pro Pro Ser Arg Glu Glu Met Thr Lys Asn Gln Val Ser Leu
625                 630                 635                 640

Thr Cys Leu Val Lys Gly Phe Tyr Pro Ser Asp Ile Ala Val Glu Trp
                645                 650                 655

Glu Ser Asn Gly Gln Pro Glu Asn Asn Tyr Lys Thr Thr Pro Pro Val
            660                 665                 670

Leu Asp Ser Asp Gly Ser Phe Phe Leu Tyr Ser Lys Leu Thr Val Asp
```

```
                675                 680                 685
Lys Ser Arg Trp Gln Gln Gly Asn Val Phe Ser Cys Ser Val Met His
        690                 695                 700
Glu Ala Leu His Asn His Tyr Thr Gln Lys Ser Leu Ser Leu Ser Pro
705                 710                 715                 720
Gly Lys

<210> SEQ ID NO 194
<211> LENGTH: 721
<212> TYPE: PRT
<213> ORGANISM: Artificial Sequence
<220> FEATURE:
<223> OTHER INFORMATION: Synthetic

<400> SEQUENCE: 194

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Gly Ser Ser Gly Glu Val Gln Leu Val Glu Ser Gly Gly Gly Leu
        115                 120                 125

Val Gln Pro Gly Gly Ser Leu Arg Leu Ser Cys Ala Ala Ser Gly Phe
    130                 135                 140

Thr Phe Ser Arg Tyr Trp Met Ser Trp Val Arg Gln Ala Pro Gly Lys
145                 150                 155                 160

Gly Leu Glu Trp Val Ala Asn Ile Lys Gln Asp Gly Ser Glu Lys Tyr
                165                 170                 175

Tyr Val Asp Ser Val Lys Gly Arg Phe Thr Ile Ser Arg Asp Asn Ala
            180                 185                 190

Lys Asn Ser Leu Tyr Leu Gln Met Asn Ser Leu Arg Ala Glu Asp Thr
        195                 200                 205

Ala Val Tyr Tyr Cys Ala Arg Glu Gly Gly Trp Phe Gly Glu Leu Ala
    210                 215                 220

Phe Asp Tyr Trp Gly Gln Gly Thr Leu Val Thr Val Ser Ser Ser Ser
225                 230                 235                 240

Gly Ser Ser Ser Gly Ser Arg Ser Gly Ser Ser Gly Gly Ser Glu
                245                 250                 255

Ile Val Leu Thr Gln Ser Pro Gly Thr Leu Ser Leu Ser Pro Gly Glu
            260                 265                 270

Arg Ala Thr Leu Ser Cys Arg Ala Ser Gln Arg Val Ser Ser Ser Tyr
        275                 280                 285

Leu Ala Trp Tyr Gln Gln Lys Pro Gly Gln Ala Pro Arg Leu Leu Ile
    290                 295                 300

Tyr Asp Ala Ser Ser Arg Ala Thr Gly Ile Pro Asp Arg Phe Ser Gly
305                 310                 315                 320
```

```
Ser Gly Ser Gly Thr Asp Phe Thr Leu Thr Ile Ser Arg Leu Glu Pro
            325                 330                 335

Glu Asp Phe Ala Val Tyr Tyr Cys Gln Gln Tyr Gly Ser Leu Pro Trp
            340                 345                 350

Thr Phe Gly Gln Gly Thr Lys Val Glu Ile Lys Ser Gly Gly Gly Gly
            355                 360                 365

Gly Glu Val Gln Leu Val Glu Ser Gly Gly Leu Val Gln Pro Gly
    370                 375                 380

Gly Ser Leu Arg Leu Ser Cys Ala Val Ser Gly Tyr Thr Phe Ser Met
385                 390                 395                 400

Asn Trp Val Arg Gln Ala Pro Gly Lys Gly Leu Glu Trp Val Ala Trp
            405                 410                 415

Ile Asn Met Tyr Thr Gly Glu Pro Thr Tyr Ala Asp Asp Phe Lys Gly
            420                 425                 430

Arg Phe Thr Ile Ser Arg Asp Asp Ser Lys Asn Thr Leu Tyr Leu Gln
            435                 440                 445

Met Asn Ser Leu Arg Ala Glu Asp Thr Ala Val Tyr Tyr Cys Ala Arg
    450                 455                 460

Leu Tyr Asn Gly Asn Ser Leu Asp Tyr Trp Gly Gln Gly Thr Leu Val
465                 470                 475                 480

Thr Val Ser Ser Gly Gly Gly Gly Ser Glu Pro Lys Ser Ser Asp Lys
            485                 490                 495

Thr His Thr Cys Pro Pro Cys Pro Ala Pro Glu Leu Leu Gly Gly Pro
            500                 505                 510

Ser Val Phe Leu Phe Pro Pro Lys Pro Lys Asp Thr Leu Met Ile Ser
            515                 520                 525

Arg Thr Pro Glu Val Thr Cys Val Val Val Asp Val Ser His Glu Asp
    530                 535                 540

Pro Glu Val Lys Phe Asn Trp Tyr Val Asp Gly Val Glu Val His Asn
545                 550                 555                 560

Ala Lys Thr Lys Pro Arg Glu Glu Gln Tyr Asn Ser Thr Tyr Arg Val
            565                 570                 575

Val Ser Val Leu Thr Val Leu His Gln Asp Trp Leu Asn Gly Lys Glu
            580                 585                 590

Tyr Lys Cys Lys Val Ser Asn Lys Ala Leu Pro Ala Pro Ile Glu Lys
            595                 600                 605

Thr Ile Ser Lys Ala Lys Gly Gln Pro Arg Glu Pro Gln Val Tyr Thr
    610                 615                 620

Leu Pro Pro Ser Arg Glu Glu Met Thr Lys Asn Gln Val Ser Leu Thr
625                 630                 635                 640

Cys Leu Val Lys Gly Phe Tyr Pro Ser Asp Ile Ala Val Glu Trp Glu
            645                 650                 655

Ser Asn Gly Gln Pro Glu Asn Asn Tyr Lys Thr Thr Pro Pro Val Leu
            660                 665                 670

Asp Ser Asp Gly Ser Phe Phe Leu Tyr Ser Lys Leu Thr Val Asp Lys
            675                 680                 685

Ser Arg Trp Gln Gln Gly Asn Val Phe Ser Cys Ser Val Met His Glu
    690                 695                 700

Ala Leu His Asn His Tyr Thr Gln Lys Ser Leu Ser Leu Ser Pro Gly
705                 710                 715                 720

Lys
```

```
<210> SEQ ID NO 195
<211> LENGTH: 720
<212> TYPE: PRT
<213> ORGANISM: Artificial Sequence
<220> FEATURE:
<223> OTHER INFORMATION: Synthetic

<400> SEQUENCE: 195

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Gly Gly Gly Ser Gly Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Thr Phe Ser Arg Tyr Trp Met Ser Trp Val Arg Gln Ala Pro Gly
145                 150                 155                 160

Lys Gly Leu Glu Trp Val Ala Asn Ile Lys Gln Asp Gly Ser Glu Lys
                165                 170                 175

Tyr Tyr Val Asp Ser Val Lys Gly Arg Phe Thr Ile Ser Arg Asp Asn
            180                 185                 190

Ala Lys Asn Ser Leu Tyr Leu Gln Met Asn Ser Leu Arg Ala Glu Asp
        195                 200                 205

Thr Ala Val Tyr Tyr Cys Ala Arg Glu Gly Gly Trp Phe Gly Glu Leu
    210                 215                 220

Ala Phe Asp Tyr Trp Gly Gln Gly Thr Leu Val Thr Val Ser Ser Gly
225                 230                 235                 240

Ser Ser Ser Gly Gly Ser Gly Ser Gly Gly Gly Gly Ser Gly Gly Gly
                245                 250                 255

Glu Ile Val Leu Thr Gln Ser Pro Gly Thr Leu Ser Leu Ser Pro Gly
            260                 265                 270

Glu Arg Ala Thr Leu Ser Cys Arg Ala Ser Gln Arg Val Ser Ser Ser
        275                 280                 285

Tyr Leu Ala Trp Tyr Gln Gln Lys Pro Gly Gln Ala Pro Arg Leu Leu
    290                 295                 300

Ile Tyr Asp Ala Ser Ser Arg Ala Thr Gly Ile Pro Asp Arg Phe Ser
305                 310                 315                 320

Gly Ser Gly Ser Gly Thr Asp Phe Thr Leu Thr Ile Ser Arg Leu Glu
                325                 330                 335

Pro Glu Asp Phe Ala Val Tyr Tyr Cys Gln Gln Tyr Gly Ser Leu Pro
            340                 345                 350

Trp Thr Phe Gly Gln Gly Thr Lys Val Glu Ile Lys Ser Gly Gly Ser
        355                 360                 365

Glu Val Gln Leu Val Glu Ser Gly Gly Gly Leu Val Gln Pro Gly Gly
```

```
            370                 375                 380
Ser Leu Arg Leu Ser Cys Ala Val Ser Gly Tyr Thr Phe Ser Met Asn
385                 390                 395                 400

Trp Val Arg Gln Ala Pro Gly Lys Gly Leu Glu Trp Val Ala Trp Ile
                405                 410                 415

Asn Met Tyr Thr Gly Glu Pro Thr Tyr Ala Asp Asp Phe Lys Gly Arg
            420                 425                 430

Phe Thr Ile Ser Arg Asp Asp Ser Lys Asn Thr Leu Tyr Leu Gln Met
        435                 440                 445

Asn Ser Leu Arg Ala Glu Asp Thr Ala Val Tyr Tyr Cys Ala Arg Leu
    450                 455                 460

Tyr Asn Gly Asn Ser Leu Asp Tyr Trp Gly Gln Gly Thr Leu Val Thr
465                 470                 475                 480

Val Ser Ser Gly Gly Gly Gly Ser Glu Pro Lys Ser Ser Asp Lys Thr
                485                 490                 495

His Thr Cys Pro Pro Cys Pro Ala Pro Glu Leu Leu Gly Gly Pro Ser
            500                 505                 510

Val Phe Leu Phe Pro Pro Lys Pro Lys Asp Thr Leu Met Ile Ser Arg
        515                 520                 525

Thr Pro Glu Val Thr Cys Val Val Val Asp Val Ser His Glu Asp Pro
    530                 535                 540

Glu Val Lys Phe Asn Trp Tyr Val Asp Gly Val Glu Val His Asn Ala
545                 550                 555                 560

Lys Thr Lys Pro Arg Glu Glu Gln Tyr Asn Ser Thr Tyr Arg Val Val
                565                 570                 575

Ser Val Leu Thr Val Leu His Gln Asp Trp Leu Asn Gly Lys Glu Tyr
            580                 585                 590

Lys Cys Lys Val Ser Asn Lys Ala Leu Pro Ala Pro Ile Glu Lys Thr
        595                 600                 605

Ile Ser Lys Ala Lys Gly Gln Pro Arg Glu Pro Gln Val Tyr Thr Leu
    610                 615                 620

Pro Pro Ser Arg Glu Glu Met Thr Lys Asn Gln Val Ser Leu Thr Cys
625                 630                 635                 640

Leu Val Lys Gly Phe Tyr Pro Ser Asp Ile Ala Val Glu Trp Glu Ser
                645                 650                 655

Asn Gly Gln Pro Glu Asn Asn Tyr Lys Thr Thr Pro Pro Val Leu Asp
            660                 665                 670

Ser Asp Gly Ser Phe Phe Leu Tyr Ser Lys Leu Thr Val Asp Lys Ser
        675                 680                 685

Arg Trp Gln Gln Gly Asn Val Phe Ser Cys Ser Val Met His Glu Ala
    690                 695                 700

Leu His Asn His Tyr Thr Gln Lys Ser Leu Ser Leu Ser Pro Gly Lys
705                 710                 715                 720

<210> SEQ ID NO 196
<211> LENGTH: 719
<212> TYPE: PRT
<213> ORGANISM: Artificial Sequence
<220> FEATURE:
<223> OTHER INFORMATION: Synthetic

<400> SEQUENCE: 196

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
```

```
                    20                  25                  30
Gly Asn Gln Lys Ser Tyr Leu Thr Trp Tyr Gln Gln Lys Pro Gly Lys
                35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
                100                 105                 110

Lys Ser Ser Gly Gly Glu Val Gln Leu Val Glu Ser Gly Gly Gly
                115                 120                 125

Leu Val Gln Pro Gly Gly Ser Leu Arg Leu Ser Cys Ala Ala Ser Gly
            130                 135                 140

Phe Thr Phe Ser Arg Tyr Trp Met Ser Trp Val Arg Gln Ala Pro Gly
145                 150                 155                 160

Lys Gly Leu Glu Trp Val Ala Asn Ile Lys Gln Asp Gly Ser Glu Lys
                165                 170                 175

Tyr Tyr Val Asp Ser Val Lys Gly Arg Phe Thr Ile Ser Arg Asp Asn
                180                 185                 190

Ala Lys Asn Ser Leu Tyr Leu Gln Met Asn Ser Leu Arg Ala Glu Asp
                195                 200                 205

Thr Ala Val Tyr Tyr Cys Ala Arg Glu Gly Gly Trp Phe Gly Glu Leu
            210                 215                 220

Ala Phe Asp Tyr Trp Gly Gln Gly Thr Leu Val Thr Val Ser Ser Ser
225                 230                 235                 240

Gly Gly Gly Ser Ser Gly Ser Gly Gly Arg Ser Gly Ser Glu Ile
                245                 250                 255

Val Leu Thr Gln Ser Pro Gly Thr Leu Ser Leu Ser Pro Gly Glu Arg
                260                 265                 270

Ala Thr Leu Ser Cys Arg Ala Ser Gln Arg Val Ser Ser Ser Tyr Leu
            275                 280                 285

Ala Trp Tyr Gln Gln Lys Pro Gly Gln Ala Pro Arg Leu Leu Ile Tyr
    290                 295                 300

Asp Ala Ser Ser Arg Ala Thr Gly Ile Pro Asp Arg Phe Ser Gly Ser
305                 310                 315                 320

Gly Ser Gly Thr Asp Phe Thr Leu Thr Ile Ser Arg Leu Glu Pro Glu
                325                 330                 335

Asp Phe Ala Val Tyr Tyr Cys Gln Gln Tyr Gly Ser Leu Pro Trp Thr
                340                 345                 350

Phe Gly Gln Gly Thr Lys Val Glu Ile Lys Ser Gly Gly Gly Gly Glu
                355                 360                 365

Val Gln Leu Val Glu Ser Gly Gly Gly Leu Val Gln Pro Gly Gly Ser
            370                 375                 380

Leu Arg Leu Ser Cys Ala Val Ser Gly Tyr Thr Phe Ser Met Asn Trp
385                 390                 395                 400

Val Arg Gln Ala Pro Gly Lys Gly Leu Glu Trp Val Ala Trp Ile Asn
                405                 410                 415

Met Tyr Thr Gly Glu Pro Thr Tyr Ala Asp Asp Phe Lys Gly Arg Phe
                420                 425                 430

Thr Ile Ser Arg Asp Asp Ser Lys Asn Thr Leu Tyr Leu Gln Met Asn
            435                 440                 445
```

```
Ser Leu Arg Ala Glu Asp Thr Ala Val Tyr Tyr Cys Ala Arg Leu Tyr
    450                 455                 460

Asn Gly Asn Ser Leu Asp Tyr Trp Gly Gln Gly Thr Leu Val Thr Val
465                 470                 475                 480

Ser Ser Gly Gly Gly Gly Ser Glu Pro Lys Ser Ser Asp Lys Thr His
                485                 490                 495

Thr Cys Pro Pro Cys Pro Ala Pro Glu Leu Leu Gly Gly Pro Ser Val
            500                 505                 510

Phe Leu Phe Pro Pro Lys Pro Lys Asp Thr Leu Met Ile Ser Arg Thr
        515                 520                 525

Pro Glu Val Thr Cys Val Val Val Asp Val Ser His Glu Asp Pro Glu
    530                 535                 540

Val Lys Phe Asn Trp Tyr Val Asp Gly Val Glu Val His Asn Ala Lys
545                 550                 555                 560

Thr Lys Pro Arg Glu Glu Gln Tyr Asn Ser Thr Tyr Arg Val Val Ser
                565                 570                 575

Val Leu Thr Val Leu His Gln Asp Trp Leu Asn Gly Lys Glu Tyr Lys
            580                 585                 590

Cys Lys Val Ser Asn Lys Ala Leu Pro Ala Pro Ile Glu Lys Thr Ile
        595                 600                 605

Ser Lys Ala Lys Gly Gln Pro Arg Glu Pro Gln Val Tyr Thr Leu Pro
    610                 615                 620

Pro Ser Arg Glu Glu Met Thr Lys Asn Gln Val Ser Leu Thr Cys Leu
625                 630                 635                 640

Val Lys Gly Phe Tyr Pro Ser Asp Ile Ala Val Glu Trp Glu Ser Asn
                645                 650                 655

Gly Gln Pro Glu Asn Asn Tyr Lys Thr Thr Pro Pro Val Leu Asp Ser
            660                 665                 670

Asp Gly Ser Phe Phe Leu Tyr Ser Lys Leu Thr Val Asp Lys Ser Arg
        675                 680                 685

Trp Gln Gln Gly Asn Val Phe Ser Cys Ser Val Met His Glu Ala Leu
    690                 695                 700

His Asn His Tyr Thr Gln Lys Ser Leu Ser Leu Ser Pro Gly Lys
705                 710                 715

<210> SEQ ID NO 197
<211> LENGTH: 723
<212> TYPE: PRT
<213> ORGANISM: Artificial Sequence
<220> FEATURE:
<223> OTHER INFORMATION: Synthetic

<400> SEQUENCE: 197

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95
```

```
Ala Tyr Phe Phe Pro Phe Thr Phe Gly Gln Gly Thr Lys Val Glu Ile
                100                 105                 110

Lys Ser Gly Ser Gly Gly Ser Glu Val Gln Leu Val Glu Ser Gly Gly
            115                 120                 125

Gly Leu Val Gln Pro Gly Gly Ser Leu Arg Leu Ser Cys Ala Ala Ser
        130                 135                 140

Gly Phe Thr Phe Ser Arg Tyr Trp Met Ser Trp Val Arg Gln Ala Pro
145                 150                 155                 160

Gly Lys Gly Leu Glu Trp Val Ala Asn Ile Lys Gln Asp Gly Ser Glu
                165                 170                 175

Lys Tyr Tyr Val Asp Ser Val Lys Gly Arg Phe Thr Ile Ser Arg Asp
            180                 185                 190

Asn Ala Lys Asn Ser Leu Tyr Leu Gln Met Asn Ser Leu Arg Ala Glu
        195                 200                 205

Asp Thr Ala Val Tyr Tyr Cys Ala Arg Glu Gly Gly Trp Phe Gly Glu
    210                 215                 220

Leu Ala Phe Asp Tyr Trp Gly Gln Gly Thr Leu Val Thr Val Ser Ser
225                 230                 235                 240

Gly Ser Gly Gly Gly Gly Ser Gly Ser Ser Gly Ser Gly Gly Gly Ser
                245                 250                 255

Gly Glu Ile Val Leu Thr Gln Ser Pro Gly Thr Leu Ser Leu Ser Pro
            260                 265                 270

Gly Glu Arg Ala Thr Leu Ser Cys Arg Ala Ser Gln Arg Val Ser Ser
        275                 280                 285

Ser Tyr Leu Ala Trp Tyr Gln Gln Lys Pro Gly Gln Ala Pro Arg Leu
    290                 295                 300

Leu Ile Tyr Asp Ala Ser Ser Arg Ala Thr Gly Ile Pro Asp Arg Phe
305                 310                 315                 320

Ser Gly Ser Gly Ser Gly Thr Asp Phe Thr Leu Thr Ile Ser Arg Leu
                325                 330                 335

Glu Pro Glu Asp Phe Ala Val Tyr Tyr Cys Gln Gln Tyr Gly Ser Leu
            340                 345                 350

Pro Trp Thr Phe Gly Gln Gly Thr Lys Val Glu Ile Lys Ser Ser Ser
        355                 360                 365

Gly Ser Ser Glu Val Gln Leu Val Glu Ser Gly Gly Gly Leu Val Gln
    370                 375                 380

Pro Gly Gly Ser Leu Arg Leu Ser Cys Ala Val Ser Gly Tyr Thr Phe
385                 390                 395                 400

Ser Met Asn Trp Val Arg Gln Ala Pro Gly Lys Gly Leu Glu Trp Val
                405                 410                 415

Ala Trp Ile Asn Met Tyr Thr Gly Glu Pro Thr Tyr Ala Asp Asp Phe
            420                 425                 430

Lys Gly Arg Phe Thr Ile Ser Arg Asp Asp Ser Lys Asn Thr Leu Tyr
        435                 440                 445

Leu Gln Met Asn Ser Leu Arg Ala Glu Asp Thr Ala Val Tyr Tyr Cys
    450                 455                 460

Ala Arg Leu Tyr Asn Gly Asn Ser Leu Asp Tyr Trp Gly Gln Gly Thr
465                 470                 475                 480

Leu Val Thr Val Ser Ser Gly Gly Gly Gly Ser Glu Pro Lys Ser Ser
                485                 490                 495

Asp Lys Thr His Thr Cys Pro Pro Cys Pro Ala Pro Glu Leu Leu Gly
            500                 505                 510
```

-continued

```
Gly Pro Ser Val Phe Leu Phe Pro Lys Pro Lys Asp Thr Leu Met
                515                 520                 525

Ile Ser Arg Thr Pro Glu Val Thr Cys Val Val Val Asp Val Ser His
    530                 535                 540

Glu Asp Pro Glu Val Lys Phe Asn Trp Tyr Val Asp Gly Val Glu Val
545                 550                 555                 560

His Asn Ala Lys Thr Lys Pro Arg Glu Glu Gln Tyr Asn Ser Thr Tyr
                565                 570                 575

Arg Val Val Ser Val Leu Thr Val Leu His Gln Asp Trp Leu Asn Gly
            580                 585                 590

Lys Glu Tyr Lys Cys Lys Val Ser Asn Lys Ala Leu Pro Ala Pro Ile
        595                 600                 605

Glu Lys Thr Ile Ser Lys Ala Lys Gly Gln Pro Arg Glu Pro Gln Val
    610                 615                 620

Tyr Thr Leu Pro Pro Ser Arg Glu Glu Met Thr Lys Asn Gln Val Ser
625                 630                 635                 640

Leu Thr Cys Leu Val Lys Gly Phe Tyr Pro Ser Asp Ile Ala Val Glu
                645                 650                 655

Trp Glu Ser Asn Gly Gln Pro Glu Asn Asn Tyr Lys Thr Thr Pro Pro
            660                 665                 670

Val Leu Asp Ser Asp Gly Ser Phe Phe Leu Tyr Ser Lys Leu Thr Val
        675                 680                 685

Asp Lys Ser Arg Trp Gln Gln Gly Asn Val Phe Ser Cys Ser Val Met
    690                 695                 700

His Glu Ala Leu His Asn His Tyr Thr Gln Lys Ser Leu Ser Leu Ser
705                 710                 715                 720

Pro Gly Lys

<210> SEQ ID NO 198
<211> LENGTH: 722
<212> TYPE: PRT
<213> ORGANISM: Artificial Sequence
<220> FEATURE:
<223> OTHER INFORMATION: Synthetic

<400> SEQUENCE: 198

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Gly Ser Gly Ser Gly Gly Glu Val Gln Leu Val Glu Ser Gly Gly
        115                 120                 125

Gly Leu Val Gln Pro Gly Gly Ser Leu Arg Leu Ser Cys Ala Ala Ser
    130                 135                 140

Gly Phe Thr Phe Ser Arg Tyr Trp Met Ser Trp Val Arg Gln Ala Pro
```

```
                145                 150                 155                 160
        Gly Lys Gly Leu Glu Trp Val Ala Asn Ile Lys Gln Asp Gly Ser Glu
                        165                 170                 175
        Lys Tyr Tyr Val Asp Ser Val Lys Gly Arg Phe Thr Ile Ser Arg Asp
                        180                 185                 190
        Asn Ala Lys Asn Ser Leu Tyr Leu Gln Met Asn Ser Leu Arg Ala Glu
                        195                 200                 205
        Asp Thr Ala Val Tyr Tyr Cys Ala Arg Glu Gly Gly Trp Phe Gly Glu
                        210                 215                 220
        Leu Ala Phe Asp Tyr Trp Gly Gln Gly Thr Leu Val Thr Val Ser Ser
        225                 230                 235                 240
        Gly Gly Gly Gly Ser Gly Ser Gly Ser Ser Arg Ser Ser Gly
                        245                 250                 255
        Gly Glu Ile Val Leu Thr Gln Ser Pro Gly Thr Leu Ser Leu Ser Pro
                        260                 265                 270
        Gly Glu Arg Ala Thr Leu Ser Cys Arg Ala Ser Gln Arg Val Ser Ser
                        275                 280                 285
        Ser Tyr Leu Ala Trp Tyr Gln Gln Lys Pro Gly Gln Ala Pro Arg Leu
                        290                 295                 300
        Leu Ile Tyr Asp Ala Ser Ser Arg Ala Thr Gly Ile Pro Asp Arg Phe
        305                 310                 315                 320
        Ser Gly Ser Gly Ser Gly Thr Asp Phe Thr Leu Thr Ile Ser Arg Leu
                        325                 330                 335
        Glu Pro Glu Asp Phe Ala Val Tyr Tyr Cys Gln Gln Tyr Gly Ser Leu
                        340                 345                 350
        Pro Trp Thr Phe Gly Gln Gly Thr Lys Val Glu Ile Lys Gly Ser Gly
                        355                 360                 365
        Gly Gly Glu Val Gln Leu Val Glu Ser Gly Gly Gly Leu Val Gln Pro
                        370                 375                 380
        Gly Gly Ser Leu Arg Leu Ser Cys Ala Val Ser Gly Tyr Thr Phe Ser
        385                 390                 395                 400
        Met Asn Trp Val Arg Gln Ala Pro Gly Lys Gly Leu Glu Trp Val Ala
                        405                 410                 415
        Trp Ile Asn Met Tyr Thr Gly Glu Pro Thr Tyr Ala Asp Asp Phe Lys
                        420                 425                 430
        Gly Arg Phe Thr Ile Ser Arg Asp Asp Ser Lys Asn Thr Leu Tyr Leu
                        435                 440                 445
        Gln Met Asn Ser Leu Arg Ala Glu Asp Thr Ala Val Tyr Tyr Cys Ala
                        450                 455                 460
        Arg Leu Tyr Asn Gly Asn Ser Leu Asp Tyr Trp Gly Gln Gly Thr Leu
        465                 470                 475                 480
        Val Thr Val Ser Ser Gly Gly Gly Ser Glu Pro Lys Ser Ser Asp
                        485                 490                 495
        Lys Thr His Thr Cys Pro Pro Cys Pro Ala Pro Glu Leu Leu Gly Gly
                        500                 505                 510
        Pro Ser Val Phe Leu Phe Pro Pro Lys Pro Lys Asp Thr Leu Met Ile
                        515                 520                 525
        Ser Arg Thr Pro Glu Val Thr Cys Val Val Val Asp Val Ser His Glu
                        530                 535                 540
        Asp Pro Glu Val Lys Phe Asn Trp Tyr Val Asp Gly Val Glu Val His
        545                 550                 555                 560
        Asn Ala Lys Thr Lys Pro Arg Glu Glu Gln Tyr Asn Ser Thr Tyr Arg
                        565                 570                 575
```

Val Val Ser Val Leu Thr Val Leu His Gln Asp Trp Leu Asn Gly Lys
            580                 585                 590

Glu Tyr Lys Cys Lys Val Ser Asn Lys Ala Leu Pro Ala Pro Ile Glu
        595                 600                 605

Lys Thr Ile Ser Lys Ala Lys Gly Gln Pro Arg Glu Pro Gln Val Tyr
    610                 615                 620

Thr Leu Pro Pro Ser Arg Glu Glu Met Thr Lys Asn Gln Val Ser Leu
625                 630                 635                 640

Thr Cys Leu Val Lys Gly Phe Tyr Pro Ser Asp Ile Ala Val Glu Trp
                645                 650                 655

Glu Ser Asn Gly Gln Pro Glu Asn Asn Tyr Lys Thr Thr Pro Pro Val
            660                 665                 670

Leu Asp Ser Asp Gly Ser Phe Phe Leu Tyr Ser Lys Leu Thr Val Asp
        675                 680                 685

Lys Ser Arg Trp Gln Gln Gly Asn Val Phe Ser Cys Ser Val Met His
    690                 695                 700

Glu Ala Leu His Asn His Tyr Thr Gln Lys Ser Leu Ser Leu Ser Pro
705                 710                 715                 720

Gly Lys

<210> SEQ ID NO 199
<211> LENGTH: 719
<212> TYPE: PRT
<213> ORGANISM: Artificial Sequence
<220> FEATURE:
<223> OTHER INFORMATION: Synthetic

<400> SEQUENCE: 199

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Trp Lys Ser Tyr Leu Thr Trp Tyr Gln Gln Lys Pro Gly Lys
        35                  40                  45

Ala Pro Lys Leu Leu Ile Tyr Trp Ala Ser Thr Leu Val Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Thr Phe Ser Arg Tyr Trp Met Ser Trp Val Arg Gln Ala Pro Gly
145                 150                 155                 160

Lys Gly Leu Glu Trp Val Ala Asn Ile Lys Gln Asp Gly Ser Glu Lys
                165                 170                 175

Tyr Tyr Val Asp Ser Val Lys Gly Arg Phe Thr Ile Ser Arg Asp Asn
            180                 185                 190

Ala Lys Asn Ser Leu Tyr Leu Gln Met Asn Ser Leu Arg Ala Glu Asp
        195                 200                 205

```
Thr Ala Val Tyr Tyr Cys Ala Arg Glu Gly Gly Trp Phe Gly Glu Leu
    210                 215                 220

Ala Phe Asp Tyr Trp Gly Gln Gly Thr Leu Val Thr Val Ser Ser Gly
225                 230                 235                 240

Gly Gly Gly Ser Gly Gly Gly Ser Gly Gly Gly Ser Glu Ile
            245                 250                 255

Val Leu Thr Gln Ser Pro Gly Thr Leu Ser Leu Ser Pro Gly Glu Arg
            260                 265                 270

Ala Thr Leu Ser Cys Arg Ala Ser Gln Arg Val Ser Ser Ser Tyr Leu
            275                 280                 285

Ala Trp Tyr Gln Gln Lys Pro Gly Gln Ala Pro Arg Leu Leu Ile Tyr
290                 295                 300

Asp Ala Ser Ser Arg Ala Thr Gly Ile Pro Asp Arg Phe Ser Gly Ser
305                 310                 315                 320

Gly Ser Gly Thr Asp Phe Thr Leu Thr Ile Ser Arg Leu Glu Pro Glu
            325                 330                 335

Asp Phe Ala Val Tyr Tyr Cys Gln Gln Tyr Gly Ser Leu Pro Trp Thr
            340                 345                 350

Phe Gly Gln Gly Thr Lys Val Glu Ile Lys Ser Gly Gly Gly Gly Glu
            355                 360                 365

Val Gln Leu Val Glu Ser Gly Gly Gly Leu Val Gln Pro Gly Gly Ser
    370                 375                 380

Leu Arg Leu Ser Cys Ala Val Ser Gly Tyr Thr Phe Ser Met Asn Trp
385                 390                 395                 400

Val Arg Gln Ala Pro Gly Lys Gly Leu Glu Trp Val Ala Trp Ile Asn
                405                 410                 415

Met Tyr Thr Gly Glu Lys Thr Tyr Ala Asp Asp Phe Lys Gly Arg Phe
            420                 425                 430

Thr Ile Ser Arg Asp Asp Ser Lys Asn Thr Leu Tyr Leu Gln Met Asn
            435                 440                 445

Ser Leu Arg Ala Glu Asp Thr Ala Val Tyr Tyr Cys Ala Arg Leu Tyr
    450                 455                 460

Asn Gly Asn Ser Leu Asp Tyr Trp Gly Gln Gly Thr Leu Val Thr Val
465                 470                 475                 480

Ser Ser Gly Gly Gly Gly Ser Glu Pro Lys Ser Ser Asp Lys Thr His
            485                 490                 495

Thr Cys Pro Pro Cys Pro Ala Pro Glu Leu Leu Gly Gly Pro Ser Val
            500                 505                 510

Phe Leu Phe Pro Pro Lys Pro Lys Asp Thr Leu Met Ile Ser Arg Thr
            515                 520                 525

Pro Glu Val Thr Cys Val Val Val Asp Val Ser His Glu Asp Pro Glu
    530                 535                 540

Val Lys Phe Asn Trp Tyr Val Asp Gly Val Glu Val His Asn Ala Lys
545                 550                 555                 560

Thr Lys Pro Arg Glu Glu Gln Tyr Asn Ser Thr Tyr Arg Val Val Ser
                565                 570                 575

Val Leu Thr Val Leu His Gln Asp Trp Leu Asn Gly Lys Glu Tyr Lys
            580                 585                 590

Cys Lys Val Ser Asn Lys Ala Leu Pro Ala Pro Ile Glu Lys Thr Ile
            595                 600                 605

Ser Lys Ala Lys Gly Gln Pro Arg Glu Pro Gln Val Tyr Thr Leu Pro
    610                 615                 620

Pro Ser Arg Glu Glu Met Thr Lys Asn Gln Val Ser Leu Thr Cys Leu
```

```
                625                 630                 635                 640
        Val Lys Gly Phe Tyr Pro Ser Asp Ile Ala Val Glu Trp Glu Ser Asn
                        645                 650                 655

Gly Gln Pro Glu Asn Asn Tyr Lys Thr Thr Pro Pro Val Leu Asp Ser
                660                 665                 670

Asp Gly Ser Phe Phe Leu Tyr Ser Lys Leu Thr Val Asp Lys Ser Arg
                        675                 680                 685

Trp Gln Gln Gly Asn Val Phe Ser Cys Ser Val Met His Glu Ala Leu
                690                 695                 700

His Asn His Tyr Thr Gln Lys Ser Leu Ser Leu Ser Pro Gly Lys
        705                 710                 715

<210> SEQ ID NO 200
        <211> LENGTH: 719
        <212> TYPE: PRT
        <213> ORGANISM: Artificial Sequence
        <220> FEATURE:
        <223> OTHER INFORMATION: Synthetic

<400> SEQUENCE: 200

Asp Ile Gln Met Thr Gln Ser Pro Ser Ser Leu Ser Ala Ser Val Gly
        1               5                   10                  15

Asp Arg Val Thr Ile Thr Cys Lys Ser Ser Gln Ser Leu Leu Asn Ser
                        20                  25                  30

Gly Asn Ile Lys Ser Tyr Leu Thr Trp Tyr Gln Gln Lys Pro Gly Lys
                    35                  40                  45

Ala Pro Lys Leu Leu Ile Tyr Trp Ala Ser Thr Leu Arg Ser Gly Val
            50                  55                  60

Pro Ser Arg Phe Ser Gly Ser Gly Ser Gly Thr Asp Tyr Thr Leu Thr
        65                  70                  75                  80

Ile Ser Ser Leu Gln Pro Glu Asp Phe Ala Thr Tyr Tyr Cys Gln Asn
                        85                  90                  95

Ala Tyr Ser Phe Pro Phe Thr Phe Gly Gln Gly Thr Lys Val Glu Ile
                    100                 105                 110

Lys Ser Gly Gly Gly Gly Glu Val Gln Leu Val Glu Ser Gly Gly Gly
            115                 120                 125

Leu Val Gln Pro Gly Gly Ser Leu Arg Leu Ser Cys Ala Ala Ser Gly
        130                 135                 140

Phe Thr Phe Ser Arg Tyr Trp Met Ser Trp Val Arg Gln Ala Pro Gly
        145                 150                 155                 160

Lys Gly Leu Glu Trp Val Ala Asn Ile Lys Gln Asp Gly Ser Glu Lys
                        165                 170                 175

Tyr Tyr Val Asp Ser Val Lys Gly Arg Phe Thr Ile Ser Arg Asp Asn
                    180                 185                 190

Ala Lys Asn Ser Leu Tyr Leu Gln Met Asn Ser Leu Arg Ala Glu Asp
            195                 200                 205

Thr Ala Val Tyr Tyr Cys Ala Arg Glu Gly Gly Trp Phe Gly Glu Leu
        210                 215                 220

Ala Phe Asp Tyr Trp Gly Gln Gly Thr Leu Val Thr Val Ser Ser Gly
        225                 230                 235                 240

Gly Gly Gly Ser Gly Gly Gly Ser Gly Gly Gly Ser Glu Ile
                        245                 250                 255

Val Leu Thr Gln Ser Pro Gly Thr Leu Ser Leu Ser Pro Gly Glu Arg
                    260                 265                 270

Ala Thr Leu Ser Cys Arg Ala Ser Gln Arg Val Ser Ser Ser Tyr Leu
```

-continued

```
            275                 280                 285
Ala Trp Tyr Gln Gln Lys Pro Gly Gln Ala Pro Arg Leu Leu Ile Tyr
290                 295                 300
Asp Ala Ser Ser Arg Ala Thr Gly Ile Pro Asp Arg Phe Ser Gly Ser
305                 310                 315                 320
Gly Ser Gly Thr Asp Phe Thr Leu Thr Ile Ser Arg Leu Glu Pro Glu
                325                 330                 335
Asp Phe Ala Val Tyr Tyr Cys Gln Gln Tyr Gly Ser Leu Pro Trp Thr
                340                 345                 350
Phe Gly Gln Gly Thr Lys Val Glu Ile Lys Ser Gly Gly Gly Gly Glu
                355                 360                 365
Val Gln Leu Val Glu Ser Gly Gly Leu Val Gln Pro Gly Gly Ser
370                 375                 380
Leu Arg Leu Ser Cys Ala Val Ser Gly Tyr Thr Phe Ser Met Asn Trp
385                 390                 395                 400
Val Arg Gln Ala Pro Gly Lys Gly Leu Glu Trp Val Ala Trp Ile Asn
                405                 410                 415
Met Tyr Thr Gly Glu Arg Thr Tyr Ala Asp Asp Phe Lys Gly Arg Phe
                420                 425                 430
Thr Ile Ser Arg Asp Asp Ser Lys Asn Thr Leu Tyr Leu Gln Met Asn
                435                 440                 445
Ser Leu Arg Ala Glu Asp Thr Ala Val Tyr Tyr Cys Ala Arg Leu Tyr
450                 455                 460
Asn Gly Asn Ser Leu Asp Tyr Trp Gly Gln Gly Thr Leu Val Thr Val
465                 470                 475                 480
Ser Ser Gly Gly Gly Gly Ser Glu Pro Lys Ser Ser Asp Lys Thr His
                485                 490                 495
Thr Cys Pro Pro Cys Pro Ala Pro Glu Leu Leu Gly Gly Pro Ser Val
                500                 505                 510
Phe Leu Phe Pro Pro Lys Pro Lys Asp Thr Leu Met Ile Ser Arg Thr
                515                 520                 525
Pro Glu Val Thr Cys Val Val Val Asp Val Ser His Glu Asp Pro Glu
                530                 535                 540
Val Lys Phe Asn Trp Tyr Val Asp Gly Val Glu Val His Asn Ala Lys
545                 550                 555                 560
Thr Lys Pro Arg Glu Glu Gln Tyr Asn Ser Thr Tyr Arg Val Val Ser
                565                 570                 575
Val Leu Thr Val Leu His Gln Asp Trp Leu Asn Gly Lys Glu Tyr Lys
                580                 585                 590
Cys Lys Val Ser Asn Lys Ala Leu Pro Ala Pro Ile Glu Lys Thr Ile
                595                 600                 605
Ser Lys Ala Lys Gly Gln Pro Arg Glu Pro Gln Val Tyr Thr Leu Pro
                610                 615                 620
Pro Ser Arg Glu Glu Met Thr Lys Asn Gln Val Ser Leu Thr Cys Leu
625                 630                 635                 640
Val Lys Gly Phe Tyr Pro Ser Asp Ile Ala Val Glu Trp Glu Ser Asn
                645                 650                 655
Gly Gln Pro Glu Asn Asn Tyr Lys Thr Thr Pro Pro Val Leu Asp Ser
                660                 665                 670
Asp Gly Ser Phe Phe Leu Tyr Ser Lys Leu Thr Val Asp Lys Ser Arg
                675                 680                 685
Trp Gln Gln Gly Asn Val Phe Ser Cys Ser Val Met His Glu Ala Leu
                690                 695                 700
```

His Asn His Tyr Thr Gln Lys Ser Leu Ser Leu Ser Pro Gly Lys
705                 710                 715

<210> SEQ ID NO 201
<211> LENGTH: 719
<212> TYPE: PRT
<213> ORGANISM: Artificial Sequence
<220> FEATURE:
<223> OTHER INFORMATION: Synthetic

<400> SEQUENCE: 201

Asp Ile Gln Met Thr Gln Ser Pro Ser Leu Ser Ala Ser Val Gly
1               5                   10                  15

Asp Arg Val Thr Ile Thr Cys Lys Ser Ser Gln Ser Leu Leu Asn Trp
            20                  25                  30

Gly Asn Gln Lys Ser Tyr Leu Thr Trp Tyr Gln Lys Pro Gly Lys
        35                  40                  45

Ala Pro Lys Leu Leu Ile Tyr Trp Ala Ser Thr Leu Phe Ser Gly Val
    50                  55                  60

Pro Ser Arg Phe Ser Gly Ser Gly Ser Gly Thr Asp Tyr Thr Leu Thr
65              70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Thr Phe Ser Arg Tyr Trp Met Ser Trp Val Arg Gln Ala Pro Gly
145                 150                 155                 160

Lys Gly Leu Glu Trp Val Ala Asn Ile Lys Gln Asp Gly Ser Glu Lys
                165                 170                 175

Tyr Tyr Val Asp Ser Val Lys Gly Arg Phe Thr Ile Ser Arg Asp Asn
            180                 185                 190

Ala Lys Asn Ser Leu Tyr Leu Gln Met Asn Ser Leu Arg Ala Glu Asp
        195                 200                 205

Thr Ala Val Tyr Tyr Cys Ala Arg Glu Gly Gly Trp Phe Gly Glu Leu
    210                 215                 220

Ala Phe Asp Tyr Trp Gly Gln Gly Thr Leu Val Thr Val Ser Ser Gly
225                 230                 235                 240

Gly Gly Gly Ser Gly Gly Gly Gly Ser Gly Gly Gly Gly Ser Glu Ile
                245                 250                 255

Val Leu Thr Gln Ser Pro Gly Thr Leu Ser Leu Ser Pro Gly Glu Arg
            260                 265                 270

Ala Thr Leu Ser Cys Arg Ala Ser Gln Arg Val Ser Ser Ser Tyr Leu
        275                 280                 285

Ala Trp Tyr Gln Gln Lys Pro Gly Gln Ala Pro Arg Leu Leu Ile Tyr
    290                 295                 300

Asp Ala Ser Ser Arg Ala Thr Gly Ile Pro Asp Arg Phe Ser Gly Ser
305                 310                 315                 320

Gly Ser Gly Thr Asp Phe Thr Leu Thr Ile Ser Arg Leu Glu Pro Glu
                325                 330                 335

Asp Phe Ala Val Tyr Tyr Cys Gln Gln Tyr Gly Ser Leu Pro Trp Thr
            340                 345                 350

```
Phe Gly Gln Gly Thr Lys Val Glu Ile Lys Ser Gly Gly Gly Glu
            355                 360                 365

Val Gln Leu Val Glu Ser Gly Gly Leu Val Gln Pro Gly Gly Ser
        370                 375                 380

Leu Arg Leu Ser Cys Ala Val Ser Gly Tyr Thr Phe Ser Met Asn Trp
385                 390                 395                 400

Val Arg Gln Ala Pro Gly Lys Gly Leu Glu Trp Val Ala Trp Ile Asn
                405                 410                 415

Met Tyr Thr Gly Glu Pro Ile Tyr Ala Asp Asp Phe Lys Gly Arg Phe
            420                 425                 430

Thr Ile Ser Arg Asp Asp Ser Lys Asn Thr Leu Tyr Leu Gln Met Asn
        435                 440                 445

Ser Leu Arg Ala Glu Asp Thr Ala Val Tyr Tyr Cys Ala Arg Leu Tyr
450                 455                 460

Asn Gly Asn Ser Leu Asp Tyr Trp Gly Gln Gly Thr Leu Val Thr Val
465                 470                 475                 480

Ser Ser Gly Gly Gly Gly Ser Glu Pro Lys Ser Ser Asp Lys Thr His
                485                 490                 495

Thr Cys Pro Pro Cys Pro Ala Pro Glu Leu Leu Gly Gly Pro Ser Val
            500                 505                 510

Phe Leu Phe Pro Pro Lys Pro Lys Asp Thr Leu Met Ile Ser Arg Thr
        515                 520                 525

Pro Glu Val Thr Cys Val Val Val Asp Val Ser His Glu Asp Pro Glu
530                 535                 540

Val Lys Phe Asn Trp Tyr Val Asp Gly Val Glu Val His Asn Ala Lys
545                 550                 555                 560

Thr Lys Pro Arg Glu Glu Gln Tyr Asn Ser Thr Tyr Arg Val Val Ser
                565                 570                 575

Val Leu Thr Val Leu His Gln Asp Trp Leu Asn Gly Lys Glu Tyr Lys
            580                 585                 590

Cys Lys Val Ser Asn Lys Ala Leu Pro Ala Pro Ile Glu Lys Thr Ile
        595                 600                 605

Ser Lys Ala Lys Gly Gln Pro Arg Glu Pro Gln Val Tyr Thr Leu Pro
610                 615                 620

Pro Ser Arg Glu Glu Met Thr Lys Asn Gln Val Ser Leu Thr Cys Leu
625                 630                 635                 640

Val Lys Gly Phe Tyr Pro Ser Asp Ile Ala Val Glu Trp Glu Ser Asn
                645                 650                 655

Gly Gln Pro Glu Asn Asn Tyr Lys Thr Thr Pro Pro Val Leu Asp Ser
            660                 665                 670

Asp Gly Ser Phe Phe Leu Tyr Ser Lys Leu Thr Val Asp Lys Ser Arg
        675                 680                 685

Trp Gln Gln Gly Asn Val Phe Ser Cys Ser Val Met His Glu Ala Leu
690                 695                 700

His Asn His Tyr Thr Gln Lys Ser Leu Ser Leu Ser Pro Gly Lys
705                 710                 715
```

<210> SEQ ID NO 202
<211> LENGTH: 476
<212> TYPE: PRT
<213> ORGANISM: Artificial Sequence
<220> FEATURE:
<223> OTHER INFORMATION: Synthetic

<400> SEQUENCE: 202

```
Asp Ile Gln Met Thr Gln Ser Pro Ser Ser Leu Ser Ala Ser Val Gly
 1               5                  10                  15

Asp Arg Val Thr Ile Thr Cys Lys Ser Gln Ser Leu Leu Asn Ser
             20                  25                  30

Gly Asn Gln Lys Ser Tyr Leu Thr Trp Tyr Gln Lys Pro Gly Lys
         35                  40                  45

Ala Pro Lys Leu Leu Ile Tyr Trp Ala Ser Thr Leu Glu Ser Gly Val
 50                  55                  60

Pro Ser Arg Phe Ser Gly Ser Gly Ser Gly Thr Asp Tyr Thr Leu Thr
 65                  70                  75                  80

Ile Ser Ser Leu Gln Pro Glu Asp Phe Ala Thr Tyr Tyr Cys Gln Asn
             85                  90                  95

Ala Tyr Phe Phe Pro Phe Thr Phe Gly Gln Gly Thr Lys Val Glu Ile
                100                 105                 110

Lys Ser Gly Gly Gly Gly Glu Val Gln Leu Val Glu Ser Gly Gly Gly
             115                 120                 125

Leu Val Gln Pro Gly Gly Ser Leu Arg Leu Ser Cys Ala Ala Ser Gly
         130                 135                 140

Phe Thr Phe Ser Arg Tyr Trp Met Ser Trp Val Arg Gln Ala Pro Gly
145                 150                 155                 160

Lys Gly Leu Glu Trp Val Ala Asn Ile Lys Gln Asp Gly Ser Glu Lys
                165                 170                 175

Tyr Tyr Val Asp Ser Val Lys Gly Arg Phe Thr Ile Ser Arg Asp Asn
             180                 185                 190

Ala Lys Asn Ser Leu Tyr Leu Gln Met Asn Ser Leu Arg Ala Glu Asp
         195                 200                 205

Thr Ala Val Tyr Tyr Cys Ala Arg Glu Gly Gly Trp Phe Gly Glu Leu
 210                 215                 220

Ala Phe Asp Tyr Trp Gly Gln Gly Thr Leu Val Thr Val Ser Ser Gly
225                 230                 235                 240

Gly Gly Gly Ser Glu Pro Lys Ser Ser Asp Lys Thr His Thr Cys Pro
                245                 250                 255

Pro Cys Pro Ala Pro Glu Leu Leu Gly Gly Pro Ser Val Phe Leu Phe
             260                 265                 270

Pro Pro Lys Pro Lys Asp Thr Leu Met Ile Ser Arg Thr Pro Glu Val
         275                 280                 285

Thr Cys Val Val Val Asp Val Ser His Glu Asp Pro Glu Val Lys Phe
 290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
             340                 345                 350

Ser Asn Lys Ala Leu Pro Ala Pro Ile Glu Lys Thr Ile Ser Lys Ala
         355                 360                 365

Lys Gly Gln Pro Arg Glu Pro Gln Val Tyr Thr Leu Pro Pro Cys Arg
 370                 375                 380

Glu Glu Met Thr Lys Asn Gln Val Ser Leu Trp Cys Leu Val Lys Gly
385                 390                 395                 400

Phe Tyr Pro Ser Asp Ile Ala Val Glu Trp Glu Ser Asn Gly Gln Pro
                405                 410                 415
```

```
Glu Asn Asn Tyr Lys Thr Thr Pro Pro Val Leu Asp Ser Asp Gly Ser
                420                 425                 430

Phe Phe Leu Tyr Ser Lys Leu Thr Val Asp Lys Ser Arg Trp Gln Gln
            435                 440                 445

Gly Asn Val Phe Ser Cys Ser Val Met His Glu Ala Leu His Asn His
        450                 455                 460

Tyr Thr Gln Lys Ser Leu Ser Leu Ser Pro Gly Lys
465                 470                 475

<210> SEQ ID NO 203
<211> LENGTH: 466
<212> TYPE: PRT
<213> ORGANISM: Artificial Sequence
<220> FEATURE:
<223> OTHER INFORMATION: Synthetic

<400> SEQUENCE: 203

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys Arg Ser Gly Gly
            100                 105                 110

Gly Gly Glu Val Gln Leu Val Glu Ser Gly Gly Gly Leu Val Gln Pro
        115                 120                 125

Gly Gly Ser Leu Arg Leu Ser Cys Ala Val Ser Gly Tyr Thr Phe Ser
130                 135                 140

Met Asn Trp Val Arg Gln Ala Pro Gly Lys Gly Leu Glu Trp Val Ala
145                 150                 155                 160

Trp Ile Asn Met Tyr Thr Gly Glu Pro Thr Tyr Ala Asp Asp Phe Lys
                165                 170                 175

Gly Arg Phe Thr Ile Ser Arg Asp Asp Ser Lys Asn Thr Leu Tyr Leu
            180                 185                 190

Gln Met Asn Ser Leu Arg Ala Glu Asp Thr Ala Val Tyr Tyr Cys Ala
        195                 200                 205

Arg Leu Tyr Asn Gly Asn Ser Leu Asp Tyr Trp Gly Gln Gly Thr Leu
210                 215                 220

Val Thr Val Ser Ser Gly Gly Gly Ser Glu Pro Lys Ser Ser Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300
```

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Cys
        355                 360                 365

Thr Leu Pro Pro Ser Arg Glu Glu Met Thr Lys Asn Gln Val Ser Leu
    370                 375                 380

Ser Cys Ala Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Val Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn Arg Phe Thr Gln Lys Ser Leu Ser Leu Ser Pro
    450                 455                 460

Gly Lys
465

<210> SEQ ID NO 204
<211> LENGTH: 476
<212> TYPE: PRT
<213> ORGANISM: Artificial Sequence
<220> FEATURE:
<223> OTHER INFORMATION: Synthetic

<400> SEQUENCE: 204

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
                20                  25                  30

Gly Asn Gln Lys Ser Tyr Leu Thr Trp Tyr Gln Asp Lys Pro Gly Lys
            35                  40                  45

Ala Pro Lys Leu Leu Ile Tyr Trp Ala Ser Thr Leu Glu Ser Gly Val
        50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Thr Phe Ser Arg Tyr Trp Met Ser Trp Val Arg Asp Ala Pro Gly
145                 150                 155                 160

Lys Gly Leu Glu Trp Val Ala Asn Ile Lys Gln Asp Gly Ser Glu Lys
                165                 170                 175

Tyr Tyr Val Asp Ser Val Lys Gly Arg Phe Thr Ile Ser Arg Asp Asn
            180                 185                 190

```
Ala Lys Asn Ser Leu Tyr Leu Gln Met Asn Ser Leu Arg Ala Glu Asp
            195                 200                 205

Thr Ala Val Tyr Tyr Cys Ala Arg Glu Gly Gly Trp Phe Gly Glu Leu
            210                 215                 220

Ala Phe Asp Tyr Trp Gly Gln Gly Thr Leu Val Thr Val Ser Ser Gly
225                 230                 235                 240

Gly Gly Gly Ser Glu Pro Lys Ser Ser Asp Lys Thr His Thr Cys Pro
            245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
            275                 280                 285

Thr Cys Val Val Val Asp Val Ser His Glu Asp Pro Glu Val Lys Phe
            290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
            325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
            355                 360                 365

Lys Gly Gln Pro Arg Glu Pro Gln Val Tyr Thr Leu Pro Pro Cys Arg
            370                 375                 380

Glu Glu Met Thr Lys Asn Gln Val Ser Leu Trp Cys Leu Val Lys Gly
385                 390                 395                 400

Phe Tyr Pro Ser Asp Ile Ala Val Glu Trp Glu Ser Asn Gly Gln Pro
            405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
            435                 440                 445

Gly Asn Val Phe Ser Cys Ser Val Met His Glu Ala Leu His Asn His
            450                 455                 460

Tyr Thr Gln Lys Ser Leu Ser Leu Ser Pro Gly Lys
465                 470                 475

<210> SEQ ID NO 205
<211> LENGTH: 466
<212> TYPE: PRT
<213> ORGANISM: Artificial Sequence
<220> FEATURE:
<223> OTHER INFORMATION: Synthetic

<400> SEQUENCE: 205

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Arg Lys Pro Gly Gln Ala Pro Arg Leu Leu
            35                  40                  45

Ile Tyr Asp Ala Ser Ser Arg Ala Thr Gly Ile Pro Asp Arg Phe Ser
            50                  55                  60

Gly Ser Gly Ser Gly Thr Asp Phe Thr Leu Thr Ile Ser Arg Leu Glu
65                  70                  75                  80
```

```
Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys Arg Ser Gly Gly
            100                 105                 110

Gly Gly Glu Val Gln Leu Val Glu Ser Gly Gly Gly Leu Val Gln Pro
        115                 120                 125

Gly Gly Ser Leu Arg Leu Ser Cys Ala Val Ser Gly Tyr Thr Phe Ser
130                 135                 140

Met Asn Trp Val Arg Arg Ala Pro Gly Lys Gly Leu Glu Trp Val Ala
145                 150                 155                 160

Trp Ile Asn Met Tyr Thr Gly Glu Pro Thr Tyr Ala Asp Asp Phe Lys
                165                 170                 175

Gly Arg Phe Thr Ile Ser Arg Asp Asp Ser Lys Asn Thr Leu Tyr Leu
            180                 185                 190

Gln Met Asn Ser Leu Arg Ala Glu Asp Thr Ala Val Tyr Tyr Cys Ala
        195                 200                 205

Arg Leu Tyr Asn Gly Asn Ser Leu Asp Tyr Trp Gly Gln Gly Thr Leu
210                 215                 220

Val Thr Val Ser Ser Gly Gly Gly Ser Glu Pro Lys Ser Ser Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Cys
        355                 360                 365

Thr Leu Pro Pro Ser Arg Glu Glu Met Thr Lys Asn Gln Val Ser Leu
370                 375                 380

Ser Cys Ala Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Val Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn Arg Phe Thr Gln Lys Ser Leu Ser Leu Ser Pro
450                 455                 460

Gly Lys
465

<210> SEQ ID NO 206
<211> LENGTH: 476
<212> TYPE: PRT
```

<213> ORGANISM: Artificial Sequence
<220> FEATURE:
<223> OTHER INFORMATION: Synthetic

<400> SEQUENCE: 206

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Asp Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Thr Phe Ser Arg Tyr Trp Met Ser Trp Val Arg Asp Ala Pro Gly
145                 150                 155                 160

Lys Gly Leu Glu Trp Val Ala Asn Ile Lys Gln Asp Gly Ser Glu Lys
                165                 170                 175

Tyr Tyr Val Asp Ser Val Lys Gly Arg Phe Thr Ile Ser Arg Asp Asn
            180                 185                 190

Ala Lys Asn Ser Leu Tyr Leu Gln Met Asn Ser Leu Arg Ala Glu Asp
        195                 200                 205

Thr Ala Val Tyr Tyr Cys Ala Arg Glu Gly Gly Trp Phe Gly Glu Leu
    210                 215                 220

Ala Phe Asp Tyr Trp Gly Gln Gly Thr Leu Val Thr Val Ser Ser Gly
225                 230                 235                 240

Gly Gly Gly Ser Glu Pro Lys Ser Ser Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Cys Arg
    370                 375                 380

Glu Glu Met Thr Lys Asn Gln Val Ser Leu Trp Cys Leu Val Lys Gly
```

```
385                 390                 395                 400
Phe Tyr Pro Ser Asp Ile Ala Val Glu Trp Glu Ser Asn Gly Gln Pro
            405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
            435                 440                 445

Gly Asn Val Phe Ser Cys Ser Val Met His Glu Ala Leu His Asn His
450                 455                 460

Tyr Thr Gln Lys Ser Leu Ser Leu Ser Pro Gly Lys
465                 470                 475

<210> SEQ ID NO 207
<211> LENGTH: 466
<212> TYPE: PRT
<213> ORGANISM: Artificial Sequence
<220> FEATURE:
<223> OTHER INFORMATION: Synthetic

<400> SEQUENCE: 207

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Lys Lys Pro Gly Gln Ala Pro Arg Leu Leu
        35                  40                  45

Ile Tyr Asp Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys Arg Ser Gly Gly
            100                 105                 110

Gly Gly Glu Val Gln Leu Val Glu Ser Gly Gly Gly Leu Val Gln Pro
        115                 120                 125

Gly Gly Ser Leu Arg Leu Ser Cys Ala Val Ser Gly Tyr Thr Phe Ser
130                 135                 140

Met Asn Trp Val Arg Lys Ala Pro Gly Lys Gly Leu Glu Trp Val Ala
145                 150                 155                 160

Trp Ile Asn Met Tyr Thr Gly Glu Pro Thr Tyr Ala Asp Asp Phe Lys
                165                 170                 175

Gly Arg Phe Thr Ile Ser Arg Asp Asp Ser Lys Asn Thr Leu Tyr Leu
            180                 185                 190

Gln Met Asn Ser Leu Arg Ala Glu Asp Thr Ala Val Tyr Tyr Cys Ala
        195                 200                 205

Arg Leu Tyr Asn Gly Asn Ser Leu Asp Tyr Trp Gly Gln Gly Thr Leu
    210                 215                 220

Val Thr Val Ser Ser Gly Gly Gly Gly Ser Glu Pro Lys Ser Ser Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
```

```
                275                 280                 285
Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Cys
        355                 360                 365

Thr Leu Pro Pro Ser Arg Glu Glu Met Thr Lys Asn Gln Val Ser Leu
    370                 375                 380

Ser Cys Ala Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Val Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn Arg Phe Thr Gln Lys Ser Leu Ser Leu Ser Pro
    450                 455                 460

Gly Lys
465

<210> SEQ ID NO 208
<211> LENGTH: 232
<212> TYPE: PRT
<213> ORGANISM: Artificial Sequence
<220> FEATURE:
<223> OTHER INFORMATION: Synthetic

<400> SEQUENCE: 208

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Cys Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
```

```
              165                 170                 175
Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 209
<211> LENGTH: 232
<212> TYPE: PRT
<213> ORGANISM: Artificial Sequence
<220> FEATURE:
<223> OTHER INFORMATION: Synthetic

<400> SEQUENCE: 209

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Cys Thr Leu Pro Pro Ser Arg Glu Glu Met Thr
    130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn Arg Phe Thr Gln Lys
            210                 215                 220

Ser Leu Ser Leu Ser Pro Gly Lys
225                 230

<210> SEQ ID NO 210
<211> LENGTH: 42
<212> TYPE: PRT
<213> ORGANISM: Artificial Sequence
<220> FEATURE:
<223> OTHER INFORMATION: Synthetic

<400> SEQUENCE: 210
```

```
Asp Gln Trp Ser Thr Gln Asp Leu Tyr Asn Asn Pro Val Thr Ala Val
1               5                   10                  15

Phe Asn Tyr Gln Gly Leu Trp Arg Ser Cys Val Arg Glu Ser Ser Gly
            20                  25                  30

Phe Thr Glu Cys Arg Gly Tyr Phe Thr Leu
        35                  40
```

<210> SEQ ID NO 211
<211> LENGTH: 261
<212> TYPE: PRT
<213> ORGANISM: Artificial Sequence
<220> FEATURE:
<223> OTHER INFORMATION: Synthetic

<400> SEQUENCE: 211

```
Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
            35                  40                  45

Leu Trp Arg Ser Cys Val Arg Glu Ser Ser Gly Phe Thr Glu Cys Arg
50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
            85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
            115                 120                 125

Gly Leu Cys Ala Ile Ala Gly Val Ser Val Phe Ala Asn Met Leu Val
            130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
            165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
            195                 200                 205

Val Ser Tyr His Ala Ser Gly His Ser Val Ala Tyr Lys Pro Gly Gly
            210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
            245                 250                 255

Lys His Asp Tyr Val
            260
```

<210> SEQ ID NO 212
<211> LENGTH: 200
<212> TYPE: PRT
<213> ORGANISM: Artificial Sequence
<220> FEATURE:
<223> OTHER INFORMATION: Synthetic

<400> SEQUENCE: 212

```
Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
                35                  40                  45

Leu Trp Arg Ser Cys Val Arg Glu Ser Ser Gly Phe Thr Glu Cys Arg
50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
                100                 105                 110

Ala Lys Ala Asn Met Thr Leu Thr Ser Gly Ile Met Phe Ile Val Ser
            115                 120                 125

Gly Leu Cys Ala Ile Ala Gly Val Ser Val Phe Ala Asn Met Leu Val
        130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala
        195                 200

<210> SEQ ID NO 213
<211> LENGTH: 42
<212> TYPE: PRT
<213> ORGANISM: Artificial Sequence
<220> FEATURE:
<223> OTHER INFORMATION: Synthetic

<400> SEQUENCE: 213

Asp Met Trp Ser Thr Gln Asp Leu Tyr Asp Asn Pro Val Thr Ser Val
1               5                   10                  15

Phe Gln Tyr Glu Gly Leu Trp Arg Ser Cys Val Arg Gln Ser Ser Gly
            20                  25                  30

Phe Thr Glu Cys Arg Pro Tyr Phe Thr Ile
            35                  40

<210> SEQ ID NO 214
<211> LENGTH: 261
<212> TYPE: PRT
<213> ORGANISM: Artificial Sequence
<220> FEATURE:
<223> OTHER INFORMATION: Synthetic

<400> SEQUENCE: 214

Met Ser Thr Thr Thr Cys Gln Val Val Ala Phe Leu Leu Ser Ile Leu
1               5                   10                  15

Gly Leu Ala Gly Cys Ile Ala Ala Thr Gly Met Asp Met Trp Ser Thr
            20                  25                  30

Gln Asp Leu Tyr Asp Asn Pro Val Thr Ser Val Phe Gln Tyr Glu Gly
                35                  40                  45

Leu Trp Arg Ser Cys Val Arg Gln Ser Ser Gly Phe Thr Glu Cys Arg
```

```
                    50                  55                  60
Pro Tyr Phe Thr Ile Leu Gly Leu Pro Ala Met Leu Gln Ala Val Arg
 65                  70                  75                  80

Ala Leu Met Ile Val Gly Ile Val Leu Gly Ala Ile Gly Leu Leu Val
                     85                  90                  95

Ser Ile Phe Ala Leu Lys Cys Ile Arg Ile Gly Ser Met Glu Asp Ser
                    100                 105                 110

Ala Lys Ala Asn Met Thr Leu Thr Ser Gly Ile Met Phe Ile Val Ser
                    115                 120                 125

Gly Leu Cys Ala Ile Ala Gly Val Ser Val Phe Ala Asn Met Leu Val
                130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                    165                 170                 175

Val Gly Trp Val Ala Gly Gly Leu Thr Leu Ile Gly Gly Val Met Met
                    180                 185                 190

Cys Ile Ala Cys Arg Gly Leu Ala Pro Glu Glu Thr Asn Tyr Lys Ala
                    195                 200                 205

Val Ser Tyr His Ala Ser Gly His Ser Val Ala Tyr Lys Pro Gly Gly
                    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                    245                 250                 255

Lys His Asp Tyr Val
                260

<210> SEQ ID NO 215
<211> LENGTH: 223
<212> TYPE: PRT
<213> ORGANISM: Artificial Sequence
<220> FEATURE:
<223> OTHER INFORMATION: Synthetic

<400> SEQUENCE: 215

Met Ala Cys Leu Gly Phe Gln Arg His Lys Ala Gln Leu Asn Leu Ala
 1               5                  10                  15

Thr Arg Thr Trp Pro Cys Thr Leu Leu Phe Leu Leu Phe Ile Pro
                 20                  25                  30

Val Phe Cys Lys Ala Met His Val Ala Gln Pro Ala Val Val Leu Ala
                 35                  40                  45

Ser Ser Arg Gly Ile Ala Ser Phe Val Cys Glu Tyr Ala Ser Pro Gly
             50                  55                  60

Lys Ala Thr Glu Val Arg Val Thr Val Leu Arg Gln Ala Asp Ser Gln
 65                  70                  75                  80

Val Thr Glu Val Cys Ala Ala Thr Tyr Met Met Gly Asn Glu Leu Thr
                     85                  90                  95

Phe Leu Asp Asp Ser Ile Cys Thr Gly Thr Ser Ser Gly Asn Gln Val
                    100                 105                 110

Asn Leu Thr Ile Gln Gly Leu Arg Ala Met Asp Thr Gly Leu Tyr Ile
                115                 120                 125

Cys Lys Val Glu Leu Met Tyr Pro Pro Pro Tyr Tyr Leu Gly Ile Gly
                130                 135                 140

Asn Gly Thr Gln Ile Tyr Val Ile Asp Pro Glu Pro Cys Pro Asp Ser
```

-continued

```
               145                 150                 155                 160
       Asp Phe Leu Leu Trp Ile Leu Ala Ala Val Ser Ser Gly Leu Phe Phe
                       165                 170                 175
       Tyr Ser Phe Leu Leu Thr Ala Val Ser Leu Ser Lys Met Leu Lys Lys
                       180                 185                 190
       Arg Ser Pro Leu Thr Thr Gly Val Tyr Val Lys Met Pro Thr Glu
                       195                 200                 205
       Pro Glu Cys Glu Lys Gln Phe Gln Pro Tyr Phe Ile Pro Ile Asn
                       210                 215                 220

<210> SEQ ID NO 216
<211> LENGTH: 288
<212> TYPE: PRT
<213> ORGANISM: Artificial Sequence
<220> FEATURE:
<223> OTHER INFORMATION: Synthetic

<400> SEQUENCE: 216

Met Gln Ile Pro Gln Ala Pro Trp Pro Val Val Trp Ala Val Leu Gln
1               5                   10                  15
Leu Gly Trp Arg Pro Gly Trp Phe Leu Asp Ser Pro Asp Arg Pro Trp
                20                  25                  30
Asn Pro Pro Thr Phe Ser Pro Ala Leu Leu Val Val Thr Glu Gly Asp
                35                  40                  45
Asn Ala Thr Phe Thr Cys Ser Phe Ser Asn Thr Ser Glu Ser Phe Val
            50                  55                  60
Ile Asn Trp Tyr Arg Met Ser Pro Ser Asn Gln Thr Asp Lys Leu Ala
65              70                  75                  80
Ala Phe Pro Glu Asp Arg Ser Gln Pro Gly Gln Asp Cys Arg Phe Arg
                85                  90                  95
Val Thr Gln Leu Pro Asn Gly Arg Asp Phe His Met Ser Val Val Arg
                100                 105                 110
Ala Arg Arg Asn Asp Ser Gly Thr Tyr Leu Cys Gly Ala Ile Ser Leu
                115                 120                 125
Ala Pro Lys Ala Gln Ile Lys Glu Ser Leu Arg Ala Glu Leu Arg Val
            130                 135                 140
Thr Glu Arg Arg Ala Glu Val Pro Thr Ala His Pro Ser Pro Ser Pro
145                 150                 155                 160
Arg Pro Ala Gly Gln Phe Gln Thr Ile Val Val Gly Val Val Gly Gly
                165                 170                 175
Leu Leu Gly Ser Leu Val Leu Leu Val Trp Val Leu Ala Val Ile Cys
                180                 185                 190
Ser Arg Ala Ala Arg Gly Thr Ile Gly Ala Arg Arg Thr Gly Gln Pro
                195                 200                 205
Leu Lys Glu Asp Pro Ser Ala Val Pro Val Phe Ser Val Asp Tyr Gly
            210                 215                 220
Glu Leu Asp Phe Gln Trp Arg Glu Lys Thr Pro Glu Pro Pro Val Pro
225                 230                 235                 240
Cys Val Pro Glu Gln Thr Glu Tyr Ala Thr Ile Val Phe Pro Ser Gly
                245                 250                 255
Met Gly Thr Ser Ser Pro Ala Arg Arg Gly Ser Ala Asp Gly Pro Arg
                260                 265                 270
Ser Ala Gly Pro Leu Arg Pro Glu Asp Gly His Cys Ser Trp Pro Leu
                275                 280                 285
```

<210> SEQ ID NO 217
<211> LENGTH: 177
<212> TYPE: PRT
<213> ORGANISM: Artificial Sequence
<220> FEATURE:
<223> OTHER INFORMATION: Synthetic

<400> SEQUENCE: 217

Met Arg Ile Phe Ala Val Phe Ile Phe Met Thr Tyr Trp His Leu Leu
1               5                   10                  15

Asn Ala Pro Tyr Asn Lys Ile Asn Gly Arg Ile Leu Val Val Asp Pro
            20                  25                  30

Val Thr Ser Glu His Glu Leu Thr Cys Gln Leu Ala Glu Gly Tyr Pro
        35                  40                  45

Lys Ala Glu Val Ile Trp Thr Ser Ser Asp His Gln Val Leu Ser Gly
    50                  55                  60

Lys Thr Thr Thr Thr Asn Ser Lys Arg Glu Glu Lys Leu Phe Asn Val
65                  70                  75                  80

Thr Ser Thr Leu Arg Ile Asn Thr Thr Asn Glu Ile Phe Tyr Cys
                85                  90                  95

Thr Phe Arg Arg Leu Asp Pro Glu Glu Asn His Thr Ala Glu Leu Val
            100                 105                 110

Ile Pro Glu Leu Pro Leu Ala His Pro Pro Asn Glu Arg Thr His Leu
        115                 120                 125

Val Ile Leu Gly Ala Ile Leu Leu Cys Leu Gly Val Ala Leu Thr Phe
    130                 135                 140

Ile Phe Arg Leu Arg Lys Gly Arg Met Met Asp Val Lys Lys Cys Gly
145                 150                 155                 160

Ile Gln Asp Thr Asn Ser Lys Lys Gly Ser Asp Thr His Leu Glu Glu
                165                 170                 175

Thr

<210> SEQ ID NO 218
<211> LENGTH: 19
<212> TYPE: PRT
<213> ORGANISM: Artificial Sequence
<220> FEATURE:
<223> OTHER INFORMATION: Synthetic

<400> SEQUENCE: 218

Met Gly Trp Ser Cys Ile Ile Leu Phe Leu Val Ala Thr Ala Thr Gly
1               5                   10                  15

Val His Ser

<210> SEQ ID NO 219
<211> LENGTH: 87
<212> TYPE: DNA
<213> ORGANISM: Artificial Sequence
<220> FEATURE:
<223> OTHER INFORMATION: Synthetic

<400> SEQUENCE: 219
agggtcacca tcacctgcaa aagcagtcag agtctgctca acagtggcaa ccagaaaagc      60
tatctgacct ggtatcaaca gaaacca                                          87

<210> SEQ ID NO 220
<211> LENGTH: 60
<212> TYPE: DNA
<213> ORGANISM: Artificial Sequence
<220> FEATURE:

<223> OTHER INFORMATION: Synthetic

<400> SEQUENCE: 220
gctccgaagc ttctgattta ttgggcatct accctcgaaa gcggagtccc ttctcgcttc    60

<210> SEQ ID NO 221
<211> LENGTH: 57
<212> TYPE: DNA
<213> ORGANISM: Artificial Sequence
<220> FEATURE:
<223> OTHER INFORMATION: Synthetic

<400> SEQUENCE: 221
gcaacttatt actgtcagaa cgcgtattct tttccgttta cgttcggaca gggtacc    57

<210> SEQ ID NO 222
<211> LENGTH: 63
<212> TYPE: DNA
<213> ORGANISM: Artificial Sequence
<220> FEATURE:
<223> OTHER INFORMATION: Synthetic

<400> SEQUENCE: 222
tcctgtgcag cttctggcta cacctttacc aactatggta tgaactgggt gcgtcaggcc    60
ccg    63

<210> SEQ ID NO 223
<211> LENGTH: 87
<212> TYPE: DNA
<213> ORGANISM: Artificial Sequence
<220> FEATURE:
<223> OTHER INFORMATION: Synthetic

<400> SEQUENCE: 223
ggcctggaat gggttgcatg gattaacatg tataccggcg aaccgaccta tgccgatgac    60
ttcaagggcc gtttcactat aagccgt    87

<210> SEQ ID NO 224
<211> LENGTH: 57
<212> TYPE: DNA
<213> ORGANISM: Artificial Sequence
<220> FEATURE:
<223> OTHER INFORMATION: Synthetic

<400> SEQUENCE: 224
gtctattatt gtgctcgcct gtataacggc aactctctgg actactgggg tcaagga    57

<210> SEQ ID NO 225
<211> LENGTH: 42
<212> TYPE: DNA
<213> ORGANISM: Artificial Sequence
<220> FEATURE:
<223> OTHER INFORMATION: Synthetic

<400> SEQUENCE: 225
gcctatgcat ccgatatcca gmtgacccag tccccgagct cc    42

<210> SEQ ID NO 226
<211> LENGTH: 78
<212> TYPE: DNA
<213> ORGANISM: Artificial Sequence
<220> FEATURE:
<223> OTHER INFORMATION: Synthetic

<400> SEQUENCE: 226

```
ggtagcggtt ccgggacgga ttwcactctg accatcagca gtctgcagcc ggaagacytc    60
gcaacttatt actgtcag                                                  78
```

<210> SEQ ID NO 227
<211> LENGTH: 78
<212> TYPE: DNA
<213> ORGANISM: Artificial Sequence
<220> FEATURE:
<223> OTHER INFORMATION: Synthetic

<400> SEQUENCE: 227

```
ctccgtttgt cctgtgcary ctctggctac acctttacca actatggtat gaactggrtc    60
cgtcaggccc cgggtaag                                                  78
```

<210> SEQ ID NO 228
<211> LENGTH: 72
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(19)
<223> OTHER INFORMATION: n is a, c, g, or t

<400> SEQUENCE: 228

```
gatgacttca agggccgtny cactwtcagc ckcgacrmct ccrmgarcac asygtaccta    60
caaatgaaca gc                                                        72
```

<210> SEQ ID NO 229
<211> LENGTH: 45
<212> TYPE: DNA
<213> ORGANISM: Artificial Sequence
<220> FEATURE:
<223> OTHER INFORMATION: Synthetic

<400> SEQUENCE: 229

```
gacactgccg tctattattg tdygargctg tataacggca actct                    45
```

<210> SEQ ID NO 230
<211> LENGTH: 21
<212> TYPE: DNA
<213> ORGANISM: Artificial Sequence
<220> FEATURE:
<223> OTHER INFORMATION: Synthetic

<400> SEQUENCE: 230

```
taaggccaag acggcctata a                                              21
```

<210> SEQ ID NO 231
<211> LENGTH: 57
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(36)
<223> OTHER INFORMATION: n is a, c, g, or t

<400> SEQUENCE: 231

```
gtctattatt gtgctcgcnn nnnnnnnnnn nnnnnwtkg actactgggg tcaagga         57
```

<210> SEQ ID NO 232

```
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(39)
<223> OTHER INFORMATION: n is a, c, g, or t

<400> SEQUENCE: 232
gtctattatt gtgctcgcnn nnnnnnnnn nnnnnnnnnw tkgactactg gggtcaagga      60

<210> SEQ ID NO 233
<211> LENGTH: 63
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(42)
<223> OTHER INFORMATION: n is a, c, g, or t

<400> SEQUENCE: 233
gtctattatt gtgctcgcnn nnnnnnnnn nnnnnnnnnn nnwtkgacta ctggggtcaa      60
gga                                                                  63

<210> SEQ ID NO 234
<211> LENGTH: 66
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(45)
<223> OTHER INFORMATION: n is a, c, g, or t

<400> SEQUENCE: 234
gtctattatt gtgctcgcnn nnnnnnnnn nnnnnnnnnn nnnnnwtkga ctactggggt      60
caagga                                                               66

<210> SEQ ID NO 235
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: n is a, c, g, or t

<400> SEQUENCE: 235
gtctattatt gtgctcgcnn stataacggc aactctctg                            39

<210> SEQ ID NO 236
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: n is a, c, g, or t

<400> SEQUENCE: 236
```
ctattattgt gctcgcctgn nsaacggcaa ctctctggac                    40

<210> SEQ ID NO 237
<211> LENGTH: 43
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(24)
<223> OTHER INFORMATION: n is a, c, g, or t

<400> SEQUENCE: 237
ctattattgt gctcgcctgt atnnsggcaa ctctctggac tac                43

<210> SEQ ID NO 238
<211> LENGTH: 46
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (26)..(27)
<223> OTHER INFORMATION: n is a, c, g, or t

<400> SEQUENCE: 238
ctattattgt gctcgcctgt ataacnnsaa ctctctggac tactgg             46

<210> SEQ ID NO 239
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: n is a, c, g, or t

<400> SEQUENCE: 239
gctcgcctgt ataacggcnn stctctggac tactggggt                     39

<210> SEQ ID NO 240
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: n is a, c, g, or t

<400> SEQUENCE: 240
cgcctgtata acggcaacnn sctggactac tggggtcaa                     39

<210> SEQ ID NO 241
<211> LENGTH: 42
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(23)
<223> OTHER INFORMATION: n is a, c, g, or t

<400> SEQUENCE: 241
gcaacttatt actgtcagaa cnnstattct tttccgttta cg                42

<210> SEQ ID NO 242
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(22)
<223> OTHER INFORMATION: n is a, c, g, or t

<400> SEQUENCE: 242
cttattactg tcagaacgcg nnstctttc cgtttacgtt c                  41

<210> SEQ ID NO 243
<211> LENGTH: 44
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(25)
<223> OTHER INFORMATION: n is a, c, g, or t

<400> SEQUENCE: 243
cttattactg tcagaacgcg tatnnstttc cgtttacgtt cgga              44

<210> SEQ ID NO 244
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: n is a, c, g, or t

<400> SEQUENCE: 244
ctgtcagaac gcgtattctn nsccgtttac gttcggacag                   40

<210> SEQ ID NO 245
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: n is a, c, g, or t

<400> SEQUENCE: 245
cacctgcaaa agcagtcagn nsctgctcaa cagtggcaac                   40

<210> SEQ ID NO 246
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: n is a, c, g, or t

<400> SEQUENCE: 246
ctgcaaaagc agtcagagtn nsctcaacag tggcaaccag                              40

<210> SEQ ID NO 247
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: n is a, c, g, or t

<400> SEQUENCE: 247
caaaagcagt cagagtctgn nsaacagtgg caaccagaaa                              40

<210> SEQ ID NO 248
<211> LENGTH: 43
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(24)
<223> OTHER INFORMATION: n is a, c, g, or t

<400> SEQUENCE: 248
caaaagcagt cagagtctgc tcnnsagtgg caaccagaaa agc                          43

<210> SEQ ID NO 249
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: n is a, c, g, or t

<400> SEQUENCE: 249
cagtcagagt ctgctcaacn nsggcaacca gaaaagctat                              40

<210> SEQ ID NO 250
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: n is a, c, g, or t

<400> SEQUENCE: 250
cagagtctgc tcaacagtnn saaccagaaa agctatctg                               39

<210> SEQ ID NO 251
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)

<223> OTHER INFORMATION: n is a, c, g, or t

<400> SEQUENCE: 251
gagtctgctc aacagtggcn nscagaaaag ctatctgacc        40

<210> SEQ ID NO 252
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(22)
<223> OTHER INFORMATION: n is a, c, g, or t

<400> SEQUENCE: 252
gtctgctcaa cagtggcaac nnsaaaagct atctgacctg g        41

<210> SEQ ID NO 253
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: n is a, c, g, or t

<400> SEQUENCE: 253
ctcaacagtg gcaaccagnn sagctatctg acctggtat        39

<210> SEQ ID NO 254
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: n is a, c, g, or t

<400> SEQUENCE: 254
caacagtggc aaccagaaan nstatctgac ctggtatcaa        40

<210> SEQ ID NO 255
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: n is a, c, g, or t

<400> SEQUENCE: 255
cagtggcaac cagaaaagcn nsctgacctg gtatcaacag        40

<210> SEQ ID NO 256
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: n is a, c, g, or t

<400> SEQUENCE: 256
ggcaaccaga aaagctatnn sacctggtat caacagaaa                                      39

<210> SEQ ID NO 257
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: n is a, c, g, or t

<400> SEQUENCE: 257
ccgaagcttc tgatttatnn sgcatctacc ctcgaaagc                                      39

<210> SEQ ID NO 258
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: n is a, c, g, or t

<400> SEQUENCE: 258
ctgatttatt gggcatctnn sctcgaaagc ggagtccct                                      39

<210> SEQ ID NO 259
<211> LENGTH: 43
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(24)
<223> OTHER INFORMATION: n is a, c, g, or t

<400> SEQUENCE: 259
gatttattgg gcatctaccc tcnnsagcgg agtcccttct cgc                                 43

<210> SEQ ID NO 260
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: n is a, c, g, or t

<400> SEQUENCE: 260
ggcctggaat gggttgcann sattaacatg tataccggc                                      39

<210> SEQ ID NO 261
<211> LENGTH: 39
<212> TYPE: DNA
<213> ORGANISM: Artificial Sequence
<220> FEATURE:
<223> OTHER INFORMATION: Synthetic
<220> FEATURE:

<221> NAME/KEY: misc_feature
<222> LOCATION: (19)..(20)
<223> OTHER INFORMATION: n is a, c, g, or t

<400> SEQUENCE: 261
gaatgggttg catggattnn satgtatacc ggcgaaccg                                    39

<210> SEQ ID NO 262
<211> LENGTH: 42
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(23)
<223> OTHER INFORMATION: n is a, c, g, or t

<400> SEQUENCE: 262
gaatgggttg catggattaa cnnstatacc ggcgaaccga cc                                42

<210> SEQ ID NO 263
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: n is a, c, g, or t

<400> SEQUENCE: 263
gttgcatgga ttaacatgnn saccggcgaa ccgacctat                                    39

<210> SEQ ID NO 264
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: n is a, c, g, or t

<400> SEQUENCE: 264
gcatggatta acatgtatnn sggcgaaccg acctatgcc                                    39

<210> SEQ ID NO 265
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: n is a, c, g, or t

<400> SEQUENCE: 265
gattaacatg tataccggcn nsccgaccta tgccgatgac                                   40

<210> SEQ ID NO 266
<211> LENGTH: 43
<212> TYPE: DNA
<213> ORGANISM: Artificial Sequence
<220> FEATURE:
<223> OTHER INFORMATION: Synthetic

```
<220> FEATURE:
<221> NAME/KEY: misc_feature
<222> LOCATION: (23)..(24)
<223> OTHER INFORMATION: n is a, c, g, or t

<400> SEQUENCE: 266
gattaacatg tataccggcg aannsaccta tgccgatgac ttc                   43

<210> SEQ ID NO 267
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: n is a, c, g, or t

<400> SEQUENCE: 267
catgtatacc ggcgaaccgn nstatgccga tgacttcaag                       40

<210> SEQ ID NO 268
<211> LENGTH: 12
<212> TYPE: PRT
<213> ORGANISM: Artificial Sequence
<220> FEATURE:
<223> OTHER INFORMATION: Synthetic

<400> SEQUENCE: 268

Arg Gly Cys Val Gly Cys Arg Gly Cys Arg Gly Cys
1               5                   10

<210> SEQ ID NO 269
<211> LENGTH: 15
<212> TYPE: PRT
<213> ORGANISM: Artificial Sequence
<220> FEATURE:
<223> OTHER INFORMATION: Synthetic

<400> SEQUENCE: 269

Arg Gly Cys Arg Gly Cys Val Gly Cys Arg Gly Cys Arg Gly Cys
1               5                   10                  15

<210> SEQ ID NO 270
<211> LENGTH: 18
<212> TYPE: PRT
<213> ORGANISM: Artificial Sequence
<220> FEATURE:
<223> OTHER INFORMATION: Synthetic

<400> SEQUENCE: 270

Arg Gly Cys Arg Gly Cys Arg Gly Cys Val Gly Cys Arg Gly Cys Arg
1               5                   10                  15

Gly Cys

<210> SEQ ID NO 271
<211> LENGTH: 45
<212> TYPE: PRT
<213> ORGANISM: Artificial Sequence
<220> FEATURE:
<223> OTHER INFORMATION: Synthetic

<400> SEQUENCE: 271

Arg Gly Cys Arg Gly Cys Arg Gly Cys Val Gly Cys Arg Gly Cys Arg
1               5                   10                  15
```

Gly Cys Arg Gly Cys Val Gly Cys Arg Gly Cys Arg Gly
            20                  25                  30

Cys Val Gly Cys Arg Gly Cys Arg Gly Cys Arg Gly Cys
            35                  40                  45

<210> SEQ ID NO 272
<211> LENGTH: 48
<212> TYPE: PRT
<213> ORGANISM: Artificial Sequence
<220> FEATURE:
<223> OTHER INFORMATION: Synthetic

<400> SEQUENCE: 272

Arg Gly Cys Arg Gly Cys Arg Gly Cys Arg Gly Cys Val Gly Cys Arg
1               5                   10                  15

Gly Cys Arg Gly Cys Arg Gly Cys Val Gly Cys Arg Gly Cys Arg Gly
            20                  25                  30

Cys Arg Gly Cys Val Gly Cys Arg Gly Cys Arg Gly Cys Arg Gly Cys
            35                  40                  45

<210> SEQ ID NO 273
<211> LENGTH: 51
<212> TYPE: PRT
<213> ORGANISM: Artificial Sequence
<220> FEATURE:
<223> OTHER INFORMATION: Synthetic

<400> SEQUENCE: 273

Arg Gly Cys Arg Gly Cys Arg Gly Cys Arg Gly Cys Val Gly Cys Arg
1               5                   10                  15

Gly Cys Arg Gly Cys Arg Gly Cys Val Gly Cys Arg Gly Cys Arg Gly
            20                  25                  30

Cys Arg Gly Cys Val Gly Cys Arg Gly Cys Arg Gly Cys Arg Gly Cys
            35                  40                  45

Arg Gly Cys
    50

<210> SEQ ID NO 274
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa is Ser, Thr, Tyr, Phe, or Trp
<220> FEATURE:
<221> NAME/KEY: MISC_FEATURE
<222> LOCATION: (12)..(12)
<223> OTHER INFORMATION: Xaa is Gln, Asn, Trp, Phe, Tyr, Ile, Met, or
      Val

<400> SEQUENCE: 274

Lys Ser Ser Gln Ser Leu Leu Asn Xaa Gly Asn Xaa Lys Ser Tyr Leu
1               5                   10                  15

Thr

<210> SEQ ID NO 275
<211> LENGTH: 7
<212> TYPE: PRT
<213> ORGANISM: Artificial Sequence
<220> FEATURE:
<223> OTHER INFORMATION: Synthetic
<220> FEATURE:

```
<221> NAME/KEY: misc_feature
<222> LOCATION: (6)..(6)
<223> OTHER INFORMATION: Xaa can be any naturally occurring amino acid

<400> SEQUENCE: 275

Trp Ala Ser Thr Leu Xaa Ser
1               5

<210> SEQ ID NO 276
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa is Ser, Thr, Phe, Tyr, or Trp

<400> SEQUENCE: 276

Gln Asn Ala Tyr Xaa Phe Pro Phe Thr
1               5

<210> SEQ ID NO 277
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is Glu, Asp, Lys, His, or Arg
<220> FEATURE:
<221> NAME/KEY: MISC_FEATURE
<222> LOCATION: (9)..(9)
<223> OTHER INFORMATION: Xaa is Pro, Lys, Arg, His, Thr, or Ser
<220> FEATURE:
<221> NAME/KEY: MISC_FEATURE
<222> LOCATION: (10)..(10)
<223> OTHER INFORMATION: Xaa is Ser, Thr, Val, Ile, or Leu

<400> SEQUENCE: 277

Trp Ile Asn Met Tyr Thr Gly Xaa Xaa Xaa Tyr Ala Asp Asp Phe Lys
1               5                   10                  15

Gly

<210> SEQ ID NO 278
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is Asn, Gln, Lys, Arg, or His

<400> SEQUENCE: 278

Leu Tyr Xaa Gly Asn Ser Leu Asp Tyr
1               5

<210> SEQ ID NO 279
<211> LENGTH: 478
<212> TYPE: PRT
<213> ORGANISM: Artificial Sequence
<220> FEATURE:
<223> OTHER INFORMATION: Synthetic

<400> SEQUENCE: 279
```

```
Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
                100                 105                 110

Lys Ser Gly Gly Gly Gly Gln Val Gln Leu Val Gln Ser Gly Ala Glu
            115                 120                 125

Val Lys Lys Pro Gly Ser Ser Val Lys Val Ser Cys Lys Thr Ser Gly
    130                 135                 140

Asp Thr Phe Ser Thr Tyr Ala Ile Ser Trp Val Arg Gln Ala Pro Gly
145                 150                 155                 160

Gln Gly Leu Glu Trp Met Gly Gly Ile Ile Pro Ile Phe Gly Lys Ala
                165                 170                 175

His Tyr Ala Gln Lys Phe Gln Gly Arg Val Thr Ile Thr Ala Asp Glu
                180                 185                 190

Ser Thr Ser Thr Ala Tyr Met Glu Leu Ser Ser Leu Arg Ser Glu Asp
        195                 200                 205

Thr Ala Val Tyr Phe Cys Ala Arg Lys Phe His Phe Val Ser Gly Ser
    210                 215                 220

Pro Phe Gly Met Asp Val Trp Gly Gln Gly Thr Thr Val Thr Val Ser
225                 230                 235                 240

Ser Gly Gly Gly Gly Ser Glu Pro Lys Ser Ser Asp Lys Thr His Thr
                245                 250                 255

Cys Pro Pro Cys Pro Ala Pro Glu Leu Leu Gly Gly Pro Ser Val Phe
                260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
        355                 360                 365

Lys Ala Lys Gly Gln Pro Arg Glu Pro Gln Val Tyr Thr Leu Pro Pro
370                 375                 380

Cys Arg Glu Glu Met Thr Lys Asn Gln Val Ser Leu Trp Cys Leu Val
385                 390                 395                 400

Lys Gly Phe Tyr Pro Ser Asp Ile Ala Val Glu Trp Glu Ser Asn Gly
                405                 410                 415
```

```
Gln Pro Glu Asn Asn Tyr Lys Thr Thr Pro Pro Val Leu Asp Ser Asp
                420                 425                 430

Gly Ser Phe Phe Leu Tyr Ser Lys Leu Thr Val Asp Lys Ser Arg Trp
            435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475

<210> SEQ ID NO 280
<211> LENGTH: 463
<212> TYPE: PRT
<213> ORGANISM: Artificial Sequence
<220> FEATURE:
<223> OTHER INFORMATION: Synthetic

<400> SEQUENCE: 280

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys Ser Gly Gly Gly Gly Glu
            100                 105                 110

Val Gln Leu Val Glu Ser Gly Gly Gly Leu Val Gln Pro Gly Gly Ser
        115                 120                 125

Leu Arg Leu Ser Cys Ala Val Ser Gly Tyr Thr Phe Ser Met Asn Trp
130                 135                 140

Val Arg Gln Ala Pro Gly Lys Gly Leu Glu Trp Val Ala Trp Ile Asn
145                 150                 155                 160

Met Tyr Thr Gly Glu Pro Thr Tyr Ala Asp Asp Phe Lys Gly Arg Phe
                165                 170                 175

Thr Ile Ser Arg Asp Asp Ser Lys Asn Thr Leu Tyr Leu Gln Met Asn
            180                 185                 190

Ser Leu Arg Ala Glu Asp Thr Ala Val Tyr Tyr Cys Ala Arg Leu Tyr
        195                 200                 205

Asn Gly Asn Ser Leu Asp Tyr Trp Gly Gln Gly Thr Leu Val Thr Val
210                 215                 220

Ser Ser Gly Gly Gly Gly Ser Glu Pro Lys Ser Ser Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Asp Val Ser His Glu Asp Pro Glu
        275                 280                 285

Val Lys Phe Asn Trp Tyr Val Asp Gly Val Glu Val His Asn Ala Lys
290                 295                 300
```

```
Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Cys Thr Leu Pro
        355                 360                 365

Pro Ser Arg Glu Glu Met Thr Lys Asn Gln Val Ser Leu Ser Cys Ala
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn Arg Phe Thr Gln Lys Ser Leu Ser Leu Ser Pro Gly Lys
    450                 455                 460

<210> SEQ ID NO 281
<211> LENGTH: 106
<212> TYPE: PRT
<213> ORGANISM: Artificial Sequence
<220> FEATURE:
<223> OTHER INFORMATION: Synthetic

<400> SEQUENCE: 281

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 282
<211> LENGTH: 11
<212> TYPE: PRT
<213> ORGANISM: Artificial Sequence
<220> FEATURE:
<223> OTHER INFORMATION: Synthetic

<400> SEQUENCE: 282

Arg Ala Ser Gln Ser Val Ser Ser Tyr Leu Ala
1               5                   10

<210> SEQ ID NO 283
<211> LENGTH: 7
<212> TYPE: PRT
<213> ORGANISM: Artificial Sequence
```

<220> FEATURE:
<223> OTHER INFORMATION: Synthetic

<400> SEQUENCE: 283

Asp Ala Ser Asn Arg Ala Thr
1               5

<210> SEQ ID NO 284
<211> LENGTH: 8
<212> TYPE: PRT
<213> ORGANISM: Artificial Sequence
<220> FEATURE:
<223> OTHER INFORMATION: Synthetic

<400> SEQUENCE: 284

Gln Gln Arg Ser Asn Trp Pro Thr
1               5

<210> SEQ ID NO 285
<211> LENGTH: 123
<212> TYPE: PRT
<213> ORGANISM: Artificial Sequence
<220> FEATURE:
<223> OTHER INFORMATION: Synthetic

<400> SEQUENCE: 285

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
        115                 120

<210> SEQ ID NO 286
<211> LENGTH: 10
<212> TYPE: PRT
<213> ORGANISM: Artificial Sequence
<220> FEATURE:
<223> OTHER INFORMATION: Synthetic

<400> SEQUENCE: 286

Gly Asp Thr Phe Ser Thr Tyr Ala Ile Ser
1               5                   10

<210> SEQ ID NO 287
<211> LENGTH: 17
<212> TYPE: PRT
<213> ORGANISM: Artificial Sequence
<220> FEATURE:
<223> OTHER INFORMATION: Synthetic

<400> SEQUENCE: 287

Gly Ile Ile Pro Ile Phe Gly Lys Ala His Tyr Ala Gln Lys Phe Gln

-continued

```
1               5                   10                  15
Gly

<210> SEQ ID NO 288
<211> LENGTH: 14
<212> TYPE: PRT
<213> ORGANISM: Artificial Sequence
<220> FEATURE:
<223> OTHER INFORMATION: Synthetic

<400> SEQUENCE: 288

Lys Phe His Phe Val Ser Gly Ser Pro Phe Gly Met Asp Val
1               5                   10

<210> SEQ ID NO 289
<211> LENGTH: 478
<212> TYPE: PRT
<213> ORGANISM: Artificial Sequence
<220> FEATURE:
<223> OTHER INFORMATION: Synthetic

<400> SEQUENCE: 289

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
                20                  25                  30

Gly Asn Gln Lys Ser Tyr Leu Thr Trp Tyr Gln Gln Lys Pro Gly Lys
            35                  40                  45

Ala Pro Lys Leu Leu Ile Tyr Trp Ala Ser Thr Leu Glu Ser Gly Val
        50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Ser Gly Gly Gly Gly Gln Val Gln Leu Val Gln Ser Gly Ala Glu
        115                 120                 125

Val Lys Lys Pro Gly Ser Ser Val Lys Val Ser Cys Lys Thr Ser Gly
    130                 135                 140

Asp Thr Phe Ser Thr Tyr Ala Ile Ser Trp Val Arg Gln Ala Pro Gly
145                 150                 155                 160

Gln Gly Leu Glu Trp Met Gly Gly Ile Ile Pro Leu Phe Gly Lys Ala
                165                 170                 175

His Tyr Ala Gln Lys Phe Gln Gly Arg Val Thr Ile Thr Ala Asp Glu
            180                 185                 190

Ser Thr Ser Thr Ala Tyr Met Glu Leu Ser Ser Leu Arg Ser Glu Asp
        195                 200                 205

Thr Ala Val Tyr Phe Cys Ala Arg Lys Phe His Phe Val Arg Gly Ser
    210                 215                 220

Pro Phe Gly Met Asp Val Trp Gly Gln Gly Thr Thr Val Thr Val Ser
225                 230                 235                 240

Ser Gly Gly Gly Gly Ser Glu Pro Lys Ser Ser Asp Lys Thr His Thr
                245                 250                 255

Cys Pro Pro Cys Pro Ala Pro Glu Leu Leu Gly Gly Pro Ser Val Phe
            260                 265                 270

Leu Phe Pro Pro Lys Pro Lys Asp Thr Leu Met Ile Ser Arg Thr Pro
```

```
                275                 280                 285
Glu Val Thr Cys Val Val Asp Val Ser His Glu Asp Pro Glu Val
        290                 295                 300
Lys Phe Asn Trp Tyr Val Asp Gly Val Glu Val His Asn Ala Lys Thr
305                 310                 315                 320
Lys Pro Arg Glu Glu Gln Tyr Asn Ser Thr Tyr Arg Val Val Ser Val
                325                 330                 335
Leu Thr Val Leu His Gln Asp Trp Leu Asn Gly Lys Glu Tyr Lys Cys
            340                 345                 350
Lys Val Ser Asn Lys Ala Leu Pro Ala Pro Ile Glu Lys Thr Ile Ser
            355                 360                 365
Lys Ala Lys Gly Gln Pro Arg Glu Pro Gln Val Tyr Thr Leu Pro Pro
370                 375                 380
Cys Arg Glu Glu Met Thr Lys Asn Gln Val Ser Leu Trp Cys Leu Val
385                 390                 395                 400
Lys Gly Phe Tyr Pro Ser Asp Ile Ala Val Glu Trp Glu Ser Asn Gly
                405                 410                 415
Gln Pro Glu Asn Asn Tyr Lys Thr Thr Pro Pro Val Leu Asp Ser Asp
            420                 425                 430
Gly Ser Phe Phe Leu Tyr Ser Lys Leu Thr Val Asp Lys Ser Arg Trp
            435                 440                 445
Gln Gln Gly Asn Val Phe Ser Cys Ser Val Met His Glu Ala Leu His
        450                 455                 460
Asn His Tyr Thr Gln Lys Ser Leu Ser Leu Ser Pro Gly Lys
465                 470                 475

<210> SEQ ID NO 290
<211> LENGTH: 463
<212> TYPE: PRT
<213> ORGANISM: Artificial Sequence
<220> FEATURE:
<223> OTHER INFORMATION: Synthetic

<400> SEQUENCE: 290

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
            20                  25                  30
Leu Ala Trp Tyr Gln Gln Lys Pro Gly Gln Ala Pro Arg Leu Leu Ile
        35                  40                  45
Tyr Asp Ala Ser Asn Arg Ala Pro Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Arg Ser Asn Trp Pro Thr
                85                  90                  95
Phe Gly Gln Gly Thr Lys Val Glu Ile Lys Ser Gly Gly Gly Gly Glu
            100                 105                 110
Val Gln Leu Val Glu Ser Gly Gly Gly Leu Val Gln Pro Gly Gly Ser
        115                 120                 125
Leu Arg Leu Ser Cys Ala Val Ser Gly Tyr Thr Phe Ser Met Asn Trp
    130                 135                 140
Val Arg Gln Ala Pro Gly Lys Gly Leu Glu Trp Val Ala Trp Ile Asn
145                 150                 155                 160
Met Tyr Thr Gly Glu Pro Thr Tyr Ala Asp Asp Phe Lys Gly Arg Phe
```

```
                    165                 170                 175
Thr Ile Ser Arg Asp Asp Ser Lys Asn Thr Leu Tyr Leu Gln Met Asn
                180                 185                 190

Ser Leu Arg Ala Glu Asp Thr Ala Val Tyr Tyr Cys Ala Arg Leu Tyr
            195                 200                 205

Asn Gly Asn Ser Leu Asp Tyr Trp Gly Gln Gly Thr Leu Val Thr Val
        210                 215                 220

Ser Ser Gly Gly Gly Gly Ser Glu Pro Lys Ser Ser Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Asp Val Ser His Glu Asp Pro Glu
        275                 280                 285

Val Lys Phe Asn Trp Tyr Val Asp Gly Val Glu Val His Asn Ala Lys
        290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Cys Thr Leu Pro
        355                 360                 365

Pro Ser Arg Glu Glu Met Thr Lys Asn Gln Val Ser Leu Ser Cys Ala
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn Arg Phe Thr Gln Lys Ser Leu Ser Leu Ser Pro Gly Lys
        450                 455                 460

<210> SEQ ID NO 291
<211> LENGTH: 106
<212> TYPE: PRT
<213> ORGANISM: Artificial Sequence
<220> FEATURE:
<223> OTHER INFORMATION: Synthetic

<400> SEQUENCE: 291

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Pro Gly Ile Pro Ala Arg Phe Ser Gly
    50                  55                  60

Ser Gly Ser Gly Thr Asp Phe Thr Leu Thr Ile Ser Ser Leu Glu Pro
```

```
                65                  70                  75                  80
Glu Asp Phe Ala Val Tyr Tyr Cys Gln Gln Arg Ser Asn Trp Pro Thr
                        85                  90                  95

Phe Gly Gln Gly Thr Lys Val Glu Ile Lys
                100                 105
```

<210> SEQ ID NO 292
<211> LENGTH: 7
<212> TYPE: PRT
<213> ORGANISM: Artificial Sequence
<220> FEATURE:
<223> OTHER INFORMATION: Synthetic

<400> SEQUENCE: 292

```
Asp Ala Ser Asn Arg Ala Pro
1               5
```

<210> SEQ ID NO 293
<211> LENGTH: 123
<212> TYPE: PRT
<213> ORGANISM: Artificial Sequence
<220> FEATURE:
<223> OTHER INFORMATION: Synthetic

<400> SEQUENCE: 293

```
Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
                20                  25                  30

Ala Ile Ser Trp Val Arg Gln Ala Pro Gly Gln Gly Leu Glu Trp Met
            35                  40                  45

Gly Gly Ile Ile Pro Leu Phe Gly Lys Ala His Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Arg Gly Ser Pro Phe Gly Met Asp Val
                100                 105                 110

Trp Gly Gln Gly Thr Thr Val Thr Val Ser Ser
        115                 120
```

<210> SEQ ID NO 294
<211> LENGTH: 17
<212> TYPE: PRT
<213> ORGANISM: Artificial Sequence
<220> FEATURE:
<223> OTHER INFORMATION: Synthetic

<400> SEQUENCE: 294

```
Gly Ile Ile Pro Leu Phe Gly Lys Ala His Tyr Ala Gln Lys Phe Gln
1               5                   10                  15

Gly
```

<210> SEQ ID NO 295
<211> LENGTH: 14
<212> TYPE: PRT
<213> ORGANISM: Artificial Sequence
<220> FEATURE:
<223> OTHER INFORMATION: Synthetic

<400> SEQUENCE: 295

Lys Phe His Phe Val Arg Gly Ser Pro Phe Gly Met Asp Val
1               5                   10

<210> SEQ ID NO 296
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa is Ile or Leu

<400> SEQUENCE: 296

Gly Ile Ile Pro Xaa Phe Gly Lys Ala His
1               5                   10

<210> SEQ ID NO 297
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is His or Arg
<220> FEATURE:
<221> NAME/KEY: misc_feature
<222> LOCATION: (6)..(6)
<223> OTHER INFORMATION: Xaa is Ser or Arg

<400> SEQUENCE: 297

Lys Phe Xaa Phe Val Xaa Gly Ser Pro Phe Gly Met Asp Val
1               5                   10

<210> SEQ ID NO 298
<211> LENGTH: 14
<212> TYPE: PRT
<213> ORGANISM: Artificial Sequence
<220> FEATURE:
<223> OTHER INFORMATION: Synthetic

<400> SEQUENCE: 298

Lys Phe Arg Phe Val Ser Gly Ser Pro Phe Gly Met Asp Val
1               5                   10

<210> SEQ ID NO 299
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Xaa is Leu or Met
<220> FEATURE:
<221> NAME/KEY: MISC_FEATURE
<222> LOCATION: (11)..(11)
<223> OTHER INFORMATION: Xaa is Ala, Ser, or Glu

<400> SEQUENCE: 299

Arg Ala Ser Gln Ser Val Ser Ser Tyr Xaa Xaa
1               5                   10

<210> SEQ ID NO 300
<211> LENGTH: 11

```
<212> TYPE: PRT
<213> ORGANISM: Artificial Sequence
<220> FEATURE:
<223> OTHER INFORMATION: Synthetic

<400> SEQUENCE: 300

Arg Ala Ser Gln Ser Val Ser Ser Tyr Leu Ser
1               5                   10

<210> SEQ ID NO 301
<211> LENGTH: 11
<212> TYPE: PRT
<213> ORGANISM: Artificial Sequence
<220> FEATURE:
<223> OTHER INFORMATION: Synthetic

<400> SEQUENCE: 301

Arg Ala Ser Gln Ser Val Ser Ser Tyr Met Ala
1               5                   10

<210> SEQ ID NO 302
<211> LENGTH: 11
<212> TYPE: PRT
<213> ORGANISM: Artificial Sequence
<220> FEATURE:
<223> OTHER INFORMATION: Synthetic

<400> SEQUENCE: 302

Arg Ala Ser Gln Ser Val Ser Ser Tyr Leu Glu
1               5                   10

<210> SEQ ID NO 303
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Xaa is Thr, Pro, Met, or Glu

<400> SEQUENCE: 303

Asp Ala Ser Asn Arg Ala Xaa
1               5

<210> SEQ ID NO 304
<211> LENGTH: 7
<212> TYPE: PRT
<213> ORGANISM: Artificial Sequence
<220> FEATURE:
<223> OTHER INFORMATION: Synthetic

<400> SEQUENCE: 304

Asp Ala Ser Asn Arg Ala Met
1               5

<210> SEQ ID NO 305
<211> LENGTH: 7
<212> TYPE: PRT
<213> ORGANISM: Artificial Sequence
<220> FEATURE:
<223> OTHER INFORMATION: Synthetic

<400> SEQUENCE: 305

Asp Ala Ser Asn Arg Ala Glu
1               5
```

<210> SEQ ID NO 306
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Ser or Ala

<400> SEQUENCE: 306

Gln Gln Arg Xaa Asn Trp Pro Thr
1               5

<210> SEQ ID NO 307
<211> LENGTH: 8
<212> TYPE: PRT
<213> ORGANISM: Artificial Sequence
<220> FEATURE:
<223> OTHER INFORMATION: Synthetic

<400> SEQUENCE: 307

Gln Gln Arg Ala Asn Trp Pro Thr
1               5

<210> SEQ ID NO 308
<211> LENGTH: 123
<212> TYPE: PRT
<213> ORGANISM: Artificial Sequence
<220> FEATURE:
<223> OTHER INFORMATION: Synthetic

<400> SEQUENCE: 308

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
        115                 120

<210> SEQ ID NO 309
<211> LENGTH: 106
<212> TYPE: PRT
<213> ORGANISM: Artificial Sequence
<220> FEATURE:
<223> OTHER INFORMATION: Synthetic

<400> SEQUENCE: 309

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

```
Leu Ala Trp Tyr Gln Gln Lys Pro Gly Gln Ala Pro Arg Leu Leu Ile
            35                  40                  45

Tyr Asp Ala Ser Asn Arg Ala Pro Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 310
<211> LENGTH: 123
<212> TYPE: PRT
<213> ORGANISM: Artificial Sequence
<220> FEATURE:
<223> OTHER INFORMATION: Synthetic

<400> SEQUENCE: 310

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Arg Gly Ser Pro Phe Gly Met Asp Val
            100                 105                 110

Trp Gly Gln Gly Thr Thr Val Thr Val Ser Ser
        115                 120

<210> SEQ ID NO 311
<211> LENGTH: 106
<212> TYPE: PRT
<213> ORGANISM: Artificial Sequence
<220> FEATURE:
<223> OTHER INFORMATION: Synthetic

<400> SEQUENCE: 311

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
```

100                 105

<210> SEQ ID NO 312
<211> LENGTH: 123
<212> TYPE: PRT
<213> ORGANISM: Artificial Sequence
<220> FEATURE:
<223> OTHER INFORMATION: Synthetic

<400> SEQUENCE: 312

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe Arg Phe Val Ser Gly Ser Pro Phe Gly Met Asp Val
            100                 105                 110

Trp Gly Gln Gly Thr Thr Val Thr Val Ser Ser
        115                 120

<210> SEQ ID NO 313
<211> LENGTH: 106
<212> TYPE: PRT
<213> ORGANISM: Artificial Sequence
<220> FEATURE:
<223> OTHER INFORMATION: Synthetic

<400> SEQUENCE: 313

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 314
<211> LENGTH: 123
<212> TYPE: PRT
<213> ORGANISM: Artificial Sequence
<220> FEATURE:
<223> OTHER INFORMATION: Synthetic

<400> SEQUENCE: 314

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Leu Phe Gly Lys Ala His Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
            115                 120

<210> SEQ ID NO 315
<211> LENGTH: 106
<212> TYPE: PRT
<213> ORGANISM: Artificial Sequence
<220> FEATURE:
<223> OTHER INFORMATION: Synthetic

<400> SEQUENCE: 315

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 316
<211> LENGTH: 123
<212> TYPE: PRT
<213> ORGANISM: Artificial Sequence
<220> FEATURE:
<223> OTHER INFORMATION: Synthetic

<400> SEQUENCE: 316

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys

```
                    85                  90                  95
Ala Arg Lys Phe His Phe Val Ser Gly Ser Pro Phe Gly Met Asp Val
               100                 105                 110

Trp Gly Gln Gly Thr Thr Val Thr Val Ser Ser
           115                 120

<210> SEQ ID NO 317
<211> LENGTH: 106
<212> TYPE: PRT
<213> ORGANISM: Artificial Sequence
<220> FEATURE:
<223> OTHER INFORMATION: Synthetic

<400> SEQUENCE: 317

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ala Asn Trp Pro Thr
                85                  90                  95

Phe Gly Gln Gly Thr Lys Val Glu Ile Lys
            100                 105

<210> SEQ ID NO 318
<211> LENGTH: 123
<212> TYPE: PRT
<213> ORGANISM: Artificial Sequence
<220> FEATURE:
<223> OTHER INFORMATION: Synthetic

<400> SEQUENCE: 318

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
               100                 105                 110

Trp Gly Gln Gly Thr Thr Val Thr Val Ser Ser
           115                 120

<210> SEQ ID NO 319
<211> LENGTH: 106
<212> TYPE: PRT
<213> ORGANISM: Artificial Sequence
<220> FEATURE:
```

<223> OTHER INFORMATION: Synthetic

<400> SEQUENCE: 319

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Met Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 320
<211> LENGTH: 123
<212> TYPE: PRT
<213> ORGANISM: Artificial Sequence
<220> FEATURE:
<223> OTHER INFORMATION: Synthetic

<400> SEQUENCE: 320

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
        115                 120

<210> SEQ ID NO 321
<211> LENGTH: 106
<212> TYPE: PRT
<213> ORGANISM: Artificial Sequence
<220> FEATURE:
<223> OTHER INFORMATION: Synthetic

<400> SEQUENCE: 321

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ser Trp Tyr Gln Gln Lys Pro Gly Gln Ala Pro Arg Leu Leu Ile
        35                  40                  45

Tyr Asp Ala Ser Asn Arg Ala Pro Gly Ile Pro Ala Arg Phe Ser Gly

```
                    50                  55                  60
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Thr
                 85                  90                  95

Phe Gly Gln Gly Thr Lys Val Glu Ile Lys
            100                 105

<210> SEQ ID NO 322
<211> LENGTH: 123
<212> TYPE: PRT
<213> ORGANISM: Artificial Sequence
<220> FEATURE:
<223> OTHER INFORMATION: Synthetic

<400> SEQUENCE: 322

Gln Val Gln Leu Val Gln Ser Gly Ala Glu Val Lys Lys Pro Gly Ser
 1               5                  10                  15

Ser Val Lys Val Ser Cys Lys Thr Ser Gly Asp Thr Phe Ser Thr Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Lys Ala His Tyr Ala Gln Lys Phe
        50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
        115                 120

<210> SEQ ID NO 323
<211> LENGTH: 106
<212> TYPE: PRT
<213> ORGANISM: Artificial Sequence
<220> FEATURE:
<223> OTHER INFORMATION: Synthetic

<400> SEQUENCE: 323

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Met Ala Trp Tyr Gln Gln Lys Pro Gly Gln Ala Pro Arg Leu Leu Ile
            35                  40                  45

Tyr Asp Ala Ser Asn Arg Ala Glu Gly Ile Pro Ala Arg Phe Ser Gly
        50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ala Asn Trp Pro Thr
                 85                  90                  95

Phe Gly Gln Gly Thr Lys Val Glu Ile Lys
            100                 105

<210> SEQ ID NO 324
<211> LENGTH: 123
```

```
<212> TYPE: PRT
<213> ORGANISM: Artificial Sequence
<220> FEATURE:
<223> OTHER INFORMATION: Synthetic

<400> SEQUENCE: 324

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
            115                 120

<210> SEQ ID NO 325
<211> LENGTH: 106
<212> TYPE: PRT
<213> ORGANISM: Artificial Sequence
<220> FEATURE:
<223> OTHER INFORMATION: Synthetic

<400> SEQUENCE: 325

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Glu Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 326
<211> LENGTH: 123
<212> TYPE: PRT
<213> ORGANISM: Artificial Sequence
<220> FEATURE:
<223> OTHER INFORMATION: Synthetic

<400> SEQUENCE: 326

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
```

```
                      35                  40                  45
Gly Gly Ile Ile Pro Leu Phe Gly Lys Ala His Tyr Ala Gln Lys Phe
         50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Lys Phe His Phe Val Ser Gly Ser Pro Phe Gly Met Asp Val
                100                 105                 110

Trp Gly Gln Gly Thr Thr Val Thr Val Ser Ser
            115                 120

<210> SEQ ID NO 327
<211> LENGTH: 106
<212> TYPE: PRT
<213> ORGANISM: Artificial Sequence
<220> FEATURE:
<223> OTHER INFORMATION: Synthetic

<400> SEQUENCE: 327

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Pro Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Thr
                 85                  90                  95

Phe Gly Gln Gly Thr Lys Val Glu Ile Lys
                100                 105

<210> SEQ ID NO 328
<211> LENGTH: 123
<212> TYPE: PRT
<213> ORGANISM: Artificial Sequence
<220> FEATURE:
<223> OTHER INFORMATION: Synthetic

<400> SEQUENCE: 328

Gln Val Gln Leu Val Gln Ser Gly Ala Glu Val Lys Lys Pro Gly Ser
 1               5                  10                  15

Ser Val Lys Val Ser Cys Lys Thr Ser Gly Asp Thr Phe Ser Thr Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Lys Ala His Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Lys Phe His Phe Val Arg Gly Ser Pro Phe Gly Met Asp Val
                100                 105                 110
```

```
Trp Gly Gln Gly Thr Thr Val Thr Val Ser Ser
        115                 120
```

<210> SEQ ID NO 329
<211> LENGTH: 106
<212> TYPE: PRT
<213> ORGANISM: Artificial Sequence
<220> FEATURE:
<223> OTHER INFORMATION: Synthetic

<400> SEQUENCE: 329

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Pro Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105
```

<210> SEQ ID NO 330
<211> LENGTH: 123
<212> TYPE: PRT
<213> ORGANISM: Artificial Sequence
<220> FEATURE:
<223> OTHER INFORMATION: Synthetic

<400> SEQUENCE: 330

```
Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Leu Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Arg Gly Ser Pro Phe Gly Met Asp Val
            100                 105                 110

Trp Gly Gln Gly Thr Thr Val Thr Val Ser Ser
        115                 120
```

<210> SEQ ID NO 331
<211> LENGTH: 106
<212> TYPE: PRT
<213> ORGANISM: Artificial Sequence
<220> FEATURE:
<223> OTHER INFORMATION: Synthetic

<400> SEQUENCE: 331

```
Glu Ile Val Leu Thr Gln Ser Pro Ala Thr Leu Ser Leu Ser Pro Gly
```

```
1               5                    10                    15
Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
            50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
                100                 105
```

BISPECIFIC ANTIBODIES TARGETING HUMAN CLAUDIN 18.2 AND PROGRAMMED DEATH-LIGAND 1 (PD-L1)

CROSS REFERENCE TO RELATED APPLICATIONS

This application claims the benefit of the filing date of U.S. Provisional Application No. 63/040,698, filed Jun. 18, 2020, the entire contents of which are incorporated by reference herein.

SEQUENCE LISTING

The application contains a Sequence Listing that has been filed electronically in the form of a text file, created Jun. 14, 2021, and named "112124-0013-70000US01_SEQ.TXT" (495,523 bytes), the contents of which are incorporated by reference herein in their entirety.

BACKGROUND OF THE INVENTION

Claudin 18 (CLDN 18.2) belongs to the claudin family, which has at least 27 members in mammals (Furuse M. et al., J Cell Biol., 1998, 141, 1539). Claudin 18 has two different splice variants, Claudin 18.1 or CLDN 18.1 and Claudin 18.2 or CLDN 18.2. Sanada Y. et al., J Pathol., 2006, 208, 633). CLDN 18.2 is a CD20-like differentiation protein overly expressed in various types of cancers, for example, gastric, esophageal, pancreatic, and non-small cell lung cancers. This molecule therefore is a valuable target for treatment of such cancers.

Programmed death-ligand 1 (PD-L1), a.k.a., cluster differentiation 274 (CD274) or B7 homolog 1 (B7-H1), is a cell surface receptor that plays a major role in immune suppression. PD-L1 binds its receptor PD-1, often expressed on activated T cells, B cells, and myeloid cells, to modulate immune system activation or suppression. PD-L1 is found to express on tumor cells, allowing for the tumor cells to evade the host immune system. Various PD-L1 inhibitors have been developed as immune-oncology therapies and showed good results in clinical settings.

SUMMARY OF THE INVENTION

The present disclosure is based, at least in part, on the development of superior anti-CLDN 18.2 antibodies and bispecific antibodies capable of binding to both CLDN 18.2 and PD-L1. Such antibodies showed improved binding affinity to CLDN 18.2 while retaining the binding to PD-L1. The bispecific antibodies also showed the same binding affinity at relatively low pH as compared to physiological pH, preserving binding affinity in the low pH tumor microenvironment. Such antibodies also demonstrated improved level of expression, minimal aggregation, and straightforward purification. Accordingly, the antibodies disclosed herein would be effective in treating diseases associated CLDN 18.2+ cells (e.g., cancer).

Accordingly, the present disclosure features, in some aspect, a bispecific antibody, comprising a first antigen-binding moiety that binds human claudin 18.2, and a second antigen-binding moiety that binds human PD-L1. The first antigen-binding moiety comprises: (a) a first heavy chain variable domain ($V_H$), which comprises the same heavy chain complementary determining regions (CDRs) as a reference anti-claudin 18.2 antibody; and (b) a first light chain variable domain ($V_L$), which comprises the same light chain CDRs as the reference anti-claudin 18.2 antibody. The reference anti-claudin 18.2 antibody can be 5C9ob, 5C9oap, 9O24, 9O41, 9O47, 9O36, 9O45, 9O51, 5C9oap-ob, 9O24-ob, 9O47-ob, 9O45-ob, 9O36-ob, 9O41-ob, 5C9oap-oac, 9O24-oac, 9O47-oac, 9O36-oac, 9O41-oac, 9O47HN, or 9O41HN.

In some embodiment, the second antigen-binding moiety that binds PD-L1 comprises: (a) a second $V_H$, which comprises the same heavy chain complementary determining regions (CDRs) as a reference anti-PD-L1 antibody; and (b) a second light chain variable domain ($V_L$), which comprises the same light chain CDRs as the reference anti-PD-L1 antibody. The reference anti-PD-L1 antibody may be durvalumab, atezolizumab, avelumab, or a 12A4 antibody (see Sequence Table 2).

In some examples, the first $V_H$ is the same as the $V_H$ chain of the reference anti-claudin 18.2 antibody, and/or the first $V_L$ is the same as the $V_L$ of the reference anti-claudin 18.2 antibody. Alternatively or in addition, the second $V_H$ is the same as the $V_H$ chain of the reference anti-PD-L1 antibody, and/or the second $V_L$ is the same as the $V_L$ of the reference anti-PD-L1 antibody.

In some embodiments, the bispecific antibody is in a one-chain format, where the first antigen-binding moiety and the second antigen-binding moiety are located on a single polypeptide. In some examples, the single polypeptide comprises, from N-terminus to C-terminus: (i) a first variable region fragment, which is the first $V_H$, the first $V_L$, the second $V_H$, or the second $V_L$; (ii) a first peptide linker (L1); (iii) a second variable region fragment, which is the first $V_H$, the first $V_L$, the second $V_H$, or the second $V_L$; (iv) a second peptide linker (L2); (v) a third variable region fragment, which is which is the first $V_H$, the first $V_L$, the second $V_H$, or the second $V_L$; (vi) a third peptide linker (L3); and (vii) a fourth variable region fragment, which is which is the first $V_H$, the first $V_L$, the second $V_H$, or the second $V_L$. The first variable region fragment, the second variable region fragment, the third variable region fragment, and the fourth variable region fragment collectively (as a whole) comprises all of the first $V_H$, the first $V_L$, the second $V_H$, and the second $V_L$. Optionally, the single polypeptide may further comprise a C-terminal fragment (e.g., an Fc fragment of an immunoglobulin molecule such as IgG), which may be linked to the fourth variable region fragment via a fourth peptide linker (L4). The L4, the C-terminal fragment, or both may comprise one or more cysterine residues for formation of disulfide bonds. Any of the peptide linkers may be a G/S rich peptide linker.

In some examples, L1 may comprise the motif of $X_1X_2X_3X_4X_5X_6$, in which:
$X_1$ represents Glycine (G), Serine (S), or absent;
$X_2$ represents Glycine (G), Serine (S), or absent;
$X_3$ represents Glycine (G), or Serine (S);
$X_4$ represents Glycine (G), Arginine (R), or Serine (S);
$X_5$ represents Glycine (G), or Serine (S); and
$X_6$ represents Glycine (G), or Serine (S);
In specific examples, $X_1$ can be absent, $X_2$ can be absent, $X_3$ can be G, $X_4$ can be G, $X_5$ can be G, $X_6$ can be G, or any combination thereof.

In some examples, $L_2$ may comprise the motif of $X_1X_2X_3X_4X_5X_6X_7X_8X_9X_{10}X_{11}X_{12}X_{13}X_{14}X_5X_{16}X_7X_{18}X_{19}X_{20}$, in which:
$X_1$ represents Glycine (G), or Serine (S);
$X_2$ represents Glycine (G), or Serine (S);
$X_3$ represents Glycine (G), or Serine (S);
$X_4$ represents Glycine (G), Serine (S), or Arginine (R);
$X_5$ represents Glycine (G), Serine (S), or Arginine (R);

$X_6$ represents Glycine (G), or Serine (S);
$X_7$ represents Glycine (G), or Serine (S);
$X_8$ represents Glycine (G) or absent;
$X_9$ represents Glycine (G) or absent;
$X_{10}$ represents Glycine (G) or absent;
$X_{11}$ represents Glycine (G), or Serine (S), or absent;
$X_{12}$ represents Glycine (G), Serine (S), Arginine (R), or absent;
$X_{13}$ represents Glycine (G), Serine (S), or Arginine (R);
$X_{14}$ represents Glycine (G), or Serine (S);
$X_{15}$ represents Glycine (G), or Serine (S);
$X_{16}$ represents Glycine (G), Serine (S), or Arginine (R);
$X_{17}$ represents Glycine (G), Serine (S), Asparagine (N), or Arginine (R);
$X_{18}$ represents Glycine (G), or Serine (S);
$X_{19}$ represents Glycine (G), or Serine (S); and
$X_{20}$ represents Glycine (G), or Serine (S).

In specific examples, at least one of $X_1$-$X_{20}$ is G. In other specific examples, each of $X_1$-$X_{20}$ independently, is G.

In some examples, $L_3$ may comprise the motif of $X_1X_2X_3X_4X_5X_6$, in which
$X_1$ represents Glycine (G), Serine (S), or absent;
$X_2$ represents Glycine (G), Serine (S), or absent;
$X_3$ represents Glycine (G), or Serine (S);
$X_4$ represents Glycine (G), Arginine (R), or Serine (S);
$X_5$ represents Glycine (G), or Serine (S); and
$X_6$ represents Glycine (G), or Serine (S).

In specific examples, $X_1$ can be G; $X_2$ can be S; $X_3$ can be G; $X_4$ can be G; $X_5$ can be G; $X_6$ can be G, or any combination thereof.

In some examples, the $L_1$-$L_3$ peptide linkers comprise the amino acid sequences of SEQ ID NOs: 121, 122, and 121, respectively. In some examples, the $L_1$-$L_3$ peptide linkers comprise the amino acid sequences of SEQ ID NOs: 121, 123, and 121, respectively. In some examples, the $L_1$-$L_3$ peptide linkers comprise the amino acid sequences of SEQ ID NOs: 124, 125, and 126, respectively. In some examples, the $L_1$-$L_3$ peptide linkers comprise the amino acid sequences of SEQ ID NOs: 121, 127, and 121, respectively. In some examples, the $L_1$-$L_3$ peptide linkers comprise the amino acid sequences of SEQ ID NOs: 121, 128, and 129, respectively. In some examples, the $L_1$-$L_3$ peptide linkers comprise the amino acid sequences of SEQ ID NOs: 121, 130, and 121, respectively. In some examples, the $L_1$-$L_3$ peptide linkers comprise the amino acid sequences of SEQ ID NOs: 131, 132, and 133, respectively. In some examples, the $L_1$-L3 peptide linkers comprise the amino acid sequences of SEQ ID NOs: 134, 135, and 126, respectively. In some examples, the $L_1$-$L_3$ peptide linkers comprise the amino acid sequences of SEQ ID NOs: 134, 136, and 137, respectively. In some examples, the $L_1$-L3 peptide linkers comprise the amino acid sequences of SEQ ID NOs: 134, 138, and 139, respectively. In some examples, the $L_1$-$L_3$ peptide linkers comprise the amino acid sequences of SEQ ID NOs: 140, 122, and 141 respectively. In some examples, the $L_1$-$L_3$ peptide linkers comprise the amino acid sequences of SEQ ID NOs: 124, 142, and 143, respectively. In some examples, the $L_1$-$L_3$ peptide linkers comprise the amino acid sequences of SEQ ID NOs: 124, 144, and 143, respectively. In some examples, the $L_1$-$L_3$ peptide linkers comprise the amino acid sequences of SEQ ID NOs: 145, 146, and 147, respectively. In some examples, the $L_1$-$L_3$ peptide linkers comprise the amino acid sequences of SEQ ID NOs: 145, 148, and 149, respectively. In some examples, the $L_1$-$L_3$ peptide linkers comprise the amino acid sequences of SEQ ID NOs: 150, 125, and 151, respectively. In some examples, the $L_1$-L3 peptide linkers comprise the amino acid sequences of SEQ ID NOs: 152, 153, and 154, respectively. In some examples, the $L_1$-L3 peptide linkers comprise the amino acid sequences of SEQ ID NOs: 155, 156, and 133, respectively. In some examples, the $L_1$-L3 peptide linkers comprise the amino acid sequences of SEQ ID NOs: 157, 158, and 121, respectively. In some examples, the $L_1$-L3 peptide linkers comprise the amino acid sequences of SEQ ID NOs: 159, 160, and 161, respectively. In some examples, the $L_1$-L3 peptide linkers comprise the amino acid sequences of SEQ ID NOs: 141, 162, and 163, respectively.

In some embodiments, a disulfide bond is formed between a variable region of the first antigen-binding moiety and a variable region in the second antigen-binding moiety. For example, the disulfide bond is formed between the first $V_L$ and the second $V_L$, or between the first $V_H$ and the second $V_H$.

In some examples, the first $V_L$ or the second $V_L$ in the bispecific antibody disclosed herein contains C at position 43 (C43) and the first $V_H$ or the second $V_H$ contains C at position 105 (C105) corresponding to the Kabat numbering. A disulfide bond is formed between C43 in the first $V_L$ and C105 in the first $V_H$. Alternatively, a disulfide bond is formed between C43 in the second $V_L$ and C105 in the second $V_H$.

In some examples, the first $V_L$ or the second $V_L$ in the bispecific antibody disclosed herein contains C at position 100 (C100) and the first $V_H$ or the second $V_H$ contains C at position 44 (C44) corresponding to the Kabat numbering. A disulfide bond is formed between C100 in the first $V_L$ and C44 in the first $V_H$. Alternatively, a disulfide bond is formed between C100 in the second $V_L$ and C44 in the second $V_H$.

In some examples, the first $V_H$ in the bispecific antibody contains C at position 3 (C3) or position 9 (C9) and the second $V_{11}$ contains C at position 42 (C42) or position 112 (C112) corresponding to the Kabat numbering. Alternatively, the second $V_H$ in the bispecific antibody contains C at position 3 (C3) or position 9 (C9) and the first $V_H$ contains C at position 42 (C42) or position 112 (C112) corresponding to the Kabat numbering. A disulfide bond can be formed between C3 and C42, between C9 and C112, or both.

In some examples, the first $V_L$ in the bispecific antibody contains C at position 43 (C43) and the first $V_H$ contains C at position 105 (C105) corresponding to the Kabat numbering. A disulfide bond is formed between C43 and C105.

In some examples, the second $V_L$ in the bispecific antibody contains C at position 43 (C43) and the second $V_H$ contains C at position 105 (C105) corresponding to the Kabat numbering. A disulfide bond is formed between C43 and C105.

In some examples, the second $V_H$ in the bispecific antibody contains C at position 3 (C3) and the first $V_H$ contains C at position 42 (C42) corresponding to the Kabat numbering. A disulfide bond is formed between C3 and C42.

In some examples, the second $V_H$ in the bispecific antibody contains C at position 9 (C9) and the first $V_H$ contains C at position 112 (C112) corresponding to the Kabat numbering. A disulfide bond is formed between C9 and C112.

In some examples, the second $V_H$ in the bispecific antibody contains C at position 44 (C44) and the second $V_L$ contains C at position 100 (C100) corresponding to the Kabat numbering. A disulfide bond is formed between C44 and C100.

In some examples, the first $V_H$ in the bispecific antibody contains C at position 44 (C44) and the first $V_L$ contains C at position 100 (C100) corresponding to the Kabat numbering. A disulfide bond is formed between C44 and C100.

In some examples, the second $V_H$ in the bispecific antibody contains C at positon 105 (C105) and the second $V_L$ contains C at position 43 (C43) corresponding to the Kabat numbering.

A disulfide bond is formed between C105 and C43.

In some examples, the first $V_H$ in the bispecific antibody contains C at position 105 (C105) and the first $V_L$ contains C at position 43 (C43) corresponding to the Kabat numbering. A disulfide bond is formed between C105 and C43.

In some embodiments, the $V_L$ of the antigen-binding moiety that binds claudin 18.2 may comprise the amino acid sequence of: DIQMTQSPSSLSASVGDRVTITCK SSQSLLNX$_1$GNQKSYLTWYQQKPGKX$_2$PKLLIYWAST LX$_3$SGVPSRFSGSGSGTDYTLTISSLQPEDFATYYCQ NAYFFPFTFGX$_4$GTKVEIK (SEQ ID NO 167), In this sequence, $X_1$ represents Serine (S), or Tryptophan (W); $X_2$ represents Alanine (A), or Cysteine (C); $X_3$ represents Glutamic acid (E), or Glutamine (Q); and $X_4$ represents Glutamine (Q), or Cysteine (C). In some examples, $X_1$ is S, $X_2$ is A, $X_3$ is E, $X_4$ is Q, or any combination thereof.

In other embodiments, the $V_L$ of the antigen-binding moiety that binds claudin 18.2 may comprise the amino acid sequence of: DIQMTQSPSSLSASVGDRVTITCK-SSQSLLNSGNQKSYLTWYQQKPGKX$_i$PKLLIYWASTL ESGVPSRFSGSGSGTDYTLTISSLQPEDFA-TYYCQNAYFFPFTFX$_2$ (SEQ ID NO: 169). In this sequence, $X_1$ represents Alanine (A), or Cysteine (C); $X_2$ represents Glutamine (Q), or Cysteine (C).

Alternatively or in addition, the $V_H$ of the antigen-binding moiety that binds claudin 18.2 may comprise the amino acid sequence of: EVQLVESGGGLVQPGGSLRLSC AVSGYTFSMNWVRQAPX$_1$KX$_2$LEWVAWINMYT GEX$_3$T YADDFKGRFTISRDDSKNTLYLQM NSLRAEDTAVYYCARLYNGNSLDYWGX$_4$GTLV TVX$_5$S (SEQ ID NO 166), in which $X_1$ represents Glycine (G), or Cysteine (C); $X_2$ represents Glycine (G), or Cysteine (C); $X_3$ represents Proline (P) or Arginine (R); $X_4$ represents Glutamine (Q), or Cysteine (C); and $X_5$ represents Serine (S), or Cysteine (C). In some examples, $X_1$ is G; $X_2$ is G; $X_3$ is P; $X_4$ is Q; $X_5$ is S, or any combination thereof.

In other embodiments, the $V_H$ of the antigen-binding moiety that binds claudin 18.2 may comprise the amino acid sequence of: EVQLVESGGGLVQPGGSL RLSCAVSGYTFSMNWVRQAPX$_1$KX$_2$LEWVAWINMY TGEPTY ADDFKGRFTISRDDSKNTLYLQ MNSLRAEDTAVYYCARLYNGNSLDYWGX$_3$GTLV TVX$_4$S (SEQ ID NO 168), in which $X_1$ is Glycine (G), or Cysteine (C); $X_2$ is Glycine (G) or Cysteine (C), $X_3$ represents amino acid residues Glutamine (Q), or Cysteine (C); and $X_3$ represents amino acid residues Serine (S), or Cysteine (C).

Alternatively or in addition, the $V_L$ of the antigen-binding moiety that binds PD-L1 comprises the amino acid sequence of: EIVLTQSPGTLSLSPGERATLSCRASQRVSSSY LAWYQQKPGQX$_1$PRLLIYDASSRATGIPD RFSGSGSGTDFTLTISRLEPEDFAVYYCQQYGSLPW TFGX$_2$GTKVEIK (SEQ ID NO 171), in which $X_1$ represents Alanine (A), or Cysteine (C); and $X_2$ represents Glutamine (Q), or Cysteine (C). In some examples, $X_1$ is A, $X_2$ is Q, or a combination thereof.

Alternatively or in addition, the $V_H$ of the antigen-binding moiety that binds PD-L1 comprises the amino acid sequence of: EVX$_1$LVESGX$_2$GLVQPGGSLRLSCA ASGFTFSRYWMSWVRQAPGKX$_3$LEWVANIKQDGSE KYYVDSVKGRFTISRDNAKNSLYLQMNSLRAED-TAVYYCAREGGWFGELAFDYWG X$_4$GTLVTVSS (SEQ ID NO 170), in which $X_1$ represents Glutamine (Q), or Cysteine (C); $X_2$ represents Glycine (G), or Cysteine (C); $X_3$ represents amino acid residues Glycine (G), or Cysteine (C); and $X_4$ represents Glutamine (Q), or Cysteine (C). In some examples, $X_1$ is Q, $X_2$ is G, $X_3$ is G, $X_4$ is Q, or any combination thereof.

Exemplary one-chain bispecific antibodies disclosed herein may comprise the amino acid sequence of SEQ ID NOs: 172, 173, 174, 175, 176, 177, 178, 179, 180, 181, 182, 183, 184, 185, 186, 187, 188, 189, 190, 191, 192, 193, 194, 195, 196, 197, 198, 199, 200, or 201.

In some embodiments, the bispecific antibody disclosed herein is in a two-chain format comprising a first polypeptide and a second polypeptide, each of which comprises one variable region of the first antigen-binding moiety and one variable region of the second antigen-binding moiety. In some examples, such a bispecific antibody may comprise (a) a first polypeptide comprises, from N-terminus to C-terminus, the first $V_L$, a first peptide linker (L1), the second $V_H$, and optionally a second peptide linker (L2); and (b) the second polypeptide comprises, from N-terminus to C-terminus, the second $V_L$, a third peptide linker (L3), and the first $V_H$, and optionally a fourth peptide linker (L4). In other examples, the bispecific antibody may comprise (a) a first polypeptide comprises, from N-terminus to C-terminus, the first $V_H$, a first peptide linker (L1), the second $V_L$, and optionally a second peptide linker (L2); and (b) a second polypeptide comprises, from N-terminus to C-terminus, the second $V_H$, a third peptide linker (L3), the first $V_L$, and optionally a fourth peptide linker (L4). In some instances, the first polypeptide further comprises a first C-terminal fragment, which may be linked to the second $V_L$ via the L2 linker. The second polypeptide further comprises a second C-terminal fragment, which may be linked to the second $V_H$ via the L4 linker. The first C-terminal fragment and the second C-terminal fragment form a dimer.

In some examples, the first C-terminal fragment is a first Fc fragment of a first IgG molecule. The second C-terminal fragment is a second Fc fragment of a second IgG molecule. The first Fc fragment and the second Fc fragment form an IgG Fc region. In some examples, the first Fc fragment comprising a first CH2 domain and a first CH3 domain, and the second Fc fragment comprises a second CH2 domain and a second CH3 domain. Either the first CH2 and the second CH2 domains each comprise an amino acid modification relative to a wild-type counterpart to form a knob and a hole. Alternatively, the first CH3 and the second CH3 domains each comprise an amino acid modification relative to a wild-type counterpart to form a knob and a hole.

In some examples, the $L_1$-$L_4$ peptide linkers in a two-chain bispecific antibody as disclosed herein may comprise the amino acid sequences of SEQ ID NOs: 121, 164, 121 and 164, respectively. In specific examples, the first polypeptide and second polypeptide comprise the amino acid sequences of SEQ ID NO: 202 and 203, SEQ ID NOs: 204 and 205, or SEQ ID NOs: 206 and 207, respectively. In other examples, the first polypeptide and the second polypeptide comprise the amino acid sequences of SEQ ID NOs:279 and 280, respectively; or the amino acid sequences of SEQ ID NOs: 289 and 290, respectively.

In other aspects, the present disclosures features an isolated antibody, which specifically binds to CLDN 18.2. In some embodiments, the antibody comprises: a light chain variable region (VL) comprising a light chain complementary determining region 1 (VL-CDR1), a light chain CDR2 (VL-CDR2), a light chain CDR3 (VL-CDR3); and a heavy chain variable region (VH) comprising a heavy chain CDR1 (VH-CDR1), a heavy chain CDR2 (VH-CDR2), and a heavy chain CDR3 (VH-CDR3).

The VL-CDR1 comprises the amino acid sequence of KSSQSLLNXIGNX$_2$KSYLT (SEQ ID NO: 274), in which X$_1$ is S, T, Y, F, or W; and X$_2$ is Q, N, W, F, Y, I, M, or V. In some examples, X$_1$ can be S or W, X$_2$ can be Q, I, or W, or any combination thereof. The VL-CDR2 comprises the amino acid sequence of WASTLX$_3$S (SEQ ID NO: 275), in which X$_3$ is any amino acid residue. In some instances, X$_3$ is E, F, M, Q, R, V, or Y. The VL-CDR3 comprises the amino acid sequence of QNAYX$_4$FPFT (SEQ ID NO: 276), in which X$_4$ is S, T, F, Y, or W. In some instances, X$_4$ is F or S.

The VH-CDR1 comprises the amino acid sequence of GYTFSMN (SEQ ID NO: 10). The VH-CDR2 comprises the amino acid sequence of WINMYTGX$_5$X$_6$X$_7$YADDFKG (SEQ ID NO: 277), in which X$_5$ E, D, K, H, or R, T; X$_6$ is P, K, R, H, T, or S; and X$_7$ is S, T, I, L, or V. In some instances, X$_5$ is E or R; X$_6$ is K, P, R, or T; and X$_7$ is T or I, or any combination thereof. The VH-CDR3 comprises the amino acid sequence of LYX$_8$GNSLDY (SEQ ID NO: 278), in which X$_8$ is N, Q, K, R, or H. In some instances, X$_8$ is N or R.

In some examples, the VL-CDR1, VL-CRD2, VL-CDR3, VH-CDR1, VH-CDR2, and VH-CDR3, respectively, comprises the amino acid sequences of SEQ ID NOs: 6, 12, 14, 10, 3, and 4.

In some examples, the VL-CDR1, VL-CRD2, VL-CDR3, VH-CDR1, VH-CDR2, and VH-CDR3, respectively, comprises the amino acid sequences of SEQ ID NOs: 6, 12, 14, 10, 3, and 18.

In some examples, the VL-CDR1, VL-CRD2, VL-CDR3, VH-CDR1, VH-CDR2, and VH-CDR3, respectively, comprises the amino acid sequences of SEQ ID NOs: 24, 25, 8, 10, 22, and 4.

In some examples, the VL-CDR1, VL-CRD2, VL-CDR3, VH-CDR1, VH-CDR2, and VH-CDR3, respectively, comprises the amino acid sequences of SEQ ID NOs: 31, 32, 8, 10, 29, and 4.

In some examples, the VL-CDR1, VL-CRD2, VL-CDR3, VH-CDR1, VH-CDR2, and VH-CDR3, respectively, comprises the amino acid sequences of SEQ ID NOs: 24, 36, 8, 10, 3, and 4.

In some examples, the VL-CDR1, VL-CRD2, VL-CDR3, VH-CDR1, VH-CDR2, and VH-CDR3, respectively, comprises the amino acid sequences of SEQ ID NOs: 40, 41, 8, 10, 22, and 4.

In some examples, the VL-CDR1, VL-CRD2, VL-CDR3, VH-CDR1, VH-CDR2, and VH-CDR3, respectively, comprises the amino acid sequences of SEQ ID NOs: 24, 47, 8, 10, 45, and 4.

In some examples, the VL-CDR1, VL-CRD2, VL-CDR3, VH-CDR1, VH-CDR2, and VH-CDR3, respectively, comprises the amino acid sequences of SEQ ID NOs: 24, 53, 8, 10, 51, and 4.

In some examples, the VL-CDR1, VL-CRD2, VL-CDR3, VH-CDR1, VH-CDR2, and VH-CDR3, respectively, comprises the amino acid sequences of SEQ ID NOs: 6, 12, 14, 10, 57, and 4.

In some examples, the VL-CDR1, VL-CRD2, VL-CDR3, VH-CDR1, VH-CDR2, and VH-CDR3, respectively, comprises the amino acid sequences of SEQ ID NOs: 24, 25, 14, 10, 22, and 4.

In some examples, the VL-CDR1, VL-CRD2, VL-CDR3, VH-CDR1, VH-CDR2, and VH-CDR3, respectively, comprises the amino acid sequences of SEQ ID NOs: 31, 32, 14, 10, 29, and 4.

In some examples, the VL-CDR1, VL-CRD2, VL-CDR3, VH-CDR1, VH-CDR2, and VH-CDR3, respectively, comprises the amino acid sequences of SEQ ID NOs: 24, 66, 14, 10, 51, and 4.

In some examples, the VL-CDR1, VL-CRD2, VL-CDR3, VH-CDR1, VH-CDR2, and VH-CDR3, respectively, comprises the amino acid sequences of SEQ ID NOs: 24, 47, 14, 10, 45, and 4.

In some examples, the VL-CDR1, VL-CRD2, VL-CDR3, VH-CDR1, VH-CDR2, and VH-CDR3, respectively, comprises the amino acid sequences of SEQ ID NOs: 24, 36, 14, 10, 3, and 4.

In some examples, the VL-CDR1, VL-CRD2, VL-CDR3, VH-CDR1, VH-CDR2, and VH-CDR3, respectively, comprises the amino acid sequences of SEQ ID NOs: 40, 41, 14, 10, 22, and 4.

In some examples, the VL-CDR1, VL-CRD2, VL-CDR3, VH-CDR1, VH-CDR2, and VH-CDR3, respectively, comprises the amino acid sequences of SEQ ID NOs: 24, 25, 14, 10, 22, and 18.

In some examples, the VL-CDR1, VL-CRD2, VL-CDR3, VH-CDR1, VH-CDR2, and VH-CDR3, respectively, comprises the amino acid sequences of SEQ ID NOs: 31, 32, 14, 10, 29, and 18.

In some examples, the VL-CDR1, VL-CRD2, VL-CDR3, VH-CDR1, VH-CDR2, and VH-CDR3, respectively, comprises the amino acid sequences of SEQ ID NOs: 24, 53, 14, 10, 51, and 18.

In some examples, the VL-CDR1, VL-CRD2, VL-CDR3, VH-CDR1, VH-CDR2, and VH-CDR3, respectively, comprises the amino acid sequences of SEQ ID NOs: 24, 47, 14, 10, 45, and 18.

In some examples, the VL-CDR1, VL-CRD2, VL-CDR3, VH-CDR1, VH-CDR2, and VH-CDR3, respectively, comprises the amino acid sequences of SEQ ID NOs: 107, 108, 5, 11, 109, and 168.

In some examples, the VL-CDR1, VL-CRD2, VL-CDR3, VH-CDR1, VH-CDR2, and VH-CDR3, respectively, comprises the amino acid sequences of SEQ ID NOs: 24, 36, 14, 10, 3, and 18.

In some examples, the VL-CDR1, VL-CRD2, VL-CDR3, VH-CDR1, VH-CDR2, and VH-CDR3, respectively, comprises the amino acid sequences of SEQ ID NOs: 40, 41, 14, 10, 22, and 18.

In some examples, the VL-CDR1, VL-CRD2, VL-CDR3, VH-CDR1, VH-CDR2, and VH-CDR3, respectively, comprises the amino acid sequences of SEQ ID NOs: 24, 53, 8, 10, 51, and 18.

In some examples, the VL-CDR1, VL-CRD2, VL-CDR3, VH-CDR1, VH-CDR2, and VH-CDR3, respectively, comprises the amino acid sequences of SEQ ID NOs: 40, 41, 8, 10, 22, and 18.

In some examples, the VL-CDR1, VL-CRD2, VL-CDR3, VH-CDR1, VH-CDR2, and VH-CDR3, respectively, comprises the amino acid sequences of SEQ ID NOs: 24, 12, 8, 10, 51, and 4.

In some examples, the VL-CDR1, VL-CRD2, VL-CDR3, VH-CDR1, VH-CDR2, and VH-CDR3, respectively, comprises the amino acid sequences of SEQ ID NOs: 24, 12, 14, 10, 51, and 18.

In some examples, the VL-CDR1, VL-CRD2, VL-CDR3, VH-CDR1, VH-CDR2, and VH-CDR3, respectively, comprises the amino acid sequences of SEQ ID NOs: 24, 12, 14, 10, 22, and 18.

In specific examples, the $V_L$ comprises the amino acid sequences of SEQ ID NOs: 13, 19, 23, 30, 35, 39, 46, 52, 59, 62, 65, 69, 72, 75, 90, or 93. Alternatively, the $V_H$ comprises the amino acid sequence selected from the group consisting of SEQ ID NOs: 9, 17, 21, 28, 44, 50, 56, 78, 80, 82, or 84. Any combination of the $V_H$ and $V_L$ chains disclosed herein is within the scope of the present disclosure. Examples include:

(1) SEQ ID NO: 13, and SEQ ID NO: 9;
(2) SEQ ID NO: 19, and SEQ ID NO: 17;
(3) SEQ ID NO: 23, and SEQ ID NO: 21;
(4) SEQ ID NO: 30, and SEQ ID NO: 28;
(5) SEQ ID NO: 35, and SEQ ID NO: 9;
(6) SEQ ID NO: 39, and SEQ ID NO: 21;
(7) SEQ ID NO: 46, and SEQ ID NO: 44;
(8) SEQ ID NO: 52, and SEQ ID NO: 50;
(9) SEQ ID NO: 13, and SEQ ID NO: 56;
(10) SEQ ID NO: 59, and SEQ ID NO: 21;
(11) SEQ ID NO: 62, and SEQ ID NO: 28;
(12) SEQ ID NO: 65, and SEQ ID NO: 50;
(13) SEQ ID NO: 69, and SEQ ID NO: 44;
(14) SEQ ID NO: 72, and SEQ ID NO: 9;
(15) SEQ ID NO: 75, and SEQ ID NO: 21;
(16) SEQ ID NO: 59, and SEQ ID NO: 78;
(17) SEQ ID NO: 62, and SEQ ID NO: 80;
(18) SEQ ID NO: 65, and SEQ ID NO: 82;
(19) SEQ ID NO: 69, and SEQ ID NO: 84;
(20) SEQ ID NO: 72, and SEQ ID NO: 17;
(21) SEQ ID NO: 75, and SEQ ID NO: 78;
(22) SEQ ID NO: 52, and SEQ ID NO: 82;
(23) SEQ ID NO: 39, and SEQ ID NO: 78;
(24) SEQ ID NO: 90, and SEQ ID NO: 50;
(25) SEQ ID NO: 93, and SEQ ID NO: 82; or
(26) SEQ ID NO: 93, and SEQ ID NO: 78.

In other embodiments, the anti-CLDN 18.2 antibody disclosed herein may comprise the same heavy chain complementary determining regions (CDRs) and the same light chain complementary determining regions (CDRs) as a reference anti-claudin 18.2 antibody. The reference (exemplary) anti-CLDN 18.2 antibody may be 5C9ob, 5C9oae, 5C9oap, 9O24, 9O36, 9O41, 9O45, 9O47, 9O51, 9O24-ob, 9O47-ob, 9O45-ob, 9O36-ob, 9O41-ob, 5C9oap-ob, 9O24oae, 9O47-oae, 9O45-oae, 9O36-oae, 9O41-oae, 9O47HN, or 9O41 HN. In some examples, the anti-CLDN 18.2 antibody may comprise the same $V_H$ and same $V_L$ and the reference antibody. Examples include anti-CLDN 18.2 antibodies having one of the following heavy chain and a light chain sequences, respectively:

(1) SEQ ID NOs: 15 and 16,
(2) SEQ ID NOs: 20 and 16,
(3) SEQ ID NOs: 26 and 27,
(4) SEQ ID NOs: 33 and 34,
(5) SEQ ID NOs: 37 and 38,
(6) SEQ ID NOs: 42 and 43,
(7) SEQ ID NOs: 48 and 49,
(8) SEQ ID NOs: 54 and 55,
(9) SEQ ID NOs: 58 and 16,
(10) SEQ ID NOs: 60 and 61,
(11) SEQ ID NOs: 63 and 64,
(12) SEQ ID NOs: 67 and 68,
(13) SEQ ID NOs: 70 and 71,
(14) SEQ ID NOs: 73 and 74,
(15) SEQ ID NOs: 76 and 77,
(16) SEQ ID NOs: 79 and 61,
(17) SEQ ID NOs: 81 and 64,
(18) SEQ ID NOs: 83 and 68,
(19) SEQ ID NOs: 83 and 71,
(20) SEQ ID NOs: 86 and 74,
(21) SEQ ID NOs: 87 and 77,
(22) SEQ ID NOs: 88 and 55,
(23) SEQ ID NOs: 89 and 43,
(24) SEQ ID NOs: 91 and 92,
(25) SEQ ID NOs: 94 and 95, or
(26) SEQ ID NOs: 96 and 95.

Any of the anti-CLDN 18.2 antibodies disclosed herein may be a full-length antibody. Alternatively, the antibody is an antigen-binding fragment thereof.

Also within the scope of the present disclosure includes an isolated nucleic acid or nucleic acid set, which collectively encode any of the anti-CLDN 18.2 antibodies or the bispecific antibodies disclosed herein. The nucleic acid or nucleic acid set can be a vector or a vector set comprising a vector(s) that comprises said nucleotide sequence. In some examples, the vector(s) can be an expression vector(s), in which said nucleotide sequences are in operably linkage to a common promoter or different promoters. In addition, provided herein is a host cell or host cell set, comprising any of the vectors or vector sets disclosed herein.

Further, provided herein is a method for preparing any of the anti-CLDN 18.2 antibodies or any of the bispecific antibodies, the method comprising culturing the host cell or host cell set as also disclosed herein under conditions allowing for expression of the antibody or bispecific antibody, and harvesting the antibody or bispecific antibody thus produced.

In yet another aspect, the present disclosure features a pharmaceutical composition, which comprises any of the bispecific antibodies disclosed herein, any of the anti-CLDN 18.2 antibodies disclosed herein, or a nucleic acid or nucleic acid set encoding such, and (ii) a pharmaceutically acceptable carrier.

In addition, the present disclosure features a method of inhibiting cells expressing CLDN 18.2, comprising contacting administering an effective amount of the pharmaceutical composition of comprising an anti-CLDN 18.2 antibody, a bispecific antibody, or a nucleic acid(s) encoding such as disclosed herein. In some embodiments, the subject is a human patient having a cancer, for example, gastric cancer, esophageal cancer, pancreatic cancer, lung cancer, ovarian cancer, colon cancer, hepatic cancer, head-neck cancer, or gallbladder cancer.

In some embodiments, the subject has undergone or is undergoing an anti-PD-1, anti-PD-L1, or anti-CTLA4 therapy. Alternatively, any of the method may further comprise administering to the subject an effective amount of an anti-PD-1, anti-PD-L1, or anti-CTLA4 therapy. In some examples, the anti-PD-1, anti-PD-L1, or anti-CTLA4 therapy may comprise an anti-PD-1, anti-PD-L1, or anti-CTLA4 antibody, respectively. Exemplary anti-PD-1 antibodies include pembrolizumab, nivolumab, and AMP-224, or an antigen-binding fragment thereof. Exemplary anti-CTLA-4 antibodies include ipilimumab, and tremetimumab, or an antigen-binding fragment thereof. Exemplary anti-PD-L1 antibodies include durvalumab, atezolizumab, and avelumab, or an antigen-binding fragment thereof.

Also within the scope of the present disclosure are any of the anti-CLDN 18.2 antibodies or bispecific antibodies for use in treating any of the target diseases disclosed herein, or uses of such antibodies for manufacturing a medicament for use in the intended treatment.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

FIGS. 1A-1C include schematic illustrations of exemplary anti-CLDN 18.2/anti-PD-L1 bispecific antibodies in single polypeptide format. FIG. 1A: monomer; FIG. 1B: dimer with disulfide bonds in the Linker 4. FIG. 1C: dimer with additional disulfide bond between heavy chain and light chain variable regions.

FIGS. 7A and 7B include charts comparing binding affinity of exemplary bispecific antibody ScDb01 to its monospecific parent antibodies as measured by ELISA. FIG. 7A: binding to CLDN 18.2. Kd values of h5C9ob and ScDB01 are 0.1327 nM and 0.2634 nM, respectively. FIG. 7B: binding to PD-L1. Kd values of Durvalumab and ScDB01 are 0.2769 nM and 0.5854 nM, respectively.

FIGS. 8A and 8B include charts comparing binding affinity of exemplary bispecific antibody ScDb01 to its monospecific parent antibodies as measured by ELISA at pH3-6. FIG. 8A: binding to CLDN 18.2. Kd values at pH3, pH4, pH4.5, and pH6 are 0.2520 nM, 0.1765 nM, 0.1600 nM, and 0.1582 nM respectively. FIG. 8B: binding to PD-L1. Kd values at pH3, pH4, pH4.5, and pH6 are 0.4884 nM, 0.3426 nM, 0.3347 nM, and 0.3518 nM respectively.

FIGS. 9A and 9B include charts comparing binding affinity of exemplary bispecific antibodies ScDb02 and ScDb04 to its monospecific parent antibodies as measured by ELISA. FIG. 9A: binding to CLDN 18.2. Kd values of ScDb02_CLDN18.2 and ScDb04_CLDN18.2 are 0.2083 nM and 0.2522 nM, respectively. FIG. 9B: binding to PD-L1. Kd values of ScDb2-PD-L1 and ScDb4_PD-L1 are 0.3998 nM and 0.5121 nM, respectively.

FIGS. 10A and 10B include charts comparing binding affinity of exemplary bispecific antibody ScDb06 to its monospecific parent antibodies as measured by ELISA. FIG. 10A: binding to CLDN 18.2. Kd values of h5C9ob and ScDB06 are 0.1327 nM and 0.2096 nM, respectively. FIG. 10B: binding to PD-L1. Kd values of ScDb06 and Durvalumab are 0.3521 nM and 0.2075 nM, respectively.

FIG. 11A: Clones DbInk2-9 and 11. Kd values of DbInk2, DbInk3, DbInk4, DbInk5, DbInk7, DbInk8, DbInk9, and DbInk11 are 0.3232 nM, 0.2943 nM, 0.2391 nM, 0.2459 nM, 0.2481 nM, 0.2587 nM, 0.2690 nM, and 0.2909 nM, respectively. FIG. 11B: Clones DbInk12-18 and ScDb01. Kd values of DbInk12, DbInk13, DbInk14, DbInk15, DbInk16, DbInk17, DbInk18, and ScDb01 are 0.2046 nM, 0.2148 nM, 0.2004 nM, 0.2317 nM, 0.2222 nM, 0.2246 nM, 0.2171 nM, and 0.2792 nM, respectively.

FIGS. 17A and 17B include charts showing complementary Dependent Cytotoxicity (CDC) effects of exemplary bispecific antibodies against cells stably expressing CLDN 18.2 (left) as compared with their monospecific parent antibody h5C9ob. FIG. 17A: DbInk2 and 3 against MCF7-CLDN 18.2 cells. The Top values of DbInk2 and DbInk3 are 906.5 and 1185, respectively. The $EC_{50}$ values of these two clones are 1.026 nM and 0.8212 nM, respectively. FIG. 17B: DbInk2 and h5C9ob against Mia Paca-CLDN 18.2 cells. The Top values of DbInk2 and h5C9ob are 1368 and 1971, respectively. The $EC_{50}$ values of these two clones are 0.3488 nM and 0.5200 nM, respectively.

FIG. 18 is a chart showing antibody-dependent cellular cytotoxicity (ADCC) effect of bispecific antibody scDb01 versus parent clone h5C9ob by a reporter assay in HEK293T cells that were stably transfected with CLDN 18.2. The $EC_{50}$ values of ScDb01 and h5C9ob are 0.01564 nM and 0.05615 nM, respectively.

FIG. 27 is a chart showing anti-Drug Antibody (ADA) assay of bispecific antibody scDb01 in CD1 mice. scDb01 was administered intravenously at 1 mg/kg.

FIGS. 28A and 28B include charts showing binding of bispecific antibody db11-21 to CLDN 18.2 (FIG. 28A) and PD-L1 (FIG. 28B) by direct ELISA assay. Kd values of db11-22 and 5C9ob over CLDN18.2 are 0.1042 nM and 0.08193 nM, respectively. Kd values of db11-22 and Durvalumab over PDL1 are 0.3782 nM and 0.2820 nM, respectively.

DETAILED DESCRIPTION OF THE INVENTION

Figure 1C:
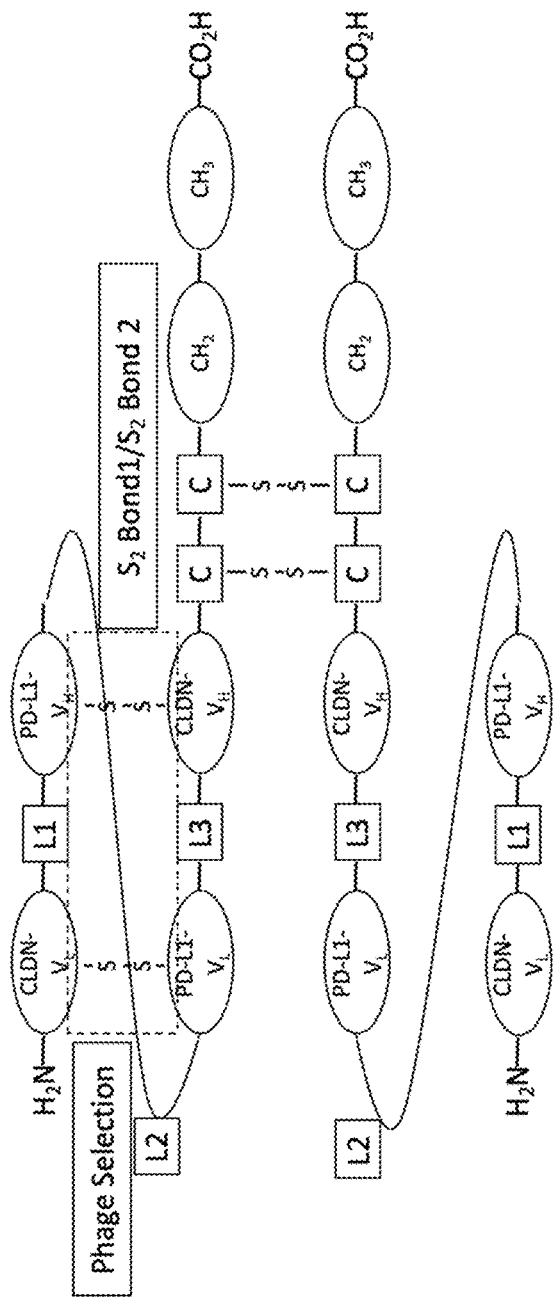
Figure 2:
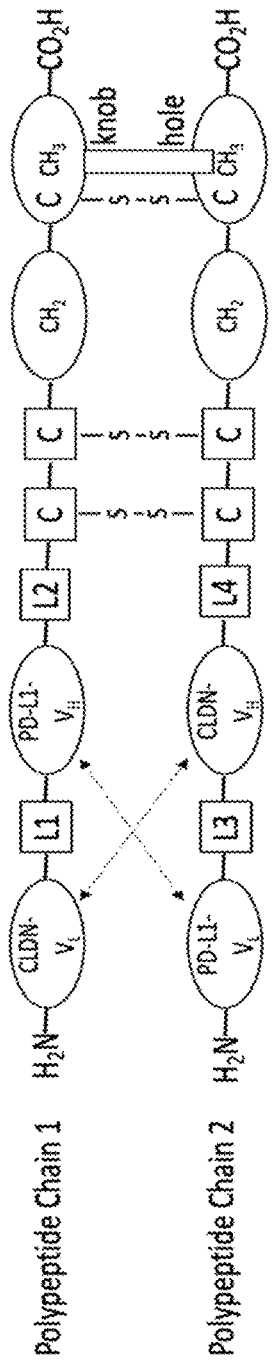
FIG. 2 is a schematic illustration of exemplary anti-CLDN 18.2/anti-PD-L1 bispecific antibodies in two polypeptides format.

The present disclosure is based on the development of antibodies having high binding affinity and specificity to human CLDN 18.2 and bispecific antibodies capable of binding to both human CLDN 18.2 and PD-L1. Such antibodies showed improved binding affinity to CLDN 18.2 while retaining the binding to PD-L1. The bispecific antibodies also showed the same binding affinity at relatively low pH as compared to physiological pH, preserving binding affinity in the low pH tumor microenvironment. Such antibodies also demonstrated good level of expression, minimal aggregation, and straightforward purification. Such anti-CLDN 18.2 antibodies and bispecific antibodies are expected to be effective in treating diseases involving CLDN 18.2-expressing cells, for example, various types of cancer as disclosed herein.

Accordingly, provided herein are anti-CLDN 18.2 antibodies and bispecific antibodies binding to human CLDN 18.2 and PD-L1, nucleic acids or nucleic acid sets encoding the antibodies, host cells comprising the nucleic acid(s), pharmaceutical compositions comprising such, methods of using such antibodies or encoding nucleic acids for treating a target disease as disclosed herein, as well as methods for producing such antibodies.

I. Anti-CLDN 18.2 Antibodies

Claudin 18.2 (CLDN 18.2) is a CD20-like differentiation protein that is overly expressed on many types of cancer as noted herein. Human CLDN 18.2 is encoded by the CLDN18 gene. The amino acid sequences of an exemplary human CLDN 18.2, including the full-length protein, a truncated version of the CLDN 18.2 (C-terminal domain deleted), and its extracellular loop 1 are provided in the Sequence Table below (SEQ ID NOs: 210-212). Structural features of other CLDN 18.2 molecules are also known in the art and can be obtained from publicly available gene database, for example, GenBank, using the provided sequences as queries.

The present disclosure provides antibodies binding to CLDN 18.2, for example, human CLDN 18.2. In some embodiments, the anti-CDLN18.2 antibodies disclosed herein are capable of binding to CDLN18.2 expressed on cell surface. As such, the antibodies disclosed herein may be used for either therapeutic or diagnostic purposes to target CLDN 18.2-positive cells (e.g., cancer cells such as those disclosed herein). As used herein, the term "anti-CLDN 18.2 antibody" refers to any antibody capable of binding to a CLDN polypeptide (e.g., a CLDN polypeptide expressed on cell surface), for a fragment thereof, which can be of a suitable source, for example, human or a non-human mammal (e.g., mouse, rat, rabbit, primate such as monkey, etc.). In some instances, the anti-CLDN 18.2 antibodies disclosed herein may be capable of binding to an extracellular domain of a CLDN 18.2, for example, the extracellular loop 1 (e.g., SEQ ID NO:210).

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody", e.g., anti-CLDN 18.2 antibody, encompasses not only intact (e.g., full-length) polyclonal or monoclonal antibodies, but also antigen-binding fragments thereof (such as Fab, Fab', F(ab')2, Fv), single-chain antibody (scFv), fusion proteins comprising an antibody portion, humanized antibodies, chimeric antibodies, diabodies, single domain antibody (e.g., nanobody), single domain antibodies (e.g., a $V_H$ only antibody), multi-specific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody, e.g., anti-CLDN 18.2 antibody, includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

A typical antibody molecule comprises a heavy chain variable region ($V_H$) and a light chain variable region ($V_L$), which are usually involved in antigen binding. The $V_H$ and $V_L$ regions can be further subdivided into regions of hypervariability, also known as "complementarity determining regions" ("CDR"), interspersed with regions that are more conserved, which are known as "framework regions" ("FR"). Each $V_H$ and $V_L$ is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the Chothia definition, the AbM definition, and/or the contact definition, all of which are well known in the art. See, e.g., Kabat, E. A., et al. (1991) *Sequences of Proteins of Immunological Interest*, Fifth Edition, U.S. Department of Health and Human Services, NIH Publication No. 91-3242, Chothia et al., (1989) Nature 342:877; Chothia, C. et al. (1987) J. Mol. Biol. 196:901-917, Al-lazikani et al (1997) J. Molec. Biol. 273:927-948; and Almagro, J. Mol. Recognit. 17:132-143 (2004). See also hgmp.nrc.ac.uk and bioinf.org.uk/abs).

The anti-CLDN 18.2 antibody described herein may be a full-length antibody, which contains two heavy chains and two light chains, each including a variable domain and a constant domain. Alternatively, the anti-CLDN 18.2 antibody can be an antigen-binding fragment of a full-length antibody. Examples of binding fragments encompassed within the term "antigen-binding fragment" of a full length antibody include (i) a Fab fragment, a monovalent fragment consisting of the $V_L$, $V_H$, $C_L$ and $C_H1$ domains; (ii) a F(ab')$_2$ fragment, a bivalent fragment including two Fab fragments linked by a disulfide bridge at the hinge region; (iii) a Ed fragment consisting of the $V_H$ and $C_H1$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain, and (vi) an isolated complementarity determining region (CDR) that retains functionality. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules known as single chain Fv (scFv). See e.g., Bird el al. (1988) *Science* 242:423-426; and Huston el al. (1988) *Proc. Natl. Acad. Sci. USA* 85:5879-5883.

The antibodies described herein can be of a suitable origin, for example, murine, rat, or human. Such antibodies are non-naturally occurring, i.e., would not be produced in an animal without human act (e.g., immunizing such an animal with a desired antigen or fragment thereof or isolated from antibody libraries). Any of the antibodies described herein, e.g., anti-CLDN 18.2 antibody, can be either monoclonal or polyclonal. A "monoclonal antibody" refers to a homogenous antibody population and a "polyclonal antibody" refers to a heterogeneous antibody population. These two terms do not limit the source of an antibody or the manner in which it is made.

In some embodiments, the anti-CLDN 18.2 antibodies are human antibodies, which may be isolated from a human antibody library or generated in transgenic mice. For example, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Amgen, Inc. (Fremont, Calif.) and HuMAb-Mouse™ and TC Mouse™ from Medarex, Inc. (Princeton, N.J.). In another alternative, antibodies may be made recombinantly by phage display or yeast technology. See, for example, U.S. Pat. Nos. 5,565,332; 5,580,717; 5,733,743; and 6,265,150; and Winter et al., (1994) *Annu. Rev. Immunol.* 12:433-455. Alternatively, the antibody library display technology, such as phage, yeast display, mammalian cell display, or mRNA display technology as known in the art can be used to produce human antibodies and antibody fragments in vitro, from immunoglobulin variable (V) domain gene repertoires from unimmunized donors.

In other embodiments, the anti-CLDN 18.2 antibodies may be humanized antibodies or chimeric antibodies. Humanized antibodies refer to forms of non-human (e.g., murine) antibodies that are specific chimeric immunoglobulins, immunoglobulin chains, or antigen-binding fragments thereof that contain minimal sequence derived from non-human immunoglobulin. In general, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. In some instances, one or more Fv framework region (FR) residues of the human immunoglobulin are replaced by corresponding non-human residues.

Furthermore, the humanized antibody may comprise residues that are found neither in the recipient antibody nor in the imported CDR or framework sequences, but are included to further refine and optimize antibody performance. In some instances, the humanized antibody may comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, or six) which are altered with respect to the original antibody, which are also termed one or more CDRs "derived from" one or more CDRs from the original antibody. Humanized antibodies may also involve affinity maturation. Methods for constructing humanized antibodies are also well known in the art. See, e.g., Queen et al., Proc. Natl. Acad. Sci. USA, 86:10029-10033 (1989).

In some embodiments, the anti-CLDN 18.2 antibody disclosed herein can be a chimeric antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region. Techniques developed for the production of "chimeric antibodies" are well known in the art. See, e.g., Morrison et al. (1984) *Proc. Natl. Acad. Sci. USA* 81, 6851; Neuberger et al. (1984) *Nature* 312, 604; and Takeda et al. (1984) *Nature* 314:452.

In some embodiments, the anti-CLDN 18.2 antibodies described herein specifically bind to the corresponding target antigen (e.g., human CLDN 18.2) or an epitope thereof. An antibody that "specifically binds" to an antigen or an epitope is a term well understood in the art. A molecule is said to exhibit "specific binding" if it reacts more frequently, more rapidly, with greater duration and/or with greater affinity with a particular target antigen than it does with alternative targets. An antibody "specifically binds" to a target antigen or epitope if it binds with greater affinity, avidity, more readily, and/or with greater duration than it binds to other substances. For example, an antibody that specifically (or preferentially) binds to an antigen (CLDN 18.2 such as human CLDN 18.2) or an antigenic epitope therein is an antibody that binds this target antigen with greater affinity, avidity, more readily, and/or with greater duration than it binds to other antigens or other epitopes in the same antigen. It is also understood with this definition that, for example, an antibody that specifically binds to a first target antigen may or may not specifically or preferentially bind to a second target antigen. As such, "specific binding" or "preferential binding" does not necessarily require (although it can include) exclusive binding. In some examples, an antibody that "specifically binds" to a target antigen or an epitope thereof may not bind to other antigens or other epitopes in the same antigen (i.e., only baseline binding activity can be detected in a conventional method).

In some embodiments, an anti-CLDN 18.2 antibody as described herein has a suitable binding affinity for the target antigen (e.g., human CLDN 18.2) or antigenic epitopes thereof. As used herein, "binding affinity" refers to the apparent association constant or $K_A$. The $K_A$ is the reciprocal of the dissociation constant ($K_D$). The anti-CLDN 18.2 antibody described herein may have a binding affinity ($K_D$) of at least 100 nM, 10 nM, 1 nM, 0.1 nM, or lower for CLDN 18.2 (e.g., human CLDN 18.2). An increased binding affinity corresponds to a decreased $K_D$. Higher affinity binding of an antibody for a first antigen relative to a second antigen can be indicated by a higher $K_A$ (or a smaller numerical value $K_D$) for binding the first antigen than the $K_A$ (or numerical value $K_D$) for binding the second antigen. In such cases, the antibody has specificity for the first antigen (e.g., a first protein in a first conformation or mimic thereof) relative to the second antigen (e.g., the same first protein in a second conformation or mimic thereof; or a second protein). Differences in binding affinity (e.g., for specificity or other comparisons) can be at least 1.5, 2, 3, 4, 5, 10, 15, 20, 37.5, 50, 70, 80, 90, 100, 500, 1000, 10,000 or 105 fold. In some embodiments, any of the anti-CLDN 18.2 antibodies may be further affinity matured to increase the binding affinity of the antibody to the target antigen or antigenic epitope thereof.

Binding affinity (or binding specificity) can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound binding protein as a function of target protein concentration. The concentration of bound binding protein ([Bound]) is generally related to the concentration of free target protein ([Free]) by the following equation:

$$[Bound]=[Free]/(Kd+[Free])$$

It is not always necessary to make an exact determination of KA, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

In some embodiments, the anti-CLDN 18.2 antibody disclosed herein has an $EC_{50}$ value of lower than 10 nM, e.g., <1 nM, <0.5 nM, or lower than 0.1 nM, for binding to CLDN 18.2-positive cells. As used herein, $EC_{50}$ values refer to the minimum concentration of an antibody required to bind to 50% of the cells in a CLDN 18.2-positive cell population. $EC_{50}$ values can be determined using conventional assays and/or assays disclosed herein. See, e.g., Examples below.

A number of exemplary anti-CLDN 18.2 antibodies, including 5C9ob, 5C9oae, 5C9oap, 9O24, 9O41, 9O47, 9O36, 9O45, 9O51, 5C9oap-ob, 9O24-ob, 9O47-ob, 9O45-ob, 9O36-ob, 9O41-ob, 5C9oap-oae, 9O24-oae, 9O47-oae, 9O36-oae, 9O41-oae, 9O47HN, and 9O41HN, are provided in the Sequence Table 1 below (CDRs for each exemplary anti-CLDN 18.2 antibody are also provided in the Sequence Table as determined by the Kabat numbering. See Kabat, E. A., et al. (1991) Sequences of Proteins of Immunological Interest, Fifth Edition, U.S. Department of Health and Human Services, NIH Publication No. 91-3242. See also www2.mrc-lmb.cam.ac.uk/vbase/alignments2.php).

In some embodiments, the anti-CLDN 18.2 antibodies described herein bind to the same epitope of a CLDN polypeptide as any of the exemplary (reference) antibodies described herein or compete against the exemplary antibody from binding to the CLDN 18.2 antigen. An "epitope" refers to the site on a target antigen that is recognized and bound by an antibody. The site can be entirely composed of amino acid components, entirely composed of chemical modifications of amino acids of the protein (e.g., glycosyl moieties), or composed of combinations thereof. Overlapping epitopes include at least one common amino acid residue. An epitope can be linear, which is typically 6-15 amino acids in length. Alternatively, the epitope can be conformational. The epitope to which an antibody binds can be determined by routine technology, for example, the epitope mapping method (see, e.g., descriptions below). An antibody that binds the same epitope as an exemplary antibody described herein may bind to exactly the same epitope or a substantially overlapping epitope (e.g., containing less than 3 non-overlapping amino acid residues, less than 2 non-overlapping amino acid residues, or only 1 non-overlapping amino acid residue) as the exemplary antibody. Whether two antibodies compete against each other from binding to the cognate antigen can be determined by a competition assay, which is well known in the art.

In some examples, the anti-CLDN 18.2 antibody comprises the same $V_H$ and/or $V_L$ CDRs as an exemplary antibody described herein. Two antibodies having the same $V_H$ and/or $V_L$ CDRs means that their CDRs are identical when determined by the same approach (e.g., the Kabat approach, the Chothia approach, the AbM approach, the Contact approach, or the IMGT approach as known in the art. See, e.g., bioinf.org.uk/abs/). Such anti-CLDN 18.2 antibodies may have the same $V_H$, the same $V_L$, or both as compared to an exemplary antibody described herein.

Also within the scope of the present disclosure are functional variants of any of the exemplary anti-CLDN 18.2 antibodies as disclosed herein. Such functional variants are substantially similar to the exemplary antibody, both structurally and functionally. A functional variant comprises substantially the same $V_H$ and $V_L$ CDRs as the exemplary antibody. For example, it may comprise only up to 8 (e.g., 8, 7, 6, 5, 4, 3, 2, or 1) amino acid residue variations in the total CDR regions of the antibody and binds the same epitope of CLDN 18.2 with substantially similar affinity (e.g., having a $K_D$ value in the same order). In some instances, the functional variants may have the same heavy chain CDR3 as the exemplary antibody, and optionally the same light chain CDR3 as the exemplary antibody. Alternatively or in addition, the functional variants may have the same heavy chain CDR2 as the exemplary antibody. Such an anti-CLDN 18.2 antibody may comprise a $V_H$ fragment having CDR amino acid residue variations in only the heavy chain CDR1, the heavy chain CDR2, or both as compared with the $V_H$ of the exemplary antibody. In some examples, the anti-CLDN 18.2 antibody may further comprise a $V_L$ fragment, which may have the same $V_L$ CDR3 as the exemplary antibody. In some examples, the antibody may have the same $V_L$ CDR1 or $V_L$ CDR2 as the exemplary antibody. Alternatively, the antibody may comprise a $V_L$ fragment having CDR amino acid residue variations in only the light chain CDR1, the light chain CDR2, or both as compared with the $V_L$ of the exemplary antibody.

Alternatively or in addition, the amino acid residue variations can be conservative amino acid residue substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S. T; (f) Q, N; and (g) E, D.

In some embodiments, the anti-CLDN 18.2 antibody may comprise heavy chain CDRs that are at least 80% (e.g., 85%, 90%, 95%, or 98%) sequence identity, individually or collectively, as compared with the $V_H$ CDRs of an exemplary antibody described herein. Alternatively or in addition, the anti-CLDN 18.2 antibody may comprise light chain CDRs that are at least 80% (e.g., 85%, 90%, 95%, or 98%) sequence identity, individually or collectively, as compared with the $V_L$ CDRs as an exemplary antibody described herein. As used herein, "individually" means that one CDR of an antibody shares the indicated sequence identity relative to the corresponding CDR of the exemplary antibody. "Collectively" means that three $V_H$ or $V_L$ CDRs of an antiody in combination share the indicated sequence identity relative the corresponding three $V_H$ or $V_L$ CDRs of the exemplary antibody in combination.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

In some embodiments, the heavy chain of any of the anti-CLDN 18.2 antibodies as described herein may further comprise a heavy chain constant region (CH) or a portion thereof (e.g., CH1, CH2, CH3, or a combination thereof). The heavy chain constant region can of any suitable origin, e.g., human, mouse, rat, or rabbit. Alternatively or in addition, the light chain of the anti-CLDN 18.2 antibody may further comprise a light chain constant region (CL), which can be any CL known in the art. In some examples, the CL is a kappa light chain. In other examples, the CL is a lambda light chain. Antibody heavy and light chain constant regions are well known in the art, e.g., those provided in the IMGT database (www.imgt.org) or at www.vbase2.org/vbstat.php., both of which are incorporated by reference herein.

In some embodiments, the anti-CLDN 18.2 antibody disclosed herein may comprise a $V_H$ chain comprising the amino acid sequence of SEQ ID NO: 9 or SEQ ID NO: 50 as provided in the Sequence Table 1. Alternatively or in addition, the anti-CLDN 18.2 antibody disclosed herein may comprise a $V_L$ chain comprising the amino acid sequence of SEQ ID NO: 13 or SEQ ID NO: 52 as provided in the Sequence Table 1. Any combination of these $V_H$ and $V_L$ chains is also within the scope of the present disclosure. In specific examples, the anti-CLDN 18.2 antibody disclosed herein may comprise a $V_H$ comprising the amino acid sequence of SEQ ID NO: 9 and a $V_L$ comprising the amino acid sequence of SEQ ID NO:13. In other specific examples, the anti-CLDN 18.2 antibody disclosed herein may comprise a $V_H$ comprising the amino acid sequence of SEQ ID NO: 50 and a $V_L$ comprising the amino acid sequence of SEQ ID NO:53.

In some embodiments, the anti-CLDN 18.2 antibody may comprise a light chain CDR1 comprising the amino acid sequence of KSSQSLLNX$_1$GNX$_2$KSYLT (SEQ ID NO: 274, in which X$_1$ is S, T, Y. F, or W; and X$_2$ is Q, N, W, F, Y, I, M, or V; a light chain CDR2 comprising the amino acid sequence of WASTLX$_3$S (SEQ ID NO: 275), in which X$_3$ is any amino acid residue; a light chain CDR3 comprising the amino acid sequence of QNAYX$_4$FPFT (SEQ ID NO: 276), in which X$_4$ is S, T, F, Y, or W; or a combination thereof.

Alternatively or in addition, the anti-CLDN 18.2 antibody may comprise a heavy chain CDR1 comprising the amino acid sequence of GYTFSMN (SEQ ID NO: 10); a heavy chain CDR2 comprising the amino acid sequence of WINMYTGX$_5$X$_6$X$_7$YADDFKG (SEQ ID NO: 277), in which X$_5$ is E, D, K, H, or R; X$_6$ is P, K, R, H, T, and X$_7$ is S, T, I, L, or V; a heavy chain CDR3 comprising the amino acid sequence of LYX$_8$GNSLDY (SEQ ID NO: 278), in which X$_8$ is N, Q, K, R, or H, or a combination thereof.

Any of the anti-CLDN 18.2 antibody as described herein, e.g., the exemplary anti-CLDN 18.2 antibodies provided here, can bind and inhibit (e.g., reduce or eliminate) the activity of CLDN 18.2-positive cells (e.g., cancer cells). In some embodiments, the anti-CLDN 18.2 antibody as described herein can bind and inhibit the activity of CLDN 18.2-positive cells (e.g., cancer cells) by at least 30% (e.g., 35%, 40%, 45%, 50%, 60%, 70%, 80%, 90%, 95% or greater, including any increment therein). The inhibitory activity of an anti-CLDN 18.2 antibody described herein can be determined by routine methods known in the art, e.g., by an assay for measuring the K$_i{}^{app}$ value.

In some examples, the K$_i{}^{app}$ value of an antibody may be determined by measuring the inhibitory effect of different concentrations of the antibody on the extent of a relevant reaction; fitting the change in pseudo-first order rate constant (v) as a function of inhibitor concentration to the modified Morrison equation (Equation 1) yields an estimate of the apparent Ki value. For a competitive inhibitor, the K$_i{}^{app}$ can be obtained from the y-intercept extracted from a linear regression analysis of a plot of K$_i{}^{app}$ versus substrate concentration.

$$v = A \cdot \frac{([E]-[I]-K_i^{app}) + \sqrt{([E]-[I]-K_i^{app})^2 + 4[E] \cdot K_i^{app}}}{2} \quad \text{(Equation 1)}$$

Where A is equivalent to v$_o$/E, the initial velocity (v$_o$) of the enzymatic reaction in the absence of inhibitor (1) divided by the total enzyme concentration (E). In some embodiments, the anti-CLDN 18.2 antibody described herein may have a Ki$^{app}$ value of 1000, 500, 100, 50, 40, 30, 20, 10, 5 pM or less for the target antigen or antigen epitope.

II. Bispecific Antibodies Binding to CLDN 18.2 and PD-L1

In some aspects, provided herein are bispecific antibodies capable of binding to CLDN 18.2 (e.g., human CLDN 18.2) and PD-L1 (e.g., human PD-L1). Such a bispecific antibody comprises two antibody portions, a first antibody portion binding to the CLDN 18.2 antigen and a second antibody portion binding to the PD-L1 antigen. The first and second antibodies portions can be derived from two parent antibodies capable of binding to the target antigens.

Parent Antibodies for Constructing Bispecific Antibodies

Any of the anti-CLDN 18.2 antibodies disclosed herein can be used as the parent antibody for the anti-CLDN 18.2 portion in the bispecific antibodies. In some embodiments, the parent antibody for the anti-CLDN 18.2 portion in the bispecific antibody may be an exemplary (reference) antibody selected from 5C9ob, 5C9oae, 5C9oap, 9O24, 9O41, 9O47, 9O36, 9O45, 9O51, 5C9oap-ob, 9O24-ob, 9O47-ob, 9O45-ob, 9O36-ob, 9O41-ob, 5C9oap-oae, 9O24-oae, 9O47-oae, 9O36-oae, 9O41-oae, 9O47HN, and 9O41HN. Their V$_H$ and V$_L$ sequences, as well as heavy chain and light chain sequences are provided in the Sequence Table 1 below. Alternatively, the parent antibody for the anti-CLDN 18.2 portion in the bispecific antibody may be a functional variant of the exemplary antibody as disclosed herein (e.g., comprising a certain degree of amino acid residue variations in one or more of the heavy chain CDRs and/or one or more of the light chain CDRs and retains similar antigen binding activity). Such functional variants are disclosed herein.

Any anti-PD-L1 antibody may be used as the parent antibody for the anti-PD-L1 portion of the bispecific antibody. Examples include, but are not limited to, durvalumab, atezolizumab, avelumab, or an 12A4 antibody. The V$_H$ and V$_L$ sequences of these exemplary anti-PD-L1 antibodies are also provided in the Sequence Table 1 and 2 below (CDRs determined following the Kabat numbering are identified in boldface). Alternatively, the parent antibody of the anti-PD-L1 portion in the bispecific antibody disclosed herein may be a functional variant of any of the exemplary anti-PD-L1 antibodies provided herein. Such functional variants are substantially similar to the exemplary antibody, both structurally and functionally. For example, it may comprise only up to 8 (e.g., 8, 7, 6, 5, 4, 3, 2, or 1) amino acid residue variations in the total CDR regions of the antibody and binds the same epitope of the example anti-PD-L1 antibody with substantially similar affinity (e.g., having a K$_D$ value in the same order). In some instances, the functional variants may have the same heavy chain CDR3 as the exemplary antibody, and optionally the same light chain CDR3 as the exemplary anti-PD-L1 antibody. Alternatively or in addition, the functional variants may have the same heavy chain CDR2 as the exemplary anti-PD-L1 antibody. Such a functional variant may comprise a V$_H$ fragment having CDR amino acid residue variations in only the heavy chain CDR1, the heavy chain CDR2, or both as compared with the V$_H$ of the exemplary anti-PD-L1 antibody. In some examples, the functional variant antibody may further comprise a V$_L$ fragment, which may have the same V$_L$ CDR3 as the exemplary anti-PD-L1 antibody. In some examples, the functional variant antibody may have the same V$_L$ CDR1 or V$_L$ CDR$_2$ as the exemplary anti-PD-L1 antibody. Alternatively, the functional variant antibody may comprise a V$_L$ fragment having CDR amino acid residue variations in only the light chain CDR1, the light chain CDR2, or both as compared with the V$_L$ of the exemplary anti-PD-L1 antibody. In some examples, the amino acid residue variations in a functional variant can be conservative amino acid residue substitutions relative to the corresponding exemplary anti-PD-L1 antibody.

In some instances, the anti-PDL1 antibody for use in making the bispecific antibodies disclosed herein is a 12A4 antibody (see Sequence Table 2). Such an anti-PDL1 antibody may comprise a heavy chain CDR1 comprising the sequence of GDTFSTYAIS (SEQ ID NO: 286), a heavy chain CDR2 comprising GIIPX$_1$FGKAH (SEQ ID NO: 296), in which X$_1$ can be I or L; and a heavy chain CDR3 comprising KFX$_1$FVX$_2$GSPFGMDV (SEQ ID NO: 297), in which X$_1$ can be H or R and X$_2$ can be S or R. Alternatively or in addition, the 12A4 anti-PDL1 antibody may comprise a light chain CDR1 comprising the sequence of RASQSVSSYX$_1$X$_2$(SEQ ID NO: 299), in which X$_1$ can be L or M and X$_2$ can be A, S, or E; a light chain CDR2 comprising the sequence of DASNRAX$_1$(SEQ ID NO: 303), in which X$_1$ can be T, P, M, or E; and a light chain CDR3 comprising the sequence of QQRX$_1$NWPT (SEQ ID No: 306), in which X$_1$ is S or A. Exemplary 12A4 anti-PDL1 antibodies are provided in Sequence Table 2, any of which can be used for constructing the bispecific antibodies disclosed herein.

In some examples, the anti-PD-L1 portion in the bispecific antibody disclosed herein may be replaced with a PD1 antagonist antibody, for example, an anti-PD1 antibody (e.g., those known in the art).

Bispecific Antibodies

A bispecific antibody as disclosed herein comprises two antigen-binding moieties, one of which binds CLDN 18.2 such as human CLDN 18.2 and the other one of which binds PD-L1 such as human PD-L1. The bispecific antibodies disclosed herein may be in any format known in the art or disclosed herein. Examples are illustrated in FIGS. 1A-1C and FIG. 2.

In some embodiments, the antigen-binding moiety for binding to the CLDN 18.2 antigen may comprise a heavy chain variable region ($V_H$), which comprises the same heavy chain CDRs and any of the parent anti-CLDN 18.2 antibodies disclosed herein, and/or a light chain variable region ($V_L$), which comprises the same light chain CDRs as the parent anti-CLDN 18.2 antibody. In some examples, the antigen-binding moiety for binding to the CLDN 18.2 antigen may comprise the same $V_H$ and/or the same $V_L$ as the parent anti-CLDN 18.2 antibody. See examples provided in the Sequence Tables 1 and 2 below.

In some embodiments, the antigen-binding moiety for binding to the PD-L1 antigen may comprise a heavy chain variable region ($V_H$), which comprises the same heavy chain CDRs and any of the parent anti-PD-L1 antibodies disclosed herein, and/or a light chain variable region ($V_L$), which comprises the same light chain CDRs as the parent anti-PD-L1 antibody. In some examples, the antigen-binding moiety for binding to the PD-L1 antigen may comprise the same $V_H$ and/or the same $V_L$ as the parent anti-PD-L1 antibody. See examples provided in the Sequence Tables 1 and 2 below.

The bispecific antibody disclosed herein may be in any suitable format as those known in the art, for example, those disclosed in Mol. Immunol. 67(2):95-106 (2015), the relevant disclosures of which are incorporated by reference for the subject matter and purpose referenced herein. Some examples are provided below.

Single-Chain Bispecific Antibody Format

In some embodiments, the bispecific antibody disclosed herein is in a single-chain format, in which the antigen-binding moiety specific to the CLDN 18.2 antigen and the antigen-binding moiety specific to the PD-L1 antigen are located on a single polypeptide. In some instances, the $V_H$ and/or $V_L$ regions of the two antigen-binding moieties may be connected by peptide linkers. See below disclosures.

One example is provided in FIGS. 1A-1C. In this setting, the $V_H$ and $V_L$ regions of one antigen-binding moiety can be flanked by the $V_H$ and $V_L$ regions of the other antigen-binding moiety. For example, the $V_H$ and $V_L$ regions of the anti-PD-L1 portion may be located in the middle of the single polypeptide and the $V_H$ and $V_L$ regions of the anti-CLDN 18.2 portion may be located at their N-terminal and C-terminal, respectively. Alternatively, the $V_H$ and $V_L$ regions of the anti-CLDN 18.2 portion may be located in the middle of the single polypeptide and the $V_H$ and $V_L$ regions of the anti-PD-L1 portion may be located at their N-terminal and C-terminal, respectively. A peptide linker may be used to link two variable regions.

In some examples, a single polypeptide bispecific antibody disclosed herein can comprise, from the N-terminus to the C-terminus, the $V_L$ of the anti-CLDN 18.2 portion, peptide linker 1 (L1), the $V_H$ of the anti-PD-L1 portion, peptide linker 2 (L2), the $V_L$ of the anti-PD-L1 portion, peptide linker 3 (L3), and the $V_H$ of the anti-CLDN 18.2 portion.

In some examples, a single polypeptide bispecific antibody disclosed herein can comprise, from the N-terminus to the C-terminus, the $V_H$ of the anti-CLDN 18.2 portion, peptide linker 1 (L1), the $V_H$ of the anti-PD-L1 portion, peptide linker 2 (L2), the $V_L$ of the anti-PD-L1 portion, peptide linker 3 (L3), and the $V_L$ of the anti-CLDN 18.2 portion.

In some examples, a single polypeptide bispecific antibody disclosed herein can comprise, from the N-terminus to the C-terminus, the $V_L$ of the anti-PD-L1 portion, peptide linker 1 (L1), the $V_H$ of the anti-CLDN 18.2 portion, peptide linker 2 (L2), the $V_L$ of the anti-CLDN 18.2 portion, peptide linker 3 (L3), and the $V_H$ of the anti-PD-L1 portion.

In some examples, a single polypeptide bispecific antibody disclosed herein can comprise, from the N-terminus to the C-terminus, the $V_H$ of the anti-PD-L1 portion, peptide linker 1 (L1), the $V_H$ of the anti-CLDN 18.2 portion, peptide linker 2 (L2), the $V_L$ of the anti-CLDN 18.2 portion, peptide linker 3 (L3), and the $V_L$ of the anti-PD-L1 portion.

In some instances, the anti-CLDN 18.2 moiety and the anti-PD-L1 moiety in a bispecific antibody disclosed herein may be designed such that one or more disulfide bonds may be formed between the two antigen-binding moieties. For example, the bispecific antibody may comprise at least one disulfide bond between the $V_H$ of one antigen-binding moiety and the $V_H$ of the other antigen-binding moiety. In other examples, the bispecific antibody may comprise at least one disulfide bond between the $V_H$ of one antigen-binding moiety and the $V_L$ of the other antigen-binding moiety. Alternatively, the bispecific antibody may comprise at least one disulfide bond between the $V_L$ of one antigen-binding moiety and the $V_L$ of the other antigen-binding moiety. See FIG. 1C. To achieve this goal, cysteine residues may be introduced into suitable positions in the $V_H$ and/or $V_L$ regions of one or both of the antigen-binding moieties. Specific examples are provided elsewhere in the present disclosure.

Exemplary one-chain bispecific antibodies capable of binding to CLDN 18.2 and PD-L1 are provide in Sequence Table 1 below.

Two-Chain Bispecific Antibody Format

In some embodiments, the bispecific antibody disclosed herein can be in a two-chain format, comprising two separate polypeptides, which collectively comprise the $V_H$ and $V_L$ regions of the anti-CLDN 18.2 moiety and the anti-PD-L1 moiety. In some examples, each of the two polypeptides in the two-chain bispecific antibody may comprise one variable region from one antigen-binding moiety and one variable region from the other antigen-binding moiety. The two variable regions in each polypeptide may be connected via a peptide linker. See FIG. 2.

In some examples, the two-chain bispecific antibody as disclosed herein may comprise (i) a first polypeptide that comprises, from the N-terminus to the C-terminus, the $V_L$ region of the anti-CLDN 18.2 moiety, a peptide linker, and the $V_H$ region of the anti-PD-L1 moiety; and (ii) a second polypeptide that comprises, from the N-terminus to the C-terminus, the $V_L$ region of the anti-PD-L1 moiety, a peptide linker, and the $V_H$ region of the anti-CLDN 18.2 moiety. In some instances, the peptide linker in the two polypeptides are identical. In other instances, they are different.

In some examples, the two-chain bispecific antibody as disclosed herein may comprise (i) a first polypeptide that comprises, from the N-terminus to the C-terminus, the $V_H$ region of the anti-CLDN 18.2 moiety, a peptide linker, and the $V_L$ region of the anti-PD-L1 moiety; and (ii) a second polypeptide that comprises, from the N-terminus to the C-terminus, the $V_H$ region of the anti-PD-L1 moiety, a peptide linker, and the $V_L$ region of the anti-CLDN 18.2 moiety. In some instances, the peptide linker in the two polypeptides are identical. In other instances, they are different.

In some examples, the two-chain bispecific antibody as disclosed herein may comprise (i) a first polypeptide that comprises, from the N-terminus to the C-terminus, the $V_H$ region of the anti-PD-L1 moiety, a peptide linker, and the $V_L$ region of the anti-CLDN 18.2 moiety; and (ii) a second polypeptide that comprises, from the N-terminus to the C-terminus, the $V_H$ region of the anti-CLDN 18.2 moiety, a peptide linker, and the $V_L$ region of the anti-PD-L1 moiety. In some instances, the peptide linker in the two polypeptides are identical. In other instances, they are different.

Peptide Linkers

Any of the bispecific antibodies disclosed herein, including the single-chain format and the two-chain format, may comprise one or more peptide linkers connecting the multiple heavy chain and/or light chain variable regions of the two antigen-binding moieties. Any peptide linker known in the art or disclosed herein may be used in the bispecific antibodies disclosed herein. Such peptide linkers typically are enriched with flexible amino acid residues, for example, Gly and Ser (G/S rich linkers), so that the fragments flanking the linker can move freely relative to one another. The peptide linkers used herein may contain about 4-30 (e.g., 5-20) amino acid residues in length. When multiple linkers are used in one bispecific antibodies, they may be of the same length in some instances. Alternatively, they have different lengths.

In some embodiments, the bispecific antibody is in the one-chain format as disclosed herein, which may comprise three peptide linkers (L1-L3, from N-terminus to C-terminus) separating the four variable regions in the bispecific antibody. The three peptide linkers may be of the same length, or of different lengths. In some examples, the three peptide linkers are identical. In other examples, they are different in sequence and/or length. For example, L2 may be longer than L1 and L3. In some instances, L1, L3, or both may contain 4-6 amino acid residues. Alternatively or in addition, L2 may contain 15-20 amino acid residues. Non-limiting examples of such peptide linkers are provided elsewhere in the instant disclosure, for example, in the Sequence Table below. Optionally, the one-chain bispecific antibody may further comprise a fourth peptide linker at the C-terminus of the last variable region (from N→C orientation) for connecting an Fc fragment (see below disclosures).

In some embodiments, the bispecific antibody is in the two-chain format disclosed herein and each of the two polypeptides in such a bispecific antibody may comprise a peptide linker separating the two variable regions therein. The peptide linkers in the two polypeptides may be of the same length and/or same sequence. Alternatively, they may differ in length, in sequence, or both. Non-limiting examples of such peptide linkers are provided in Sequence Table 1 below.

Fragments for Dimer Formation

Any of the bispecific antibodies disclosed herein may comprise a C-terminal fragment to form a dimer. In some instances, such a C-terminal fragment may be an Fc fragment or a portion thereof (e.g., comprising the CH2 domain, the CH3, domain, or both) from an immunoglobulin molecule. The C-terminal fragment may be obtained from any suitable Ig subfamily (e.g., IgG, IgA, IgE, IgD, or IgM). In some examples, the C-terminal fragment may be an Fc fragment from an IgG (e.g., IgG1) such as human IgG molecule.

When the bispecific antibody is in the one-chain format, such a bispecific antibody may comprise the C-terminal fragment, which may be linked to the last variable region (in N→C orientation) via a peptide linker (L4). See FIGS. 1A and 1B. The L4 linker may comprise one or more cysteine residues such that one or more disulfide bonds can be formed between two copies of the single-chain bispecific antibody to form a homodimer. In some instances, the L4 linker may be the hinge domain of an Ig or mimic the hinge domain of an Ig.

When the bispecific antibody is in the two-chain format, each polypeptide of such a bispecific antibody may comprise a C-terminal fragment, which can be linked to the C-terminal variable region via a peptide linker. See FIG. 2. In some examples, the C-terminal fragment may be the Fc fragment of an Ig, for example, IgG (e.g., human IgG). In some instances, the Fc fragments are of a naturally-occurring IgG molecule. In other instances, the Fc fragments may comprise one or more mutations to enhance heterodimer formation (between the two polypeptides of the bispecific antibody) and reduce or eliminate formation of homodimers (between two copies of one polypeptide of the bispecific antibody).

In some examples, the Fc fragment in the first polypeptide of the two-chain bispecific antibody and the Fc fragment in the second polypeptide of the bispecific antibody may comprise one or more knob/hole modifications in the CH2 domain, in the CH3 domain, or in both the CH2 and CH3 domains. Typically, the terms "a knob and a hole" or "knobs-into-holes" are used interchangeably herein. Knobs-into-holes amino acid changes is a rational design strategy known in the art for heterodimerization of the heavy (H) chains in the production of bispecific IgG antibodies. Carter, J. Immunol. Methods, 248(1-2):7-15 (2001), the relevant disclosures of which are incorporated by reference herein for the purpose and subject matter referenced herein.

In one example, the "knobs-into-holes" provides an approach as described in, e.g., Ridgway J B B et al., (1996) Protein Engineering, 9(7): 617-21 and U.S. Pat. No. 5,731,168, the relevant disclosures of each of which are incorporated by reference herein for the purpose and subject matter referenced herein. This approach has been shown to promote the formation of heterodimers of the first polypeptide and the second polypeptide chain, and hinder the assembly of corresponding homodimers. In one aspect, a knob is created by replacing small amino side chains at the interface between CH3 domains with larger ones, whereas a hole is constructed by replacing large side chains with smaller ones.

In a specific example, the "knob" mutation comprises T366W and the "hole" mutations comprise T366S, L368A and Y407V (Atwell S el al., (1997) J. Mol. Biol. 270: 26-35). In another specific embodiment, the "knob" mutations comprise T366W, S354C and the "hole" mutations comprise T366S, L368A, Y407V and Y349C, so that a disulfide bond is formed between the corresponding cysteine residues S354C and Y349C, further promoting heterodimer formation. Unless otherwise indicated, the Kabat numbering system is used in the present disclosure for describing positions of amino acid residues in an antibody molecule.

In another example, the first polypeptide chain 1 (knob) contains the Q38D or Q38E substitution in the $V_L$ region of anti-CDLN 18.2 antibody and Q39D or Q39E in the $V_H$ region of anti-PD-L1 antibody, while the second polypeptide chain 2 (hole) contains the Q38R or Q38K substitution in the $V_L$ region of anti-PD-L1 antibody and Q39R or Q39K in the $V_H$ region of anti-CDLN 18.2 antibody, so that the polar interactions between the negatively charged D/E and the positively charged R/K further promote the heterodimer formation.

In yet another example, the "knob" mutations comprise T366W, (S354C) and the "hole" mutations comprise T366S, L368A, Y407V, (Y349C), H435R, and Y436F. Herein, the Fc with H435R and Y436F substitutions (i.e., Fc*) has a reduced binding affinity to Protein A. Thus, the homodimers comprising two unsubstituted CH3 domains (i.e., Fc*Fc*), the homodimers comprising two H435R/Y436F substituted CH3 domains (i.e., Fc*Fc*), and the heterodimer comprising one unsubstituted CH3 domain and one H435R/Y436F substituted CH3 domain (i.e., Fc*Fc) can be better separated by a protein A chromatography method.

Non-limiting exemplary bispecific antibodies as disclosed herein, including one-chain format and two-chain format, are provided in the Sequence Tables 1 and 2 below.

III. Methods for Producing Anti-CLDN 18.2 Antibodies and Bispecific Antibodies

Any of the anti-CLDN 18.2 antibodies or anti-CLDN 18.2/anti-PD-L1 bispecific antibodies described herein can be made by any method known in the art. See, for example, Harlow and Lane, (1998) Antibodies: A Laboratory Manual, Cold Spring Harbor Laboratory, New York. In some embodiments, the anti-CLDN 18.2 antibody may be produced by the conventional hybridoma technology. Alternatively, the anti-CLDN 18.2 antibody may be identified from a suitable library (e.g., a human antibody library). In some instances, high affinity fully human CLDN 18.2 binders may be obtained from a human antibody library, for example, affinity maturation libraries (e.g., having variations in one or more of the CDR regions). See also Examples below. There are a number of routine methods known in the art to identify and isolate antibodies capable of binding to the target antigens described herein, including phage display, yeast display, ribosomal display, or mammalian display technology.

If desired, an antibody (monoclonal or polyclonal) of interest (e.g., produced by a hybridoma cell line or isolated from an antibody library) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to, e.g., humanize the antibody or to improve the affinity (affinity maturation), or other characteristics of the antibody. For example, the constant region may be engineered to more resemble human constant regions to avoid immune response if the antibody is from a non-human source and is to be used in clinical trials and treatments in humans. Alternatively or in addition, it may be desirable to genetically manipulate the antibody sequence to obtain greater affinity and/or specificity to the target antigen and greater efficacy in enhancing the activity of CLDN 18.2. It will be apparent to one of skill in the art that one or more polynucleotide changes can be made to the antibody and still maintain its binding specificity to the target antigen.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). Once isolated, the DNA may be placed into one or more expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) Proc. Natl. Acad. Sci. USA 81, 6851; Neuberger et al. (1984) Nature 312, 604; and Takeda et al. (1984) Nature 314:452.

Methods for constructing humanized antibodies are also well known in the art. See, e.g., Queen et al., Proc. Natl. Acad. Sci. USA, 86:10029-10033 (1989). In one example, variable regions of $V_H$ and $V_L$ of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected. The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704, 692) can be adapted to produce a phage-display, yeast-display, mammalian cell-display, or mRNA-display scFv library and scFv clones specific to CLDN 18.2 can be identified from the library following routine procedures.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence, to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries).

Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of CLDN 18.2 have been replaced (swapped) with sequences from a closely related, but antigenically distinct protein (such as another member of the tumor necrosis factor receptor family). By assessing binding of the antibody to the mutant CLDN 18.2, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art. In some examples, an anti-CLDN 18.2 antibody or a bispecific antibody as disclosed herein can be prepared by recombinant technology as exemplified below.

Nucleic acids encoding the heavy and light chain of an anti-CLDN 18.2 antibody or a bispecific antibody as described herein can be cloned into one expression vector, each nucleotide sequence being in operable linkage to a suitable promoter. In one example, each of the nucleotide sequences encoding the heavy chain and light chain is in operable linkage to a distinct prompter. Alternatively, the nucleotide sequences encoding the heavy chain and the light chain can be in operable linkage with a single promoter, such that both heavy and light chains are expressed from the same promoter. When necessary, an internal ribosomal entry site (IRES) can be inserted between the heavy chain and light chain encoding sequences.

In some examples, the nucleotide sequences encoding the two chains of the antibody are cloned into two vectors, which can be introduced into the same or different cells. When the two chains are expressed in different cells, each of them can be isolated from the host cells expressing such and the isolated heavy chains and light chains can be mixed and incubated under suitable conditions allowing for the formation of the antibody.

Generally, a nucleic acid sequence encoding one or all chains of an antibody can be cloned into a suitable expression vector in operable linkage with a suitable promoter using methods known in the art. For example, the nucleotide sequence and vector can be contacted, under suitable conditions, with a restriction enzyme to create complementary ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector. The selection of expression vectors/promoter would depend on the type of host cells for use in producing the antibodies.

A variety of promoters can be used for expression of the antibodies described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter, and the herpes simplex tk virus promoter.

Regulatable promoters can also be used. Such regulatable promoters include those using the lac repressor from *E. coli* as a transcription modulator to regulate transcription from lac operator-bearing mammalian cell promoters [Brown, M. et al., *Cell*, 49:603-612 (1987)], those using the tetracycline repressor (tetR) [Gossen, M., and Bujard, H., *Proc. Natl. Acad. Sci. USA* 89:5547-5551 (1992); Yao, F. et al., *Human Gene Therapy*, 9:1939-1950 (1998); Shockelt, P., et al., *Proc. Natl. Acad. Sci. USA*, 92:6522-6526 (1995)]. Other systems include FK506 dimer, VP16 or p65 using astradiol, RU486, diphenol murislerone, or rapamycin. Inducible systems are available from Invitrogen, Clontech and Ariad.

Regulatable promoters that include a repressor with the operon can be used. In one embodiment, the lac repressor from *E. coli* can function as a transcriptional modulator to regulate transcription from lac operator-bearing mammalian cell promoters [M. Brown et al., *Cell*, 49:603-612 (1987); Gossen and Bujard (1992); M. Gossen et al., *Natl. Acad. Sci. USA*, 89:5547-5551 (1992)] combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter (Yao et al., *Human Gene Therapy*, 10(16):1392-1399 (2003)). One particular advantage of this tetracycline inducible switch is that it does not require the use of a tetracycline repressor-mammalian cells transactivator or repressor fusion protein, which in some instances can be toxic to cells (Gossen et al., *Natl. Acad. Sci. USA*, 89:5547-5551 (1992); Shockett et al., *Proc. Natl. Acad. Sci. USA,* 92:6522-6526 (1995)), to achieve its regulatable effects.

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art.

Examples of polyadenylation signals useful to practice the methods described herein include, but are not limited to, human collagen I polyadenylation signal, human collagen II polyadenylation signal, and SV40 polyadenylation signal.

One or more vectors (e.g., expression vectors) comprising nucleic acids encoding any of the antibodies may be introduced into suitable host cells for producing the antibodies. The host cells can be cultured under suitable conditions for expression of the antibody or any polypeptide chain thereof. Such antibodies or polypeptide chains thereof can be recovered by the cultured cells (e.g., from the cells or the culture supernatant) via a conventional method, e.g., affinity purification. If necessary, polypeptide chains of the antibody can be incubated under suitable conditions for a suitable period of time allowing for production of the antibody.

In some embodiments, methods for preparing an antibody described herein involve a recombinant expression vector that encodes both the heavy chain and the light chain of an anti-CLDN 18.2 antibody, or encodes both chains of a two-chain bispecific antibody as also described herein. The recombinant expression vector can be introduced into a suitable host cell (e.g., a dhfr– CHO cell) by a conventional method, e.g., calcium phosphate-mediated transfection. Positive transformant host cells can be selected and cultured under suitable conditions allowing for the expression of the two polypeptide chains that form the antibody, which can be recovered from the cells or from the culture medium. When necessary, the two chains recovered from the host cells can be incubated under suitable conditions allowing for the formation of the antibody.

In one example, two recombinant expression vectors are provided, one encoding the heavy chain of the anti-CLDN 18.2 antibody or one of the two chains of a two-chain bispecific antibody disclosed herein and the other encoding the light chain of the anti-CLND18.2 antibody or the other chain of the bispecific antibody. Both of the two recombinant expression vectors can be introduced into a suitable host cell (e.g., dhfr– CHO cell) by a conventional method, e.g., calcium phosphate-mediated transfection. Alternatively, each of the expression vectors can be introduced into a suitable host cells. Positive transformants can be selected and cultured under suitable conditions allowing for the expression of the polypeptide chains of the antibody. When the two expression vectors are introduced into the same host cells, the antibody produced therein can be recovered from the host cells or from the culture medium. If necessary, the polypeptide chains can be recovered from the host cells or from the culture medium and then incubated under suitable conditions allowing for formation of the antibody. When the two expression vectors are introduced into different host cells, each of them can be recovered from the corresponding host cells or from the corresponding culture media. The two polypeptide chains can then be incubated under suitable conditions for formation of the antibody.

Standard molecular biology techniques are used to prepare the recombinant expression vector, transfect the host cells, select for transformants, culture the host cells and recovery of the antibodies from the culture medium. For example, some antibodies can be isolated by affinity chromatography with a Protein A or Protein G coupled matrix.

Any of the nucleic acids encoding the heavy chain, the light chain, or both of an anti-CLDN 18.2 antibody or any of the bispecific antibodies as described herein, vectors (e.g., expression vectors) containing such; and host cells comprising the vectors are within the scope of the present disclosure.

IV. Therapeutic Applications

Any of the anti-CLDN 18.2 antibodies or bispecific antibodies disclosed herein can be used for therapeutic, diagnostic, and/or research purposes, all of which are within the scope of the present disclosure.

Pharmaceutical Compositions

The antibodies, as well as the encoding nucleic acids or nucleic acid sets, vectors comprising such, or host cells comprising the vectors, as described herein can be mixed with a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover. The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™ (polysorbate surfactant), PLURONICS™ or polyethylene glycol (PEG).

In some examples, the pharmaceutical composition described herein comprises liposomes containing the antibodies (or the encoding nucleic acids) which can be prepared by methods known in the art, such as described in Epstein, et al., *Proc. Natl. Acad. Sci. USA* 82:3688 (1985); Hwang, et al., *Proc. Natl. Acad. Sci. USA* 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The antibodies, or the encoding nucleic acid(s), may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation. For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., TWEEN™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 m, particularly 0.1 and 0.5 m, and have a pH in the range of 5.5 to 8.0.

The emulsion compositions can be those prepared by mixing an antibody with Intralipid™ or the components thereof (soybean oil, egg phospholipids, glycerol and water). Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

Therapeutic Applications

To practice the method disclosed herein, an effective amount of the pharmaceutical composition described herein, comprising any of the anti-CLDN 18.2 antibodies or any of the bispecific antibodies, can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes.

The subject to be treated by the methods described herein can be a mammal, more preferably a human or a non-human primate. Mammals include, but are not limited to, farm animals, sport animals, pets, primates, horses, dogs, cats, mice and rats. A human subject who needs the treatment may be a human patient having, at risk for, or suspected of having a target disease/disorder characterized by carrying CLDN+ disease cells. Examples of such target diseases/disorders include, gastric cancer, esophageal cancer, pancreatic cancer, non-small cell lung cancer, ovarian cancer, colon cancer, hepatic cancer, head-neck cancer, and cancer of the gallbladder.

A subject having a target cancer can be identified by routine medical examination, e.g., laboratory tests, organ functional tests, CT scans, or ultrasounds. In some embodiments, the subject to be treated by the method described herein may be a human cancer patient who has undergone or is subjecting to an anti-cancer therapy, for example, chemotherapy, radiotherapy, immunotherapy, or surgery.

A subject suspected of having any of such target disease/disorder might show one or more symptoms of the disease/disorder. A subject at risk for the disease/disorder can be a subject having one or more of the risk factors for that disease/disorder.

As used herein, "an effective amount" refers to the amount of each active agent required to confer therapeutic effect on the subject, either alone or in combination with one or more other active agents. Determination of whether an amount of the antibody achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a target disease/disorder. Alternatively, sustained continuous release formulations of an antibody may be appropriate. Various formulations and devices for achieving sustained release are known in the art.

In one example, dosages for an antibody as described herein may be determined empirically in individuals who have been given one or more administration(s) of the antibody. Individuals are given incremental dosages of the agonist. To assess efficacy of the agonist, an indicator of the disease/disorder can be followed.

Generally, for administration of any of the antibodies described herein, an initial candidate dosage can be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of an antibody as described herein will depend on the specific antibody, antibodies, and/or non-antibody peptide (or compositions thereof) employed, the type and severity of the disease/disorder, whether the antibody is administered for preventive or therapeutic purposes, previous therapy, the patient's clinical history and response to the agonist, and the discretion of the attending physician. Typically the clinician will administer an antibody, until a dosage is reached that achieves the desired result. In some embodiments, the desired result is an increase in anti-tumor immune response in the tumor microenvironment. Methods of determining whether a dosage resulted in the desired result would be evident to one of skill in the art. Administration of one or more antibodies can be continuous or intermittent, depending, for example, upon the recipient's physiological condition, whether the purpose of the administration is therapeutic or prophylactic, and other factors known to skilled practitioners. The administration of an antibody may be essentially continuous over a preselected period of time or may be in a series of spaced dose, e.g., either before, during, or after developing a target disease or disorder.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity or prolonging survival. Alleviating the disease or prolonging survival does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some examples, the pharmaceutical composition is administered intraocularly or intravitreally.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipient is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution. In one embodiment, any of the antibodies disclosed herein may be administered via site-specific or targeted local delivery techniques. Examples of site-specific or targeted local delivery techniques include various implantable depot sources of the antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing one or more nucleic acids such as expression vectors for producing any of the anti-CLDN 18.2 antibodies or bispecific antibodies can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Nat. Acad. Sci. USA (1990) 87:3655; Wu et al., J. Biol. Chem. (1991) 266:338.

Therapeutic compositions containing a polynucleotide (e.g., those encoding the antibodies described herein) can be administered in a range of about 100 ng to about 200 mg of DNA for local administration in a gene therapy protocol. In some embodiments, concentration ranges of about 500 ng to about 50 mg, about 1 µg to about 2 mg, about 5 µg to about 500 µg, and about 20 µg to about 100 µg of DNA or more can also be used during a gene therapy protocol.

The therapeutic polynucleotides described herein can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters and/or enhancers. Expression of the coding sequence can be either constitutive or regulated. Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

The particular dosage regimen, i.e., dose, timing and repetition, used in the method described herein will depend on the particular subject and that subject's medical history.

In some embodiments, more than one antibody, or a combination of an antibody and another suitable therapeutic agent, may be administered to a subject in need of the treatment. The antibody can also be used in conjunction with other agents that serve to enhance and/or complement the effectiveness of the agents. Treatment efficacy for a target disease/disorder such as those disclosed herein can be assessed by methods well-known in the art.

In some embodiments, any of the anti-CLDN 18.2 antibodies or any of the bispecific antibodies disclosed herein may be co-used with another anti-cancer agent, for example, a chemotherapeutic agent, an immunotherapeutic agent, or a combination thereof. For example, any of the anti-CLDN 18.2 antibodies disclosed herein may be used in combination with an immune checkpoint inhibitor, such as an anti-PD-1 antibody or an anti-PDL1 antibody. Alternatively, the anti-CLDN 18.2 antibody may be used in combination with an anti-CTLA4 antibody.

As used herein, the term "combination," "combined," and related terms refers to the simultaneous or sequential administration of multiple therapeutic agents in accordance with this disclosure. For example, any of the anti-CLDN 18.2 antibodies or any of the bispecific antibodies as disclosed herein may be administered with another therapeutic agent simultaneously or sequentially in separate unit dosage forms or together in a single unit dosage form.

Diagnostic Applications

Any of the anti-CLDN 18.2 antibodies disclosed here may be used for detecting and quantifying CLDN 18.2 protein levels in a biological sample using a conventional method, for example, any immunohistological method known to those of skill in the art (see, e.g., Jalkanen, et al., *J. Cell. Biol.* 101:976-985 (1985); Jalkanen et al., *J. Cell Biol.* 105:3087-3096 (1987)). Other antibody-based methods useful for detecting CLDN 18.2 protein expression include immunoassays, such as the enzyme linked immunosorbent assay (ELISA), immunoprecipitation, or Western blotting. Suitable assays are described in more detail elsewhere herein.

The term "biological sample" means any biological sample obtained from an individual, cell line, tissue culture, or other source of cells potentially expressing CLDN 18.2. Methods for obtaining tissue biopsies and body fluids from mammals are well known in the art.

To perform the method disclosed herein, any of the anti-CDLN18.2 antibodies as disclosed herein can be brought in contact with a sample suspected of containing a target antigen as disclosed herein, for example, a human CDLN18.2 protein or a CDLN18.2$^+$ cell. In general, the term "contacting" or "in contact" refers to an exposure of the anti-CDLN18.2 antibody disclosed herein with the sample suspected of containing the target antigen for a suitable period under suitable conditions sufficient for the formation of a complex between the anti-CLDN 18.2 antibody and the target antigen in the sample, if any. The antibody-antigen complex thus formed, if any, can be determined via a routine approach. Detection of such an antibody-antigen complex after the incubation is indicative of the presence of the target antigen in the sample. When needed, the amount of the antibody-antigen complex can be quantified, which is indicative of the level of the target antigen in the sample.

In some examples, the anti-CLDN 18.2 antibodies as described herein can be conjugated to a detectable label, which can be any agent capable of releasing a detectable signal directly or indirectly. The presence of such a detectable signal or intensity of the signal is indicative of presence or quantity of the target antigen in the sample. Alternatively, a secondary antibody specific to the anti-CDLN18.2 antibody or specific to the target antigen may be used in the methods disclosed herein. For example, when the anti-CDLN18.2 antibody used in the method is a full-length antibody, the secondary antibody may bind to the constant region of the anti-CLDN 18.2 antibody. In other instances, the secondary antibody may bind to an epitope of the target antigen that is different from the binding epitope of the anti-CDLN18.2 antibody. Any of the secondary antibodies disclosed herein may be conjugated to a detectable label.

Any suitable detectable label known in the art can be used in the assay methods described herein. In some embodiments, a detectable label can be a label that directly releases a detectable signal. Examples include a fluorescent label or a dye. A fluorescent label comprises a fluorophore, which is a fluorescent chemical compound that can re-emit light upon light excitation. Examples of fluorescent label include, but are not limited to, xanthene derivatives (e.g., fluorescein, rhodamine, OREGON GREEN™ (fluorinated fluorescein dye), eosin, and Texas red), cyanine derivatives (e.g., cyanine, indocarbocyanine, oxacarbocyanine, thiacarbocyanine, and merocyanine), squaraine derivatives and ring-substituted squaraines (e.g., Seta and Square dyes), squaraine rotaxane derivatives such as SeTau dyes, naphthalene derivatives (e.g., dansyl and prodan derivatives), coumarin derivatives, oxadiazole derivatives (e.g., pyridyloxazole, nitrobenzoxadiazole and benzoxadiazole), anthracene derivatives (e.g., anthraquinones, including DRAQ5™ (far-red fluorescent anthraquinone dye), DRAQ7™ (far-red fluorescent anthraquinone dye) and CYTRAK ORANGE™ (orange fluorescent anthraquinone dye)), pyrene derivatives such as CASCADE BLUE™ (acetyl azide, trisodium salt), oxazine derivatives (e.g., Nile red, Nile blue, cresyl violet, and oxazine 170), acridine derivatives (e.g., proflavin, acridine orange, and acridine yellow), arylmethine derivatives (e.g., auramine, crystal violet, and malachite green), and tetrapyrrole derivatives (e.g., porphin, phthalocyanine, and bilirubin). A dye can be a molecule comprising a chromophore, which is responsible for the color of the dye. In some examples, the detectable label can be fluorescein isothiocyanate (FITC), phycoerythrin (PE), biotin, Allophycocyanin (APC) or Alexa Fluor® 488.

In some embodiments, the detectable label may be a molecule that releases a detectable signal indirectly, for example, via conversion of a reagent to a product that directly releases the detectable signal. In some examples, such a detectable label may be an enzyme (e.g., β-galactosidase, HRP or AP) capable of producing a colored product from a colorless substrate.

V. Kits Comprising Anti-CLDN 18.2 Antibody or Bispecific Antibody

The present disclosure also provides kits comprising any of the anti-CLDN 18.2 antibodies or any of the bispecific antibodies disclosed herein. Such kits can be used for any of the applications of such antibodies as disclosed herein, for example, for use in treating or alleviating a target disease, such as a cancer as disclosed herein, or for detecting presence or measuring the amount of CLDN 18.2 protein or CLDN18/2$^+$ cells in a biological sample. Such kits can include one or more containers comprising an anti-CLDN 18.2 antibody or a bispecific antibody as those described herein.

In some embodiments, the kit can comprise instructions for use in accordance with any of the methods described herein. The included instructions can comprise a description of administration of the anti-CDLN18.2 antibody or the bispecific antibody to treat, delay the onset, or alleviate a target disease as those described herein. The kit may further comprise a description of selecting an individual suitable for treatment based on identifying whether that individual has the target disease. In still other embodiments, the instructions comprise a description of administering an antibody to an individual at risk of the target disease.

The instructions relating to the use of the anti-CLDN 18.2 antibody or the bispecific antibody generally include information as to dosage, dosing schedule, and route of administration for the intended treatment. The containers may be unit doses, bulk packages (e.g., multi-dose packages) or sub-unit doses. Instructions supplied in the kits of the present disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating the disease, such as cancer or immune disorders (e.g., an autoimmune disease). Instructions may be provided for practicing any of the methods described herein. The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-CLDN 18.2 antibody or a bispecific antibody as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introuction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty, ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higgins eds. (1985»; *Transcription and Translation* (B. D. Hames & S. J. Higgins, eds. (1984»; *Animal Cell Culture* (R. I. Freshney, ed. (1986»; *Immobilized Cells and Enzymes* (IRL Press, (1986»; and B. Perbal, *A practical Guide To Molecular Cloning* (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Assays Used in Examples

Production of Recombinant Antibodies cDNAs encoding the variable domains of the heavy chain and light chain were amplified from phagemid selected from the phage display screening from antibody humanization and maturation using PCR technology. An extra sequence encoding a signal peptide, for example, the leader sequence MGWSCIILFLVATATGVHS (SEQ ID NO: 218), was added to the 5' end of these nucleotides by PCR. To construct a plasmid to express the whole IgG, the above fragments can be ligated in reading frame with a cDNA fragment encoding human IgG1 constant domain of heavy chain or light chain, and inserted into a mammalian expression vector like pCDNA3.4 to construct the pCDNA3.4-HC and pCDNA3.4-LC.

To transiently express an antibody, 1 µg of plasmids of pCDNA3.4-HC and pCDNA3.4-LC mixture can be used to transfect Expi293F cells. The expressed IgG can be purified from the medium using affinity chromatography with protein A resin. Eluted IgG can be checked by gel electrophoresis and high-performance liquid chromatography (HPLC) to ensure purity. The buffer solution can be exchanged into PBS, and the concentration can be determined by OD280 using 1.4 extinction coefficient. The monoclonal antibodies can be aliquoted and stored at −80° C.

Enzyme-Linked Immunosorbent Assay (ELISA)

ELISA assay was employed to determine the binding properties of the bispecific antibodies to their antigens. Briefly, the wells of the microtiter plates were coated with recombinant CLDN 18.2 or PD-L1 protein. After blocking with 5% BSA in PBS, the wells were reacted with the bispecific antibodies, or their parental anti-CLDN 18.2 antibody, or anti-PD-L1 antibody durvalumab, at ambient temperature for two hours. The wells were then reacted with goat anti human IgG antibody conjugated with horseradish peroxidase (HRP). After washing, the plates were developed with TMB substrate and stopped with 2M sulfuric acid or 1M phosphoric acid, and the ODs were analyzed at 450 nM.

Competitive ELISA

The microtiter plates were coated with PD-L1 protein and blocked with 5% BSA in PBS. The wells were then reacted with an aliquot of the bispecific antibodies pre-incubated with PD-L1 of various concentrations at room temperature. The wells were then reacted with goat anti human IgG antibody conjugated with HRP. After washing, the plates were developed with TMB substrate and stopped with 2M sulfuric acid or 1M phosphoric acid, and the ODs were then analyzed at 450 nM.

In-Cell ELISA

HEK293T cells that over express CLDN 18.2 were seeded into 96-well microplates at $1\times10^5$ cells per well. After culturing overnight to allow the cells to adhere to the wells, 10% paraformaldehyde was used to fix and cross link the cells to the plates. The wells were then blocked with BSA and reacted with the bispecific antibodies at ambient temperature for two hours. The wells were then be reacted with goat anti human IgG antibody conjugated with HRP. After washing, the plates were developed with TMB substrate and stopped with 2M sulfuric acid or 1M phosphoric acid, and the ODs are then analyzed at 450 nM.

Complement Dependent Cytotoxicity (CDC)

Bispecific antibodies were evaluated for their ability to mediate CDC using the CYTOTOX-GLO™ Cytotoxicity Assay (Promega) by measuring the stable "glow-type" luminescent signal. Briefly, $1\times10^5$ to $5\times10^5$ cells stably transfected with plasmid encoding CLDN 18.2 can be washed and incubated with various concentrations of the bispecific antibody for 120 min at room temperature or at 37° C. Human serum or plasma with complements can then be added to a final concentration of 25% (v/v) and the cells incubated at 37° C. for 4 hours. After adding Cyto-Glo cytotoxicity assay reagent, the luminescence signal was measured using a Bio-Tek plate reader. The percentage specific lysis was calculated as follows: % specific lysis= (fluorescence sample−fluorescence background)/(fluorescence maximal lysis-fluorescence background)×100.

Antibody Dependent Cellular Cytotoxicity (ADCC) Assay

ADCC assay was performed using ADCC Reporter Bioassay (Promega), which uses an engineered Jurkat cells that stably express the FcγRIIIa receptor V158 variant (high affinity) and an NFAT response element driving expression of firefly luciferase as the effector cells. The transfected cells that stably express CLDN 18.2 at a density of $1\times10^5$/mL were incubated with bispecific antibodies at various concentrations for 1 hour. Engineered Jurkat effector cells are then added to each well at a ratio of E:T (effector cell:target cell=10:1), and the cells mixture was incubated for 6 hours at 37° C. under 5% CO2 and 90% humidity. The luminescence signal resulting from the expression of luciferase driven by NFAF response element was analyzed by Bio-tek synergy 4.

Antibody Phage Display Selection

Library sorting was carried out according to a procedure modified from the published protocols (Miller et al. *PLOS one*, 7: e43746 (2012); Fellouse F. A. et al *J. Mol. Biol.* 373, 924 (2007); Sherman et al *J. Mol. Biol.* 426, 2145 (2014)). In a typical procedure in the first round, 0.1-0.5 nmol of the biotinylated CLDN 18.2 was immobilized on the streptavidin-coated magnetic beads, blocked with biotin, and incubated with phage library for 15 min in 1 mL binding buffer (PBS Buffer supplemented with 0.05% TWEEN™ 20, 0.5% BSA). The beads were then separated from the solution with a magnet, washed twice with the binding buffer, and directly used to transduce the XL1-blue cells to amplify the phages. In the subsequent rounds, purified phages were first incubated with streptavidin beads in the binding buffer for 30 min to remove the bead binders and the supernatant was then incubated for 15 min with 50 nM biotinylated CLDN 18.2 in 100 µL binding buffer, supplemented with 0.5 µM CLDN 18.1. Streptavidin magnetic beads were then added to the solution for 15 min to allow the capture of the RNA target complex together with the bound phages. The beads were then eluted with 100 mM DTT or 0.1 M Gly-HCl (pH 2.1) buffer followed by neutralization with 1M TRIS-CL™ buffer (pH 8; tris(hydroxymethyl)aminomethane hydrochloride).

Phage ELISA Screening

After 3-5 rounds of selection, individual clones were analyzed by phage ELISA. Forty-eight or more individual colonies were picked from a fresh LB/Amp plate, inoculated in 400 µL of 2YT medium containing 100 µg/mL ampicillin and $10^{10}$ PFU/mL M13KO7 helper phage in a 96-well deep-well plate, and grown at 37° C. overnight with shaking at 300 rpm. The deep-well plate was then centrifuged for 15 min at 3500 rpm to pellet the cells. The supernatant was diluted 3-fold to prepare a phage solution in Binding Buffer. A 96-well MAXISORP™ plate was coated with 100 µL of 2 µg/mL neutravidin in 100 mM sodium bicarbonate coating buffer (pH 9.6) overnight at 4° C. The coating solution was removed and the MAXISORP™ plate was blocked for 1 h with 200 µL/well of 1% (w/v) BSA in PBS. After the blocking solution was removed, the MAXISORP™ plate was washed with PBS with 0.05% (v/v) TWEEN™ 20 and incubated with 100 µL/well of 25 nM CLDN 18.2 in Binding Buffer for 30 min at room temperature. For each well containing CLDN 18.2 target, a control well with CLDN 18.1 was prepared in parallel. The MAXISORP™ plate was then washed with Binding Buffer, incubated with 100 µL/well phage solution at room temperature for 30 min. After washing with Binding Buffer, the MAXISORP™ plate was incubated with 100 µL/well anti-M13/horseradish peroxidase conjugate (diluted 5000× in Binding Buffer) at room temperature for 30 min. After another washing step with Binding Buffer, the MAXISORP™ plate was incubated with 100 µL/well Ultra TMB-ELISA Substrates for 5-10 min, quenched with 100 µL/well of 1 M phosphoric acid, and read spectrophotometrically at 450 nm in a microplate reader.

Competitive Phage ELISA

MAXISORP™ ELISA plate was coated with CLDN 18.2 overnight at 4° C. and blocked with BSA for 1 hour at RT. Serial dilutions of CLDN 18.2 were incubated with subsaturating concentrations of phage at RT for 1 hour, and then added to the blocked and washed ELISA plate. After 15 min incubation and washing, anti-M13 antibody/HRP conjugate was added and incubated for 30 min, then developed with TMB for 5-10 min and quenched with 1 M phosphoric acid. Binding signal was analyzed by the plate reader.

Mouse Pharmacokinetic Assay

CD1 mice received a single IV dose of 1 mg/kg and 5 mg/kg of bispecific antibody via the tail vein in the PK study. The terminal blood sample was collected via cardiac puncture from each animal in each dosing group at the following time points (2 mice/time point): 15 min, 2 h, 8 h, 1, 2, 3, 7, 14 day and processed for serum for the PK analysis through ELISA analysis.

Anti-Drug Antibody (ADA) Assay

CD1 mice received a single IV dose of 1 mg/kg or 5 mg/kg of bispecific antibody via the tail vein. The blood sample was collected via cardiac puncture in each dosing group at the specified time points. To determine the ADA level of these blood samples, the bispecific antibodies were coated to 96-well microtiter plates. After blocking with BSA, the wells were incubated with mice plasma diluted with RMD (50×), and then reacted with anti-mouse IgG antibody conjugated with HRP. After washing, the plates were developed with TMB substrate and stopped with 2M sulfuric acid or 1M phosphoric acid. The ODs were analyzed at 450 nM.

Example 1: Generation of Mouse Anti-CLDN 18.2 Antibody 5C9

(A) Immunization

Female Balb/C mice were injected intravenously with plasmid encoding full-length CLDN 18.2 (SEQ ID No: 211) with Freund's adjuvant (complete suspension). A total of 3 injections were given within a 3-week interval. At the final DNA injection, or during the injections, 3 to 5 million of 293T cells or 3T3 cells that express the full-length CLDN 18.2 were also injected intravenously. Three or four days after this boost, the mice were euthanized and their spleens were harvested for fusion.

(B) Hybridoma Production

To produce monoclonal hybridomas, mouse myeloma cell Sp2/0 were grown to a logarithmic growth phase and fused with immunized mouse spleen cells at a ratio of 1:2 or 1:3 in the presence of polyethylene glycol/Dimethyl sulfoxide (PEG/DMSO; 45%/5%) solution (HYBRI-MAX™, Sigma, P7181, D2650). The hybridoma cells were selected in hypoxanthine-aminopterin-thymidine (HAT) (Sigma, H0262) media for 7 days. Media containing HT was added and the hybridoma cells were incubated for additional 7-10 days. Hybrids were initially screened for antibody production after 2-3 weeks of fusion and again after additional 2 weeks. Hybridomas were further cloned three times and picked from a plating density of 0.5 cells/well.

(C) Selection of Positive Clones

The clones that secret antibodies against CLDN 18.2 were screened by ELISA assays using HEK293T cells that express full-length CLDN 18.2. The native HEK293T cells were used as control. The clones that secret antibodies bound to HEK293T-CLDN 18.2 but not to HEK293T were selected. Then, the selected clones were subjected to second screen using HEK293-CLDN 18.2 cells and HEK293-CLDN 18.1 cells. The clones that secret antibodies bound to HEK293T-CLDN 18.2 but not HEK293T-CLDN 18.1 were selected for subcloning until all sub single clone was positive for HEK293T-CLDN 18.2 specifically.

(D) Preparation of Mouse Antibodies

To produce monoclonal antibody for characterization, the selected monoclonal hybridoma cells were injected into the peritoneal cavity of Balb/C mice to produce monoclonal antibody in the ascitic fluid. The antibody was purified using Protein A/G affinity chromatography to provide mouse antibody 5C9 that comprises two heavy chain variable domains (VHs) comprising the amino acid sequence of SEQ ID NO:1 and two light chain variable domains (VLs) comprising the amino acid sequence of SEQ ID NO:5.

Example 2: Preparation of Humanized Anti-CLDN 18.2 Antibody h5C9o Framework

The framework of human consensus sequences of heavy chain subgroup III (humIII) and light chain κ subgroup I (humκI) was chosen based on the success of the blockbuster antibody therapeutic drugs, HERCEPTIN® (trastuzumab) and HUMIRA® (adalimumab) (Carter P, Presta et al *Proc. Natl. Acad. Sci. USA* 89, 4285-4289 (1992); Presta L G, et al *J. Immunol* 151, 2623-2632 (1993); Kabat, E. A., et al, Sequences of Proteins of Immunological Interest. 5th ed. Public Health Service, National Institutes of Health, Bethesda, MD (1991) for the humanization of the anti-CLDN 18.2 antibodies.

To generate a template pSY1 for future CDR swap, the humIII and hum κI genes were inserted into a phagemid designed to display human Fab on the surface of M13 bacteriophage. Two open reading frames were used to encode for two Fab chains separately under the control of phoA promoters. The first open reading frame encoded for the light chain and second one encoded for the heavy chain fused to the C-terminal domain of the M13 minor coat protein P3. Both peptide chains were directed for secretion by N-terminal stII signal sequences.

Single Stranded DNA (ssDNA) Template pSY1 was then electroporated into CJ236 cells (uracil deglycosidase deficient) on a micropulser electroporator (Bio-Rad 1652100). Single colony was used to inoculate 1 mL 2YT starting culture with 100 μg/mL ampicillin and 10 μg/mL chloramphenicol and the resulting culture was shaken at 37° C. for 6 h. M13KO7 helper phage (~$10^{10}$ pfu) was added and after 10 min shaking at 37° C., 300 μL of the mixture was transferred to 30 μL 2YT with 100 μg/mL ampicillin and 0.25 mg/mL uridine. After 18 h growth at 37° C., phages were purified and the uracil-containing ssDNA was isolated with the E.Z.N.A® M13 DNA Mini Kit (Omega Biotek Inc).

CDR Swap to Generate the Humanized h5C9o

Kunkel mutagenesis (Kunkel T. A. *Proc Natl Acad Sci USA* 82, 488-92 (1985); Sidhu S. S et al *Methods Enzymol* 328, 333-63 (2000)) was employed to construct the CDR swap version of the humanized anti CLDN 18.2 antibody h5C9o. The following primers were designed to swap the CDRs of 5C9 antibody into pSY1:

```
(for CDR-L1)
                                       (SEQ ID NO: 219)
AGGGTCACCATCACCTGCAAAAGCAGTCAGAGTCTGCTCAACAGTGGCAA

CCAGAAAAGCTATCTGACCTGGTATCAACAGAAACCA, (for CDR-L2)
                                       (SEQ ID NO: 220)
GCTCCGAAGCTTCTGATTTATTGGGCATCTACCCTCGAAAGCGGAGTCCC

TTCTCGCTTC, (for CDR-L3)
                                       (SEQ ID NO: 221)
GCAACTTATTACTGTCAGAACGCGTATTCTTTTCCGTTTACGTTCGGACA

GGGTACC, (for CDR-H1)
                                       (SEQ ID NO: 222)
TCCTGTGCAGCTTCTGGCTACACCTTTACCAACTATGGTATGAACTGGGT

GCGTCAGGCCCCG, (for CDR-H2)
                                       (SEQ ID NO: 223)
GGCCTGGAATGGGTTGCATGGATTAACATGTATACCGGCGAACCGACCTA

TGCCGATGACTTCAAGGGCCGTTTCACTATAAGCCGT, (for CDR-H3)
                                       (SEQ ID NO: 224)
GTCTATTATTGTGCTCGCCTGTATAACGGCAACTCTCTGGACTACTGGGG

TCAAGGA.
```

The nucleotide fragments coding for the CDR regions based on Kabat numbering are underlined.

The six primers were phosphorylated individually using T4 Polynucleotide kinase (NEB) at 37° C. for 1 h. The phosphorylated primers were annealed to the uracil-containing ssDNA template at 90° C. for 1 min, 50° C. for 3 min and placed on ice. The oligonucleotides were extended with T7 DNA polymerase and ligated with T4 DNA ligase at 37° C. for 1.5 h to form covalently closed circular DNA. The DNA was desalted and affinity purified with Qiagen QIAQUICK® DNA purification kit and transformed into XL-1 blue cells (uracil glycosidase containing strain) by heat shock transformation. Small scale DNA was purified using Qiagen miniprep kit and sent for sequencing to confirm the sequence. Plasmid h5C9a was then used to prepare uracil-containing ssDNA for humanization library construction.

Humanization Library Construction

Based on the published work (Baca M, et al *J. Biol. Chem.* 272, 10678-10684 (1997)) and referenced by some marketed therapeutic antibodies such trastuzumab, a library was designed to include the mouse and frequent human amino acid compositions at the following sites, VL: M4 (MTG), F71 (TWC), F83 (YTC); VH: A24 (RYC), V37 (RTC), F67 (NYC), 169 (WTC), R71 (CKC), D73 (RMC), K75 (RMG), N76 (ARC), L78 (SYG), A93 (DYG), R94 (ARG). Degenerate codons (underlined in the below sequences) used for each site are shown in the parentheses. M=A or C, W=A or T, R=A or G, Y=C or T, N=A, C, G, or T, K=G or T, S=G or C, and D=A, G, or T. The following primers were designed to introduce these degenerate codons in the desired sites via Kunkel mutagenesis:

```
(hLibL1)
                                   (SEQ ID NO: 225)
GCCTATGCATCCGATATCCAGMTGACCCAGTCCCCGAGCTCC, (hLibL2)
                                   (SEQ ID NO: 226)
GGTAGCGGTTCCGGGACGGATTWCACTCTGACCATCAGCAGTCTGCAGCC

GGAAGACYTCGCAACTTATTACTGTCAG, (hLibH1)
                                   (SEQ ID NO: 227)
CTCCGTTTGTCCTGTGCARYCTCTGGCTACACCTTTACCAACTATGGTAT

GAACTGGRTCCGTCAGGCCCCGGGTAAG, (hLibH2)
                                   (SEQ ID NO: 228)
GATGACTTCAAGGGCCGTNYCACTWTCAGCCKCGACRMCTCCRMGARCAC

ASYGTACCTACAAATGAACAGC, (hLibH3)
                                   (SEQ ID NO: 229)
GACACTGCCGTCTATTATTGTDYGARGCTGTATAACGGCAACTCT.
```

Phosphorylation of the primers and Kunkel mutagenesis were carried out as described (Sidhu S. S et al *Methods Enzymol* 328, 333-63 (2000)). Covalently closed circular DNA obtained was electroporated into electrocompetent SS320 cells to prepare h5C9 humanization Fab library as described (Sidhu et al. 2000). The tittered apparent diversity was $1.9 \times 10^9$, larger than $3.2 \times 10^6$, the designed theoretical diversity.

Selection of the Humanized h5C9 Clones

Selection was carried out similar to that have been described previously (Ye J. D., et al *Proc Natl Acad Sci USA* 105, 82-87 (2008)). Biotinylated full-length CLDN 18.2 was used as the antigen. In the first round, 0.5 nmol of biotinylated CLDN 18.2 was immobilized on magnetic beads (Promega) and incubated with $10^{12-13}$ cfu of phages for 15 min in 1 ml of PD (1×PBS with 0.1% DDM), supplemented with 0.4% BSA and 0.2 mg/mL streptavidin. The solution was then removed, and the beads were washed twice with PD and amplified for later rounds of selection. In the subsequent rounds, purified phage pools were first incubated with streptavidin beads for 15 min, and the supernatant was used in the subsequent selection on a KingFisher magnetic particle processor (Thermo Fisher). Phages ($10^{10-11}$ cfu) were incubated for 15 min with decreasing concentrations of biotinylated CLDN 18.2 (20-0.1 nM) and increasing concentrations of CLDN 18.1 (400-800 nM). Streptavidin magnetic beads were then added to the solution for 15 min to allow the capture of the biotinylated CLDN 18.2 together with the bound phages. The beads were washed five times with PD, and eluted in 100 mM DTT for 15 min. After each round of selection, recovered phages were amplified as described (Sidhu S. S et al *Methods Enzymol* 328, 333-63 (2000)). After five rounds of selection, phage ELISA were performed to identify positive clones and sequenced. H5C9o was obtained and comprised two copies of the heavy chain variable domain ($V_H$) comprising the amino acid sequence of SEQ ID NO:9 and two copies of the light chain variable domain ($V_L$) comprising the amino acid sequence of SEQ ID NO: 11.

Example 3: Preparation of Anti-CLDN 18.2-5C9ob, 5C9oae, and 5C9oap

Construction of the h5C9oAMH9_12 Library

The first library focused on CDR-H3 was constructed as follows. Position right upstream of 101 (100a in the current CDR), according to the Kabat numbering system, was given a diversity of the frequent four amino acids: FILM. Position 95-100 were randomized with a customized codon XYZ, X=G (0.45), A (0.23), T (0.11), C (0.21), Y=G (0.31), A (0.34), T (0.17), C (0.18), Z=G (0.24), C (0.76). This codon is similar to the one that mimics the natural AA composition in CDR H3 at position 95-100a_z (Lee C. V., et al *J. Mol. Biol.* 340, 1073-1093 (2004)) with reduced representation in cysteine and stop codon. The length of the CDR-H3 was allowed to vary between 9 and 12 residues with each additional residue encoded by XYZ codon. The theoretical size of the library is $1.5 \times 10^{14}$. Given the large size, therefore diluted binding clones in the library, the position 95-100a of CDR-H3 sequence was replaced with TAAGGCCAA-GACGGCCTATAA (SEQ ID NO: 230) and used this new construct to prepare the template for library construction. This allowed for the effective removal of the parent h5C9o from the affinity maturation library. The following primers were used in Kunkel mutagenesis to construct this library:

```
                                   (SEQ ID NO: 231)
GTCTATTATTGTGCTCGCXYZXYZXYZXYZXYZXYZWTKGACTACTGGGG

TCAAGGA, (SEQ ID NO: 232)
GTCTATTATTGTGCTCGCXYZXYZXYZXYZXYZXYZXYZWTKGACTACTG

GGGTCAAGGA, (SEQ ID NO: 233)
GTCTATTATTGTGCTCGCXYZXYZXYZXYZXYZXYZXYZXYZWTKGACTA

CTGGGGTCAAGGA, (SEQ ID NO: 234)
GTCTATTATTGTGCTCGCXYZXYZXYZXYZXYZXYZXYZXYZXYZWTKGA

CTACTGGGGTCAAGGA.
```

Library construction was carried out as described above and the apparent diversity was $1.5 \times 10^{10}$.

Antigen binding requires a concerted action from the direct binding of contact residues and structural support from framework residues in all CDR regions. Therefore, if possible, it is beneficial to be able to screen residues on multiple CDRs at the same time. In addition to the potential improvement in antigen binding affinity and specificity, being able to sample multiple CDR sequence spaces at the same time may have a better chance to obtain antibodies with more compact and stable structures. Our capability of making large sized synthetic antibody libraries with minimal effort allows us to screen multiple CDR sequences within the same library. Two libraries were constructed in this endeavor.

Construction of the h5C9oAM_CDRW_L3_H3 Library

This library aims at screening for CDRs L3 and H3 at the same time. A single amino acid CDR walking (Yang W. P., et al *J. Mol. Biol.* 254, 392-403 (1995)) was adopted to randomize positions 95-100 in CDR-H3 and positions 91-94 in CDR-L3, according to the Kabat numbering system. Each position was randomized individually at a given CDR with the degenerate codon NNS to encode all 20 amino acids. Primers comprising the nucleotide sequences of SEQ ID NOs: 235-244 (see Sequence Table 1 below) were used in Kunkel mutagenesis to construct this library. Library construction was carried out as described above and the apparent diversity was $1.0 \times 10^9$, which is larger than $2.5 \times 10^4$, the designed diversity.

Construction of the h5C9AM_CDRW_L1_L2_-H2 Library

This library is constructed for screening for CDRs L1, L2 and H2 at the same time. Similar to the previous library, a single amino acid CDR walking strategy (Yang W. P., et al *J. Mol. Biol.* 254, 392-403 (1995)) was adopted. The randomized positions included 27-33 in CDR-L1, positions 50, 53 and 55 in CDR-L2, and positions 50, 52-54, 56-58 in CDR-H2. Each position was also randomized individually at a given CDR with the degenerate codon NNS to encode all 20 amino acids. Primers comprising the nucleotide sequences of SEQ ID NOs: 245-267 (see Sequence Table 1) were used in Kunkel mutagenesis to construct this library. Library construction was carried out as described above and the apparent diversity was $1.1 \times 10^{10}$, which is larger than $9.4 \times 10^6$, the designed diversity.

Selection of the Affinity Maturated Antibodies

The above three affinity maturation libraries were used separately when selected against CLDN 18.2. The basic procedure is similar to that described in Example 2 with the following modification. The biotinylated antigen concentration used in the selection ranged from 1 nM to 10 pM. With 10 pM biotinylation antigen concentration, after capture of the antigen/antibody complex on the heads, the heads were washed with PD and >1000 fold of non-biotinylated antigen was incubated with the beads for 0.5-1 hour at RT. Then washed and eluted as described above. This off-rate selection allows the selection of antibodies with slower off-rate, potentially beneficial to its in vivo activity.

The humanized antibodies 5C9ob, 5C9oae, or 5C9oap were obtained and compromised two copies of the heavy chain variable domain ($V_H$) comprising the amino acid sequence of SEQ ID NO:9, SEQ ID NO:17, or SEQ ID NO:21 and two copies of the light chain variable domain ($V_L$) comprising the amino acid sequence of SEQ ID NO:13, SEQ ID NO: 19 or SEQ ID NO:23, respectively.

Example 4: General Method for Monovalent Affinity Maturation of Anti-CLDN 18.2 Antibodies Single Stranded DNA (ssDNA) Template of h5C9o Plasmid of h5C9o was electroporated into CJ236 cells (uracil deglycosidase deficient) on a micropulser electroporator (Bio-Rad 1652100). Single colony was used to inoculate 1 mL 2YT starting culture with 100 µg/mL ampicillin and 10 µg/mL chloramphenicol and the resulting culture was shaken at 37° C. for 6 h. M13KO7 helper phage (~$10^{10}$ pfu) was added and after 10 min shaking at 37° C., 300 µL of the mixture was transferred to 30 µL 2YT with 100 µg/mL ampicillin and 0.25 mg/mL uridine. After 18 h growth at 37° C., phages were purified and the uracil-containing ssDNA was isolated with the E.Z.N.A.® M13 DNA Mini Kit (Omega Biotek Inc).

Construction of the h5C9AMmv_CDRW_L1_L2_H2 Library

This library is constructed to screen for CDRs L1, L2 and H2 at the same time. A single amino acid CDR walking strategy (Yang W. P., et al *J. Mol. Biol.* 254, 392-403 (1995)) was adopted. The randomized positions included 27-33 in CDR-L1, positions 50-56 in CDR-L2, and positions 50, 52-54, 56-58 in CDR-H2. Each position was randomized individually at a given CDR with the degenerate codon NNS to encode all 20 amino acids. Randomization was incorporated into h5C9o ssDNA template via Kunkel mutagenesis (Kunkel T. A. *Proc Natl Acad Sci USA* 82, 488-92 (1985); Sidhu S. S et al *Methods Enzymol* 328, 333-63 (2000)). Phosphorylation of the primers and Kunkel mutagenesis were carried out as described (Sidhu S. S et al *Methods Enzymol* 328, 333-63 (2000)). Covalently closed circular DNA obtained was electroporated into electrocompetent SS320 cells to prepare h5C9 humanization Fab library as described (Sidhu S. S et al *Methods Enzymol* 328, 333-63 (2000)). The tittered apparent diversity was $1 \times 10^9$, larger than $2.2 \times 10^7$, the designed theoretical diversity.

Selection of the Affinity Maturated Antibodies

Selection was carried out similar to that have been described previously (Ye J. D., et al *Proc Natl Acad Sci USA* 105, 82-87 (2008)). Biotinylated full-length CLDN 18.2 was used as the antigen. In each round except for the first round, purified phage pools were first incubated with streptavidin beads for 15 min, and the supernatant was used in the subsequent selection on a KingFisher magnetic particle processor (Thermo Fisher). Phages ($10^{10-11}$ cfu) were incubated for 1 hour with biotinylated CLDN 18.2 (100, 10, and 100 pM for the first, second and third round respectively). Streptavidin magnetic beads were then added to the solution for 1.5 min to allow the capture of the biotinylated CLDN 18.2 together with the bound phages. In the first and second round, after capture of the antigen/antibody complex on the beads, the beads were washed with PBS supplemented with 0.1% DDM (PD) and >1000 fold of non-biotinylated antigen was incubated with the beads for 0.5-1 hour at RT. The beads were then washed five times with PD, and eluted in 100 mM DTT for 15 min. After each round of selection, recovered phages were amplified as described (Sidhu S. S et al *Methods Enzymol* 328, 333-63 (2000)). After three rounds of selection, phage ELISA were performed to identify positive clones and sequenced.

Clone identification from the h5C9AMmv_CDRW_L1_L2_H2 Library

Figure 3:
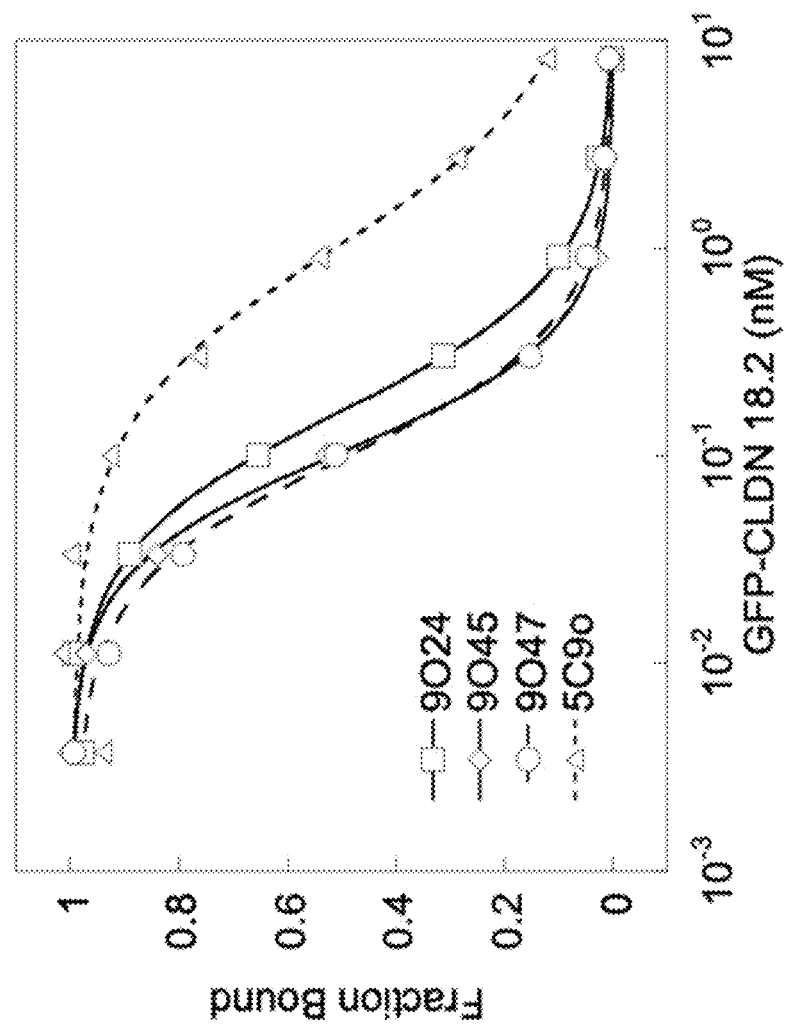
FIG. 3 is a chart showing binding to CLDN 18.2 of exemplary affinity matured antibodies measured by competitive phage ELISA.

Screening h5C9AMmv_CDRW_L1_L2_H2 library identified clones (9O24, 9O36, 9O41, 9O45, and 9O47) that have improved binding to CLDN 18.2 compared to the parent antibody. Their binding affinities of clones 9O24, 9O36, 9O41, 9O45, and 9O47 to CLDN 18.2 versus clones h5C9o, 5C9oae, and 5C9oap were measured by competitive phage ELISA, and are shown in Table 1 and FIG. 3.

Combining Beneficial Mutations from Different CDRs

Figure 4:
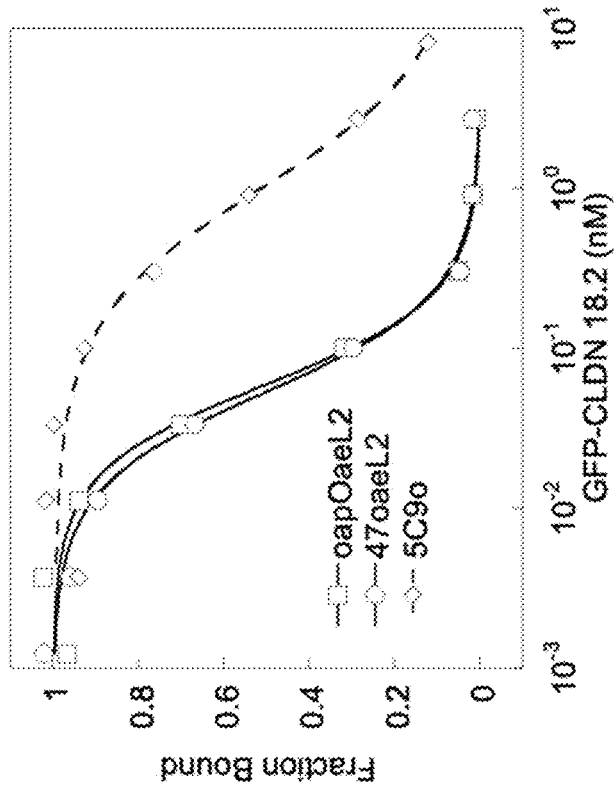
FIG. 4 is a chart showing binding affinity of antibodies having combined mutations to the CLDN 18.2 antigen. Diamond: h5C9o. Circle: 9O47. Square: 9O47-5C9oae combination clone.

Clones 5C9ob and 5C9oae were demonstrated to bind to CLDN 18.2 with improved affinities compared to the parent clone h5C9o. These two clones contain mutations in CDR L3 and CDR H3. To test whether these mutations have additive effect with the mutations in other CDR regions, 5C9ob and 5C9oae mutations were added to clones 5C9oap, 9O24, 9O36, 9O41, 9O45, and 9O47 via Kunkel mutagenesis. Their binding affinities to CLDN 18.2 were measured with competitive phage ELISA and are listed in Table 1. Exemplar plots of the competitive phage ELISA is shown in FIG. 4.

cells, cultured in Expi293™ expression medium, using ExpiFectamine™ as a transfection reagent, as described by the LifeTech protocol (Life Technologies™, Carlsbad, CA). Expifectamine™ transfection enhancers 1 and 2 were added on day 2 of culture as described in LifeTech protocol. Cultures were incubated at 37° C., 8% C02, and 130 rpm through day 7. Cultures were harvested by centrifugation

TABLE 1

Binding affinities of the affinity matured and combination clones measured by competitive phage ELISA.

| mutations | Clone | | | | | | |
|---|---|---|---|---|---|---|---|
| | 5C9o | 5C9oap | 9O24 | 9O36 | 9O41 | 9O45 | 9O47 |
| None | 1.07 | No data | 0.144 | 0.108 | 0.167 | 0.104 | 0.095 |
| 5C9ob | 0.221 | 0.100 | 0.139 | 0.111 | 0.177 | 0.096 | 0.098 |
| 5C9oae | No data | 0.060 | 0.067 | 0.064 | No binding | 0.071 | 0.059 |
| LC55E (L2) | 1.07 | No data | No data | No data | No data | No data | 0.141 |
| oaeL2 | No data | 0.0593 | 0.0604 | 0.0590 | No data | 0.0562 | 0.0533 |

CDR LC 55E Mutation for Solubility Screening

Figure 5:
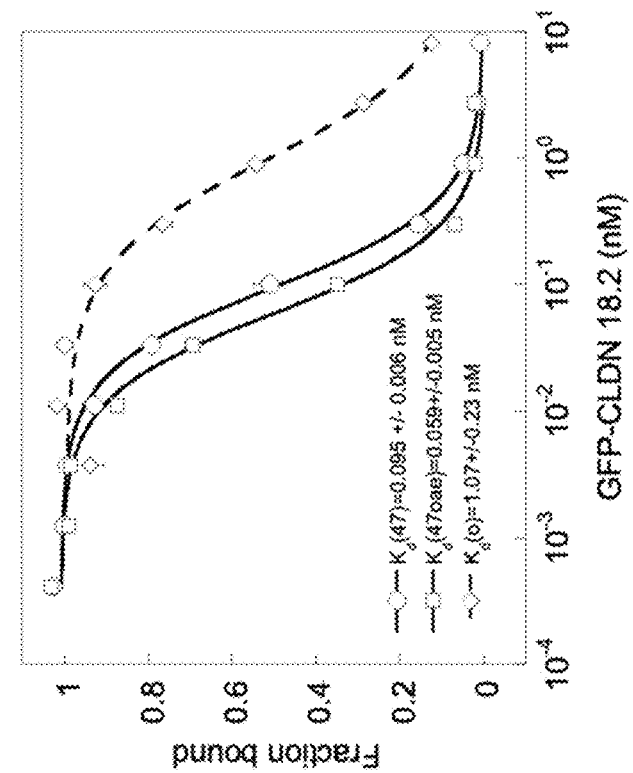
FIG. 5 is a chart showing binding of antibodies with 5C9oae combined mutations and L2 mutation to CLDN 18.2 as measured by competitive phage ELISA. Diamond: h5C9o. Circle: 9O47 with 5C9oae and L2 mutations. Square: 5C9oap with 5C9oae and L2 mutations.

To identify clones with improved solubility, CDR light chain residue 55 (LC55E or L2) was mutated back to Glu on clones 9O47, 5C9oap-oae, 9O24-oae, 9O36-oae, 9O45-oae, and 9O47-oae. Their binding affinities were measured by competitive phage ELISA and are summarized in Table 1. Exemplar plots of the competitive phage ELISA is shown in FIG. 5.

Example 5: Construction and Characterization of Exemplary Single-Chain Bispecific Antibodies that Bind to CLDN 18.2 and PD-L1

Construction of Exemplary Single-Chain Bispecific Antibodies by Direct Synthesis A number of exemplary anti-CLDN 18.2 and PD-L1 bispecific antibodies, including clones scDb01, scDb02, scDb03, scDb04, scDb05, scDb06, scDb07, scDb08, scDb09, scDb9O24, scDb9O41, and scDb9O47 were constructed, using one of anti-CLDN 18.2 clones 5C9ob, 5C9oap, 9O24, 9O41, and 9O47 and anti-PD-L1 antibody durvalumab as the parent antibodies. The constructs and each component of the exemplary bispecific antibodies are summarized in Table 2 below.

Clones scDb01, scDb02, scDb03, scDb04, scDb05, scDb06, scDb07, scDb08, scDb09, scDb9O24, scDb9O41, and scDb9O47 were synthesized from GenScript and comprise a single polypeptide chain, including a light chain variable region of an anti-claudin 18.2 antibody 5C9ob, 5C9oap, 9O24, 9O41, or 9O47, a glycine-rich linker 1 (L1), a heavy chain variable region of an anti-PD-L1 antibody durvalumab, a glycine-rich linker 2 (L2), a light chain variable region of an anti-PD-L1 antibody durvalumab, a glycine-rich linker 3 (L3), a heavy chain variable region of an anti-claudin 18.2 antibody 5C9ob, 5C9oap, 9O24, 9O41, or 9O47, a glycine-rich linker 4 (L4), and a Fc region comprising heavy chain constant region 2 ($CH_2$) and constant region 3 ($CH_3$).

To construct the expression cassettes for the exemplary bispecific antibodies described above, the coding sequences for these polypeptides with the addition of a secretion signal peptide at the N-terminal were synthesized and cloned into a pCDNA3.4 vector, pCDNA3.4 expression plasmids encoding the above-noted bispecific antibodies were generated and transfected into 30 mL cultures of Expi293F™ followed by 0.2 µM sterile filtration and stored at 4° C. Clones were batch purified using a protein A column.

Generation of the Linker Enhanced scDb Clones DbInk1-18

The linker optimization was achieved through displaying single chain bispecific antibodies (scDbs) on phage with all three linkers randomized and selection with alternating CLDN 18.2 and PD-L1 as antigens. See disclosures in following sections.

Generation of the scDb01 Template

A phagemid pSY1 displaying the antibody gene between NsiI and FseI sites was double digested with NsiI and FseI, gel purified, and ligated to scDb gene insert with proper double digestion to generate pSY4. Uracil containing single stranded DNA template was then generated with a procedure similar to that described (Sidhu S. S et al *Methods Enzymol* 328, 333-63 (2000)).

Linker Library Construction scDb01 contains three glycine-rich linkers: Linker 1 (SGGGG, SEQ ID 121), Linker 2 (GGGGSGGGGSGGGGS, SEQ ID 122), and Linker 3 (SGGGG, SEQ ID 121). To generate scDb constructs with improved properties, these three linkers were randomized in a large single library. Degenerate codon RGC (R=A or G) was used to encode Gly and Ser while VGC (V=A, C or G) was used to encode Gly, Ser and Arg. VGC codons were placed at select locations to increase the hydrophilicity of the linkers. Three different lengths were also allowed at each linker location. Thus, Kunkel primers contain RGCVGCRGCRGC (SEQ ID 268), RGCRGCVGCRGCRGC (SEQ ID 269), or RGCRGCRGCVGCRGCRGC (SEQ ID 270) for Linker 1 and Linker 3; RGCRGCRGCVGCRGCRGCRGC VGCRGCRGCRGCVGCRGCRGCRGC (SEQ ID 271), RGCRGCRGCRGCVGCRGCRGCRGCVGCRGCRGC RGCVGCRGCRGCRGC (SEQ 272), or RGCRGCRGCRGCVGCRGCRGCRGCVGCRGCRGC RGCVGCRGCRGCRGC (SEQ ID 273) for Linker 2;

Phosphorylation of the primers and Kunkel mutagenesis were carried out as described (Sidhu S. S et al *Methods Enzymol* 328, 333-63 (2000)). Covalently closed circular DNA obtained was electroporated into electrocompetent SS320 cells to prepare scDb linker library as described (Sidhu et al. 2000). The tittered apparent diversity was $1.81 \times 10^{10}$, comparable to $2.2 \times 10^{10}$, the designed theoretical diversity.

Selection of the Linker Enhanced scDb Clones

Selection was carried out similar to that have been described previously (Ye J. D., et al *Proc Natl Acad Sci USA* 105, 82-87 (2008)). Biotinylated full-length CLDN 18.2 and PD-L1 were alternatingly used as the antigen.

In each selection round except for the first round, purified phage pools were first incubated with streptavidin beads for 15 min, and the supernatant was used in the subsequent selection on a KingFisher magnetic particle processor (Thermo Fisher). Phages ($10^{12}$ for the first round, $10^{9-10}$ cfu for later rounds) were incubated for 15 min with proper amount of antigen (1 nM biotinylated CLDN 18.2 in the first round; 0.2 nM biotinylated PD-L1 in the second round; 0.1 nM biotinylated CLDN 18.2 in the third round). Streptavidin magnetic beads were then added to the solution for 15 min to allow the capture of the biotinylated antigen together with the bound phages. The beads were washed five times with PD (PBS/DDM), and eluted in 100 mM DTT for 15 min. After each round of selection, recovered phages were amplified as described (Sidhu S. S et al *Methods Enzymol* 328, 333-63 (2000)). After three rounds of selection, single clones were miniprepped and sequenced.

Construction of Exemplary Bispecific Antibodies that Contain Disulfide Bond

A disulfide bond between the VH residue 44 (C44) and VL residue 100 (C100) was engineered into both anti-CLDN 18.2-5C9ob and anti-PD-L1 durvalumab scFv regions for 2 clones, scDb02 and scDb 06. Another disulfide bond between the VH residue 105 (C105) and VL residue 43 (C43) was engineered into both anti-CLDN 18.2-5C9ob and anti-PD-L1 durvalumab scFv regions for clone scDb03. Yet another disulfide bond between the VH residue 42 (C42) in anti-CLDN 18.2 5C9ob and VH residue 3 (C3) was engineered into the bispecific antibody for clone sDb04. In a further exemplary modification, another disulfide bond between the VH residue 112 (C112) in anti-CLDN 18.2 5C9ob and VH residue 9 (C9) was engineered into the bispecific antibody for clone scDb05.

Figure 6:
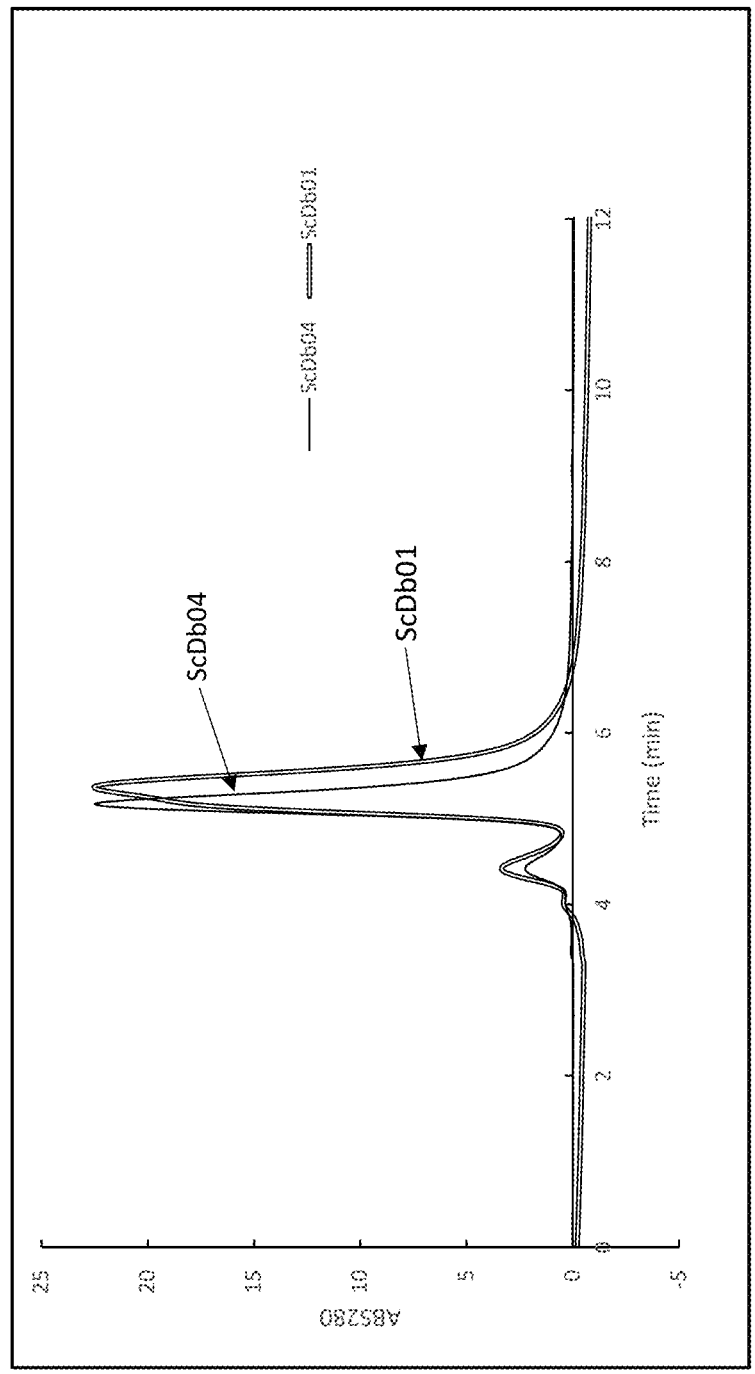
FIG. 6 is a diagram showing exemplary bispecific antibodies with disulfide bond insertions as analyzed by HPLC with an SEC column.
Figure 11A:
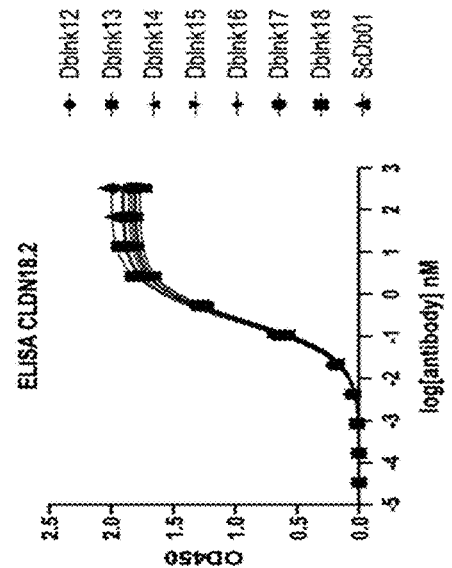
FIGS. 11A and 11B include charts showing binding of various bispecific antibodies to CLDN 18.2.
Figure 11B:
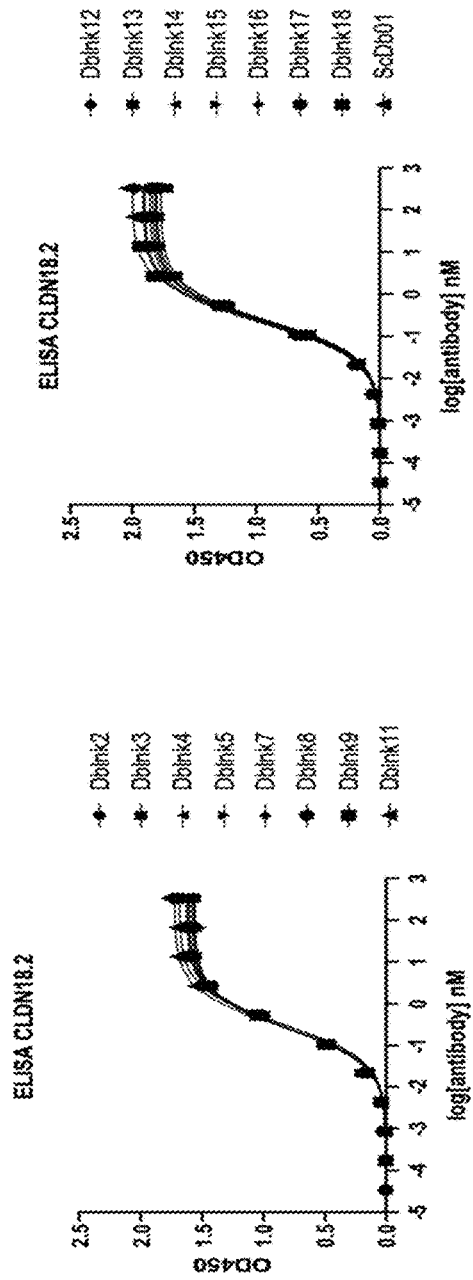
Figure 12A:
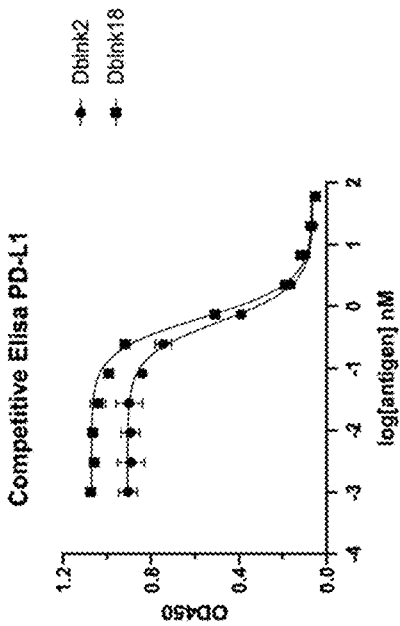
FIGS. 12A and 12B include charts showing binding of bispecific antibodies DbInk2 and DbInk18 to PD-L1 by direct ELISA (FIG. 12A) and competitive ELISA (FIG. 12B). Kd values of DbInk2 and DbInk18 are 0.8825 nM and 0.4925 nM, respectively. $IC_{50}$ values of DbInk2 and DbInk18 are 0.5732 nM and 0.6517 nM, respectively.
Figure 12B:
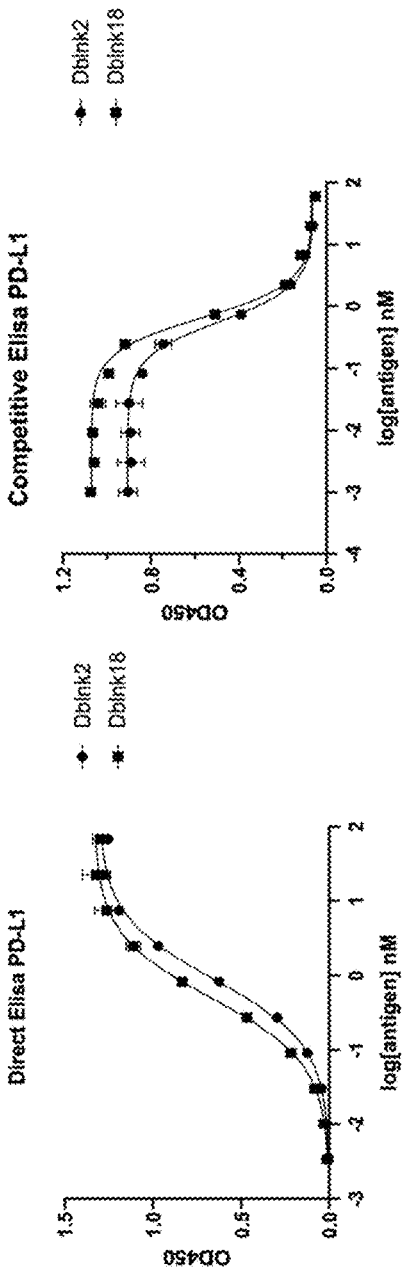
Figure 13A:
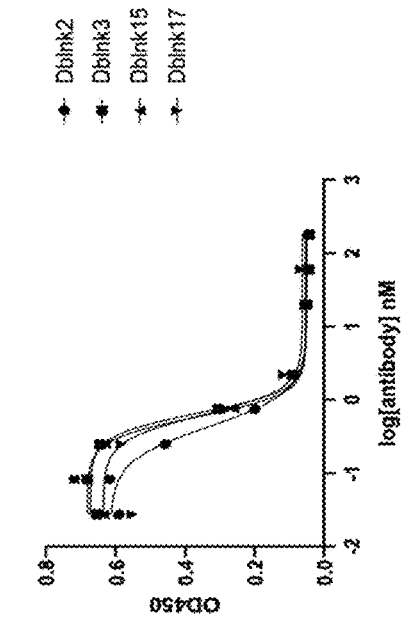
FIGS. 13A and 13B include charts showing binding of bispecific antibodies DbInk3, DbInk15, and DbInk 17 to PD-L1 by direct ELISA (FIG. 13A) and competitive ELISA (FIG. 13B). Kd values of DbInk2, DbINK3, DbInk15, and DbInk17 are 0.6418 nM, 0.4981 nM, 0.4604 nM, and 0.4374 nM, respectively. $IC_{50}$ values of DbInk2, DbINK3, DbInk15, and DbInk17 are 0.4264 nM, 0.6556 nM, 0.5804 nM, and 0.6517 nM, respectively.
Figure 13B:
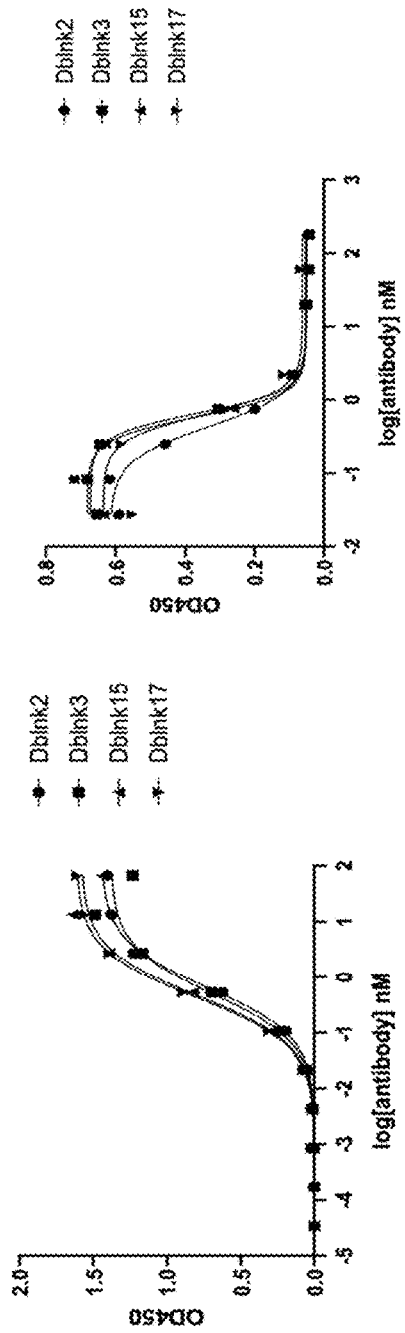

HPLC analysis with a SEC column of the bispecific antibodies containing scFvs with disulfides showed dramatic reduction of the high molecular weight peaks, bringing the ranges down to 1-2% (FIG. 6). This reduction of aggregation applied across all concentrations tested.

A summary of exemplary single-chain bispecific antibodies containing all components and sequence IDs are shown in Table 2.

TABLE 2

Components of Exemplary Single-Chain Bispecific Antibodies

| Bispecific Antibody | CLDN 18.2-VL SEQ ID | L1 SEQ ID | PD-L1 VH SEQ ID | L2 SEQ ID | PD-L1 VL SEQ ID | L3 SEQ ID | CLDN 18.2-VH SEQ ID | L4 SEQ ID | $CH_2CH_3$ SEQ ID |
|---|---|---|---|---|---|---|---|---|---|
| scDb01 | 13 | 121 | 97 | 122 | 101 | 121 | 9 | 164 | 165 |
| scDb02 | 13 | 121 | 97 | 122 | 101 | 121 | 9 | 164 | 165 |
| scDb03 | 13 | 121 | 97 | 122 | 101 | 121 | 9 | 164 | 165 |
| scDb04 | 13 | 121 | 97 | 122 | 101 | 121 | 9 | 164 | 165 |
| scDb05 | 13 | 121 | 97 | 122 | 101 | 121 | 9 | 164 | 165 |
| scDb06 | 13 | 121 | 97 | 123 | 101 | 121 | 9 | 164 | 165 |
| scDb07 | 23 | 121 | 97 | 122 | 101 | 121 | 21 | 164 | 165 |
| scDb08 | 13 | 124 | 97 | 125 | 101 | 126 | 9 | 164 | 165 |
| scDb09 | 23 | 124 | 97 | 125 | 101 | 126 | 21 | 164 | 165 |
| Dblnk1 | 13 | 121 | 97 | 127 | 101 | 121 | 9 | 164 | 165 |
| Dblnk2 | 13 | 121 | 97 | 128 | 101 | 129 | 9 | 164 | 165 |
| Dblnk3 | 13 | 121 | 97 | 130 | 101 | 121 | 9 | 164 | 165 |
| Dblnk4 | 13 | 131 | 97 | 132 | 101 | 133 | 9 | 164 | 165 |
| Dblnk5 | 13 | 134 | 97 | 135 | 101 | 126 | 9 | 164 | 165 |
| Dblnk6 | 13 | 134 | 97 | 136 | 101 | 137 | 9 | 164 | 165 |
| Dblnk7 | 13 | 134 | 97 | 138 | 101 | 139 | 9 | 164 | 165 |
| Dblnk8 | 13 | 140 | 97 | 122 | 101 | 141 | 9 | 164 | 165 |
| Dblnk9 | 13 | 124 | 97 | 142 | 101 | 143 | 9 | 164 | 165 |
| Dblnk10 | 13 | 124 | 97 | 144 | 101 | 143 | 9 | 164 | 165 |
| Dblnk11 | 13 | 145 | 97 | 146 | 101 | 147 | 9 | 164 | 165 |
| Dblnk12 | 13 | 145 | 97 | 148 | 101 | 149 | 9 | 164 | 165 |
| Dblnk13 | 13 | 150 | 97 | 125 | 101 | 151 | 9 | 164 | 165 |
| Dblnk14 | 13 | 152 | 97 | 153 | 101 | 154 | 9 | 164 | 165 |
| Dblnk15 | 13 | 155 | 97 | 156 | 101 | 133 | 9 | 164 | 165 |
| Dblnk16 | 13 | 157 | 97 | 158 | 101 | 121 | 9 | 164 | 165 |
| Dblnk17 | 13 | 159 | 97 | 160 | 101 | 161 | 9 | 164 | 165 |
| Dblnk18 | 13 | 141 | 97 | 162 | 101 | 163 | 9 | 164 | 165 |
| scDb9O24 | 30 | 121 | 97 | 122 | 101 | 121 | 28 | 164 | 165 |
| scDb9O41 | 39 | 121 | 97 | 122 | 101 | 121 | 21 | 164 | 165 |
| scDb9O47 | 52 | 121 | 97 | 122 | 101 | 121 | 50 | 164 | 165 |

The binding characters of exemplary anti-CLDN 18.2/anti-PDL1 bispecific antibodies were evaluated by direct ELISA assay to CLDN 18.2 and PD-L1 according to the general experimental methods. The data are summarized in Table 3 and FIGS. 7A-14.

TABLE 3

Disassociation constant of Exemplary Single-Chain Bispecific Antibodies

| Bispecific Antibody | Direct ELISA Kd to CLDN 18.2 (nM) | Direct ELISA Kd to PD-L1 (nM) | Competitive ELISA Kd to PD-L1 (nM) |
|---|---|---|---|
| scDb01 | 0.26 | 0.59 | |
| scDb02 | 0.21 | 0.4 | |
| scDb04 | 0.25 | 0.51 | |

TABLE 3-continued

Disassociation constant of Exemplary Single-Chain Bispecific Antibodies

| Bispecific Antibody | Direct ELISA Kd to CLDN 18.2 (nM) | Direct ELISA Kd to PD-L1 (nM) | Competitive ELISA Kd to PD-L1 (nM) |
|---|---|---|---|
| scDb06 | 0.21 | 0.35 | |
| Dblnk2 | 0.32 | 0.64 | 0.57 |
| Dblnk3 | 0.29 | 0.5 | 0.66 |
| Dblnk4 | 0.24 | | |
| Dblnk5 | 0.25 | | |
| Dblnk7 | 0.25 | | |
| Dblnk8 | 0.26 | | |
| Dblnk9 | 0.27 | | |
| Dblnk11 | 0.29 | | |
| Dblnk12 | 0.2 | | |
| Dblnk13 | 0.21 | | |
| Dblnk14 | 0.2 | | |
| Dblnk15 | 0.23 | 0.46 | 0.58 |
| Dblnk16 | 0.22 | | |
| Dblnk17 | 0.22 | 0.44 | 0.62 |
| Dblnk18 | 0.22 | 0.49 | 0.65 |
| H5C9ob | 0.13 | | |

Figure 14:
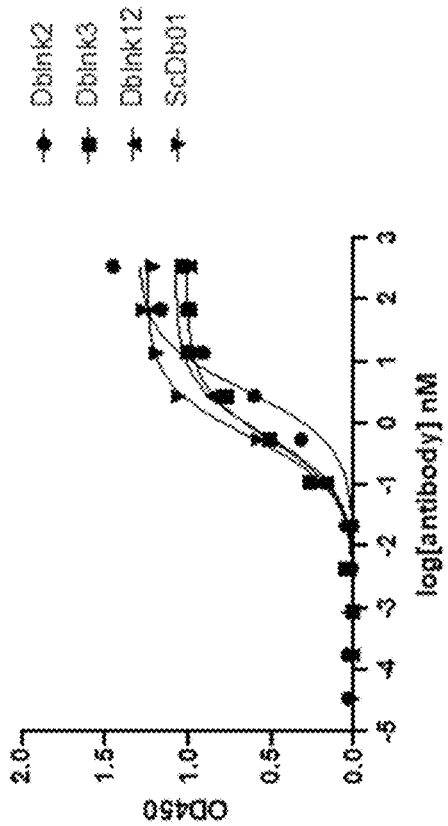
FIG. 14 is a chart showing binding of bispecific antibodies DbInk2, 3, 17 and scDb01 to HEK293T cells stably expressing surface CLDN 18.2 by InCell ELISA.

The bispecific antibody ScDb01 has a similar Kd to CLDN 18.2 and PDL1 at different pH (pH3, pH4, pH4.5 and pH6) (FIG. 8). The binding of exemplary bispecific antibodies to HEK293T-CLDN 18.2 was also evaluated by In-Cell analysis. As shown in FIG. 14, DbInk 2, DbInk 3, DbInk12, and ScDb01 showed similar binding to HEK293 cells that stably expressed CLDN 18.2. See also Table 4 below for Bmax and Kd values of the exemplary antibody clones.

TABLE 4

Bmax and Kd Values of Exemplary Clones

| | DbInk2 | DbInk3 | DbInk12 | ScDb01 |
|---|---|---|---|---|
| Bmax (nM) | 1.301 | 1.008 | 1.075 | 1.251 |
| Kd (nM) | 3.230 | 0.5226 | 0.6319 | 0.5817 |

Figure 15:
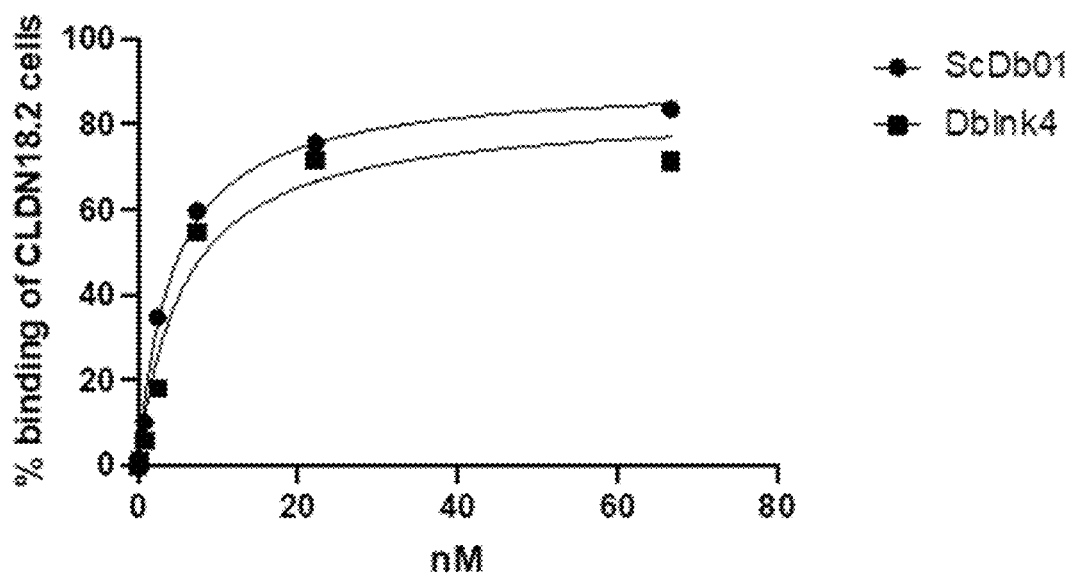
FIG. 15 is a chart showing binding of bispecific antibodies scDb01 and DbInk4 to MCF cells stably expressing CLDN 18.2 by FACS analysis.
Figure 16:
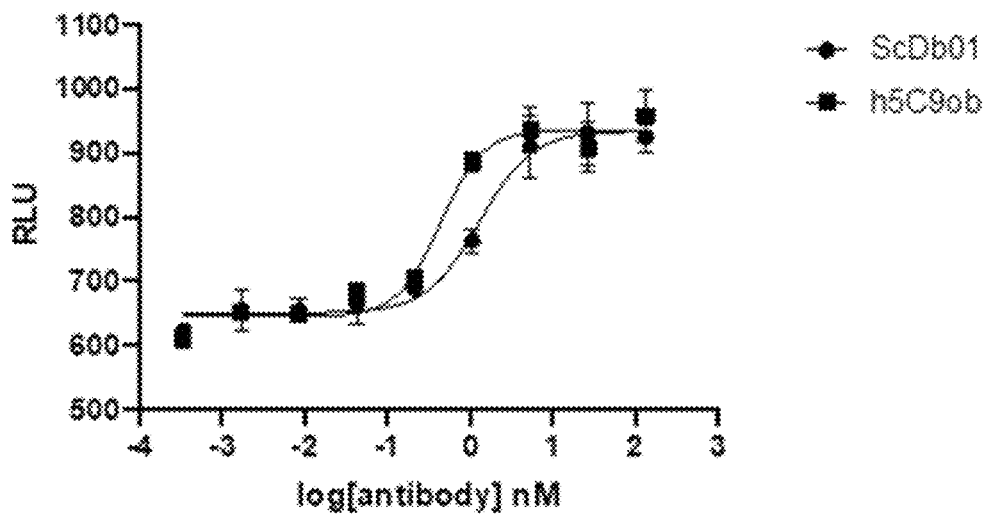
FIG. 16 is a chart showing complementary Dependent Cytotoxicity (CDC) effects of scDb01 and its parent monoclonal antibody h5C9ob against HEK293T cells stably expressing CLDN 18.2.
Figure 19:
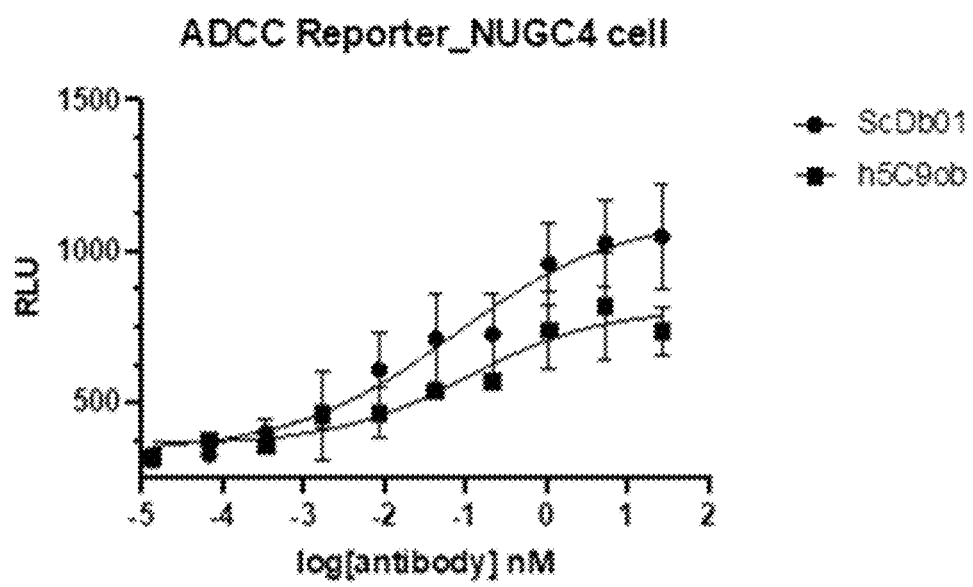
FIG. 19 is a chart showing antibody-dependent cellular cytotoxicity (ADCC) effect of bispecific antibody scDb01 versus parent clone h5C9ob by a reporter assay in NUGC4 cells. The Top values of ScDb01 and h5C9ob are 1116 and 809.1, respectively. Top values refer to relative light units (RLU) for live cell luminescence. The $EC_{50}$ values of these two clones are 0.07403 nM and 0.1057 nM, respectively.
Figure 20:
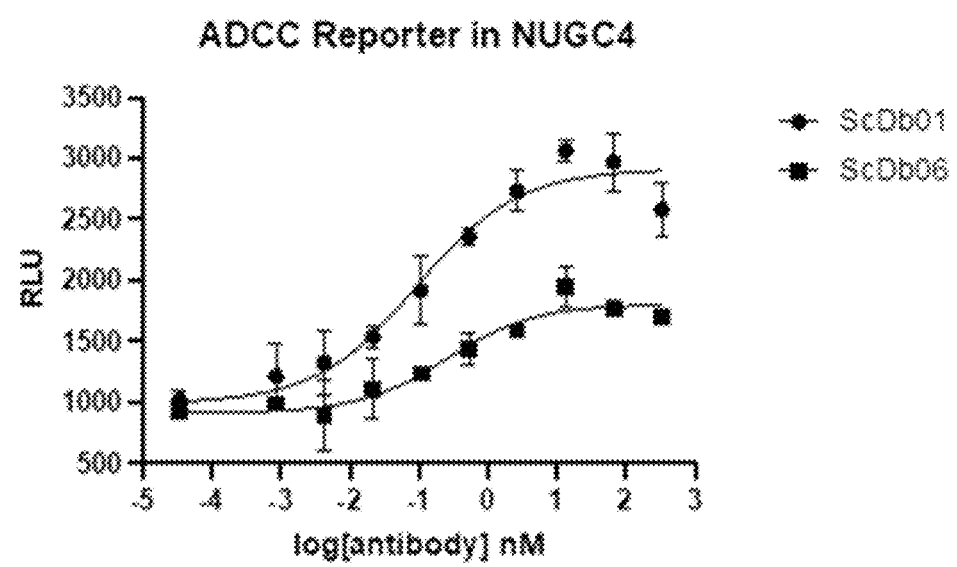
FIG. 20 is a chart showing antibody-dependent cellular cytotoxicity (ADCC) effects of bispecific antibodies scDb01 and scDb06 by a reporter assay in NUGC4 cells. The Top values of ScDb01 and ScDb06 are 2912 and 1805, respectively. Top values refer to relative light units (RLU) for live cell luminescence. The $EC_{50}$ values of these two clones are 0.09345 nM and 0.2550 nM, respectively.
Figure 21:
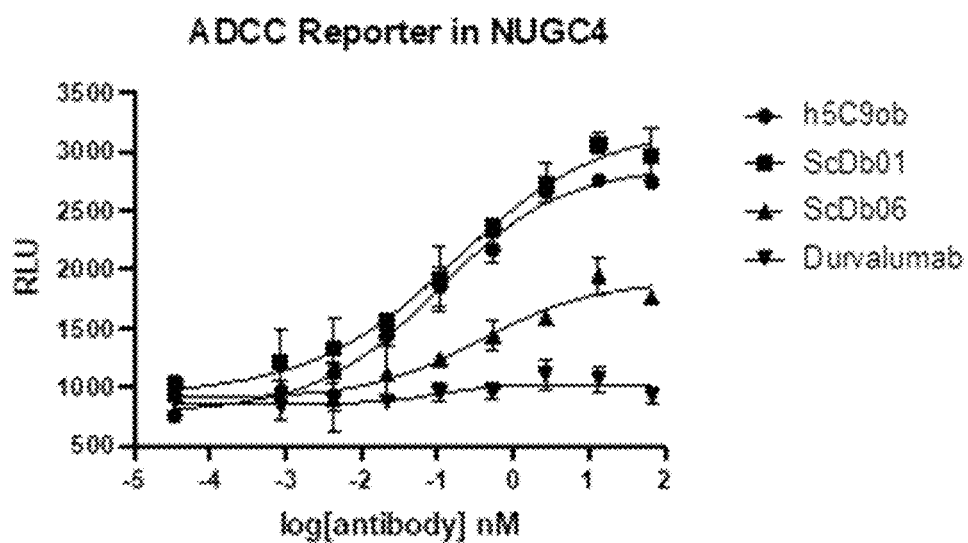
FIG. 21 is a chart showing antibody-dependent cellular cytotoxicity (ADCC) effects of bispecific antibodies scDb01 and scDb06 and parent antibodies h5C9ob, and durvalumab by a reporter assay in NUGC4 cells. The Top values of h5C9ob, ScDb01, ScDb06, and Durvalumab are 2870, 3221, 1905, and 1023, respectively. Top values refer to relative light units (RLU) for live cell luminescence. The $EC_{50}$ values of h5C9ob, ScDb01, ScDb06, and Durvalumab are 0.1015 nM, 0.1710 nM, 0.3860 nM, and 0.1033 nM, respectively.
Figure 22:
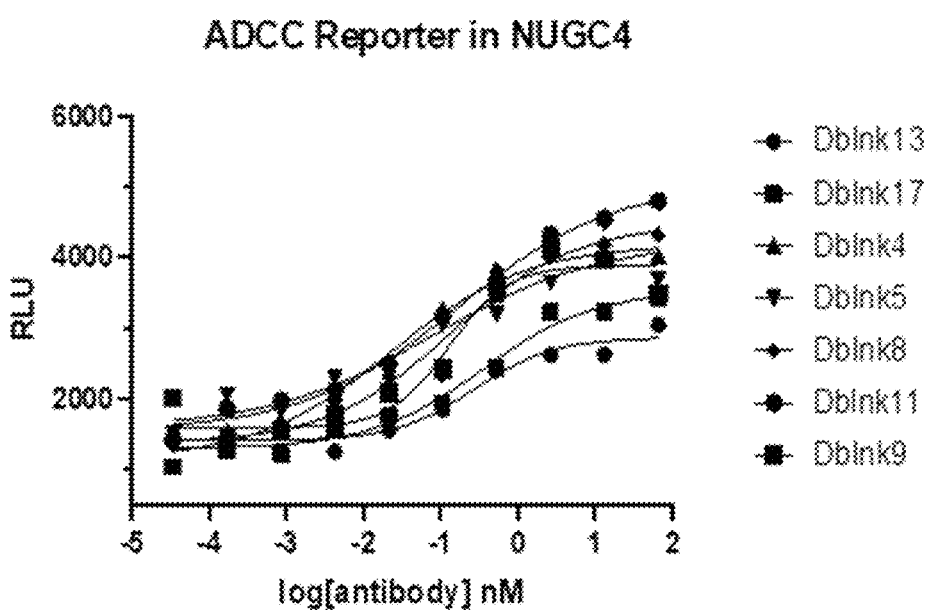
FIG. 22 is a chart showing antibody-dependent cellular cytotoxicity (ADCC) effects of bispecific antibodies DbInk13, 17, 4, 5, 8, 11, and 9 by a reporter assay in NUGC4 cells. The $EC_{50}$ values of DbInk13, DbInk 17, DbInk 4, DbInk 5, DbInk 8, DbInk 11, and DbInk 9 are 0.2741 nM, 0.3507 nM, 0.02283 nM, 0.08135 nM, 0.01340 nM, 0.1673 nM, and 0.1279 nM, respectively.
Figure 23A:
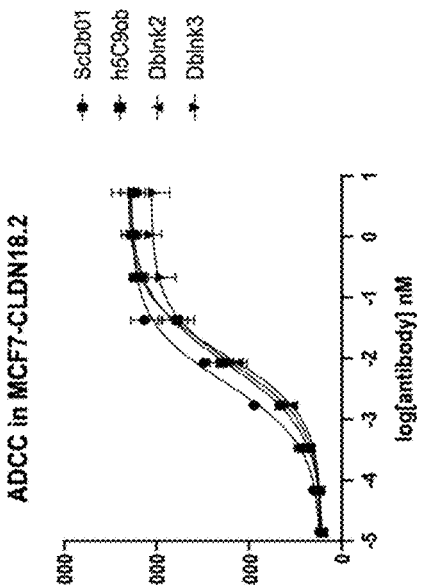
FIGS. 23A and 23B include charts showing antibody-dependent cellular cytotoxicity (ADCC) effects of bispecific antibodies DbInk2, 3, 12 and scDb01 by a reporter assay in HEK293T cells stably expressing CLDN 18.2 (FIG. 23A) and the ADCC effects of bispecific antibodies scDb01, h5C9ob, DbInk2, and DbInk3 in MCF7 cells stably expressing CLDN 18.2 (FIG. 23B). The Top values of DbInk2, DbInk3, DbInk12, and ScDb01 are 9318, 8939, 8873, and 8094, respectively. Top values refer to relative light units (RLU) for live cell luminescence. The $EC_{50}$ values of DbInk2, DbInk3, DbInk12, and ScDb01 are 0.009373 nM, 0.001045 nM, 0.004838 nM, and 0.004201 nM, respectively.
Figure 23B:
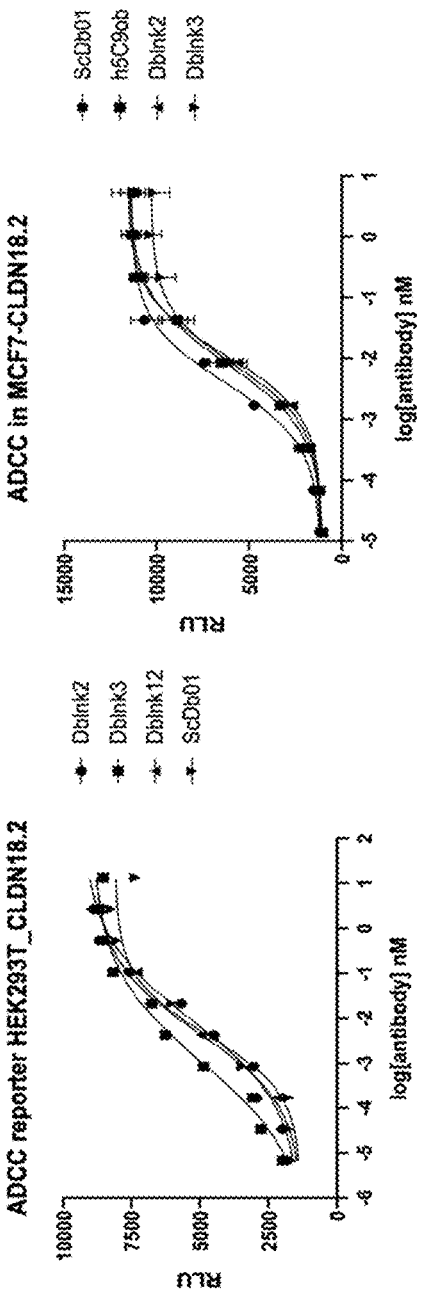
Figure 24A:
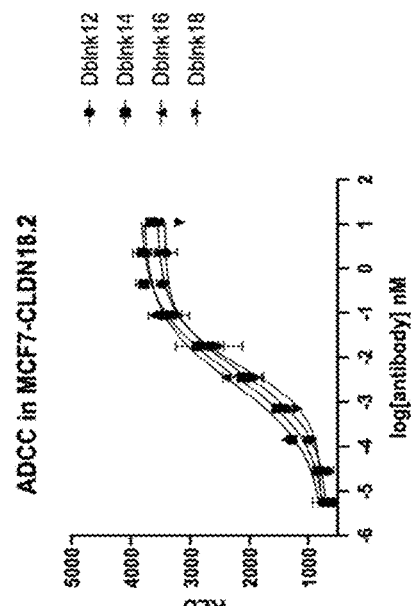
FIGS. 24A and 24B include charts showing antibody-dependent cellular cytotoxicity (ADCC) effects of bispecific antibodies scDb01, h5C9ob, DbInk4, and DbInk9 (FIG. 24A) and DbInk 12, 14, 16, and 18 (FIG. 24B) by a reporter assay in MCF7 cells stably expressing CLDN 18.2. The $EC_{50}$ values of scDb01, h5C9ob, DbInk4, and DbInk9 are 0.002033 nM, 0.004432 nM, 0.001734 nM, and 0.002644, respectively. The $EC_{50}$ values of DbInk12, DbInk14, DbInk16, and DbInk18 are 0.004411 nM, 0.004089 nM, 0.002550 nM, and 0.005795 nM, respectively.
Figure 24B:
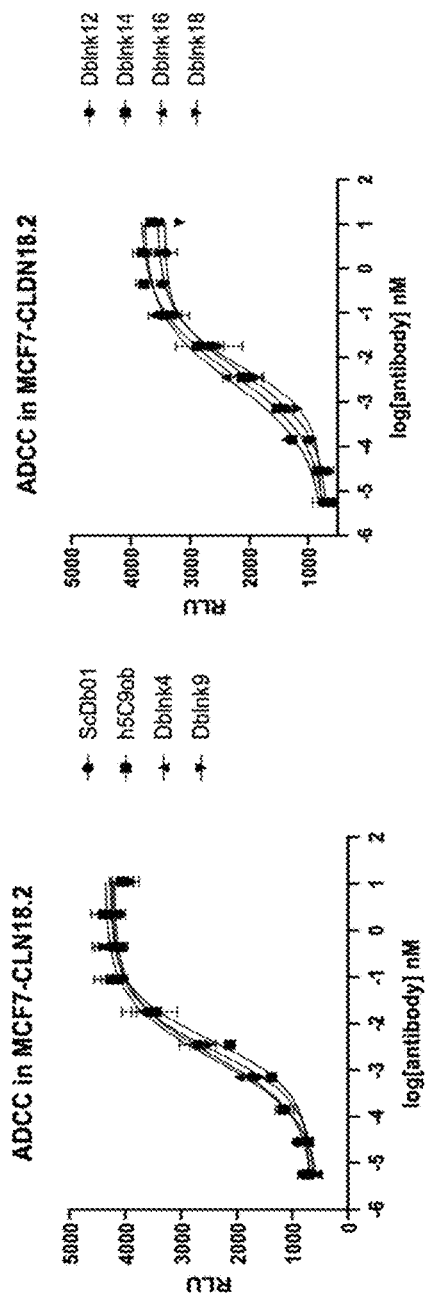

FACS analyses of ScDb01 and DbInk4 in MCF7 cells stably overexpressed CLDN 18.2 demonstrated a similar binding character. See FIG. 15.

Flow cytometry was used to evaluate the binding of bispecific antibodies to living cells expressing CLDN 18.2. The MCF7 cell line that stably expressed CLDN 18.2 (MCF7-CLDN 18.2) was incubated with various concentrations of bispecific antibodies in PBS containing 3% BSA in PBS at 4° C. for 60 min. After washing, the cells were stained with DyLight 650-labeled anti-IgG antibody and analyzed by flow cytometry with a FACS instrument (BD, Accuri™ C6 Plus) using light and side scatter properties to gate on single living cells. The MCF7-CLDN 18.2 cells were detected in a different fluorescence channel since the recombinant CLDN 18.2 is fused with the GFP at its C-terminal. Fluorescence marker was plotted on the horizontal axis against antibody binding on the vertical axis. It was shown that the ratio of MCF7_CLDN 18.2 cells that binds to bispecific antibodies scDb01 and DbInk4 increased with increased antibody concentrations, reaching 75% and 70% at 3.3 μg/ml, respectively.

Complementary Dependent Cytotoxicity (CDC) and Antibody-Dependent Cellular Cytotoxicity (ADCC) of some exemplary bispecific antibodies versus their parent monoclonal antibody h5C9ob or durvalumab were evaluated in HEK293T, MCF7 and MiaPaca cells that were stably transfected with CLDN 18.2, or NUGC4 cells according to the general protocols. All data are shown in Table 5 and FIGS. 16-24.

TABLE 5

Antibody Dependent Cellular Cytotoxicity (ADCC) and Complementary Dependent Cytotoxicity of Exemplary Single-Chain Bispecific Antibodies

| Bispecific Antibody | CDC in HEK293-CLDN 18.2, EC$_{50}$ (nM) | CDC in MCF7-CLDN 18.2, EC$_{50}$ (nM) | CDC in MiaPaCa-CLDN 18.2, EC$_{50}$ (nM) | ADCC Reporter in HEK293-CLDN18.2, EC$_{50}$ (nM) | ADCC Reporter in MCF7-CLDN 18.2, EC$_{50}$ (nM) | ADCC Reporter in NUGC4, EC$_{50}$ (nM) | ADCC in NUGC4, EC$_{50}$ (nM) |
|---|---|---|---|---|---|---|---|
| scDb01 | 1.29 | | | 0.004 | 0.003 | 0.093 | 0.074 |
| scDb06 | | | | | | 0.255 | |
| Dblnk2 | | 1.0 | 0.35 | 0.0094 | 0.011 | | |
| Dblnk3 | | 0.82 | | 0.001 | 0.0075 | | |
| Dblnk4 | | | | | 0.002 | 0.022 | |
| Dblnk5 | | | | | | 0.081 | |
| Dblnk8 | | | | | | 0.134 | |
| Dblnk9 | | | | | 0.003 | 0.13 | |
| Dblnk11 | | | | | | 0.17 | |
| Dblnk12 | | | | 0.005 | 0.0044 | 0.005 | |
| Dblnk13 | | | | | | 0.27 | |
| Dblnk14 | | | | | 0.004 | | |
| Dblnk16 | | | | | 0.0025 | | |
| Dblnk17 | | | | | | 0.35 | |
| Dblnk18 | | | | | 0.0058 | | |
| H5C9ob | 0.43 | | 0.52 | 0.056 | 0.006 | 0.105 | 0.106 |
| Durvalumab | | | | | | 0.1 | |

Figure 25:
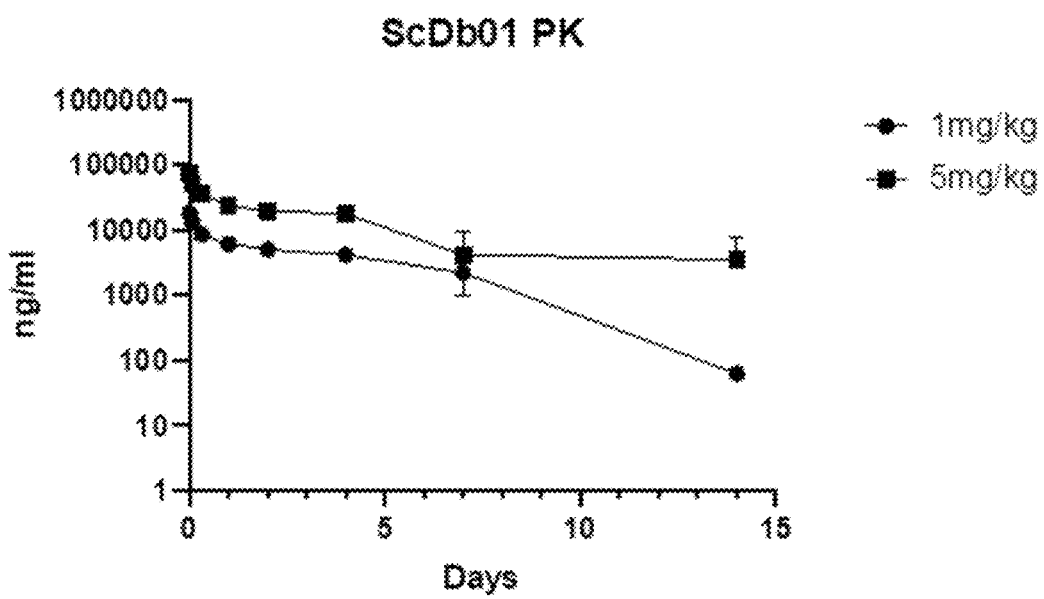
FIG. 25 is a chart showing pharmacokinetic features of bispecific antibody scDb01 in CD1 mice. scDb01 was administered intravenously at 1 and 5 mg/kg, respectively.
Figure 26:
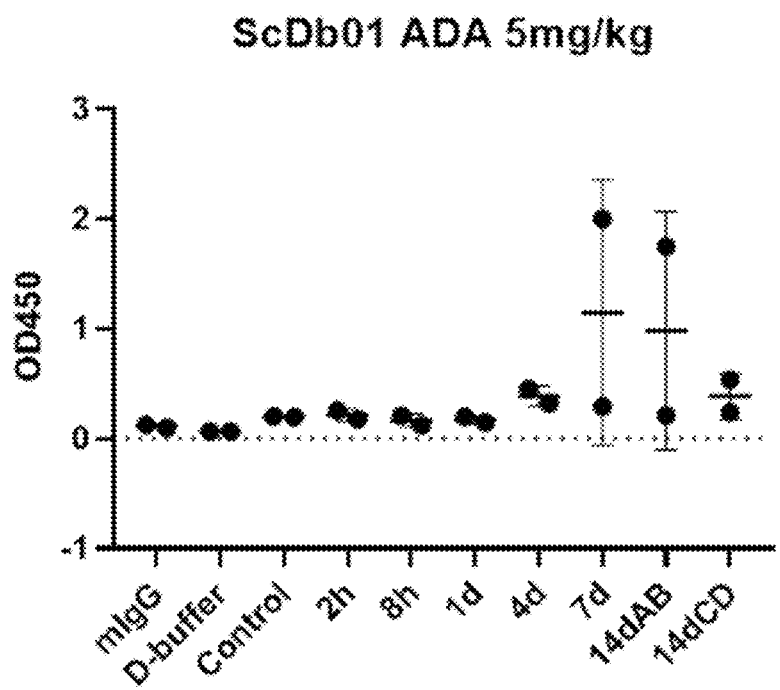
FIG. 26 is a chart showing anti-Drug Antibody (ADA) assay of bispecific antibody scDb01 in CD1 mice. scDb01 was administered intravenously at 5 mg/kg.
Figure 29:
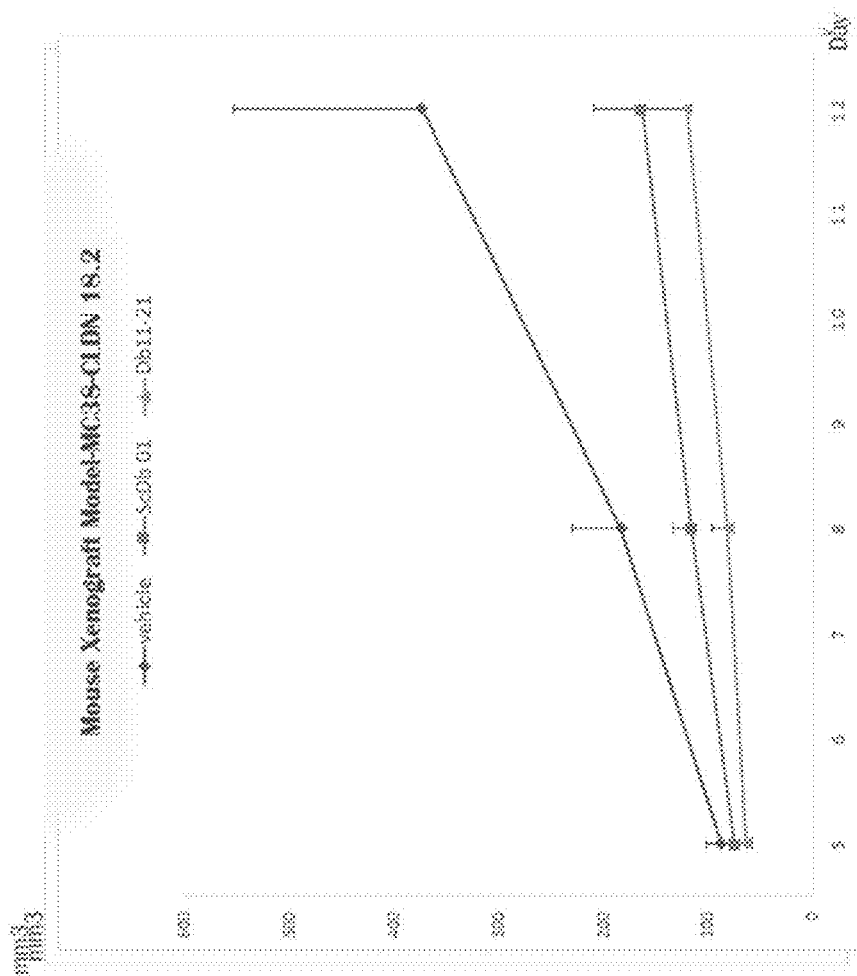
FIG. 29 is a chart showing a mouse xenograft model of bispecific antibodies scDb01 and db11-21, along with PBS vehicle control in C57 mice. Both bispecific antibodies were administered intravenously at 10 mg/kg on day 6 following inoculation.

Pharmacokinetic properties and Anti-Drug Antibody (ADA) of bispecific antibody scDb01 were evaluated in CD1 mice, and shown in FIGS. 25-27. At least scDb01 demonstrated a good pharmacokinetic characteristics and minimal immunogenicity in CD1 mice at 1 and 5 mg/kg dose, respectively.

Example 6: Construction and Characterization of Exemplary Heterodimeric Bispecific Antibodies that Bind CLDN 18.2 and PD-L1

Another exemplary set of anti-CLDN 18.2/PD-L1 bispecific antibodies as shown in Table 6 was constructed as follows. The first expression vector encodes a light chain variable region of an anti-claudin 18.2 5C9ob, a glycine-rich linker 1 (L1), and a heavy chain variable region of an anti-PD-L1 antibody durvalumab fused to a knob-Fc region of human IgG. The second expression vector encodes a light chain variable region of an anti-PD-L1 antibody durvalumab, a glycine-rich linker 3 (L3), and a heavy chain variable region of an anti-claudin 18.2 5C9ob fused to a hole-Fc region of human IgG. Both expression vectors were synthesized and cloned into pCDNA3.4 vector from GenScript. The amino acid sequences of each of the exemplary bispecific antibodies are also provided in the Table 6.

TABLE 6

Components of Exemplary Heterodimeric Bispecific Antibody Db11/Db21

| Bispecific Polypeptide Db11 | CLDN 18.2-VL SEQ ID 13 | L1 SEQ ID 121 | PD-L1 VH SEQ ID 97 | L2 SEQ ID 164 | Knob CH$_2$CH$_3$ SEQ ID 208 |
|---|---|---|---|---|---|
| Bispecific Polypeptide Db21 | PD-L1 VL SEQ ID 101 | L3 SEQ ID 121 | CLDN 18.2-VH SEQ ID 9 | L4 SEQ ID 164 | Hole CH$_2$CH$_3$ SEQ ID 209 |

To generate the above-noted bispecific antibodies, the two pCDNA3.4 expression plasmids, each encoding one chain of the above-noted bispecific antibodies, were co-transfected into 500 mL cultures of Expi293F™ cells, cultured in Expi293™ expression medium, using ExpiFectamine™ as a transfection reagent, as described by the LifeTech protocol (Life Technologies™, Carlsbad, CA). Expifectamine™ transfection enhancers 1 and 2 were added on day 2 of culture as described in LifeTech protocol. Cultures were incubated at 37° C., 8% CO$_2$, and 130 rpm through day 7. Cultures were harvested by centrifugation followed by 0.2 μM sterile filtration and stored at 4° C. Clones were batch purified using a protein A column.

In vivo efficacy of the bispecific antibodies scDb01 and db11-21 were evaluated in a mouse Xenograft model and showed in FIG. 27. C57 mice (n=8) were inoculated with MC38-CLDN 18.2 cells (1×10E6). On day 6 following the inoculation, the animals were administered intravenously scD01, db11-21, or PBS vehicle (10 mg/kg) twice a week. The size of tumor was measured every 3-day. Both scDb01 and db11-21 inhibited the tumor growth significantly as compared to the vehicle with a p-value of 0.07 and 0.006, respectively.

Figure 30A:
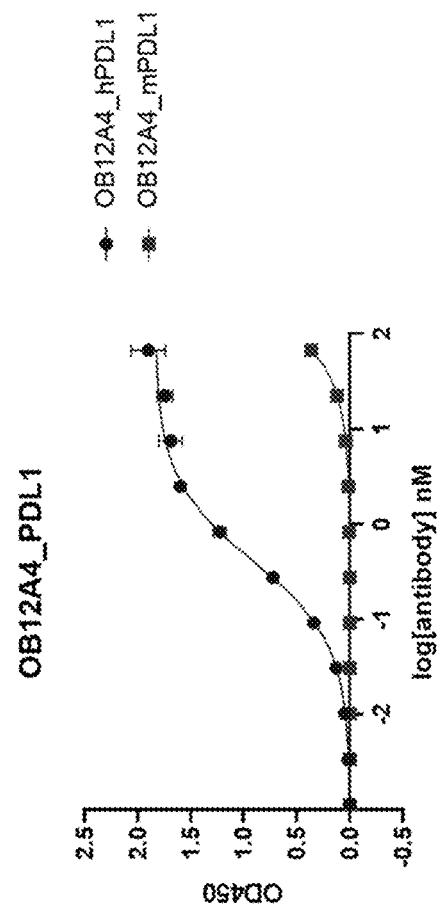
FIGS. 30A and 30B include charts showing binding of bispecific antibody OB12A4 to CLDN18.2 (FIG. 30A) and to human and mouse PDL1 (FIG. 30B). The Kd value over CLDN18.2 is 0.2123 nM. The Kd values over human and mouse PDL1 are 0.4122 nM and ~11059 nM, respectively.
Figure 30B:
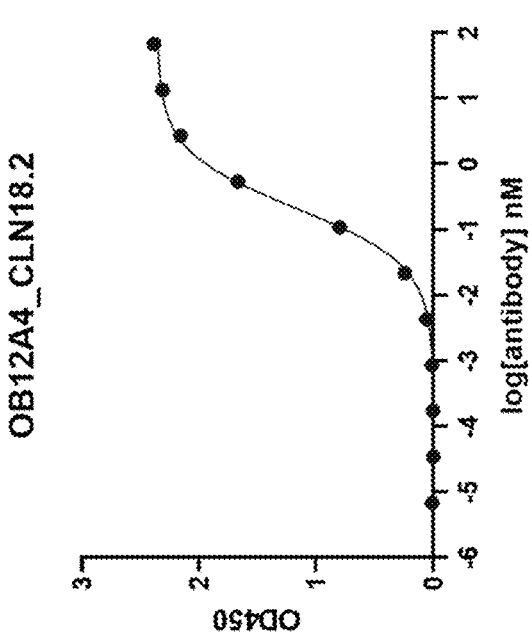

Additional exemplary 2-chain bispecific antibodies, OB12A4 and OB-12A4-bad, were constructed following the same methods disclosed herein. These two bispecific antibodies are in the format illustrated in FIG. 2. Amino acid sequences of the components of these two bispecific antibodies are provided in the Sequence Table 2 below. The binding activities of the bispecific antibodies to both CLDN18.2 and PD-L1 were examined by ELISA following the methods disclosed herein. The results are shown in FIGS. 30A and 30B. The bispecific antibodies show high binding affinity to CLDN18.2 and human PDL1 but little binding activity to mouse PDL1.

TABLE 1

| | | | Sequence | |
|---|---|---|---|---|
| Ab # | Ori ID | | SEQ ID | SEQUENCE |
| 1 | 5C9-CLDN-VH | | 1 | VKLQESGPELKKPGETVKISCKASGYTFTNYGMNWVKQAPGKGLKWMGWINMYTGEPTYADDFKGRFAFSLETSASTAYLQINNLKNEDTATYFCSRLYNGNSLDYWGQGTSLTVSSAKTTPKLVYPLAP |
| | 5C9-CLDN-VH-CDR1 | | 2 | GYTFTNYGMN |
| | 5C9-CLDN-VH-CDR2 | | 3 | WINMYTGEPTYADDFKG |
| | 5C9-CLDN-VH-CDR3 | | 4 | LYNGNSLDY |
| | 5C9-CLDN-VL | | 5 | GDILLTQSPLSLTVTAGEKVTMSCKSSQSLLNSGNQKSYLTWYQQKPGQPPKLLLYWASTRESGVPARFTGSGSGTDFSLTISSVQTEDLAVYYCQNAYSFPFTFGSGTKLEINRADAAPTGSIF |
| | 5C9-CLDN-VL-CDR1 | | 6 | KSSQSLLNSGNQKSYLT |
| | 5C9-CLDN-VL-CDR2 | | 7 | WASTRES |
| | 5C9-CLDN-VL-CDR3 | | 8 | QNAYSFPFT |
| 2 | h5C9o-CLDN-VH | | 9 | EVQLVESGGGLVQPGGSLRLSCAVSGYTFSMNWVRQAPGKGLEWVAWINMYTGEPTYADDFKGRFTISRDDSKNTLYLQMNSLRAEDTAVYYCARLYNGNSLDYWGQGTLVTVSS |
| | h5C9o-CLDN-VH-CDR1 | | 10 | GYTFSMN |
| | h5C9o-CLDN-VH-CDR2 | | 3 | WINMYTGEPTYADDFKG |
| | h5C9o-CLDN-VH-CDR3 | | 4 | LYNGNSLDY |
| | h5C9o-CLDN-VL | | 11 | DIQMTQSPSSLSASVGDRVTITCKSSQSLLNSGNQKSYLTWYQQKPGKAPKLLIYWASTLESGVPSRFSGSGSGTDYTLTISSLQPEDFATYYCQNAYSFPFTFGQGTKVEIKR |
| | h5C9o-CLDN-VL-CDR1 | | 6 | KSSQSLLNSGNQKSYLT |
| | h5C9o-CLDN-VL-CDR2 | | 12 | WASTLES |
| | h5C9o-CLDN-VL-CDR3 | | 8 | QNAYSFPFT |

TABLE 1-continued

| Ab # | Ori ID | SEQ ID | SEQUENCE |
|---|---|---|---|
| 3 | 5C9ob-CLDN-VH | 9 | EVQLVESGGGLVQPGGSLRLSCAVSGYTFSMNWVRQAPG KGLEWVAWINMYTGEPTYADDFKGRFTISRDDSKNTLYL QMNSLRAEDTAVYYCARLYNGNSLDYWGQGTLVTVSS |
| | 5C9ob-CLDN-VH-CDR1 | 10 | GYTFSMN |
| | 5C9ob-CLDN-VH-CDR2 | 3 | WINMYTGEPTYADDFKG |
| | 5C9ob-CLDN-VH-CDR3 | 4 | LYNGNSLDY |
| | 5C9ob-CLDN-VL | 13 | DIQMTQSPSSLSASVGDRVTITCKSSQSLLNSGNQKSYL TWYQQKPGKAPKLLIYWASTLESGVPSRFSGSGSGTDYT LTISSLQPEDFATYYCQNAYFFPFTFGQGTKVEIK |
| | 5C9ob-CLDN-VL-CDR1 | 6 | KSSQSLLNSGNQKSYLT |
| | 5C9ob-CLDN-VL-CDR2 | 12 | WASTLES |
| | 5C9ob-CLDN-VL-CDR3 | 14 | QNAYFFPFT |
| | 5C9ob-CLDN-heavy chain | 15 | EVQLVESGGGLVQPGGSLRLSCAVSGYITSMNWVRQAPG KGLEWVAWINMYTGEPTYADDFKGRFTISRDDSKNTLYL QMNSLRAEDTAVYYCARLYNGNSLDYWGQGTLVTVSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKRVEPKSCDKTHTCPPCPAPELLG GPSVFLFPPKPKDTLMISRTPEVTCVVVDVSHEDPEVKF NWYVDGVEVHNAKTKPREEQYNSTYRVVSVLTVLHQDWL NGKEYKCKVSNKALPAPIEKTISKAKGQPREPQVYTLPP SRDELTKNQVSLTCLVKGFYPSDIAVEWESNGQPENNYK TTPPVLDSDGSFFLYSKLTVDKSRWQQGNVFSCSVMHEA LHNHYTQKSLSLSPGK |
| | 5C9ob-CLDN-light chain | 16 | DIQMTQSPSSLSASVGDRVTITCKSSQSLLNSGNQKSYL TWYQQKPGKAPKLLIYWASTLESGVPSRFSGSGSGTDYT LTISSLQPEDFATYYCQNAYFFPFTFGQGTKVEIKRTVA APSVFIFPPSDEQLKSGTASVVCLLNNFYPREAKVQWKV DNALQSGNSQESVTEQDSKDSTYSLSSTLTLSKADYEKH KVYACEVTHQGLSSPVTKSFNRGEC |
| 4 | 5C9oae-CLDN-VH | 17 | EVQLVESGGGLVQPGGSLRLSCAVSGYTFSMNWVRQAPG KGLEWVAWINMYTGEPTYADDFKGRFTISRDDSKNTLYL QMNSLRAEDTAVYYCARLYRGNSLDYWGQGTLVTVSS |
| | 5C9oae-CLDN-VH-CDR1 | 10 | GYTFSMN |
| | 5C9oae-CLDN-VH-CDR2 | 3 | WINMYTGEPTYADDFKG |
| | 5C9oae-CLDN-VH-CDR3 | 18 | LYRGNSLDY |
| | 5C9oae-CLDN-VL | 19 | DIQMTQSPSSLSASVGDRVTITCKSSQSLLNSGNQKSYL TWYQQKPGKAPKLLIYWASTLESGVPSRFSGSGSGTDYT LTISSLQPEDFATYYCQNAYFFPFTFGQGTKVEIKR |
| | 5C9oae-CLDN-VL-CDR1 | 6 | KSSQSLLNSGNQKSYLT |
| | 5C9oae-CLDN-VL-CDR2 | 12 | WASTLES |
| | 5C9oae-CLDN-VL-CDR3 | 14 | QNAYFFPFT |
| | 5C9oae-CLDN-heavy chain | 20 | EVQLVESGGGLVQPGGSLRLSCAVSGYTFSMNWVRQAPG KGLEWVAWINMYTGEPTYADDFKGRFTISRDDSKNTLYL QMNSLRAEDTAVYYCARLYRGNSLDYWGQGTLVTVSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKKVEPKSCDKTHTCPPCPAPELLG GPSVFLFPPKPKDTLMISRTPEVTCVVVDVSHEDPEVKF NWYVDGVEVHNAKTKPREEQYNSTYRVVSVLTVLHQDWL NGKEYKCKVSNKALPAPIEKTISKAKGQPREPQVYTLPP SRDELTKNQVSLTCLVKGFYPSDIAVEWESNGQPENNYK TTPPVLDSDGSFFLYSKLTVDKSRWQQGNVFSCSVMHEA LHNHYTQKSLSLSPGK |
| | 5C9oae-CLDN-light chain | 16 | DIQMTQSPSSLSASVGDRVTITCKSSQSLLNSGNQKSYL TWYQQKPGKAPKLLIYWASTLESGVPSRFSGSGSGTDYT LTISSLQPEDFATYYCQNAYFFPFTFGQGTKVEIKRTVA APSVFIFPPSDEQLKSGTASVVCLLNNFYPREAKVQWKV DNALQSGNSQESVTEQDSKDSTYSLSSTLTLSKADYEKH KVYACEVTHQGLSSPVTKSFNRGEC |
| 5 | 5C9oap-CLDN-VH | 21 | EVQLVESGGGLVQPGGSLRLSCAVSGYTFSMNWVRQAPG KGLEWVAWINMYTGERTYADDFKGRFTISRDDSKNTLYL QMNSLRAEDTAVYYCARLYNGNSLDYWGQGTLVTVSS |
| | 5C9oap-CLDN-VH-CDR1 | 10 | GYTFSMN |
| | 5C9oap-CLDN-VH-CDR2 | 22 | WINMYTGERTYADDFKG |
| | 5C9oap-CLDN-VH-CDR3 | 4 | LYNGNSLDY |
| | 5C9oap-CLDN-VL | 23 | DIQMTQSPSSLSASVGDRVTITCKSSQSLLNWGNQKSYL TWYQQKPGKAPKLLIYWASTLQSGVPSRFSGSGSGTDYT LTISSLQPEDFATYYCQNAYSFPFTFGQGTKVEIKR |
| | 5C9oap-CLDN-VL-CDR1 | 24 | KSSQSLLNWGNQKSYLT |
| | 5C9oap-CLDN-VL-CDR2 | 25 | WASTLQS |
| | 5C9oap-CLDN-VL-CDR3 | 8 | QNAYSFPFT |
| | 5C9oap-CLDN-heavy chain | 26 | EVQLVESGGGLVQPGGSLRLSCAVSGYTFSMNWVRQAPG KGLEWVAWINMYTGERTYADDFKGRFTISRDDSKNTLYL |

TABLE 1-continued

| Ab # | Ori ID | SEQ ID | SEQUENCE |
|---|---|---|---|
| | | | QMNSLRAEDTAVYYCARLYNGNSLDYWGQGTLVTVSSAS
TKGPSVFPLAPSSKSTSGGTAALGCLVKDYFPEPVTVSW
NSGALTSGVHTFPAVLQSSGLYSLSSVVTVPSSSLGTQT
YICNVNHKPSNTKVDKKVEPKSCDKTHTCPPCPAPELLG
GPSVFLFPPKPKDTLMISRTPEVTCVVVDVSHEDPEVKF
NWYVDGVEVHNAKTKPREEQYNSTYRVVSVLTVLHQDWL
NGKEYKCKVSNKALPAPIEKTISKAKGQPREPQVYTLPP
SREEMTKNQVSLTCLVKGFYPSDIAVEWESNGQPENNYK
TTPPVLDSDGSFFLYSKLTVDKSRWQQGNVFSCSVMHEA
LHNHYTQKSLSLSPGK |
| | 5C9oap-CLDN-light chain | 27 | DIQMTQSPSSLSASVGDRVTITCKSSQSLLNWGNQKSYL
TWYQQKPGKAPKLLIYWASTLQSGVPSRFSGSGSGTDYT
LTISSLQPEDFATYYCQNAYSFPPTFGQGTKVEIKRTVA
APSVFIFPPSDEQLKSGTASVVCLLNNFYPREAKVQWKV
DNALQSGNSQESVTEQDSKDSTYSLSSTLTLSKADYEKH
KVYACEVTHQGLSSPVTKSFNRGEC |
| 6 | 9024-CLDN-VH | 28 | EVQLVESGGGLVQPGGSLRLSCAVSGYTFSMNWVRQAPG
KGLEWVAWINMYTGEKTYADDFKGRFTISRDDSKNTLYL
QMNSLRAEDTAVYYCARLYNGNSLDYWGQGTLVTVSS |
| | 9024-CLDN-VH-CDR1 | 10 | GYTFSMN |
| | 9024-CLDN-VH-CDR2 | 29 | WINMYTGEKTYADDFKG |
| | 9024-CLDN-VH-CDR3 | 4 | LYNGNSLDY |
| | 9024-CLDN-VL | 30 | DIQMTQSPSSLSASVGDRVTITC**KSSQSLLNSGNWKSYL
TWYQQKPGKAPKLLIYWASTLVS**GVPSRFSGSGSGTDYT
LTISSLQPEDFATYYCQNAYSFPFTFGQGTKVEIK |
| | 9024-CLDN-VL-CDR1 | 31 | KSSQSLLNSGNWKSYLT |
| | 9024-CLDN-VL-CDR2 | 32 | WASTLVS |
| | 9024-CLDN-VL-CDR3 | 8 | QNAYSFPFT |
| | 9024-CLDN-heavy chain | 33 | EVQLVESGGGLVQPGGSLRLSCAVSGYTFSMNWVRQAPG
KGLEWVAWINMYTGEKTYADDFKGRFTISRDDSKNTLYL
QMNSLRAEDTAVYYCARLYNGNSLDYWGQGTLVTVSSAS
TKGPSVFPLAPSSKSTSGGTAALGCLVKDYFPEPVTVSW
NSGALTSGVHTFPAVLQSSGLYSLSSVVTVPSSSLGTQT
YICNVNHKPSNTKVDKRVEPKSCDKTHTCPPCPAPELLG
GPSVFLFPPKPKDTLMISRTPEVTCVVVDVSHEDPEVKF
NWYVDGVEVHNAKTKPREEQYNSTYRVVSVLTVLHQDWL
NGKEYKCKVSNKALPAPIEKTISKAKGQPREPQVYTLPP
SREEMTKNQVSLTCLVKGFYPSDIAVEWESNGQPENNYK
TTPPVLDSDGSFFLYSKLTVDKSRWQQGNVFSCSVMHEA
LHNHYTQKSLSLSPGK |
| | 9024-CLDN-light chain | 34 | DIQMTQSPSSLSASVGDRVTITCKSSQSLLNSGNWKSYL
TWYQQKPGKAPKLLIYWASTLVSGVPSRFSGSGSGTDYT
LTISSLQPEDFATYYCQNAYSFPFTFGQGTKVEIKRTVA
APSVFIFPPSDEQLKSGTASVVCLLNNFYPREAKVQWKV
DNALQSGNSQESVTEQDSKDSTYSLSSTLTLSKADYEKH
KVYACEVTHQGLSSPVTKSFNRGEC |
| 7 | 9036-CLDN-VH | 9 | EVQLVESGGGLVQPGGSLRLSCAVSGYTFSMNWVRQAPG
KGLEWVAWINMYTGEPTYADDFKGRFTISRDDSKNTLYL
QMNSLRAEDTAVYYCARLYNGNSLDYWGQGTLVTVSS |
| | 9036-CLDN-VH-CDR1 | 10 | GYTFSMN |
| | 9036-CLDN-VH-CDR2 | 3 | WINMYTGEPTYADDFKG |
| | 9036-CLDN-VH-CDR3 | 4 | LYNGNSLDY |
| | 9036-CLDN-VL | 35 | DIQMTQSPSSLSASVGDRVTITC**KSSQSLLNWGNQKSYL
TWYQQKPGKAPKLLIYWASTLMS**GVPSRFSGSGSGTDYT
LTISSLQPEDFATYYCQNAYSFPFTFGQGTKVEIK |
| | 9036-CLDN-VL-CDR1 | 24 | KSSQSLLNWGNQKSYLT |
| | 9036-CLDN-VL-CDR2 | 36 | WASTLMS |
| | 9036-CLDN-VL-CDR3 | 8 | QNAYSFPFT |
| | 9036-CLDN-heavy chain | 37 | EVQLVESGGGLVQPGGSLRLSCAVSGYTFSMNWVRQAPG
KGLEWVAWINMYTGEPTYADDFKGRFTISRDDSKNTLYL
QMNSLRAEDTAVYYCARLYNGNSLDYWGQGTLVTVSSAS
TKGPSVFPLAPSSKSTSGGTAALGCLVKDYFPEPVTVSW
NSGALTSGVHTFPAVLQSSGLYSLSSVVTVPSSSLGTQT
YICNVNHKPSNTKVDKRVEPKSCDKTHTCPPCPAPELLG
GPSVFLFPPKPKDTLMISRTPEVTCVVVDVSHEDPEVKF
NWYVDGVEVHNAKTKPREEQYNSTYRVVSVLTVLHQDWL
NGKEYKCKVSNKALPAPIEKTISKAKGQPREPQVYTLPP
SREEMTKNQVSLTCLVKGFYPSDIAVEWESNGQPENNYK
TTPPVLDSDGSFFLYSKLTVDKSRWQQGNVFSCSVMHEA
LHNHYTQKSLSLSPGK |
| | 9036-CLDN-light chain | 38 | DIQMTQSPSSLSASVGDRVTITCKSSQSLLNWGNQKSYL
TWYQQKPGKAPKLLIYWASTLMSGVPSRFSGSGSGTDYT
LTISSLQPEDFATYYCQNAYSFPFTFGQGTKVEIKRTVA
APSVFIFPPSDEQLKSGTASVVCLLNNFYPREAKVQWKV |

TABLE 1-continued

| Ab # | Ori ID | SEQ ID | SEQUENCE |
|---|---|---|---|
| | | | DNALQSGNSQESVTEQDSKDSTYSLSSTLTLSKADYEKH KVYACEVTHQGLSSPVTKSFNRGEC |
| 8 | 9041-CLDN-VH | 21 | EVQLVESGGGLVQPGGSLRLSCAVSGYTFSMNWVRQAPG KGLEWVAWINMYTGERTYADDFKGRFTISRDDSKNTLYL QMNSLRAEDTAVYYCARLYNGNSLDYWGQGTLVTVSS |
| | 9041-CLDN-VH-CDR1 | 10 | GYTFSMN |
| | 9041-CLDN-VH-CDR2 | 22 | WINMYTGERTYADDFKG |
| | 9041-CLDN-VH-CDR3 | 4 | LYNGNSLDY |
| | 9041-CLDN-VL | 39 | DIQMTQSPSSLSASVGDRVTITCKSSQSLLNSGNIKSYL TWYQQKPGKAPKLLIYWASTLRSGVPSRFSGSGSGTDYT LTISSLQPEDFATYYCQNAYSFPFTFGQGTKVEIK |
| | 9041-CLDN-VL-CDR1 | 40 | KSSQSLLNSGNIKSYLT |
| | 9041-CLDN-VL-CDR2 | 41 | WASTLRS |
| | 9041-CLDN-VL-CDR3 | 8 | QNAYSFPFT |
| | 9041-CLDN-heavy chain | 42 | EVQLVESGGGLVQPGGSLRLSCAVSGYTFSMNWVRQAPG KGLEWVAWINMYTGERTYADDFKGRFTISRDDSKNTLYL QMNSLRAEDTAVYYCARLYNGNSLDYWGQGTLVTVSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKRVEPKSCDKTHTCPPCPAPELLG GPSVFLFPPKPKDTLMISRTPEVTCVVVDVSHEDPEVKF NWYVDGVEVHNAKTKPREEQYNSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK |
| | 9041-CLDN-light chain | 43 | DIQMTQSPSSLSASVGDRVTITCKSSQSLLNSGNIKSYL TWYQQKPGKAPKLLIYWASTLRSGVPSRFSGSGSGTDYT LTISSLQPEDFATYYCQNAYSFPFTFGQGTKVEIKRTVA APSVFIFPPSDEQLKSGTASVVCLLNNFYPREAKVQWKV DNALQSGNSQESVTEQDSKDSTYSLSSTLTLSKADYEKH KVYACEVTHQGLSSPVTKSFNRGEC |
| 9 | 9045-CLDN-VH | 44 | EVQLVESGGGLVQPGGSLRLSCAVSGYTFSMNWVRQAPG KGLEWVAWINMYTGETTYADDFKGRFTISRDDSKNTLYL QMNSLRAEDTAVYYCARLYNGNSLDYWGQGTLVTVSS |
| | 9045-CLDN-VH-CDR1 | 10 | GYTFSMN |
| | 9045-CLDN-VH-CDR2 | 45 | WINMYTGETTYADDFKG |
| | 9045-CLDN-VH-CDR3 | 4 | LYNGNSLDY |
| | 9045-CLDN-VL | 46 | DIQMTQSPSSLSASVGDRVTITCKSSQSLLNWGNQKSYL TWYQQKPGKAPKLLIYWASTLYSGVPSRFSGSGSGTDYT LTISSLQPEDFATYYCQNAYSFPFTFGQGTKVEIK |
| | 9045-CLDN-VL-CDR1 | 24 | KSSQSLLNWGNQKSYLT |
| | 9045-CLDN-VL-CDR2 | 47 | WASTLYS |
| | 9045-CLDN-VL-CDR3 | 8 | QNAYSFPFT |
| | 9045-CLDN-heavy chain | 48 | EVQLVESGGGLVQPGGSLRLSCAVSGYTFSMNWVRQAPG KGLEWVAWINMYTGETTYADDFKGRFTISRDDSKNTLYL QMNSLRAEDTAVYYCARLYNGNSLDYWGQGTLVTVSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKRVEPKSCDKTHTCPPCPAPELLG GPSVFLFPPKPKDTLMISRTPEVTCVVVDVSHEDPEVKF NWYVDGVEVHNAKTKPREEQYNSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK |
| | 9045-CLDN-light chain | 49 | DIQMTQSPSSLSASVGDRVTITCKSSQSLLNWGNQKSYL TWYQQKPGKAPKLLIYWASTLYSGVPSRFSGSGSGTDYT LTISSLQPEDFATYYCQNAYSFPFTFGQGTKVEIKRTVA APSVFIFPPSDEQLKSGTASVVCLLNNFYPREAKVQWKV DNALQSGNSQESVTEQDSKDSTYSLSSTLTLSKADYEKH KVYACEVTHQGLSSPVTKSFNRGEC |
| 10 | 9047-CLDN-VH | 50 | EVQLVESGGGLVQPGGSLRLSCAVSGYTFSMNWVRQAPG KGLEWVAWINMYTGEPIYADDFKGRFTISRDDSKNTLYL QMNSLRAEDTAVYYCARLYNGNSLDYWGQGTLVTVSS |
| | 9047-CLDN-VH-CDR1 | 10 | GYTFSMN |
| | 9047-CLDN-VH-CDR2 | 51 | WINMYTGEPIYADDFKG |
| | 9047-CLDN-VH-CDR3 | 4 | LYNGNSLDY |
| | 9047-CLDN-VL | 52 | DIQMTQSPSSLSASVGDRVTITCKSSQSLLNWGNQKSYL TWYQQKPGKAPKLLIYWASTLFSGVPSRFSGSGSGTDYT LTISSLQPEDFATYYCQNAYSFPFTFGQGTKVEIK |

TABLE 1-continued

| Ab # | Ori ID | SEQ ID | SEQUENCE |
|---|---|---|---|
| | 9047-CLDN-VL-CDR1 | 24 | KSSQSLLNWGNQKSYLT |
| | 9047-CLDN-VL-CDR2 | 53 | WASTLFS |
| | 9047-CLDN-VL-CDR3 | 8 | QNAYSFPFT |
| | 9047-CLDN-heavy chain | 54 | EVQLVESGGGLVQPGGSLRLSCAVSGYTFSMNWVRQAPG KGLEWVAWINMYTGEPIYADDFKGRFTISRDDSKNTLYL QMNSLRAEDTAVYYCARLYNGNSLDYWGQGTLVTVSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKRVEPKSCDKTHTCPPCPAPELLG GPSVFLFPPKPKDTLMISRTPEVTCVVVDVSHEDPEVKF NWYVDGVEVHNAKTKPREEQYNSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK |
| | 9047-CLDN-light chain | 55 | DIQMTQSPSSLSASVGDRVTITCKSSQSLLNWGNQKSYL TWYQQKPGKAPKLLIYWASTLFSGVPSRFSGSGSGTDYT LTISSLQPEDFATYYCQNAYSFPFTFGQGTKVEIKRTVA APSVFIFPPSDEQLKSGTASVVCLLNNFYPREAKVQWKV DNALQSGNSQESVTEQDSKDSTYSLSSTLTLSKADYEKH KVYACEVTHQGLSSPVTKSFNRGEC |
| 11 | 9051-CLDN-VH | 56 | EVQLVESGGGLVQPGGSLRLSCAVSGYTFSMNWVRQAPG KGLEWVAWINMYTGRPTYADDFKGRFTISRDDSKNTLYL QMNSLRAEDTAVYYCARLYNGNSLDYWGQGTLVTVSS |
| | 9051-CLDN-VH-CDR1 | 10 | GYTFSMN |
| | 9051-CLDN-VH-CDR2 | 57 | WINMYTGRPTYADDFKG |
| | 9051-CLDN-VH-CDR3 | 4 | LYNGNSLDY |
| | 9051-CLDN-VL | 13 | DIQMTQSPSSLSASVGDRVTITCKSSQSLLNSGNQKSYL TWYQQKPGKAPKLLIYWASTLESGVPSRFSGSGSGTDYT LTISSLQPEDFATYYCQNAYFFPFTFGQGTKVEIK |
| | 9051-CLDN-VL-CDR1 | 6 | KSSQSLLNSGNQKSYLT |
| | 9051-CLDN-VL-CDR2 | 12 | WASTLES |
| | 9051-CLDN-VL-CDR3 | 14 | QNAYFFPFT |
| | 9051-CLDN-heavy chain | 58 | EVQLVESGGGLVQPGGSLRLSCAVSGYTFSMNWVRQAPG KGLEWVAWINMYTGRPTYADDFKGRFTISRDDSKNTLYL QMNSLRAEDTAVYYCARLYNGNSLDYWGQGTLVTVSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKRVEPKSCDKTHTCPPCPAPELLG GPSVFLFPPKPKDTLMISRTPEVTCVVVDVSHEDPEVKF NWYVDGVEVHNAKTKPREEQYNSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK |
| | 9051-CLDN-light chain | 16 | DIQMTQSPSSLSASVGDRVTITCKSSQSLLNSGNQKSYL TWYQQKPGKAPKLLIYWASTLESGVPSRFSGSGSGTDYT LTISSLQPEDFATYYCQNAYFFPFTFGQGTKVEIKRTVA APSVFIFPPSDEQLKSGTASVVCLLNNFYPREAKVQWKV DNALQSGNSQESVTEQDSKDSTYSLSSTLTLSKADYEKH KVYACEVTHQGLSSPVTKSFNRGEC |
| 12 | 5C9oap-ob-CLDN-VH | 21 | EVQLVESGGGLVQPGGSLRLSCAVSGYTFSMNWVRQAPG KGLEWVAWINMYTGERTYADDFKGRFTISRDDSKNTLYL QMNSLRAEDTAVYYCARLYNGNSLDYWGQGTLVTVSS |
| | 5C9oap-ob-CLDN-VH-CDR1 | 10 | GYTFSMN |
| | 5C9oap-ob-CLDN-VH-CDR2 | 22 | WINMYTGERTYADDFKG |
| | 5C9oap-ob-CLDN-VH-CDR3 | 4 | LYNGNSLDY |
| | 5C9oap-ob-CLDN-VL | 59 | DIQMTQSPSSLSASVGDRVTITCKSSQSLLNWGNQKSYL TWYQQKPGKAPKLLIYWASTLQSGVPSRFSGSGSGTDYT LTISSLQPEDFATYYCQNAYFFPFTFGQGTKVEIK |
| | 5C9oap-ob-CLDN-VL-CDR1 | 24 | KSSQSLLNWGNQKSYLT |
| | CLDN-VL-5C9oap-ob-CDR2 | 25 | WASTLQS |
| | 5C9oap-ob-CLDN-VL-CDR3 | 14 | QNAYFFPFT |
| | 5C9oap-ob-CLDN-heavy chain | 60 | EVQLVESGGGLVQPGGSLRLSCAVSGYITSMNWVRQAPG KGLEWVAWINMYTGERTYADDFKGRFTISRDDSKNTLYL QMNSLRAEDTAVYYCARLYNGNSLDYWGQGTLVTVSSAS TKGPSVFPLAPSSKSTSGGTAALGCLVKDYFPEPVTVSW NSGALTSGVHTFPAVLQSSGLYSLSSVVTVPSSSLGTQT |

TABLE 1-continued

| Ab # | Ori ID | SEQ ID | SEQUENCE |
|---|---|---|---|
| | | | YICNVNHKPSNTKVDKRVEPKSCDKTHTCPPCPAPELLG GPSVFLFPPKPKDTLMISRTPEVTCVVVDVSHEDPEVKF NWYVDGVEVHNAKTKPREEQYNSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK |
| | 5C9oap-ob-CLDN-light chain | 61 | DIQMTQSPSSLSASVGDRVTITCKSSQSLLNWGNQKSYL TWYQQKPGKAPKLLIYWASTLQSGVPSRFSGSGSGTDYT LTISSLQPEDFATYYCQNAYFFPFTFGQGTKVEIKRTVA APSVFIFPPSDEQLKSGTASVVCLLNNFYPREAKVQWKV DNALQSGNSQESVTEQDSKDSTYSLSSTLTLSKADYEKH KVYACEVTHQGLSSPVTKSFNRGEC |
| 13 | 9024-ob-CLDN-VH | 28 | EVQLVESGGGLVQPGGSLRLSCAVSGYTFSMNWVRQAPG KGLEWVAWINMYTGEKTYADDFKGRFTISRDDSKNTLYL QMNSLRAEDTAVYYCARLYNGNSLDYWGQGTLVTVSS |
| | 9024-ob-CLDN-VH-CDR1 | 10 | GYTFSMN |
| | 9024-ob-CLDN-VH-CDR2 | 29 | WINMYTGEKTYADDFKG |
| | 9024-ob-CLDN-VH-CDR3 | 4 | LYNGNSLDY |
| | 9024-ob-CLDN-VL | 62 | DIQMTQSPSSLSASVGDRVTITCKSSQSLLNSGNWKSYL TWYQQKPGKAPKLLIYWASTLVSGVPSRFSGSGSGTDYT LTISSLQPEDFATYYCQNAYFFPFTFGQGTKVEIK |
| | 9024-ob-CLDN-VL-CDR1 | 31 | KSSQSLLNSGNWKSYLT |
| | 9024-ob-CLDN-VL-CDR2 | 32 | WASTLVS |
| | 9024-ob-CLDN-VL-CDR3 | 14 | QNAYFFPFT |
| | 9024-ob-CLDN-heavy chain | 63 | EVQLVESGGGLVQPGGSLRLSCAVSGYITSMNWVRQAPG KGLEWVAWINMYTGEKTYADDFKGRFTISRDDSKNTLYL QMNSLRAEDTAVYYCARLYNGNSLDYWGQGTLVTVSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKRVEPKSCDKTHTCPPCPAPELLG GPSVFLFPPKPKDTLMISRTPEVTCVVVDVSHEDPEVKF NWYVDGVEVHNAKTKPREEQYNSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK |
| | 9024-ob-CLDN-light chain | 64 | DIQMTQSPSSLSASVGDRVTITCKSSQSLLNSGNWKSYL TWYQQKPGKAPKLLIYWASTLVSGVPSRFSGSGSGTDYT LTISSLQPEDFATYYCQNAYFFPFTFGQGTKVEIKRTVA APSVFIFPPSDEQLKSGTASVVCLLNNFYPREAKVQWKV DNALQSGNSQESVTEQDSKDSTYSLSSTLTLSKADYEKH KVYACEVTHQGLSSPVTKSFNRGEC |
| 14 | 9047-ob-CLDN-VH | 50 | EVQLVESGGGLVQPGGSLRLSCAVSGYTFSMNWVRQAPG KGLEWVAWINMYTGEPIYADDFKGRFTISRDDSKNTLYL QMNSLRAEDTAVYYCARLYNGNSLDYWGQGTLVTVSS |
| | 9047-ob-CLDN-VH-CDR1 | 10 | GYTFSMN |
| | 9047-ob-CLDN-VH-CDR2 | 51 | WINMYTGEPIYADDFKG |
| | 9047-ob-CLDN-VH-CDR3 | 4 | LYNGNSLDY |
| | 9047-ob-CLDN-VL | 65 | DIQMTQSPSSLSASVGDRVTITCKSSQSLLNWGNQKSYL TWYQQKPGKAPKLLIYWASTLFSGVPSRFSGSGSGTDYT LTISSLQPEDFATYYCQNAYFFPFTFGQGTKVEIK |
| | 9047-ob-CLDN-VL-CDR1 | 24 | KSSQSLLNWGNQKSYLT |
| | 9047-ob-CLDN-VL-CDR2 | 66 | YWASTLFS |
| | 9047-ob-CLDN-VL-CDR3 | 14 | QNAYFFPFT |
| | 9047-ob-CLDN-heavy chain | 67 | EVQLVESGGGLVQPGGSLRLSCAVSGYTFSMNWVRQAPG KGLEWVAWINMYTGEPIYADDFKGRFTISRDDSKNTLYL QMNSLRAEDTAVYYCARLYNGNSLDYWGQGTLVTVSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKRVEPKSCDKTHTCPPCPAPELLG GPSVFLFPPKPKDTLMISRTPEVTCVVVDVSHEDPEVKF NWYVDGVEVHNAKTKPREEQYNSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK |
| | 9047-ob-CLDN-light chain | 68 | DIQMTQSPSSLSASVGDRVTITCKSSQSLLNWGNQKSYL TWYQQKPGKAPKLLIYWASTLFSGVPSRFSGSGSGTDYT LTISSLQPEDFATYYCQNAYFFPFTFGQGTKVEIKRTVA APSVFIFPPSDEQLKSGTASVVCLLNNFYPREAKVQWKV DNALQSGNSQESVTEQDSKDSTYSLSSTLTLSKADYEKH KVYACEVTHQGLSSPVTKSFNRGEC |

TABLE 1-continued

Sequence

| Ab # | Ori ID | SEQ ID | SEQUENCE |
|---|---|---|---|
| 15 | 9045-ob-CLDN-VH | 44 | EVQLVESGGGLVQPGGSLRLSCAVSGYTFSMNWVRQAPG<br>KGLEWVAWINMYTGETTYADDFKGRFTISRDDSKNTLYL<br>QMNSLRAEDTAVYYCARLYNGNSLDYWGQGTLVTVSS |
|  | 9045-ob-CLDN-VH-CDR1 | 10 | GYTFSMN |
|  | 9045-ob-CLDN-VH-CDR2 | 45 | WINMYTGETTYADDFKG |
|  | 9045-ob-CLDN-VH-CDR3 | 4 | LYNGNSLDY |
|  | 9045-ob-CLDN-VL | 69 | DIQMTQSPSSLSASVGDRVTITCKSSQSLLNWGNQKSYL<br>TWYQQKPGKAPKLLIYWASTLYSGVPSRFSGSGSGTDYT<br>LTISSLQPEDFATYYCQNAYFFPFTFGQGTKVEIK |
|  | 9045-ob-CLDN-VL-CDR1 | 24 | KSSQSLLNWGNQKSYLT |
|  | 9045-ob-CLDN-VL-CDR2 | 47 | WASTLYS |
|  | 9045-ob-CLDN-VL-CDR3 | 14 | QNAYFFPFT |
|  | 9045-ob-CLDN-heavy chain | 70 | EVQLVESGGGLVQPGGSLRLSCAVSGYTFSMNWVRQAPG<br>KGLEWVAWINMYTGETTYADDFKGRFTISRDDSKNTLYL<br>QMNSLRAEDTAVYYCARLYNGNSLDYWGQGTLVTVSSAS<br>TKGPSVFPLAPSSKSTSGGTAALGCLVKDYFPEPVTVSW<br>NSGALTSGVHTFPAVLQSSGLYSLSSVVTVPSSSLGTQT<br>YICNVNHKPSNTKVDKRVEPKSCDKTHTCPPCPAPELLG<br>GPSVFLFPPKPKDTLMISRTPEVTCVVVDVSHEDPEVKF<br>NWYVDGVEVHNAKTKPREEQYNSTYRVVSVLTVLHQDWL<br>NGKEYKCKVSNKALPAPIEKTISKAKGQPREPQVYTLPP<br>SREEMTKNQVSLTCLVKGFYPSDIAVEWESNGQPENNYK<br>TTPPVLDSDGSFFLYSKLTVDKSRWQQGNVFSCSVMHEA<br>LHNHYTQKSLSLSPGK |
|  | 9045-ob-CLDN-light chain | 71 | DIQMTQSPSSLSASVGDRVTITCKSSQSLLNWGNQKSYL<br>TWYQQKPGKAPKLLIYWASTLYSGVPSRFSGSGSGTDYT<br>LTISSLQPEDFATYYCQNAYFFPFTFGQGTKVEIKRTVA<br>APSVFIFPPSDEQLKSGTASVVCLLNNFYPREAKVQWKV<br>DNALQSGNSQESVTEQDSKDSTYSLSSTLTLSKADYEKH<br>KVYACEVTHQGLSSPVTKSFNRGEC |
| 16 | 9036-ob-CLDN-VH | 9 | EVQLVESGGGLVQPGGSLRLSCAVSGYTFSMNWVRQAPG<br>KGLEWVAWINMYTGEPTYADDFKGRFTISRDDSKNTLYL<br>QMNSLRAEDTAVYYCARLYNGNSLDYWGQGTLVTVSS |
|  | 9036-ob-CLDN-VH-CDR1 | 10 | GYTFSMN |
|  | 9036-ob-CLDN-VH-CDR2 | 3 | WINMYTGEPTYADDFKG |
|  | 9036-ob-CLDN-VH-CDR3 | 4 | LYNGNSLDY |
|  | 9036-ob-CLDN-VL | 72 | DIQMTQSPSSLSASVGDRVTITCKSSQSLLNWGNQKSYL<br>TWYQQKPGKAPKLLIYWASTLMSGVPSRFSGSGSGTDYT<br>LTISSLQPEDFATYYCQNAYFFPFTFGQGTKVEIK |
|  | 9036-ob-CLDN-VL-CDR1 | 24 | KSSQSLLNWGNQKSYLT |
|  | 9036-ob-CLDN-VL-CDR2 | 36 | WASTLMS |
|  | 9036-ob-CLDN-VL-CDR3 | 14 | QNAYFFPFT |
|  | 9036-ob-CLDN-heavy chain | 73 | EVQLVESGGGLVQPGGSLRLSCAVSGYTFSMNWVRQAPG<br>KGLEWVAWINMYTGEPTYADDFKGRFTISRDDSKNTLYL<br>QMNSLRAEDTAVYYCARLYNGNSLDYWGQGTLVTVSSAS<br>TKGPSVFPLAPSSKSTSGGTAALGCLVKDYFPEPVTVSW<br>NSGALTSGVHTFPAVLQSSGLYSLSSVVTVPSSSLGTQT<br>YICNVNHKPSNTKVDKRVEPKSCDKTHTCPPCPAPELLG<br>GPSVFLFPPKPKDTLMISRTPEVTCVVVDVSHEDPEVKF<br>NWYVDGVEVHNAKTKPREEQYNSTYRVVSVLTVLHQDWL<br>NGKEYKCKVSNKALPAPIEKTISKAKGQPREPQVYTLPP<br>SREEMTKNQVSLTCLVKGFYPSDIAVEWESNGQPENNYK<br>TTPPVLDSDGSFFLYSKLTVDKSRWQQGNVFSCSVMHEA<br>LHNHYTQKSLSLSPGK |
|  | 9036-ob-CLDN-light chain | 74 | DIQMTQSPSSLSASVGDRVTITCKSSQSLLNWGNQKSYL<br>TWYQQKPGKAPKLLIYWASTLMSGVPSRFSGSGSGTDYT<br>LTISSLQPEDFATYYCQNAYFFPFTFGQGTKVEIKRTVA<br>APSVFIFPPSDEQLKSGTASVVCLLNNFYPREAKVQWKV<br>DNALQSGNSQESVTEQDSKDSTYSLSSTLTLSKADYEKH<br>KVYACEVTHQGLSSPVTKSFNRGEC |
| 17 | 9041-ob-CLDN-VH | 21 | EVQLVESGGGLVQPGGSLRLSCAVSGYTFSMNWVRQAPG<br>KGLEWVAWINMYTGERTYADDFKGRFTISRDDSKNTLYL<br>QMNSLRAEDTAVYYCARLYNGNSLDYWGQGTLVTVSS |
|  | 9041-ob-CLDN-VH-CDR1 | 10 | GYTFSMN |
|  | 9041-ob-CLDN-VH-CDR2 | 22 | WINMYTGERTYADDFKG |
|  | 9041-ob-CLDN-VH-CDR3 | 4 | LYNGNSLDY |
|  | 9041-ob-CLDN-VL | 75 | DIQMTQSPSSLSASVGDRVTITCKSSQSLLNSGNIKSYL<br>TWYQQKPGKAPKLLIYWASTLRSGVPSRFSGSGSGTDYT<br>LTISSLQPEDFATYYCQNAYFFPFTFGQGTKVEIK |
|  | 9041-ob-CLDN-VL-CDR1 | 40 | KSSQSLLNSGNIKSYLT |
|  | 9041-ob-CLDN-VL-CDR2 | 41 | WASTLRS |
|  | 9041-ob-CLDN-VL-CDR3 | 14 | QNAYFFPFT |
|  | 9041-ob-CLDN-heavy chain | 76 | EVQLVESGGGLVQPGGSLRLSCAVSGYITSMNWVRQAPG<br>KGLEWVAWINMYTGERTYADDFKGRFTISRDDSKNTLYL |

TABLE 1-continued

| Ab # | Ori ID | SEQ ID | SEQUENCE |
|---|---|---|---|
| | | | QMNSLRAEDTAVYYCARLYNGNSLDYWGQGTLVTVSSAS
TKGPSVFPLAPSSKSTSGGTAALGCLVKDYFPEPVTVSW
NSGALTSGVHTFPAVLQSSGLYSLSSVVTVPSSSLGTQT
YICNVNHKPSNTKVDKRVEPKSCDKTHTCPPCPAPELLG
GPSVFLFPPKPKDTLMISRTPEVTCVVVDVSHEDPEVKF
NWYVDGVEVHNAKTKPREEQYNSTYRVVSVLTVLHQDWL
NGKEYKCKVSNKALPAPIEKTISKAKGQPREPQVYTLPP
SREEMTKNQVSLTCLVKGFYPSDIAVEWESNGQPENNYK
TTPPVLDSDGSFFLYSKLTVDKSRWQQGNVFSCSVMHEA
LHNHYTQKSLSLSPGK |
| | 9041-ob-CLDN-light chain | 77 | DIQMTQSPSSLSASVGDRVTITCKSSQSLLNSGNIKSYL
TWYQQKPGKAPKLLIYWASTLRSGVPSRFSGSGSGTDYT
LTISSLQPEDFATYYCQNAYFFPFTFGQGTKVEIKRTVA
APSVFIFPPSDEQLKSGTASVVCLLNNFYPREAKVQWKV
DNALQSGNSQESVTEQDSKDSTYSLSSTLTLSKADYEKH
KVYACEVTHQGLSSPVTKSFNRGEC |
| 18 | 5C9oap-oae-CLDN-VH | 78 | EVQLVESGGGLVQPGGSLRLSCAVSGYTFSMNWVRQAPG
KGLEWVAWINMYTGERTYADDFKGRFTISRDDSKNTLYL
QMNSLRAEDTAVYYCARLYRGNSLDYWGQGTLVTVSS |
| | 5C9oap-oae-CLDN-VH-CDR1 | 10 | GYTFSMN |
| | 5C9oap-oae-CLDN-VH-CDR2 | 22 | WINMYTGERTYADDFKG |
| | 5C9oap-oae-CLDN-VH-CDR3 | 18 | LYRGNSLDY |
| | 5C9oap-oae-CLDN-VL | 59 | DIQMTQSPSSLSASVGDRVTITC**KSSQSLLNWGNQKSYL
TWYQQKPGKAPKLLIYWASTLQS**GVPSRFSGSGSGTDYT
LTISSLQPEDFATYYCQNAYFFPFTFGQGTKVEIK |
| | 5C9oap-oae-CLDN-VL-CDR1 | 24 | KSSQSLLNWGNQKSYLT |
| | 5C9oap-oae-CLDN-VL-CDR2 | 25 | WASTLQS |
| | 5C9oap-oae-CLDN-VL-CDR3 | 14 | QNAYFFPFT |
| | 5C9oap-oae-CLDN-heavy chain | 79 | EVQLVESGGGLVQPGGSLRLSCAVSGYITSMNWVRQAPG
KGLEWVAWINMYTGERTYADDFKGRFTISRDDSKNTLYL
QMNSLRAEDTAVYYCARLYRGNSLDYWGQGTLVTVSSAS
TKGPSVFPLAPSSKSTSGGTAALGCLVKDYFPEPVTVSW
NSGALTSGVHTFPAVLQSSGLYSLSSVVTVPSSSLGTQT
YICNVNHKPSNTKVDKRVEPKSCDKTHTCPPCPAPELLG
GPSVFLFPPKPKDTLMISRTPEVTCVVVDVSHEDPEVKF
NWYVDGVEVHNAKTKPREEQYNSTYRVVSVLTVLHQDWL
NGKEYKCKVSNKALPAPIEKTISKAKGQPREPQVYTLPP
SREEMTKNQVSLTCLVKGFYPSDIAVEWESNGQPENNYK
TTPPVLDSDGSFFLYSKLTVDKSRWQQGNVFSCSVMHEA
LHNHYTQKSLSLSPGK |
| | 5C9oap-oae-CLDN-light chain | 61 | DIQMTQSPSSLSASVGDRVTITCKSSQSLLNWGNQKSYL
TWYQQKPGKAPKLLIYWASTLQSGVPSRFSGSGSGTDYT
LTISSLQPEDFATYYCQNAYFFPFTFGQGTKVEIKRTVA
APSVFIFPPSDEQLKSGTASVVCLLNNFYPREAKVQWKV
DNALQSGNSQESVTEQDSKDSTYSLSSTLTLSKADYEKH
KVYACEVTHQGLSSPVTKSFNRGEC |
| 19 | 9024-oae-CLDN-VH | 80 | EVQLVESGGGLVQPGGSLRLSCAVSGYTFSMNWVRQAPG
KGLEWVAWINMYTGEKTYADDFKGRFTISRDDSKNTLYL
QMNSLRAEDTAVYYCARLYRGNSLDYWGQGTLVTVSS |
| | 9024-oae-CLDN-VH-CDR1 | 10 | GYTFSMN |
| | 9024-oae-CLDN-VH-CDR2 | 29 | WINMYTGEKTYADDFKG |
| | 9024-oae-CLDN-VH-CDR3 | 18 | LYRGNSLDY |
| | 9024-oae-CLDN-VL | 62 | DIQMTQSPSSLSASVGDRVTITC**KSSQSLLNSGNWKSYL
TWYQQKPGKAPKLLIYWASTLVS**GVPSRFSGSGSGTDYT
LTISSLQPEDFATYYCQNAYFFPFTFGQGTKVEIK |
| | 9024-oae-CLDN-VL-CDR1 | 31 | KSSQSLLNSGNWKSYLT |
| | 9024-oae-CLDN-VL-CDR2 | 32 | WASTLVS |
| | 9024-oae-CLDN-VL-CDR3 | 14 | QNAYFFPFT |
| | 9024-oae-CLDN-heavy chain | 81 | EVQLVESGGGLVQPGGSLRLSCAVSGYITSMNWVRQAPG
KGLEWVAWINMYTGEKTYADDFKGRFTISRDDSKNTLYL
QMNSLRAEDTAVYYCARLYRGNSLDYWGQGTLVTVSSAS
TKGPSVFPLAPSSKSTSGGTAALGCLVKDYFPEPVTVSW
NSGALTSGVHTFPAVLQSSGLYSLSSVVTVPSSSLGTQT
YICNVNHKPSNTKVDKRVEPKSCDKTHTCPPCPAPELLG
GPSVFLFPPKPKDTLMISRTPEVTCVVVDVSHEDPEVKF
NWYVDGVEVHNAKTKPREEQYNSTYRVVSVLTVLHQDWL
NGKEYKCKVSNKALPAPIEKTISKAKGQPREPQVYTLPP
SREEMTKNQVSLTCLVKGFYPSDIAVEWESNGQPENNYK |

TABLE 1-continued

| Ab # | Ori ID | SEQ ID | SEQUENCE |
|---|---|---|---|
| | | | TTPPVLDSDGSFFLYSKLTVDKSRWQQGNVFSCSVMHEALHNHYTQKSLSLSPGK |
| | 9024-oae-CLDN-light chain | 64 | DIQMTQSPSSLSASVGDRVTITCKSSQSLLNSGNWKSYLTWYQQKPGKAPKLLIYWASTLVSGVPSRFSGSGSGTDYTLTISSLQPEDFATYYCQNAYFFPFTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 20 | 9047-oae-CLDN-VH | 82 | EVQLVESGGGLVQPGGSLRLSCAVSGYTFSMNWVRQAPGKGLEWVAWINMYTGEPIYADDFKGRFTISRDDSKNTLYLQMNSLRAEDTAVYYCARLYRGNSLDYWGQGTLVTVSS |
| | 9047-oae-CLDN-VH-CDR1 | 10 | GYTFSMN |
| | 9047-oae-CLDN-VH-CDR2 | 51 | WINMYTGEPIYADDFKG |
| | 9047-oae-CLDN-VH-CDR3 | 18 | LYRGNSLDY |
| | 9047-oae-CLDN-VL | 65 | DIQMTQSPSSLSASVGDRVTITCKSSQSLLNWGNQKSYLTWYQQKPGKAPKLLIYWASTLFSGVPSRFSGSGSGTDYTLTISSLQPEDFATYYCQNAYFFPFTFGQGTKVEIK |
| | 9047-oae-CLDN-VL-CDR1 | 24 | KSSQSLLNWGNQKSYLT |
| | 9047-oae-CLDN-VL-CDR2 | 53 | WASTLFS |
| | 9047-oae-CLDN-VL-CDR3 | 14 | QNAYFFPFT |
| | 9047-oae-CLDN-heavy chain | 83 | EVQLVESGGGLVQPGGSLRLSCAVSGYTFSMNWVRQAPGKGLEWVAWINMYTGEPIYADDFKGRFTISRDDSKNTLYLQMNSLRAEDTAVYYCARLYRGNSLDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | 9047-oae-CLDN-light chain | 68 | DIQMTQSPSSLSASVGDRVTITCKSSQSLLNWGNQKSYLTWYQQKPGKAPKLLIYWASTLFSGVPSRFSGSGSGTDYTLTISSLQPEDFATYYCQNAYFFPFTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 21 | 9045-oae-CLDN-VH | 84 | EVQLVESGGGLVQPGGSLRLSCAVSGYTFSMNWVRQAPGKGLEWVAWINMYTGETTYADDFKGRFTISRDDSKNTLYLQMNSLRAEDTAVYYCARLYRGNSLDYWGQGTLVTVSS |
| | 9045-oae-CLDN-VH-CDR1 | 10 | GYTFSMN |
| | 9045-oae-CLDN-VH-CDR2 | 45 | WINMYTGETTYADDFKG |
| | 9045-oae-CLDN-VH-CDR3 | 18 | LYRGNSLDY |
| | 9045-oae-CLDN-VL | 69 | DIQMTQSPSSLSASVGDRVTITCKSSQSLLNWGNQKSYLTWYQQKPGKAPKLLIYWASTLYSGVPSRFSGSGSGTDYTLTISSLQPEDFATYYCQNAYFFPFTFGQGTKVEIK |
| | 9045-oae-CLDN-VL-CDR1 | 24 | KSSQSLLNWGNQKSYLT |
| | 9045-oae-CLDN-VL-CDR2 | 47 | WASTLYS |
| | 9045-oae-CLDN-VL-CDR3 | 14 | QNAYFFPFT |
| | 9045-oae-CLDN-heavy chain | 85 | EVQLVESGGGLVQPGGSLRLSCAVSGYTFSMNWVRQAPGKGLEWVAWINMYTGETTYADDFKGRFTISRDDSKNTLYLQMNSLRAEDTAVYYCARLYRGNSLDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | 9045-oae-CLDN-light chain | 71 | DIQMTQSPSSLSASVGDRVTITCKSSQSLLNWGNQKSYLTWYQQKPGKAPKLLIYWASTLYSGVPSRFSGSGSGTDYTLTISSLQPEDFATYYCQNAYFFPFTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 22 | 9036-oae-CLDN-VH | 17 | EVQLVESGGGLVQPGGSLRLSCAVSGYTFSMNWVRQAPGKGLEWVAWINMYTGEPTYADDFKGRFTISREDSKNTLYLQMNSLRAEDTAVYYCARLYRGNSLDYWGQGTLVTVSS |
| | 9036-oae-CLDN-VH-CDR1 | 10 | GYTFSMN |
| | 9036-oae-CLDN-VH-CDR2 | 3 | WINMYTGEPTYADDFKG |

TABLE 1-continued

| Ab # | Ori ID | SEQ ID | SEQUENCE |
|---|---|---|---|
| | 9036-oae-CLDN-VH-CDR3 | 18 | LYRGNSLDY |
| | 9036-oae-CLDN-VL | 72 | DIQMTQSPSSLSASVGERVTITCKSSQSLLNWGNQKSYL TWYQQKPGKAPKLLIYWASTLMSGVPSRFSGSGSGTEYT LTISSLQPEDFATYYCQNAYFFPFTFGQGTKVEIK |
| | 9036-oae-CLDN-VL-CDR1 | 24 | KSSQSLLNWGNQKSYLT |
| | 9036-oae-CLDN-VL-CDR2 | 36 | WASTLMS |
| | 9036-oae-CLDN-VL-CDR3 | 14 | QNAYFFPFT |
| | 9036-oae-CLDN-heavy chain | 86 | EVQLVESGGGLVQPGGSLRLSCAVSGYTFSMNWVRQAPG KGLEWVAWINMYTGEPTYADDFKGRFTISRDDSKNTLYL QMNSLRAEDTAVYYCARLYRGNSLDYWGQGTLVTVSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKRVEPKSCDKTHTCPPCPAPELLG GPSVFLFPPKPKDTLMISRTPEVTCVVVDVSHEDPEVKF NWYVDGVEVHNAKTKPREEQYNSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK |
| | 9036-oae-CLDN-light chain | 74 | DIQMTQSPSSLSASVGDRVTITCKSSQSLLNWGNQKSYL TWYQQKPGKAPKLLIYWASTLMSGVPSRFSGSGSGTDYT LTISSLQPEDFATYYCQNAYFFPFTFGQGTKVEIKRTVA APSVFIFPPSDEQLKSGTASVVCLLNNFYPREAKVQWKV DNALQSGNSQESVTEQDSKDSTYSLSSTLTLSKADYEKH KVYACEVTHQGLSSPVTKSFNRGEC |
| 23 | 9041-oae-CLDN-VH | 78 | EVQLVESGGGLVQPGGSLRLSCAVSGYTFSMNWVRQAPG KGLEWVAWINMYTGERTYADDFKGRFTISREDSKNTLYL QMNSLRAEDTAVYYCARLYRGNSLDYWGQGTLVTVSS |
| | 9041-oae-CLDN-VH-CDR1 | 10 | GYTFSMN |
| | 9041-oae-CLDN-VH-CDR2 | 22 | WINMYTGERTYADDFKG |
| | 9041-oae-CLDN-VH-CDR3 | 18 | LYRGNSLDY |
| | 9041-oae-CLDN-VL | 75 | DIQMTQSPSSLSASVGERVTITCKSSQSLLNSGNIKSYL TWYQQKPGKAPKLLIYWASTLRSGVPSRFSGSGSGTEYT LTISSLQPEDFATYYCQNAYFFPFTFGQGTKVEIK |
| | 9041-oae-CLDN-VL-CDR1 | 40 | KSSQSLLNSGNIKSYLT |
| | 9041-oae-CLEN-VL-CDR2 | 41 | WASTLRS |
| | 9041-oae-CLDN-VL-CDR3 | 14 | QNAYFFPFT |
| | 9041-oae-CLEN-heavy chain | 87 | EVQLVESGGGLVQPGGSLRLSCAVSGYTFSMNWVRQAPG KGLEWVAWINMYTGERTYADDFKGRFTISRDDSKNTLYL QMNSLRAEDTAVYYCARLYRGNSLDYWGQGTLVTVSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKRVEPKSCDKTHTCPPCPAPELLG GPSVFLFPPKPKDTLMISRTPEVTCVVVDVSHEDPEVKF NWYVDGVEVHNAKTKPREEQYNSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK |
| | 9041-oae-CLDN-light chain | 77 | DIQMTQSPSSLSASVGDRVTITCKSSQSLLNSGNIKSYL TWYQQKPGKAPKLLIYWASTLRSGVPSRFSGSGSGTDYT LTISSLQPEDFATYYCQNAYFFPFTFGQGTKVEIKRTVA APSVFIFPPSDEQLKSGTASVVCLLNNFYPREAKVQWKV DNALQSGNSQESVTEQDSKDSTYSLSSTLTLSKADYEKH KVYACEVTHQGLSSPVTKSFNRGEC |
| 24 | 9047HN-CLDN-VH | 82 | EVQLVESGGGLVQPGGSLRLSCAVSGYTFSMNWVRQAPG KGLEWVAWINMYTGEPIYADDFKGRFTISRDDSKNTLYL QMNSLRAEDTAVYYCARLYRGNSLDYWGQGTLVTVSS |
| | 9047HN-CLDN-VH-CDR1 | 10 | GYTFSMN |
| | 9047HN-CLDN-VH-CDR2 | 51 | WINMYTGEPIYADDFKG |
| | 9047HN-CLDN-VH-CDR3 | 18 | LYRGNSLDY |
| | 9047HN-CLDN-VL | 52 | DIQMTQSPSSLSASVGDRVTITCKSSQSLLNWGNQKSYL TWYQQKPGKAPKLLIYWASTLFSGVPSRFSGSGSGTDYT LTISSLQPEDFATYYCQNAYSFPFTFGQGTKVEIK |
| | 9047HN-CLDN-VL-CDR1 | 24 | KSSQSLLNWGNQKSYLT |
| | 9047HN-CLDN-VL-CDR2 | 53 | WASTLFS |
| | 9047HN-CLDN-VL-CDR3 | 8 | QNAYSFPFT |
| | 9047HN-CLDN-heavy chain | 88 | EVQLVESGGGLVQPGGSLRLSCAVSGYTFSMNWVRQAPG KGLEWVAWINMYTGEPIYADDFKGRFTISRDDSKNTLYL QMNSLRAEDTAVYYCARLYRGNSLDYWGQGTLVTVSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKRVEPKSCDKTHTCPPCPAPELLG GPSVFLFPPKPKDTLMISRTPEVTCVVVDVSHEDPEVKF |

TABLE 1-continued

| Ab # | Ori ID | SEQ ID | SEQUENCE |
|---|---|---|---|
| | | | NWYVDGVEVHNAKTKPREEQYNSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK |
| | 9047HN-CLDN-light chain | 55 | DIQMTQSPSSLSASVGDRVTITCKSSQSLLNWGNQKSYL TWYQQKPGKAPKLLIYWASTLFSGVPSRFSGSGSGTDYT LTISSLQPEDFATYYCQNAYSFPFTFGQGTKVEIKRTVA APSVFIFPPSDEQLKSGTASVVCLLNNFYPREAKVQWKV DNALQSGNSQESVTEQDSKDSTYSLSSTLTLSKADYEKH KVYACEVTHQGLSSPVTKSFNRGEC |
| 25 | 9041HN-CLDN-VH | 78 | EVQLVESGGGLVQPGGSLRLSCAVSGYTFSMNWVRQAPG KGLEWVAWINMYTGERTYADDFKGRFTISRDDSKNTLYL QMNSLRAEDTAVYYCARLYRGNSLDYWGQGTLVTVSS |
| | 9041HN-CLDN-VH-CDR1 | 10 | GYTFSMN |
| | 9041HN-CLDN-VH-CDR2 | 22 | WINMYTGERTYADDFKG |
| | 9041HN-CLDN-VH-CDR3 | 18 | LYRGNSLDY |
| | 9041HN-CLDN-VL | 39 | DIQMTQSPSSLSASVGDRVTITCKSSQSLLNSGNIKSYL TWYQQKPGKAPKLLIYWASTLRSGVPSRFSGSGSGTDYT LTISSLQPEDFATYYCQNAYSFPFTFGQGTKVEIK |
| | 9041HN-CLDN-VL-CDR1 | 40 | KSSQSLLNSGNIKSYLT |
| | 9041HN-CLDN-VL-CDR2 | 41 | WASTLRS |
| | 9041HN-CLDN-VL-CDR3 | 8 | QNAYSFPFT |
| | 9041HN-CLDN-heavy chain | 89 | EVQLVESGGGLVQPGGSLRLSCAVSGYTFSMNWVRQAPG KGLEWVAWINMYTGERTYADDFKGRFTISRDDSKNTLYL QMNSLRAEDTAVYYCARLYRGNSLDYWGQGTLVTVSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKRVEPKSCDKTHTCPPCPAPELLG GPSVFLFPPKPKDTLMISRTPEVTCVVVDVSHEDPEVKF NWYVDGVEVHNAKTKPREEQYNSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK |
| | 9041HN-CLDN-light chain | 43 | DIQMTQSPSSLSASVGDRVTITCKSSQSLLNSGNIKSYL TWYQQKPGKAPKLLIYWASTLRSGVPSRFSGSGSGTDYT LTISSLQPEDFATYYCQNAYSFPFTFGQGTKVEIKRTVA APSVFIFPPSDEQLKSGTASVVCLLNNFYPREAKVQWKV DNALQSGNSQESVTEQDSKDSTYSLSSTLTLSKADYEKH KVYACEVTHQGLSSPVTKSFNRGEC |
| 26 | 9047E-CLDN-VH | 50 | EVQLVESGGGLVQPGGSLRLSCAVSGYTFSMNWVRQAPG KGLEWVAWINMYTGEPIYADDFKGRFTISRDDSKNTLYL QMNSLRAEDTAVYYCARLYNGNSLDYWGQGTLVTVSS |
| | 9047E-CLDN-VH-CDR1 | 10 | GYTFSMN |
| | 9047E-CLDN-VH-CDR2 | 51 | WINMYTGEPIYADDFKG |
| | 9047E-CLDN-VH-CDR3 | 4 | LYNGNSLDY |
| | 9047E-CLDN-VL | 90 | DIQMTQSPSSLSASVGDRVTITCKSSQSLLNWGNQKSYL TWYQQKPGKAPKLLIYWASTLESGVPSRFSGSGSGTDYT LTISSLQPEDFATYYCQNAYSFPFTFGQGTKVEIK |
| | 9047E-CLDN-VL-CDR1 | 24 | KSSQSLLNWGNQKSYLT |
| | 9047E-CLDN-VL-CDR2 | 12 | WASTLES |
| | 9047E-CLDN-VL-CDR3 | 8 | QNAYSFPFT |
| | 9047E-CLDN-heavy chain | 91 | EVQLVESGGGLVQPGGSLRLSCAVSGYTFSMNWVRQAPG KGLEWVAWINMYTGEPIYADDFKGRFTISRDDSKNTLYL QMNSLRAEDTAVYYCARLYNGNSLDYWGQGTLVTVSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKRVEPKSCDKTHTCPPCPAPELLG GPSVFLFPPKPKDTLMISRTPEVTCVVVDVSHEDPEVKF NWYVDGVEVHNAKTKPREEQYNSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK |
| | 9047E-CLDN-light chain | 92 | DIQMTQSPSSLSASVGDRVTITCKSSQSLLNWGNQKSYL TWYQQKPGKAPKLLIYWASTLESGVPSRFSGSGSGTDYT LTISSLQPEDFATYYCQNAYSFPFTFGQGTKVEIKRTVA APSVFIFPPSDEQLKSGTASVVCLLNNFYPREAKVQWKV DNALQSGNSQESVTEQDSKDSTYSLSSTLTLSKADYEKH KVYACEVTHQGLSSPVTKSFNRGEC |

TABLE 1-continued

| Ab # | Ori ID | SEQ ID | SEQUENCE |
|---|---|---|---|
| 27 | 9047-oaeE-CLDN-VH | 82 | EVQLVESGGGLVQPGGSLRLSCAVSGYTFSMNWVRQAPG KGLEWVAWINMYTGEPIYADDFKGRFTISRDDSKNTLYL QMNSLRAEDTAVYYCARLYRGNSLDYWGQGTLVTVSS |
|  | 9047-oaeE-CLDN-VH-CDR1 | 10 | GYTFSMN |
|  | 9047-oaeE-CLDN-VH-CDR2 | 51 | WINMYTGEPIYADDFKG |
|  | 9047-oaeE-CLDN-VH-CDR3 | 18 | LYRGNSLDY |
|  | 9047-oaeE-CLDN-VL | 93 | DIQMTQSPSSLSASVGDRVTITCKSSQSLLNWGNQKSYL TWYQQKPGKAPKLLIYWASTLESGVPSRFSGSGSGTDYT LTISSLQPEDFATYYCQNAYFFPFTFGQGTKVEIK |
|  | 9047-oaeE-CLDN-VL-CDR1 | 24 | KSSQSLLNWGNQKSYLT |
|  | 9047-oaeE-CLDN-VL-CDR2 | 12 | WASTLES |
|  | 9047-oaeE-CLDN-VL-CDR3 | 14 | QNAYFFPFT |
|  | 9047-oaeE-CLDN-heavy chain | 94 | EVQLVESGGGLVQPGGSLRLSCAVSGYTFSMNWVRQAPG KGLEWVAWINMYTGEPIYADDFKGRFTISRDDSKNTLYL QMNSLRAEDTAVYYCARLYRGNSLDYWGQGTLVTVSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKRVEPKSCDKTHTCPPCPAPELLG GPSVFLFPPKPKDTLMISRTPEVTCVVVDVSHEDPEVKF NWYVDGVEVHNAKTKPREEQYNSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK |
|  | 9047-oaeE-CLDN-light chain | 95 | DIQMTQSPSSLSASVGDRVTITCKSSQSLLNWGNQKSYL TWYQQKPGKAPKLLIYWASTLESGVPSRFSGSGSGTDYT LTISSLQPEDFATYYCQNAYFFPFTFGQGTKVEIKRTVA APSVFIFPPSDEQLKSGTASVVCLLNNFYPREAKVQWKV DNALQSGNSQESVTEQDSKDSTYSLSSTLTLSKADYEKH KVYACEVTHQGLSSPVTKSFNRGEC |
| 28 | 5C9oap-oaeE-CLDN-VH | 78 | EVQLVESGGGLVQPGGSLRLSCAVSGYTFSMNWVRQAPG KGLEWVAWINMYTGERTYADDFKGRFTISRDDSKNTLYL QMNSLRAEDTAVYYCARLYRGNSLDYWGQGTLVTVSS |
|  | 5C9oap-oaeE-CLDN-VH-CDR1 | 10 | GYTFSMN |
|  | 5C9oap-oaeE-CLDN-VH-CDR2 | 22 | WINMYTGERTYADDFKG |
|  | 5C9oap-oaeE-CLDN-VH-CDR3 | 18 | LYRGNSLDY |
|  | 5C9oap-oaeE-CLDN-VL | 93 | DIQMTQSPSSLSASVGDRVTITCKSSQSLLNWGNQKSYL TWYQQKPGKAPKLLIYWASTLESGVPSRFSGSGSGTDYT LTISSLQPEDFATYYCQNAYFFPFTFGQGTKVEIK |
|  | 5C9oap-oaeE-CLDN-VL-CDR1 | 24 | KSSQSLLNWGNQKSYLT |
|  | 5C9oap-oaeE-CLDN-VL-CDR2 | 12 | WASTLES |
|  | 5C9oap-oaeE-CLDN-VL-CDR3 | 14 | QNAYFFPFT |
|  | 5C9oap-oaeE-CLDN-heavy chain | 96 | EVQLVESGGGLVQPGGSLRLSCAVSGYTFSMNWVRQAPG KGLEWVAWINMYTGERTYADDFKGRFTISRDDSKNTLYL QMNSLRAEDTAVYYCARLYRGNSLDYWGQGTLVTVSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKRVEPKSCDKTHTCPPCPAPELLG GPSVFLFPPKPKDTLMISRTPEVTCVVVDVSHEDPEVKF NWYVDGVEVHNAKTKPREEQYNSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK |
|  | 5C9oap-oaeE-CLDN-light chain | 95 | DIQMTQSPSSLSASVGDRVTITCKSSQSLLNWGNQKSYL TWYQQKPGKAPKLLIYWASTLESGVPSRFSGSGSGTDYT LTISSLQPEDFATYYCQNAYFFPFTFGQGTKVEIKRTVA APSVFIFPPSDEQLKSGTASVVCLLNNFYPREAKVQWKV DNALQSGNSQESVTEQDSKDSTYSLSSTLTLSKADYEKH KVYACEVTHQGLSSPVTKSFNRGEC |

TABLE 1-continued

| Ab # | Ori ID | SEQ ID | SEQUENCE |
|---|---|---|---|
| 29 | Durvalumab-VH | 97 | EVQLVESGGGLVQPGGSLRLSCAASGFTFSRYWMSWVRQ APGKGLEWVANIKQDGSEKYYVDSVKGRFTISRDNAKNS LYLQMNSLRAEDTAVYYCAREGGWFGELAFDYWGQGTLV TVSS |
| | Durvalumab-VH-CDR1 | 98 | GFTFSRYWMS |
| | Durvalumab-VH-CDR2 | 99 | NIKQDGSEKYYVDSVKG |
| | Durvalumab-VH-CDR3 | 100 | EGGWFGELAFDY |
| | Durvalumab-VL | 101 | EIVLTQSPGTLSLSPGERATLSCRASQRVSSSYLAWYQQ KPGQAPRLLIYDASSRATGIPDRFSGSGSGTDFTLTISR LEPEDFAVYYCQQYGSLPWTFGQGTKVEIK |
| | Durvalumab-VL-CDR1 | 102 | RASQRVSSSYLA |
| | Durvalumab-VL-CDR2 | 103 | DASSRAT |
| | Durvalumab-VL-CDR3 | 104 | QQYGSLPWT |
| 30 | Avelumab-VH | 105 | EVQLLESGGGLVQPGGSLRLSCAASGFTFSSYIMMWVRQ APGKGLEWVSSIYPSGGITFYADTVKGRFTISRDNSKNT LYLQMNSLRAEDTAVYYCARIKLGTVTTVDYWGQGTLVT VSS |
| | Avelumab-VH-CDR1 | 106 | GFTFSSYIMM |
| | Avelumab-VH-CDR2 | 107 | SIYPSGGITFYADTVKG |
| | Avelumab-VH-CDR3 | 108 | IKLGTVTTVDY |
| | Avelumab-VL | 109 | QSALTQPASVSGSPGQSITISCTGTSSDVGGYNYVSWYQ QHPGKAPKLMIYDVSNRPSGVSNRFSGSKSGNTASLTIS GLQAEDEADYYCSSYTSSSTRVFGTGTKVTVL |
| | Avelumab-VL-CDR1 | 110 | TGTSSDVGGYNYVS |
| | Avelumab-VL-CDR2 | 111 | DVSNRPS |
| | Avelumab-VL-CDR3 | 112 | SSYTSSSTRV |
| 31 | Atezolizumab-VH | 113 | EVQLVESGGGLVQPGGSLRLSCAASGFTFSDSWIHWVRQ APGKGLEWVAWISPYGGSTYYADSVKGRFTISADTSKNT AYLQMNSLRAEDTAVYYCARRHWPGGFDYWGQGTLVTVS S |
| | Atezolizumab-VH-CDR1 | 114 | GFTFSDSWIH |
| | Atezolizumab-VH-CDR2 | 115 | WISPYGGSTYYADSVKG |
| | Atezolizumab-VH-CDR3 | 116 | RHWPGGFDY |
| | Atezolizumab-VL | 117 | DIQMTQSPSSLSASVGDRVTITCRASQDVSTAVAWYQQK PGKAPKLLIYSASFLYSGVPSRFSGSGSGTDFTLTISSL QPEDFATYYCQQYLYHPATFGQGTKVEIK |
| | Atezolizumab-VL-CDR1 | 118 | RASQDVSTAVA |
| | Atezolizumab-VL-CDR2 | 119 | SASFLYS |
| | Atezolizumab-VL-CDR3 | 120 | QQYLYHPAT |
| 32 | ScDb01-L1 | 121 | SGGGG |
| | ScDb01-L2 | 122 | GGGGSGGGGSGGGGS |
| | ScDb01-L3 | 121 | SGGGG |
| 33 | ScDb06-L2 | 123 | GGGGSGGGGSGGGGSGGGGS |
| 34 | ScDb08-L1 | 124 | GSSRSS |
| | ScDb08-L2 | 125 | GSGSSSSRSSSGSGGG |
| | ScDb08-L3 | 126 | SGGRGG |
| 35 | Dblnk1-L2 | 127 | GSSGSSSRGGSGSSS |
| 36 | Dblnk2-L2 | 128 | SSSGSGGGSGGGGGG |
| | Dblnk2-L3 | 129 | GSSGS |
| 37 | Dblnk3-L2 | 130 | GGGGSGSGSSGSSSG |
| | Dblnk4-L1 | 131 | GGGGSG |
| | Dblnk4-L2 | 132 | GSSSGGGSGGSSSSS |
| | Dblnk4-L3 | 133 | SGGS |
| 38 | Dblnk5-L1 | 134 | GGGS |
| | Dblnk5-L2 | 135 | SSGSGGGSSSGSSGG |
| 39 | Dblnk6-L2 | 136 | SGGRSGSGSGSNGGG |
| | Dblnk6-L3 | 137 | GGSGGG |
| 40 | Dblnk7-L2 | 138 | GSSGRGSSGGSGGSSG |

TABLE 1-continued

| Ab # | Ori ID | SEQ ID | SEQUENCE |
|---|---|---|---|
| 41 | Dblnk7-L3 | 139 | GGSG |
| 42 | Dblnk8-L1 | 140 | GGGSS |
|  | Dblnk8-L3 | 141 | GSGSGG |
| 43 | Dblnk9-L2 | 142 | SGSSGSSSSGSGSG |
|  | Dblnk9-L3 | 143 | SSGSGG |
| 44 | Dblnk10-L2 | 144 | SGSSGSSSGSGSG |
| 45 | Dblnk11-L1 | 145 | GSGS |
|  | Dblnk11-L2 | 146 | SSGGSSGSSGSGSSGG |
|  | Dblnk11-L3 | 147 | SGGGS |
| 46 | Dblnk12-L2 | 148 | SSSSSGGGGSGGSSSG |
| 47 | Dblnk12-L3 | 149 | SSSGGG |
| 48 | Dblnk13-L1 | 150 | GGGGG |
|  | Dblnk13-L3 | 151 | SGGSGG |
| 49 | Dblnk14-L1 | 152 | GSSG |
|  | Dblnk14-L2 | 153 | SSGSSSGSRSGSSSGGS |
|  | Dblnk14-L3 | 154 | SGGGGG |
| 50 | Dblnk15-L1 | 155 | GGGSG |
|  | Dblnk15-L2 | 156 | GSSSGGSSGSGGGGGGG |
| 51 | Dblnk16-L1 | 157 | SSSGG |
|  | Dblnk16-L2 | 158 | SGGGSSGSGGGRSGS |
| 52 | Dblnk17-L1 | 159 | SGSGGS |
|  | Dblnk17-L2 | 160 | GSGGGGSSGSSGSGGSG |
|  | Dblnk17-L3 | 161 | SSSGSS |
| 53 | Dblnk18-L2 | 162 | GGGGSSGSGSSSRSSGG |
|  | Dblnk18-L3 | 163 | GSGGG |
|  | Dblnk18-L4 | 164 | GGGGS |
|  | CH₂CH₃ (Fc) | 165 | EPKSSDKTHTCPPCPAPELLGGPSVFLFPPKPKDTLMIS RTPEVTCVVVDVSHEDPEVKFNWYVDGVEVHNAKTKPRE EQYNSTYRVVSVLTVLHQDWLNGKEYKCKVSNKALPAPI EKTISKAKGQPREPQVYTLPPSREEMTKNQVSLTCLVKG FYPSDIAVEWESNGQPENNYKTTPPVLDSDGSFFLYSKL TVDKSRWQQGNVFSCSVMHEALHNHYTQKSLSLSPGK |
| 54 | CLDN-VH-General Formula 1 | 166 | EVQLVESGGGLVQPGGSLRLSCAVSGYTFSMNWVRQAPX$_1$ KX$_2$LEWVAWINMYTGEX$_3$TYADDFKGRFTISRDDSKNTL YLQMNSLRAEDTAVYYCARLYNGNSLDYWGX$_4$GTLVTVX$_5$ S (X$_1$ is G or C; X$_2$ is G or C; X$_3$ is P or R; X$_4$ is Q or C; and X$_5$ is S or C) |
|  | CLDN-VL-General Formula 1 | 167 | DIQMTQSPSSLSASVGDRVTITCKSSQSLLNX$_1$GNQKSY LTWYQQKPGKX$_2$PKLLIYWASTLX$_3$SGVPSRFSGSGSGTD YTLTISSLQPEDFATYYCQNAYFFPFTFGX$_4$GTKVEIK (X$_1$ is S or W; X$_2$ is A or C; X$_3$ is E or Q; and X$_4$ is Q or C) |
| 55 | CLDN-VH-General Formula 2 | 168 | EVQLVESGGGLVQPGGSLRLSCAVSGYTFSMNWVRQAPX$_1$ KX$_2$LEWVAWINMYTGEPTYADDFKGRFTISRDDSKNTLY LQMNSLRAEDTAVYYCARLYNGNSLDYWGX$_3$GTLVTVX$_4$S (X$_1$ is G or C; X$_2$ is G or C; X$_3$ is Q or C; and X$_4$ is S or C) |
|  | CLDN-VL-General Formula 2 | 169 | DIQMTQSPSSLSASVGDRVTITCKSSQSLLNSGNQKSYL TWYQQKPGKX$_1$PKLLIYWASTLESGVPSRFSGSGSGTDY TLTISSLQPEDFATYYCQNAYFFPFTFGX$_2$GTKVEIK (X$_1$ is A or C, X$_2$ is Q or C) |
| 56 | PD-L1-VH-General Formula | 170 | EVX$_1$LVESGX$_2$GLVQPGGSLRLSCAASGFTFSRYWMSWVR QAPGKX$_3$LEWVANIKQDGSEKYYVDSVKGRFTISRDNAK NSLYLQMNSLRAEDTAVYYCAREGGWFGELAFDYWGX$_4$G TLVTVSS (X$_1$ Q or C; X$_2$ is G or C; X$_3$ G or C; and X$_4$ G or C) |
|  | PD-L1-VL-General Formula | 171 | EIVLTQSPGTLSLSPGERATLSCRASQRVSSSYLAWYQQ KPGQX$_1$PRLLIYDASSRATGIPDRFSGSGSGTDFTLTIS RLEPEDFAVYYCQQYGSLPWTFGX$_2$GTKVEIK (X$_1$ A or C; X$_2$ is Q or C) |

TABLE 1-continued

| Ab # | Ori ID | SEQ ID | SEQUENCE |
|---|---|---|---|
| 57 | ScDb01 | 172 | DIQMTQSPSSLSASVGDRVTITCKSSQSLLNSGNQKSYL<br>TWYQQKPGKAPKLLIYWASTLESGVPSRFSGSGSGTDYT<br>LTISSLQPEDFATYYCQNAYFFPFTFGQGTKVEIKSGGG<br>GEVQLVESGGGLVQPGGSLRLSCAASGFTFSRYWMSWVR<br>QAPGKGLEWVANIKQDGSEKYYVDSVKGRFTISRDNAKN<br>SLYLQMNSLRAEDTAVYYCAREGGWFGELAFDYWGQGTL<br>VTVSSGGGGSGGGGSGGGGSEIVLTQSPGTLSLSPGERA<br>TLSCRASQRVSSSYLAWYQQKPGQAPRLLIYDASSRATG<br>IPDRFSGSGSGTDFTLTISRLEPEDFAVYYCQQYGSLPW<br>TFGQGTKVEIKSGGGGEVQLVESGGGLVQPGGSLRLSCA<br>VSGYTFSMNWVRQAPGKGLEWVAWINMYTGEPTYADDFK<br>GRFTISRDDSKNTLYLQMNSLRAEDTAVYYCARLYNGNS<br>LDYWGQGTLVTVSSGGGGSEPKSSDKTHTCPPCPAPELL<br>GGPSVFLFPPKPKDTLMISRTPEVTCVVVDVSHEDPEVK<br>FNWYVDGVEVHNAKTKPREEQYNSTYRVVSVLTVLHQDW<br>LNGKEYKCKVSNKALPAPIEKTISKAKGQPREPQVYTLP<br>PSREEMTKNQVSLTCLVKGFYPSDIAVEWESNGQPENNY<br>KTTPPVLDSDGSFFLYSKLTVDKSRWQQGNVFSCSVMHE<br>ALHNHYTQKSLSLSPGK |
| 58 | ScDb02 | 173 | DIQMTQSPSSLSASVGDRVTITCKSSQSLLNSGNQKSYL<br>TWYQQKPGKAPKLLIYWASTLESGVPSRFSGSGSGTDYT<br>LTISSLQPEDFATYYCQNAYFFPFTFGCGTKVEIKSGGG<br>GEVQLVESGGGLVQPGGSLRLSCAASGFITSRYWMSWVR<br>QAPGKCLEWVANIKQDGSEKYYVDSVKGRFTISRDNAKN<br>SLYLQMNSLRAEDTAVYYCAREGGWFGELAFDYWGQGTL<br>VTVSSGGGGSGGGGSGGGGSEIVLTQSPGTLSLSPGERA<br>TLSCRASQRVSSSYLAWYQQKPGQAPRLLIYDASSRATG<br>IPDRFSGSGSGTDFTLTISRLEPEDFAVYYCQQYGSLPW<br>TFGCGTKVEIKSGGGGEVQLVESGGGLVQPGGSLRLSCA<br>VSGYTFSMNWVRQAPGKCLEWVAWINMYTGEPTYADDFK<br>GRFTISRDDSKNTLYLQMNSLRAEDTAVYYCARLYNGNS<br>LDYWGQGTLVTVSSGGGGSEPKSSDKTHTCPPCPAPELL<br>GGPSVFLFPPKPKDTLMISRTPEVTCVVVDVSHEDPEVK<br>FNWYVDGVEVHNAKTKPREEQYNSTYRVVSVLTVLHQDW<br>LNGKEYKCKVSNKALPAPIEKTISKAKGQPREPQVYTLP<br>PSREEMTKNQVSLTCLVKGFYPSDIAVEWESNGQPENNY<br>KTTPPVLDSDGSFFLYSKLTVDKSRWQQGNVESCSVMHE<br>ALHNHYTQKSLSLSPGK |
| 59 | ScDb03 | 174 | DIQMTQSPSSLSASVGDRVTITCKSSQSLLNSGNQKSYL<br>TWYQQKPGKCPKLLIYWASTLESGVPSRFSGSGSGTDYT<br>LTISSLQPEDFATYYCQNAYFFPFTFGQGTKVEIKSGGG<br>GEVQLVESGGGLVQPGGSLRLSCAASGFITSRYWMSWVR<br>QAPGKGLEWVANIKQDGSEKYYVDSVKGRFTISRDNAKN<br>SLYLQMNSLRAEDTAVYYCAREGGWFGELAFDYWGCGTL<br>VTVSSGGGGSGGGGSGGGGSEIVLTQSPGTLSLSPGERA<br>TLSCRASQRVSSSYLAWYQQKPGQCPRLLIYDASSRATG<br>IPDRFSGSGSGTDFTLTISRLEPEDFAVYYCQQYGSLPW<br>TFGQGTKVEIKSGGGGEVQLVESGGGLVQPGGSLRLSCA<br>VSGYTFSMNWVRQAPGKGLEWVAWINMYTGEPTYADDFK<br>GRFTISRDDSKNTLYLQMNSLRAEDTAVYYCARLYNGNS<br>LDYWGCGTLVTVSSGGGGSEPKSSDKTHTCPPCPAPELL<br>GGPSVFLFPPKPKDTLMISRTPEVTCVVVDVSHEDPEVK<br>FNWYVDGVEVHNAKTKPREEQYNSTYRVVSVLTVLHQDW<br>LNGKEYKCKVSNKALPAPIEKTISKAKGQPREPQVYTLP<br>PSREEMTKNQVSLTCLVKGFYPSDIAVEWESNGQPENNY<br>KTTPPVLDSDGSFFLYSKLTVDKSRWQQGNVESCSVMHE<br>ALHNHYTQKSLSLSPGK |
| 60 | ScDb04 | 175 | DIQMTQSPSSLSASVGDRVTITCKSSQSLLNSGNQKSYL<br>TWYQQKPGKAPKLLIYWASTLESGVPSRFSGSGSGTDYT<br>LTISSLQPEDFATYYCQNAYFFPFTFGQGTKVEIKSGGG<br>GEVCLVESGGGLVQPGGSLRLSCAASGFITSRYWMSWVR<br>QAPGKGLEWVANIKQDGSEKYYVDSVKGRFTISRDNAKN<br>SLYLQMNSLRAEDTAVYYCAREGGWFGELAFDYWGQGTL<br>VTVSSGGGGSGGGGSGGGGSEIVLTQSPGTLSLSPGERA<br>TLSCRASQRVSSSYLAWYQQKPGQAPRLLIYDASSRATG<br>IPDRFSGSGSGTDFTLTISRLEPEDFAVYYCQQYGSLPW<br>TFGQGTKVEIKSGGGGEVQLVESGGGLVQPGGSLRLSCA<br>VSGYTFSMNWVRQAPCKGLEWVAWINMYTGEPTYADDFK<br>GRFTISRDDSKNTLYLQMNSLRAEDTAVYYCARLYNGNS<br>LDYWGQGTLVTVSSGGGGSEPKSSDKTHTCPPCPAPELL<br>GGPSVFLFPPKPKDTLMISRTPEVTCVVVDVSHEDPEVK<br>FNWYVDGVEVHNAKTKPREEQYNSTYRVVSVLTVLHQDW<br>LNGKEYKCKVSNKALPAPIEKTISKAKGQPREPQVYTLP |

TABLE 1-continued

| Ab # | Ori ID | SEQ ID | Sequence |
|---|---|---|---|
| | | | PSREEMTKNQVSLTCLVKGFYPSDIAVEWESNGQPENNY<br>KTTPPVLDSDGSFFLYSKLTVDKSRWQQGNVESCSVMHE<br>ALHNHYTQKSLSLSPGK |
| 61 | ScDb05 | 176 | DIQMTQSPSSLSASVGDRVTITCKSSQSLLNSGNQKSYL<br>TWYQQKPGKAPKLLIYWASTLESGVPSRFSGSGSGTDYT<br>LTISSLQPEDFATYYCQNAYFFPFTFGQGTKVEIKSGGG<br>GEVQLVESGCGLVQPGGSLRLSCAASGFITSRYWMSWVR<br>QAPGKGLEWVANIKQDGSEKYYVDSVKGRFTISRDNAKN<br>SLYLQMNSLRAEDTAVYYCAREGGWFGELAFDYWGQGTL<br>VTVSSGGGGSGGGGSGGGGSEIVLTQSPGTLSLSPGERA<br>TLSCRASQRVSSSYLAWYQQKPGQAPRLLIYDASSRATG<br>IPDRFSGSGSGTDFTLTISRLEPEDFAVYYCQQYGSLPW<br>TFGQGTKVEIKSGGGGEVQLVESGGGLVQPGGSLRLSCA<br>VSGYTFSMNWVRQAPGKGLEWVAWINMYTGEPTYADDFK<br>GRFTISRDDSKNTLYLQMNSLRAEDTAVYYCARLYNGNS<br>LDYWGQGTLVTVCSGGGGSEPKSSDKTHTCPPCPAPELL<br>GGPSVFLFPPKPKDTLMISRTPEVTCVVVDVSHEDPEVK<br>FNWYVDGVEVHNAKTKPREEQYNSTYRVVSVLTVLHQDW<br>LNGKEYKCKVSNKALPAPIEKTISKAKGQPREPQVYTLP<br>PSREEMTKNQVSLTCLVKGFYPSDIAVEWESNGQPENNY<br>KTTPPVLDSDGSFFLYSKLTVDKSRWQQGNVESCSVMHE<br>ALHNHYTQKSLSLSPGK |
| 62 | ScDb06 | 177 | DIQMTQSPSSLSASVGDRVTITCKSSQSLLNSGNQKSYL<br>TWYQQKPGKAPKLLIYWASTLESGVPSRFSGSGSGTDYT<br>LTISSLQPEDFATYYCQNAYFFPFTFGCGTKVEIKSGGG<br>GEVQLVESGGGLVQPGGSLRLSCAASGFTFSRYWMSWVR<br>QAPGKCLEWVANIKQDGSEKYYVDSVKGRFTISRDNAKN<br>SLYLQMNSLRAEDTAVYYCAREGGWFGELAFDYWGQGTL<br>VTVSSGGGGSGGGGSGGGGSGGGGSEIVLTQSPGTLSLS<br>PGERATLSCRASQRVSSSYLAWYQQKPGQAPRLLIYDAS<br>SRATGIPDRFSGSGSGTDFTLTISRLEPEDFAVYYCQQY<br>GSLPWTFGCGTKVEIKSGGGGEVQLVESGGGLVQPGGSL<br>RLSCAVSGYTFSMNWVRQAPGKCLEWVAWINMYTGEPTY<br>ADDFKGRFTISRDDSKNTLYLQMNSLRAEDTAVYYCARL<br>YNGNSLDYWGQGTLVTVSSGGGGSEPKSSDKTHTCPPCP<br>APELLGGPSVFLFPPKPKDTLMISRTPEVTCVVVDVSHE<br>DPEVKFNWYVDGVEVHNAKTKPREEQYNSTYRVVSVLTV<br>LHQDWLNGKEYKCKVSNKALPAPIEKTISKAKGQPREPQ<br>VYTLPPSREEMTKNQVSLTCLVKGFYPSDIAVEWESNGQ<br>PENNYKTTPPVLDSDGSFFLYSKLTVDKSRWQQGNVFSC<br>SVMHEALHNHYTQKSLSLSPGK |
| 63 | ScDb07 | 178 | DIQMTQSPSSLSASVGDRVTITCKSSQSLLNWGNQKSYL<br>TWYQQKPGKAPKLLIYWASTLQSGVPSRFSGSGSGTDYT<br>LTISSLQPEDFATYYCQNAYFFPFTFGQGTKVEIKSGGG<br>GEVQLVESGGGLVQPGGSLRLSCAASGFTFSRYWMSWVR<br>QAPGKGLEWVANIKQDGSEKYYVDSVKGRFTISRDNAKN<br>SLYLQMNSLRAEDTAVYYCAREGGWFGELAFDYWGQGTL<br>VTVSSGGGGSGGGGSGGGGSEIVLTQSPGTLSLSPGERA<br>TLSCRASQRVSSSYLAWYQQKPGQAPRLLIYDASSRATG<br>IPDRFSGSGSGTDFTLTISRLEPEDFAVYYCQQYGSLPW<br>TFGQGTKVEIKSGGGGEVQLVESGGGLVQPGGSLRLSCA<br>VSGYTFSMNWVRQAPGKGLEWVAWINMYTGERTYADDFK<br>GRFTISRDDSKNTLYLQMNSLRAEDTAVYYCARLYNGNS<br>LDYWGQGTLVTVSSGGGGSEPKSSDKTHTCPPCPAPELL<br>GGPSVFLFPPKPKDTLMISRTPEVTCVVVDVSHEDPEVK<br>FNWYVDGVEVHNAKTKPREEQYNSTYRVVSVLTVLHQDW<br>LNGKEYKCKVSNKALPAPIEKTISKAKGQPREPQVYTLP<br>PSREEMTKNQVSLTCLVKGFYPSDIAVEWESNGQPENNY<br>KTTPPVLDSDGSFFLYSKLTVDKSRWQQGNVESCSVMHE<br>ALHNHYTQKSLSLSPGK |
| 64 | ScDb08 | 179 | DIQMTQSPSSLSASVGDRVTITCKSSQSLLNSGNQKSYL<br>TWYQQKPGKAPKLLIYWASTLESGVPSRFSGSGSGTDYT<br>LTISSLQPEDFATYYCQNAYFFPFTFGQGTKVEIKSSR<br>SSEVQLVESGGGLVQPGGSLRLSCAASGFTFSRYWMSWV<br>RQAPGKGLEWVANIKQDGSEKYYVDSVKGRFTISRDNAK<br>NSLYLQMNSLRAEDTAVYYCAREGGWFGELAFDYWGQGT<br>LVTVSSGSGSSSSSRSSSGSGGGEIVLTQSPGTLSLSPG<br>ERATLSCRASQRVSSSYLAWYQQKPGQAPRLLIYDASSR<br>ATGIPDRFSGSGSGTDFTLTISRLEPEDFAVYYCQQYGS<br>LPWTFGQGTKVEIKSGGRGGEVQLVESGGGLVQPGGSLR<br>LSCAVSGYTFSMNWVRQAPGKGLEWVAWINMYTGEPTYA<br>DDFKGRFTISRDDSKNTLYLQMNSLRAEDTAVYYCARLY |

TABLE 1-continued

| Ab # | Ori ID | SEQ ID | SEQUENCE |
|---|---|---|---|
| | | | NGNSLDYWGQGTLVTVSSGGGGSEPKSSDKTHTCPPCPA<br>PELLGGPSVFLFPPKPKDTLMISRTPEVTCVVVDVSHED<br>PEVKFNWYVDGVEVHNAKTKPREEQYNSTYRVVSVLTVL<br>HQDWLNGKEYKCKVSNKALPAPIEKTISKAKGQPREPQV<br>YTLPPSREEMTKNQVSLTCLVKGFYPSDIAVEWESNGQP<br>ENNYKTTPPVLDSDGSFFLYSKLTVDKSRWQQGNVFSCS<br>VMHEALHNHYTQKSLSLSPGK |
| 65 | ScDb09 | 180 | DIQMTQSPSSLSASVGDRVTITCKSSQSLLNWGNQKSYL<br>TWYQQKPGKAPKLLIYWASTLQSGVPSRFSGSGSGTDYT<br>LTISSLQPEDFATYYCQNAYFFPFTFGQGTKVEIKGSSR<br>SSEVQLVESGGGLVQPGGSLRLSCAASGFTFSRYWMSWV<br>RQAPGKGLEWVANIKQDGSEKYYVDSVKGRFTISRDNAK<br>NSLYLQMNSLRAEDTAVYYCAREGGWFGELAFDYWGQGT<br>LVTVSSGSGSSSSRSSSGSGGGEIVLTQSPGTLSLSPG<br>ERATLSCRASQRVSSSYLAWYQQKPGQAPRLLIYDASSR<br>ATGIPDRFSGSGSGTDFTLTISRLEPEDFAVYYCQQYGS<br>LPWTFGQGTKVEIKSGGRGGEVQLVESGGGLVQPGGSLR<br>LSCAVSGYTFSMNWVRQAPGKGLEWVAWINMYTGERTYA<br>DDFKGRFTISRDDSKNTLYLQMNSLRAEDTAVYYCARLY<br>NGNSLDYWGQGTLVTVSSGGGGSEPKSSDKTHTCPPCPA<br>PELLGGPSVFLFPPKPKDTLMISRTPEVTCVVVDVSHED<br>PEVKFNWYVDGVEVHNAKTKPREEQYNSTYRVVSVLTVL<br>HQDWLNGKEYKCKVSNKALPAPIEKTISKAKGQPREPQV<br>YTLPPSREEMTKNQVSLTCLVKGFYPSDIAVEWESNGQP<br>ENNYKTTPPVLDSDGSFFLYSKLTVDKSRWQQGNVFSCS<br>VMHEALHNHYTQKSLSLSPGK |
| 66 | Dblnk1 | 181 | DIQMTQSPSSLSASVGDRVTITCKSSQSLLNSGNQKSYL<br>TWYQQKPGKAPKLLIYWASTLESGVPSRFSGSGSGTDYT<br>LTISSLQPEDFATYYCQNAYFFPFTFGQGTKVEIKSGGG<br>GEVQLVESGGGLVQPGGSLRLSCAASGFTFSRYWMSWVR<br>QAPGKGLEWVANIKQDGSEKYYVDSVKGRFTISRDNAKN<br>SLYLQMNSLRAEDTAVYYCAREGGWFGELAFDYWGQGTL<br>VTVSSGSGSSSRGGSGSSSEIVLTQSPGTLSLSPGERA<br>TLSCRASQRVSSSYLAWYQQKPGQAPRLLIYDASSRATG<br>IPDRFSGSGSGTDFTLTISRLEPEDFAVYYCQQYGSLPW<br>TFGQGTKVEIKSGGGGEVQLVESGGGLVQPGGSLRLSCA<br>VSGYTFSMNWVRQAPGKGLEWVAWINMYTGEPTYADDFK<br>GRFTISRDDSKNTLYLQMNSLRAEDTAVYYCARLYNGNS<br>LDYWGQGTLVTVSSGGGGSEPKSSDKTHTCPPCPAPELL<br>GGPSVFLFPPKPKDTLMISRTPEVTCVVVDVSHEDPEVK<br>FNWYVDGVEVHNAKTKPREEQYNSTYRVVSVLTVLHQDW<br>LNGKEYKCKVSNKALPAPIEKTISKAKGQPREPQVYTLP<br>PSREEMTKNQVSLTCLVKGFYPSDIAVEWESNGQPENNY<br>KTTPPVLDSDGSFFLYSKLTVDKSRWQQGNVFSCSVMHE<br>ALHNHYTQKSLSLSPGK |
| 67 | Dblnk2 | 182 | DIQMTQSPSSLSASVGDRVTITCKSSQSLLNSGNQKSYL<br>TWYQQKPGKAPKLLIYWASTLESGVPSRFSGSGSGTDYT<br>LTISSLQPEDFATYYCQNAYFFPFTFGQGTKVEIKSGGG<br>GEVQLVESGGGLVQPGGSLRLSCAASGFTFSRYWMSWVR<br>QAPGKGLEWVANIKQDGSEKYYVDSVKGRFTISRDNAKN<br>SLYLQMNSLRAEDTAVYYCAREGGWFGELAFDYWGQGTL<br>VTVSSSSSGSGGGGSGGGGGEIVLTQSPGTLSLSPGER<br>ATLSCRASQRVSSSYLAWYQQKPGQAPRLLIYDASSRAT<br>GIPDRFSGSGSGTDFTLTISRLEPEDFAVYYCQQYGSLP<br>WTFGQGTKVEIKSSGSEVQLVESGGGLVQPGGSLRLSC<br>AVSGYTFSMNWVRQAPGKGLEWVAWINMYTGEPTYADDF<br>KGRFTISRDDSKNTLYLQMNSLRAEDTAVYYCARLYNGN<br>SLDYWGQGTLVTVSSGGGGSEPKSSDKTHTCPPCPAPEL<br>LGGPSVFLFPPKPKDTLMISRTPEVTCVVVDVSHEDPEV<br>KFNWYVDGVEVHNAKTKPREEQYNSTYRVVSVLTVLHQD<br>WLNGKEYKCKVSNKALPAPIEKTISKAKGQPREPQVYTL<br>PPSREEMTKNQVSLTCLVKGFYPSDIAVEWESNGQPENN<br>YKTTPPVLDSDGSFFLYSKLTVDKSRWQQGNVFSCSVMH<br>EALHNHYTQKSLSLSPGK |
| 68 | Dblnk3 | 183 | DIQMTQSPSSLSASVGDRVTITCKSSQSLLNSGNQKSYL<br>TWYQQKPGKAPKLLIYWASTLESGVPSRFSGSGSGTDYT<br>LTISSLQPEDFATYYCQNAYFFPFTFGQGTKVEIKSGGG<br>GEVQLVESGGGLVQPGGSLRLSCAASGFTFSRYWMSWVR<br>QAPGKGLEWVANIKQDGSEKYYVDSVKGRFTISRDNAKN<br>SLYLQMNSLRAEDTAVYYCAREGGWFGELAFDYWGQGTL<br>VTVSSGGGGSGSGSSGSSSEIVLTQSPGTLSLSPGERA<br>TLSCRASQRVSSSYLAWYQQKPGQAPRLLIYDASSRATG |

TABLE 1-continued

| Ab # | Ori ID | SEQ ID | SEQUENCE |
|---|---|---|---|
| | | | IPDRFSGSGSGTDFTLTISRLEPEDFAVYYCQQYGSLPW TFGQGTKVEIKSGGGGEVQLVESGGGLVQPGGSLRLSCA VSGYTFSMNWVRQAPGKGLEWVAWINMYTGEPTYADDFK GRFTISRDDSKNTLYLQMNSLRAEDTAVYYCARLYNGNS LDYWGQGTLVTVSSGGGGSEPKSSDKTHTCPPCPAPELL GGPSVFLFPPKPKDTLMISRTPEVTCVVVDVSHEDPEVK FNWYVDGVEVHNAKTKPREEQYNSTYRVVSVLTVLHQDW LNGKEYKCKVSNKALPAPIEKTISKAKGQPREPQVYTLP PSREEMTKNQVSLTCLVKGFYPSDIAVEWESNGQPENNY KTTPPVLDSDGSFFLYSKLTVDKSRWQQGNVFSCSVMHE ALHNHYTQKSLSLSPGK |
| 69 | Dblnk4 | 184 | DIQMTQSPSSLSASVGDRVTITCKSSQSLLNSGNQKSYL TWYQQKPGKAPKLLIYWASTLESGVPSRFSGSGSGTDYT LTISSLQPEDFATYYCQNAYFFPFTFGQGTKVEIKGGGG SGEVQLVESGGGLVQPGGSLRLSCAASGFTFSRYWMSWV RQAPGKGLEWVANIKQDGSEKYYVDSVKGRFTISRDNAK NSLYLQMNSLRAEDTAVYYCAREGGWFGELAFDYWGQGT LVTVSSGSSSGGGSGGSSSSSSEIVLTQSPGTLSLSPGE RATLSCRASQRVSSSYLAWYQQKPGQAPRLLIYDASSRA TGIPDRFSGSGSGTDFTLTISRLEPEDFAVYYCQQYGSL PWTFGQGTKVEIKSGGSEVQLVESGGGLVQPGGSLRLSC AVSGYTFSMNWVRQAPGKGLEWVAWINMYTGEPTYADDF KGRFTISRDDSKNTLYLQMNSLRAEDTAVYYCARLYNGN SLDYWGQGTLVTVSSGGGGSEPKSSDKTHTCPPCPAPEL LGGPSVFLFPPKPKDTLMISRTPEVTCVVVDVSHEDPEV KFNWYVDGVEVHNAKTKPREEQYNSTYRVVSVLTVLHQD WLNGKEYKCKVSNKALPAPIEKTISKAKGQPREPQVYTL PPSREEMTKNQVSLTCLVKGFYPSDIAVEWESNGQPENN YKTTPPVLDSDGSFFLYSKLTVDKSRWQQGNVFSCSVMH EALHNHYTQKSLSLSPGK |
| 70 | Dblnk5 | 185 | DIQMTQSPSSLSASVGDRVTITCKSSQSLLNSGNQKSYL TWYQQKPGKAPKLLIYWASTLESGVPSRFSGSGSGTDYT LTISSLQPEDFATYYCQNAYFFPFTFGQGTKVEIKGGGS EVQLVESGGGLVQPGGSLRLSCAASGFTFSRYWMSWVRQ APGKGLEWVANIKQDGSEKYYVDSVKGRFTISRDNAKNS LYLQMNSLRAEDTAVYYCAREGGWFGELAFDYWGQGTLV TVSSSGSGGGGSSSGSSSGGEIVLTQSPGTLSLSPGERAT LSCRASQRVSSSYLAWYQQKPGQAPRLLIYDASSRATGI PDRFSGSGSGTDFTLTISRLEPEDFAVYYCQQYGSLPWT FGQGTKVEIKSGGRGGEVQLVESGGGLVQPGGSLRLSCA VSGYTFSMNWVRQAPGKGLEWVAWINMYTGEPTYADDFK GRFTISRDDSKNTLYLQMNSLRAEDTAVYYCARLYNGNS LDYWGQGTLVTVSSGGGGSEPKSSDKTHTCPPCPAPELL GGPSVFLFPPKPKDTLMISRTPEVTCVVVDVSHEDPEVK FNWYVDGVEVHNAKTKPREEQYNSTYRVVSVLTVLHQDW LNGKEYKCKVSNKALPAPIEKTISKAKGQPREPQVYTLP PSREEMTKNQVSLTCLVKGFYPSDIAVEWESNGQPENNY KTTPPVLDSDGSFFLYSKLTVDKSRWQQGNVFSCSVMHE ALHNHYTQKSLSLSPGK |
| 71 | Dblnk6 | 186 | DIQMTQSPSSLSASVGDRVTITCKSSQSLLNSGNQKSYL TWYQQKPGKAPKLLIYWASTLESGVPSRFSGSGSGTDYT LTISSLQPEDFATYYCQNAYFFPFTFGQGTKVEIKGGGS EVQLVESGGGLVQPGGSLRLSCAASGFTFSRYWMSWVRQ APGKGLEWVANIKQDGSEKYYVDSVKGRFTISRDNAKNS LYLQMNSLRAEDTAVYYCAREGGWFGELAFDYWGQGTLV TVSSSGGRSGSGSGSNGGGEIVLTQSPGTLSLSPGERAT LSCRASQRVSSSYLAWYQQKPGQAPRLLIYDASSRATGI PDRFSGSGSGTDFTLTISRLEPEDFAVYYCQQYGSLPWT FGQGTKVEIKGGSGGGEVQLVESGGGLVQPGGSLRLSCA VSGYTFSMNWVRQAPGKGLEWVAWINMYTGEPTYADDFK GRFTISRDDSKNTLYLQMNSLRAEDTAVYYCARLYNGNS LDYWGQGTLVTVSSGGGGSEPKSSDKTHTCPPCPAPELL GGPSVFLFPPKPKDTLMISRTPEVTCVVVDVSHEDPEVK FNWYVDGVEVHNAKTKPREEQYNSTYRVVSVLTVLHQDW LNGKEYKCKVSNKALPAPIEKTISKAKGQPREPQVYTLP PSREEMTKNQVSLTCLVKGFYPSDIAVEWESNGQPENNY KTTPPVLDSDGSFFLYSKLTVDKSRWQQGNVFSCSVMHE ALHNHYTQKSLSLSPGK |
| 72 | Dblnk7 | 187 | DIQMTQSPSSLSASVGDRVTITCKSSQSLLNSGNQKSYL TWYQQKPGKAPKLLIYWASTLESGVPSRFSGSGSGTDYT LTISSLQPEDFATYYCQNAYFFPFTFGQGTKVEIKGGGS EVQLVESGGGLVQPGGSLRLSCAASGFTFSRYWMSWVRQ |

TABLE 1-continued

| Ab # | Ori ID | SEQ ID | SEQUENCE |
|---|---|---|---|
| | | | APGKGLEWVANIKQDGSEKYYVDSVKGRFTISRDNAKNS LYLQMNSLRAEDTAVYYCAREGGWFGELAFDYWGQGTLV TVSSGSSGRGSSGGSGGSSGEIVLTQSPGTLSLSPGERA TLSCRASQRVSSSYLAWYQQKPGQAPRLLIYDASSRATG IPDRFSGSGSGTDFTLTISRLEPEDFAVYYCQQYGSLPW TFGQGTKVEIKGGSEVQLVESGGGLVQPGGSLRLSCAV SGYTFSMNWVRQAPGKGLEWVAWINMYTGEPTYADDFKG RFTISRDDSKNTLYLQMNSLRAEDTAVYYCARLYNGNSL DYWGQGTLVTVSSGGGGSEPKSSDKTHTCPPCPAPELLG GPSVFLFPPKPKDTLMISRTPEVTCVVVDVSHEDPEVKF NWYVDGVEVHNAKTKPREEQYNSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK |
| 73 | Dblnk8 | 188 | DIQMTQSPSSLSASVGDRVTITCKSSQSLLNSGNQKSYL TWYQQKPGKAPKLLIYWASTLESGVPSRFSGSGSGTDYT LTISSLQPEDFATYYCQNAYFFPFTFGQGTKVEIKGGGS SEVQLVESGGGLVQPGGSLRLSCAASGFTFSRYWMSWVR QAPGKGLEWVANIKQDGSEKYYVDSVKGRFTISRDNAKN SLYLQMNSLRAEDTAVYYCAREGGWFGELAFDYWGQGTL VTVSSGGGGSGGGGSGGGGSEIVLTQSPGTLSLSPGERA TLSCRASQRVSSSYLAWYQQKPGQAPRLLIYDASSRATG IPDRFSGSGSGTDFTLTISRLEPEDFAVYYCQQYGSLPW TFGQGTKVEIKGSGSGGEVQLVESGGGLVQPGGSLRLSC AVSGYTFSMNWVRQAPGKGLEWVAWINMYTGEPTYADDF KGRFTISRDDSKNTLYLQMNSLRAEDTAVYYCARLYNGN SLDYWGQGTLVTVSSGGGGSEPKSSDKTHTCPPCPAPEL LGGPSVFLFPPKPKDTLMISRTPEVTCVVVDVSHEDPEV KFNWYVDGVEVHNAKTKPREEQYNSTYRVVSVLTVLHQD WLNGKEYKCKVSNKALPAPIEKTISKAKGQPREPQVYTL PPSREEMTKNQVSLTCLVKGFYPSDIAVEWESNGQPENN YKTTPPVLDSDGSFFLYSKLTVDKSRWQQGNVFSCSVMH EALHNHYTQKSLSLSPGK |
| 74 | Dblnk9 | 189 | DIQMTQSPSSLSASVGDRVTITCKSSQSLLNSGNQKSYL TWYQQKPGKAPKLLIYWASTLESGVPSRFSGSGSGTDYT LTISSLQPEDFATYYCQNAYFFPFTFGQGTKVEIKGSSR SSEVQLVESGGGLVQPGGSLRLSCAASGFTFSRYWMSWV RQAPGKGLEWVANIKQDGSEKYYVDSVKGRFTISRDNAK NSLYLQMNSLRAEDTAVYYCAREGGWFGELAFDYWGQGT LVTVSSGSSGSSSSSGSGSGEIVLTQSPGTLSLSPGER ATLSCRASQRVSSSYLAWYQQKPGQAPRLLIYDASSRAT GIPDRFSGSGSGTDFTLTISRLEPEDFAVYYCQQYGSLP WTFGQGTKVEIKSSGSGGEVQLVESGGGLVQPGGSLRLS CAVSGYTFSMNWVRQAPGKGLEWVAWINMYTGEPTYADD FKGRFTISRDDSKNTLYLQMNSLRAEDTAVYYCARLYNG NSLDYWGQGTLVTVSSGGGGSEPKSSDKTHTCPPCPAPE LLGGPSVFLFPPKPKDTLMISRTPEVTCVVVDVSHEDPE VKFNWYVDGVEVHNAKTKPREEQYNSTYRVVSVLTVLHQ DWLNGKEYKCKVSNKALPAPIEKTISKAKGQPREPQVYT LPPSREEMTKNQVSLTCLVKGFYPSDIAVEWESNGQPEN NYKTTPPVLDSDGSFFLYSKLTVDKSRWQQGNVFSCSVM HEALHNHYTQKSLSLSPGK |
| 75 | Dblnk10 | 190 | DIQMTQSPSSLSASVGDRVTITCKSSQSLLNSGNQKSYL TWYQQKPGKAPKLLIYWASTLESGVPSRFSGSGSGTDYT LTISSLQPEDFATYYCQNAYFFPFTFGQGTKVEIKGSSR SSEVQLVESGGGLVQPGGSLRLSCAASGFTFSRYWMSWV RQAPGKGLEWVANIKQDGSEKYYVDSVKGRFTISRDNAK NSLYLQMNSLRAEDTAVYYCAREGGWFGELAFDYWGQGT LVTVSSSGSSGSSSSSGSGSGEIVLTQSPGTLSLSPGER ATLSCRASQRVSSSYLAWYQQKPGQAPRLLIYDASSRAT GIPDRFSGSGSGTDFTLTISRLEPEDFAVYYCQQYGSLP WTFGQGTKVEIKSSGSGGEVQLVESGGGLVQPGGSLRLS CAVSGYTFSMNWVRQAPGKGLEWVAWINMYTGEPTYADD FKGRFTISRDDSKNTLYLQMNSLRAEDTAVYYCARLYNG NSLDYWGQGTLVTVSSGGGGSEPKSSDKTHTCPPCPAPE LLGGPSVFLFPPKPKDTLMISRTPEVTCVVVDVSHEDPE VKFNWYVDGVEVHNAKTKPREEQYNSTYRVVSVLTVLHQ DWLNGKEYKCKVSNKALPAPIEKTISKAKGQPREPQVYT LPPSREEMTKNQVSLTCLVKGFYPSDIAVEWESNGQPEN NYKTTPPVLDSDGSFFLYSKLTVDKSRWQQGNVFSCSVM HEALHNHYTQKSLSLSPGK |

TABLE 1-continued

| Ab # | Ori ID | SEQ ID | SEQUENCE |
|---|---|---|---|
| 76 | Dblnk11 | 191 | DIQMTQSPSSLSASVGDRVTITCKSSQSLLNSGNQKSYL<br>TWYQQKPGKAPKLLIYWASTLESGVPSRFSGSGSGTDYT<br>LTISSLQPEDFATYYCQNAYFFPFTFGQGTKVEIKGSGS<br>EVQLVESGGGLVQPGGSLRLSCAASGFTFSRYWMSWVRQ<br>APGKGLEWVANIKQDGSEKYYVDSVKGRFTISRDNAKNS<br>LYLQMNSLRAEDTAVYYCAREGGWFGELAFDYWGQGTLV<br>TVSSSSGGSSGSSGSGSSGGEIVLTQSPGTLSLSPGERA<br>TLSCRASQRVSSSYLAWYQQKPGQAPRLLIYDASSRATG<br>IPDRFSGSGSGTDFTLTISRLEPEDFAVYYCQQYGSLPW<br>TFGQGTKVEIKSGGGSEVQLVESGGGLVQPGGSLRLSCA<br>VSGYTFSMNWVRQAPGKGLEWVAWINMYTGEPTYADDFK<br>GRFTISRDDSKNTLYLQMNSLRAEDTAVYYCARLYNGNS<br>LDYWGQGTLVTVSSGGGGSEPKSSDKTHTCPPCPAPELL<br>GGPSVFLFPPKPKDTLMISRTPEVTCVVVDVSHEDPEVK<br>FNWYVDGVEVHNAKTKPREEQYNSTYRVVSVLTVLHQDW<br>LNGKEYKCKVSNKALPAPIEKTISKAKGQPREPQVYTLP<br>PSREEMTKNQVSLTCLVKGFYPSDIAVEWESNGQPENNY<br>KTTPPVLDSDGSFFLYSKLTVDKSRWQQGNVFSCSVMHE<br>ALHNHYTQKSLSLSPGK |
| 77 | Dblnk12 | 192 | DIQMTQSPSSLSASVGDRVTITCKSSQSLLNSGNQKSYL<br>TWYQQKPGKAPKLLIYWASTLESGVPSRFSGSGSGTDYT<br>LTISSLQPEDFATYYCQNAYFFPFTFGQGTKVEIKGSGS<br>EVQLVESGGGLVQPGGSLRLSCAASGFTFSRYWMSWVRQ<br>APGKGLEWVANIKQDGSEKYYVDSVKGRFTISRDNAKNS<br>LYLQMNSLRAEDTAVYYCAREGGWFGELAFDYWGQGTLV<br>TVSSSSSSGGGGSGGSSSGEIVLTQSPGTLSLSPGERA<br>TLSCRASQRVSSSYLAWYQQKPGQAPRLLIYDASSRATG<br>IPDRFSGSGSGTDFTLTISRLEPEDFAVYYCQQYGSLPW<br>TFGQGTKVEIKSSSGGGEVQLVESGGGLVQPGGSLRLSC<br>AVSGYTFSMNWVRQAPGKGLEWVAWINMYTGEPTYADDF<br>KGRFTISRDDSKNTLYLQMNSLRAEDTAVYYCARLYNGN<br>SLDYWGQGTLVTVSSGGGGSEPKSSDKTHTCPPCPAPEL<br>LGGPSVFLFPPKPKDTLMISRTPEVTCVVVDVSHEDPEV<br>KFNWYVDGVEVHNAKTKPREEQYNSTYRVVSVLTVLHQD<br>WLNGKEYKCKVSNKALPAPIEKTISKAKGQPREPQVYTL<br>PPSREEMTKNQVSLTCLVKGFYPSDIAVEWESNGQPENN<br>YKTTPPVLDSDGSFFLYSKLTVDKSRWQQGNVFSCSVMH<br>EALHNHYTQKSLSLSPGK |
| 78 | Dblnk13 | 193 | DIQMTQSPSSLSASVGDRVTITCKSSQSLLNSGNQKSYL<br>TWYQQKPGKAPKLLIYWASTLESGVPSRFSGSGSGTDYT<br>LTISSLQPEDFATYYCQNAYFFPFTFGQGTKVEIKGGGG<br>GEVQLVESGGGLVQPGGSLRLSCAASGFTFSRYWMSWVR<br>QAPGKGLEWVANIKQDGSEKYYVDSVKGRFTISRDNAKN<br>SLYLQMNSLRAEDTAVYYCAREGGWFGELAFDYWGQGTL<br>VTVSSGSGSSSSRSSSGSGGGEIVLTQSPGTLSLSPGE<br>RATLSCRASQRVSSSYLAWYQQKPGQAPRLLIYDASSRA<br>TGIPDRFSGSGSGTDFTLTISRLEPEDFAVYYCQQYGSL<br>PWTFGQGTKVEIKSGGSGGEVQLVESGGGLVQPGGSLRL<br>SCAVSGYTFSMNWVRQAPGKGLEWVAWINMYTGEPTYAD<br>DFKGRFTISRDDSKNTLYLQMNSLRAEDTAVYYCARLYN<br>GNSLDYWGQGTLVTVSSGGGGSEPKSSDKTHTCPPCPAP<br>ELLGGPSVFLFPPKPKDTLMISRTPEVTCVVVDVSHEDP<br>EVKFNWYVDGVEVHNAKTKPREEQYNSTYRVVSVLTVLH<br>QDWLNGKEYKCKVSNKALPAPIEKTISKAKGQPREPQVY<br>TLPPSREEMTKNQVSLTCLVKGFYPSDIAVEWESNGQPE<br>NNYKTTPPVLDSDGSFFLYSKLTVDKSRWQQGNVFSCSV<br>MHEALHNHYTQKSLSLSPGK |
| 79 | Dblnk14 | 194 | DIQMTQSPSSLSASVGDRVTITCKSSQSLLNSGNQKSYL<br>TWYQQKPGKAPKLLIYWASTLESGVPSRFSGSGSGTDYT<br>LTISSLQPEDFATYYCQNAYFFPFTFGQGTKVEIKGSSG<br>EVQLVESGGGLVQPGGSLRLSCAASGFTFSRYWMSWVRQ<br>APGKGLEWVANIKQDGSEKYYVDSVKGRFTISRDNAKNS<br>LYLQMNSLRAEDTAVYYCAREGGWFGELAFDYWGQGTLV<br>TVSSSSGSSSGSRSGSSSGGSEIVLTQSPGTLSLSPGER<br>ATLSCRASQRVSSSYLAWYQQKPGQAPRLLIYDASSRAT<br>GIPDRFSGSGSGTDFTLTISRLEPEDFAVYYCQQYGSLP<br>WTFGQGTKVEIKSGGGGGEVQLVESGGGLVQPGGSLRLS<br>CAVSGYTFSMNWVRQAPGKGLEWVAWINMYTGEPTYADD<br>FKGRFTISRDDSKNTLYLQMNSLRAEDTAVYYCARLYNG<br>NSLDYWGQGTLVTVSSGGGGSEPKSSDKTHTCPPCPAPE<br>LLGGPSVFLFPPKPKDTLMISRTPEVTCVVVDVSHEDPE<br>VKFNWYVDGVEVHNAKTKPREEQYNSTYRVVSVLTVLHQ<br>DWLNGKEYKCKVSNKALPAPIEKTISKAKGQPREPQVYT |

TABLE 1-continued

| Ab # | Ori ID | SEQ ID | SEQUENCE |
|---|---|---|---|
| | | | LPPSREEMTKNQVSLTCLVKGFYPSDIAVEWESNGQPEN
NYKTTPPVLDSDGSFFLYSKLTVDKSRWQQGNVFSCSVM
HEALHNHYTQKSLSLSPGK |
| 80 | Dblnk15 | 195 | DIQMTQSPSSLSASVGDRVTITCKSSQSLLNSGNQKSYL
TWYQQKPGKAPKLLIYWASTLESGVPSRFSGSGSGTDYT
LTISSLQPEDFATYYCQNAYFFPFTFGQGTKVEIKGGGS
GEVQLVESGGGLVQPGGSLRLSCAASGFTFSRYWMSWVR
QAPGKGLEWVANIKQDGSEKYYVDSVKGRFTISRDNAKN
SLYLQMNSLRAEDTAVYYCAREGGWFGELAFDYWGQGTL
VTVSSGSSSGGSSGSGGGGGGGEIVLTQSPGTLSLSPGE
RATLSCRASQRVSSSYLAWYQQKPGQAPRLLIYDASSRA
TGIPDRFSGSGSGTDFTLTISRLEPEDFAVYYCQQYGSL
PWTFGQGTKVEIKSGGSEVQLVESGGGLVQPGGSLRLSC
AVSGYTFSMNWVRQAPGKGLEWVAWINMYTGEPTYADDF
KGRFTISRDDSKNTLYLQMNSLRAEDTAVYYCARLYNGN
SLDYWGQGTLVTVSSGGGGSEPKSSDKTHTCPPCPAPEL
LGGPSVFLFPPKPKDTLMISRTPEVTCVVVDVSHEDPEV
KFNWYVDGVEVHNAKTKPREEQYNSTYRVVSVLTVLHQD
WLNGKEYKCKVSNKALPAPIEKTISKAKGQPREPQVYTL
PPSREEMTKNQVSLTCLVKGFYPSDIAVEWESNGQPENN
YKTTPPVLDSDGSFFLYSKLTVDKSRWQQGNVFSCSVMH
EALHNHYTQKSLSLSPGK |
| 81 | Dblnk16 | 196 | DIQMTQSPSSLSASVGDRVTITCKSSQSLLNSGNQKSYL
TWYQQKPGKAPKLLIYWASTLESGVPSRFSGSGSGTDYT
LTISSLQPEDFATYYCQNAYFFPFTFGQGTKVEIKSSSG
GEVQLVESGGGLVQPGGSLRLSCAASGFTFSRYWMSWVR
QAPGKGLEWVANIKQDGSEKYYVDSVKGRFTISRDNAKN
SLYLQMNSLRAEDTAVYYCAREGGWFGELAFDYWGQGTL
VTVSSSGGGSSGSGGGRSGSEIVLTQSPGTLSLSPGERA
TLSCRASQRVSSSYLAWYQQKPGQAPRLLIYDASSRATG
IPDRFSGSGSGTDFTLTISRLEPEDFAVYYCQQYGSLPW
TFGQGTKVEIKSGGGGEVQLVESGGGLVQPGGSLRLSCA
VSGYTFSMNWVRQAPGKGLEWVAWINMYTGEPTYADDFK
GRFTISRDDSKNTLYLQMNSLRAEDTAVYYCARLYNGNS
LDYWGQGTLVTVSSGGGGSEPKSSDKTHTCPPCPAPELL
GGPSVFLFPPKPKDTLMISRTPEVTCVVVDVSHEDPEVK
FNWYVDGVEVHNAKTKPREEQYNSTYRVVSVLTVLHQDW
LNGKEYKCKVSNKALPAPIEKTISKAKGQPREPQVYTLP
PSREEMTKNQVSLTCLVKGFYPSDIAVEWESNGQPENNY
KTTPPVLDSDGSFFLYSKLTVDKSRWQQGNVFSCSVMHE
ALHNHYTQKSLSLSPGK |
| 82 | Dblnk17 | 197 | DIQMTQSPSSLSASVGDRVTITCKSSQSLLNSGNQKSYL
TWYQQKPGKAPKLLIYWASTLESGVPSRFSGSGSGTDYT
LTISSLQPEDFATYYCQNAYFFPFTFGQGTKVEIKSGSG
GSEVQLVESGGGLVQPGGSLRLSCAASGFTFSRYWMSWV
RQAPGKGLEWVANIKQDGSEKYYVDSVKGRFTISRDNAK
NSLYLQMNSLRAEDTAVYYCAREGGWFGELAFDYWGQGT
LVTVSSGSGGGSSGSSGSGGSEIVLTQSPGTLSLSPG
ERATLSCRASQRVSSSYLAWYQQKPGQAPRLLIYDASSR
ATGIPDRFSGSGSGTDFTLTISRLEPEDFAVYYCQQYGS
LPWTFGQGTKVEIKSSSGGSEVQLVESGGGLVQPGGSLR
LSCAVSGYTFSMNWVRQAPGKGLEWVAWINMYTGEPTYA
DDFKGRFTISRDDSKNTLYLQMNSLRAEDTAVYYCARLY
NGNSLDYWGQGTLVTVSSGGGGSEPKSSDKTHTCPPCPA
PELLGGPSVFLFPPKPKDTLMISRTPEVTCVVVDVSHED
PEVKFNWYVDGVEVHNAKTKPREEQYNSTYRVVSVLTVL
HQDWLNGKEYKCKVSNKALPAPIEKTISKAKGQPREPQV
YTLPPSREEMTKNQVSLTCLVKGFYPSDIAVEWESNGQP
ENNYKTTPPVLDSDGSFFLYSKLTVDKSRWQQGNVFSCS
VMHEALHNHYTQKSLSLSPGK |
| 83 | Dblnk18 | 198 | DIQMTQSPSSLSASVGDRVTITCKSSQSLLNSGNQKSYL
TWYQQKPGKAPKLLIYWASTLESGVPSRFSGSGSGTDYT
LTISSLQPEDFATYYCQNAYFFPFTFGQGTKVEIKGSGS
GGEVQLVESGGGLVQPGGSLRLSCAASGFTFSRYWMSWV
RQAPGKGLEWVANIKQDGSEKYYVDSVKGRFTISRDNAK
NSLYLQMNSLRAEDTAVYYCAREGGWFGELAFDYWGQGT
LVTVSSGGGGSSGSGSSSRSSGGEIVLTQSPGTLSLSPG
ERATLSCRASQRVSSSYLAWYQQKPGQAPRLLIYDASSR
ATGIPDRFSGSGSGTDFTLTISRLEPEDFAVYYCQQYGS
LPWTFGQGTKVEIKGSGGGEVQLVESGGGLVQPGGSLRL
SCAVSGYTFSMNWVRQAPGKGLEWVAWINMYTGEPTYAD
DFKGRFTISRDDSKNTLYLQMNSLRAEDTAVYYCARLYN |

TABLE 1-continued

| Ab # | Ori ID | SEQ ID | SEQUENCE |
|---|---|---|---|
| | | | GNSLDYWGQGTLVTVSSGGGGSEPKSSDKTHTCPPCPAP<br>ELLGGPSVFLFPPKPKDTLMISRTPEVTCVVVDVSHEDP<br>EVKFNWYVDGVEVHNAKTKPREEQYNSTYRVVSVLTVLH<br>QDWLNGKEYKCKVSNKALPAPIEKTISKAKGQPREPQVY<br>TLPPSREEMTKNQVSLTCLVKGFYPSDIAVEWESNGQPE<br>NNYKTTPPVLDSDGSFFLYSKLTVDKSRWQQGNVFSCSV<br>MHEALHNHYTQKSLSLSPGK |
| 84 | ScDb9024 | 199 | DIQMTQSPSSLSASVGDRVTITCKSSQSLLNSGNWKSYL<br>TWYQQKPGKAPKLLIYWASTLVSGVPSRFSGSGSGTDYT<br>LTISSLQPEDFATYYCQNAYSFPPTFGQGTKVEIKSGGG<br>GEVQLVESGGGLVQPGGSLRLSCAASGFTFSRYWMSWVR<br>QAPGKGLEWVANIKQDGSEKYYVDSVKGRFTISRDNAKN<br>SLYLQMNSLRAEDTAVYYCAREGGWFGELAFDYWGQGTL<br>VTVSSGGGGSGGGGSGGGGSEIVLTQSPGTLSLSPGERA<br>TLSCRASQRVSSSYLAWYQQKPGQAPRLLIYDASSRATG<br>IPDRFSGSGSGTDFTLTISRLEPEDFAVYYCQQYGSLPW<br>TFGQGTKVEIKSGGGGEVQLVESGGGLVQPGGSLRLSCA<br>VSGYTFSMNWVRQAPGKGLEWVAWINMYTGEKTYADDFK<br>GRFTISRDDSKNTLYLQMNSLRAEDTAVYYCARLYNGNS<br>LDYWGQGTLVTVSSGGGGSEPKSSDKTHTCPPCPAPELL<br>GGPSVFLFPPKPKDTLMISRTPEVTCVVVDVSHEDPEVK<br>FNWYVDGVEVHNAKTKPREEQYNSTYRVVSVLTVLHQDW<br>LNGKEYKCKVSNKALPAPIEKTISKAKGQPREPQVYTLP<br>PSREEMTKNQVSLTCLVKGFYPSDIAVEWESNGQPENNY<br>KTTPPVLDSDGSFFLYSKLTVDKSRWQQGNVFSCSVMHE<br>ALHNHYTQKSLSLSPGK |
| 85 | ScDb9041 | 200 | DIQMTQSPSSLSASVGDRVTITCKSSQSLLNSGNIKSYL<br>TWYQQKPGKAPKLLIYWASTLRSGVPSRFSGSGSGTDYT<br>LTISSLQPEDFATYYCQNAYSFPPTFGQGTKVEIKSGGG<br>GEVQLVESGGGLVQPGGSLRLSCAASGFTFSRYWMSWVR<br>QAPGKGLEWVANIKQDGSEKYYVDSVKGRFTISRDNAKN<br>SLYLQMNSLRAEDTAVYYCAREGGWFGELAFDYWGQGTL<br>VTVSSGGGGSGGGGSGGGGSEIVLTQSPGTLSLSPGERA<br>TLSCRASQRVSSSYLAWYQQKPGQAPRLLIYDASSRATG<br>IPDRFSGSGSGTDFTLTISRLEPEDFAVYYCQQYGSLPW<br>TFGQGTKVEIKSGGGGEVQLVESGGGLVQPGGSLRLSCA<br>VSGYTFSMNWVRQAPGKGLEWVAWINMYTGERTYADDFK<br>GRFTISRDDSKNTLYLQMNSLRAEDTAVYYCARLYNGNS<br>LDYWGQGTLVTVSSGGGGSEPKSSDKTHTCPPCPAPELL<br>GGPSVFLFPPKPKDTLMISRTPEVTCVVVDVSHEDPEVK<br>FNWYVDGVEVHNAKTKPREEQYNSTYRVVSVLTVLHQDW<br>LNGKEYKCKVSNKALPAPIEKTISKAKGQPREPQVYTLP<br>PSREEMTKNQVSLTCLVKGFYPSDIAVEWESNGQPENNY<br>KTTPPVLDSDGSFFLYSKLTVDKSRWQQGNVFSCSVMHE<br>ALHNHYTQKSLSLSPGK |
| 86 | ScDb9047 | 201 | DIQMTQSPSSLSASVGDRVTITCKSSQSLLNWGNQKSYL<br>TWYQQKPGKAPKLLIYWASTLFSGVPSRFSGSGSGTDYT<br>LTISSLQPEDFATYYCQNAYSFPPTFGQGTKVEIKSGGG<br>GEVQLVESGGGLVQPGGSLRLSCAASGFTFSRYWMSWVR<br>QAPGKGLEWVANIKQDGSEKYYVDSVKGRFTISRDNAKN<br>SLYLQMNSLRAEDTAVYYCAREGGWFGELAFDYWGQGTL<br>VTVSSGGGGSGGGGSGGGGSEIVLTQSPGTLSLSPGERA<br>TLSCRASQRVSSSYLAWYQQKPGQAPRLLIYDASSRATG<br>IPDRFSGSGSGTDFTLTISRLEPEDFAVYYCQQYGSLPW<br>TFGQGTKVEIKSGGGGEVQLVESGGGLVQPGGSLRLSCA<br>VSGYTFSMNWVRQAPGKGLEWVAWINMYTGEPIYADDFK<br>GRFTISRDDSKNTLYLQMNSLRAEDTAVYYCARLYNGNS<br>LDYWGQGTLVTVSSGGGGSEPKSSDKTHTCPPCPAPELL<br>GGPSVFLFPPKPKDTLMISRTPEVTCVVVDVSHEDPEVK<br>FNWYVDGVEVHNAKTKPREEQYNSTYRVVSVLTVLHQDW<br>LNGKEYKCKVSNKALPAPIEKTISKAKGQPREPQVYTLP<br>PSREEMTKNQVSLTCLVKGFYPSDIAVEWESNGQPENNY<br>KTTPPVLDSDGSFFLYSKLTVDKSRWQQGNVFSCSVMHE<br>ALHNHYTQKSLSLSPGK |
| 87 | Db11 | 202 | DIQMTQSPSSLSASVGDRVTITCKSSQSLLNSGNQKSYL<br>TWYQQKPGKAPKLLIYWASTLESGVPSRFSGSGSGTDYT<br>LTISSLQPEDFATYYCQNAYFFPPTFGQGTKVEIKSGGG<br>GEVQLVESGGGLVQPGGSLRLSCAASGFITSRYWMSWVR<br>QAPGKGLEWVANIKQDGSEKYYVDSVKGRFTISRDNAKN<br>SLYLQMNSLRAEDTAVYYCAREGGWFGELAFDYWGQGTL<br>VTVSSGGGGSEPKSSDKTHTCPPCPAPELLGGPSVFLFP<br>PKPKDTLMISRTPEVTCVVVDVSHEDPEVKFNWYVDGVE |

TABLE 1-continued

| Ab # | Ori ID | SEQ ID | SEQUENCE |
|---|---|---|---|
| | | | VHNAKTKPREEQYNSTYRVVSVLTVLHQDWLNGKEYKCK VSNKALPAPIEKTISKAKGQPREPQVYTLPPCREEMTKN QVSLWCLVKGFYPSDIAVEWESNGQPENNYKTTPPVLDS DGSFFLYSKLTVDKSRWQQGNVESCSVMHEALHNHYTQK SLSLSPGK |
| | Db21 | 203 | EIVLTQSPGTLSLSPGERATLSCRASQRVSSSYLAWYQQ KPGQAPRLLIYDASSRATGIPDRFSGSGSGTDFTLTISR LEPEDFAVYYCQQYGSLPWTFGQGTKVEIKRSGGGEVQ LVESGGGLVQPGGSLRLSCAVSGYITSMNWVRQAPGKGL EWVAWINMYTGEPTYADDFKGRFTISRDDSKNTLYLQMN SLRAEDTAVYYCARLYNGNSLDYWGQGTLVTVSSGGGGS EPKSSDKTHTCPPCPAPELLGGPSVFLFPPKPKDTLMIS RTPEVTCVVVDVSHEDPEVKFNWYVDGVEVHNAKTKPRE EQYNSTYRVVSVLTVLHQDWLNGKEYKCKVSNKALPAPI EKTISKAKGQPREPQVCTLPPSREEMTKNQVSLSCAVKG FYPSDIAVEWESNGQPENNYKTTPPVLDSDGSFFLVSKL TVDKSRWQQGNVESCSVMHEALHNRFTQKSLSLSPGK |
| 88 | Db12 | 204 | DIQMTQSPSSLSASVGDRVTITCKSSQSLLNSGNQKSYL TWYQDKPGKAPKLLIYWASTLESGVPSRFSGSGSGTDYT LTISSLQPEDFATYYCQNAYFFPFTFGQGTKVEIKSGGG GEVQLVESGGGLVQPGGSLRLSCAASGFITSRYWMSWVR DAPGKGLEWVANIKQDGSEKYYVDSVKGRFTISRDNAKN SLYLQMNSLRAEDTAVYYCAREGGWFGELAFDYWGQGTL VTVSSGGGGSEPKSSDKTHTCPPCPAPELLGGPSVFLFP PKPKDTLMISRTPEVTCVVVDVSHEDPEVKFNWYVDGVE VHNAKTKPREEQYNSTYRVVSVLTVLHQDWLNGKEYKCK VSNKALPAPIEKTISKAKGQPREPQVYTLPPCREEMTKN QVSLWCLVKGFYPSDIAVEWESNGQPENNYKTTPPVLDS DGSFFLYSKLTVDKSRWQQGNVESCSVMHEALHNHYTQK SLSLSPGK |
| | Db22 | 205 | EIVLTQSPGTLSLSPGERATLSCRASQRVSSSYLAWYQR KPGQAPRLLIYDASSRATGIPDRFSGSGSGTDFTLTISR LEPEDFAVYYCQQYGSLPWTFGQGTKVEIKRSGGGEVQ LVESGGGLVQPGGSLRLSCAVSGYITSMNWVRRAPGKGL EWVAWINMYTGEPTYADDFKGRFTISRDDSKNTLYLQMN SLRAEDTAVYYCARLYNGNSLDYWGQGTLVTVSSGGGGS EPKSSDKTHTCPPCPAPELLGGPSVFLFPPKPKDTLMIS RTPEVTCVVVDVSHEDPEVKFNWYVDGVEVHNAKTKPRE EQYNSTYRVVSVLTVLHQDWLNGKEYKCKVSNKALPAPI EKTISKAKGQPREPQVCTLPPSREEMTKNQVSLSCAVKG FYPSDIAVEWESNGQPENNYKTTPPVLDSDGSFFLVSKL TVDKSRWQQGNVESCSVMHEALHNRFTQKSLSLSPGK |
| 89 | Db13 | 206 | DIQMTQSPSSLSASVGDRVTITCKSSQSLLNSGNQKSYL TWYQDKPGKAPKLLIYWASTLESGVPSRFSGSGSGTDYT LTISSLQPEDFATYYCQNAYFFPFTFGQGTKVEIKSGGG GEVQLVESGGGLVQPGGSLRLSCAASGFTFSRYWMSWVR DAPGKGLEWVANIKQDGSEKYYVDSVKGRFTISRDNAKN SLYLQMNSLRAEDTAVYYCAREGGWFGELAFDYWGQGTL VTVSSGGGGSEPKSSDKTHTCPPCPAPELLGGPSVFLFP PKPKDTLMISRTPEVTCVVVDVSHEDPEVKFNWYVDGVE VHNAKTKPREEQYNSTYRVVSVLTVLHQDWLNGKEYKCK VSNKALPAPIEKTISKAKGQPREPQVYTLPPCREEMTKN QVSLWCLVKGFYPSDIAVEWESNGQPENNYKTTPPVLDS DGSFFLYSKLTVDKSRWQQGNVFSCSVMHEALHNHYTQK SLSLSPGK |
| | Db23 | 207 | EIVLTQSPGTLSLSPGERATLSCRASQRVSSSYLAWYQK KPGQAPRLLIYDASSRATGIPDRFSGSGSGTDFTLTISR LEPEDFAVYYCQQYGSLPWTFGQGTKVEIKRSGGGGEVQ LVESGGGLVQPGGSLRLSCAVSGYTFSMNWVRKAPGKGL EWVAWINMYTGEPTYADDFKGRFTISRDDSKNTLYLQMN SLRAEDTAVYYCARLYNGNSLDYWGQGTLVTVSSGGGGS EPKSSDKTHTCPPCPAPELLGGPSVFLFPPKPKDTLMIS RTPEVTCVVVDVSHEDPEVKFNWYVDGVEVHNAKTKPRE EQYNSTYRVVSVLTVLHQDWLNGKEYKCKVSNKALPAPI EKTISKAKGQPREPQVCTLPPSREEMTKNQVSLSCAVKG FYPSDIAVEWESNGQPENNYKTTPPVLDSDGSFFLVSKL TVDKSRWQQGNVESCSVMHEALHNRFTQKSLSLSPGK |
| | $CH_2CH_3$ (Knob) | 208 | EPKSSDKTHTCPPCPAPELLGGPSVFLFPPKPKDTLMIS RTPEVTCVVVDVSHEDPEVKFNWYVDGVEVHNAKTKPRE EQYNSTYRVVSVLTVLHQDWLNGKEYKCKVSNKALPAPI EKTISKAKGQPREPQVYTLPPCREEMTKNQVSLWCLVKG FYPSDIAVEWESNGQPENNYKTTPPVLDSDGSFFLYSKL TVDKSRWQQGNVFSCSVMHEALHNHYTQKSLSLSPGK |

TABLE 1-continued

| Ab # | Ori ID | SEQ ID | SEQUENCE |
|---|---|---|---|
|  | CH₂CH₃ (Hole) | 209 | EPKSSDKTHTCPPCPAPELLGGPSVFLFPPKPKDTLMIS RTPEVTCVVVDVSHEDPEVKFNWYVDGVEVHNAKTKPRE EQYNSTYRVVSVLTVLHQDWLNGKEYKCKVSNKALPAPI EKTISKAKGQPREPQVCTLPPSREEMTKNQVSLSCAVKG FYPSDIAVEWESNGQPENNYKTTPPVLDSDGSFFLVSKL TVDKSRWQQGNVFSCSVMHEALHNRFTQKSLSLSPGK |
| 90 | Extracellular Loop 1 of claudin 18.2 | 210 | DQWSTQDLYNNPVTAVFNYQGLWRSCVRESSGFTECRGY FTL |
| 91 | Full Length Protein of claudin 18.2 | 211 | MAVTACQGLGFVVSLIGIAGIIAATCMDQWSTQDLYNNP VTAVFNYQGLWRSCVRESSGFTECRGYFTLLGLPAMLQA VRALMIVGIVLGAIGLLVSIFALKCIRIGSMEDSAKANM TLTSGIMFIVSGLCAIAGVSVFANMLVTNFWMSTANMYT GMGGMVQTVQTRYTFGAALFVGWVAGGLTLIGGVMMCIA CRGLAPEETNYKAVSYHASGHSVAYKPGGFKASTGFGSN TKNKKIYDGGARTEDEVQSYPSKHDYV |
| 92 | C-terminal Deleted Domain of claudin 18.2 | 212 | MAVTACQGLGFVVSLIGIAGIIAATCMDQWSTQDLYNNP VTAVFNYQGLWRSCVRESSGFTECRGYFTLLGLPAMLQA VRALMIVGIVLGAIGLLVSIFALKCIRIGSMEDSAKANM TLTSGIMFIVSGLCAIAGVSVFANMLVTNFWMSTANMYT GMGGMVQTVQTRYTFGAALFVGWVAGGLTLIGGVMMCIA CRGLA |
| 93 | Extracellular Loop 1 of claudin 18.1 | 213 | DMWSTQDLYDNPVTSVFQYEGLWRSCVRQSSGFTECRPY FTI |
| 94 | Full Length Protein of claudin 18.1 | 214 | MSTTTCQVVAFLLSILGLAGCIAATGMDMWSTQDLYDNP VTSVFQYEGLWRSCVRQSSGFTECRPYFTILGLPAMLQA VRALMIVGIVLGAIGLLVSIFALKCIRIGSMEDSAKANM TLTSGIMFIVSGLCAIAGVSVFANMLVTNFWMSTANMYT GMGGMVQTVQTRYTFGAALFVGWVAGGLTLIGGVMMCIA CRGLAPEETNYKAVSYHASGHSVAYKPGGFKASTGFGSN TKNKKIYDGGARTEDEVQSYPSKHDYV |
| 95 | CTLA4 polypeptide | 215 | MACLGFQRHKAQLNLATRTWPCTLLFFLLFIPVFCKAMH VAQPAVVLASSRGIASFVCEYASPGKATEVRVTVLRQAD SQVTEVCAATYMMGNELTFLDDSICTGTSSGNQVNLTIQ GLRAMDTGLYICKVELMYPPPYYLGIGNGTQIYVIDPEP CPDSDFLLWILAAVSSGLFFYSFLLTAVSLSKMLKKRSP LTTGVYVKMPPTEPECEKQFQPYFIPIN |
| 96 | PD-1 polypeptide | 216 | MQIPQAPWPV VWAVLQLGWR PGWFLDSPDR PWNPPTFSPALLVVTEGDNA TFTCSFSNTSESFVINWYRM SPSNQTDKLA AFPEDRSQPG QDCRFRVTQL PNGRDFHMSV VRARRNDSGTYLCGAISLAP KAQIKESLRA ELRVTERRAE VPTAHPSPSP RPAGQFQTIV VGVVGGLLGSLVLLVWVLAV ICSRAARGTI GARRTGQPLK EDPSAVPVFS VDYGELDFQW REKTPEPPVP CVPEQTEYAT IVFPSGMGTS SPARRGSADG PRSAGPLRPE DGHCSWPL |
| 97 | PD-L1 polypeptide | 217 | MRIFAVFIFMTYWHLLNAPYNKINGRILVVDPVTSEHEL TCQLAEGYPKAEVIWTSSDHQVLSGKTTTTNSKREEKLF NVTSTLRINTTTNEIFYCTFRRLDPEENHTAELVIPELP LAHPPNERTHLVILGAILLCLGVALTFIFRLRKG RMMDVKKCGI QDTNSKKGSD THLEET |
| 98 | A leader sequence for signal peptide | 218 | MGWSCIILFLVATATGVHS |
| 99 | CDR swap primer for CDR-L1 | 219 | AGGGTCACCATCACCTGCAAAAGCAGTCAGAGTCTGCTC AACAGTGGCAACCAGAAAAGCTATCTGACCTGGTATCAA CAGAAACCA |
|  | CDR swap primer for CDR-L2 | 220 | GCTCCGAAGCTTCTGATTTATTGGGCATCTACCCTCGAA AGCGGAGTCCCTTCTCGCTTC |
|  | CDR swap primer for CDR-L3 | 221 | GCAACTTATTACTGTCAGAACGCGTATTCTTTTCCGTTT ACGTTCGGACAGGGTACC |
|  | CDR swap primer for CDR-H1 | 222 | TCCTGTGCAGCTTCTGGCTACACCTTTACCAACTATGGT ATGAACTGGGTGCGTCAGGCCCCG |
|  | CDR swap primer for CDR-H2 | 223 | GGCCTGGAATGGGTTGCATGGATTAACACGTATACCGGC GAACCGACCTATGCCGATGACTTCAAGGGCCGTTTCACT ATAAGCCGT |

TABLE 1-continued

| Ab # | Ori ID | SEQ ID | SEQUENCE |
|---|---|---|---|
| | CDR swap primer for CDR-H3 | 224 | GTCTATTATTGTGCTCGCCTGTATAACGGCAACTCTCTGGACTACTGGGGTCAAGGA |
| 100 | Primer for degenerate codon of hLibL1 | 225 | GCCTATGCATCCGATATCCAGMTGACCCAGTCCCCGAGCTCC |
| | Primer for degenerate codon of hLibL2 | 226 | GGTAGCGGTTCCGGGACGGATTWCACTCTGACCATCAGCAGTCTGCAGCCGGAAGACYTCGCAACTTATTACTGTCAG |
| | Primer for degenerate codon of hLibH1 | 227 | CTCCGTTTGTCCTGTGCARYCTCTGGCTACACCTTTACCAACTATGGTATGAACTGGRTCCGTCAGGCCCCGGGTAAG |
| | Primer for degenerate codon of hLibH2 | 228 | GATGACTTCAAGGGCCGTNYCACTWTCAGCCKCGACRMCTCCRMGARCACASYGTACCTACAAATGAACAGC |
| | Primer for degenerate codon of hLibH3 | 229 | GACACTGCCGTCTATTATTGTDYGARGCTGTATAACGGCAACTCT |
| 101 | Substituting sequence to CDR-H3 | 230 | TAAGGCCAAGACGGCCTATAA |
| 102 | Kunkel mutagenesis primer 1 | 231 | GTCTATTATTGTGCTCGCXYZXYZXYZXYZXYZXYZWTKGACTACTGGGGTCAAGGA |
| | Kunkel mutagenesis primer 2 | 232 | GTCTATTATTGTGCTCGCXYZXYZXYZXYZXYZXYZXYZWTKGACTACTGGGGTCAAGGA |
| | Kunkel mutagenesis primer 3 | 233 | GTCTATTATTGTGCTCGCXYZXYZXYZXYZXYZXYZXYZXYZWTKGACTACTGGGGTCAAGGA |
| | Kunkel mutagenesis primer 4 | 234 | GTCTATTATTGTGCTCGCXYZXYZXYZXYZXYZXYZXYZXYZXYZWTKGACTACTGGGGTCAAGGA |
| 103 | HC Primer 1 for h5C9oAM_CDRW_L3_H3 library | 235 | GTCTATTATTGTGCTCGCNNSTATAACGGCAACTCTCTG |
| | HC Primer 2 for h5C9oAM_CDRW_L3_H3 library | 236 | CTATTATTGTGCTCGCCTGNNSAACGGCAACTCTCTGGAC |
| | HC Primer 3 for h5C9oAM_CDRW_L3_H3 library | 237 | CTATTATTGTGCTCGCCTGTATNNSGGCAACTCTCTGGACTAC |
| | HC Primer 4 for h5C9oAM_CDRW_L3_H3 library | 238 | CTATTATTGTGCTCGCCTGTATAACNNSAACTCTCTGGACTACTGG |
| | HC Primer 5 for h5C9oAM_CDRW_L3_H3 library | 239 | GCTCGCCTGTATAACGGCNNSTCTCTGGACTACTGGGGT |
| | HC Primer 6 for h5C9oAM_CDRW_L3_H3 library | 240 | CGCCTGTATAACGGCAACNNSCTGGACTACTGGGGTCAA |
| | LC Primer 1 for h5C9oAM_CDRW_L3_H3 library | 241 | GCAACTTATTACTGTCAGAACNNSTATTCTTTTCCGTTTACG |
| | LC Primer 2 for h5C9oAM_CDRW_L3_H3 library | 242 | CTTATTACTGTCAGAACGCGNNSTCTTTTCCGTTTACGTTC |
| | LC Primer 3 for h5C9oAM_CDRW_L3_H3 library | 243 | CTTATTACTGTCAGAACGCGTATNNSTTTCCGTTTACGTTCGGA |
| | LC Primer 4 for h5C9oAM_CDRW_L3_H3 library | 244 | CTGTCAGAACGCGTATTCTNNSCCGTTTACGTTCGGACAG |
| 104 | L1 Primer 1 for h5C9AM_CDRW_L1_L2_H2 library | 245 | CACCTGCAAAAGCAGTCAGNNSCTGCTCAACAGTGGCAAC |
| | L1 Primer 2 for h5C9AM_CDRW_L1_L2_H2 library | 246 | CTGCAAAAGCAGTCAGAGTNNSCTCAACAGTGGCAACCAG |
| | L1 Primer 3 for h5C9AM_CDRW_L1_L2_H2 library | 247 | CAAAAGCAGTCAGAGTCTGNNSAACAGTGGCAACCAGAAA |
| | L1 Primer 4 for h5C9AM_CDRW_L1_L2_H2 library | 248 | CAAAAGCAGTCAGAGTCTGCTCNNSAGTGGCAACCAGAAAAGC |

TABLE 1-continued

| Ab # | Ori ID | SEQ ID | SEQUENCE |
|---|---|---|---|
| | L1 Primer 5 for h5C9AM CDRW L1 L2 H2 library | 249 | CAGTCAGAGTCTGCTCAACNNSGGCAACCAGAAAAGCTAT |
| | L1 Primer 6 for h5C9AM_CDRW_L1_L2 H2 library | 250 | CAGAGTCTGCTCAACAGTNNSAACCAGAAAAGCTATCTG |
| | L1 Primer 7 for h5C9AM_CDRW_L1_L2 H2 library | 251 | GAGTCTGCTCAACAGTGGCNNSCAGAAAAGCTATCTGACC |
| | L1 Primer 8 for h5C9AM CDRW L1 L2 H2 library | 252 | GTCTGCTCAACAGTGGCAACNNSAAAAGCTATCTGACCTGG |
| | L1 Primer 9 for h5C9AM CDRW L1 L2 H2 library | 253 | CTCAACAGTGGCAACCAGNNSAGCTATCTGACCTGGTAT |
| | L1 Primer 10 for h5C9AM_CDRW_L1_L2 H2 library | 254 | CAACAGTGGCAACCAGAAANNSTATCTGACCTGGTATCAA |
| | L1 Primer 11 for h5C9AM CDRW L1 L2 H2 library | 255 | CAGTGGCAACCAGAAAAGCNNSCTGACCTGGTATCAACAG |
| | L1 Primer 12 for h5C9AM CDRW L1 L2 H2 library | 256 | GGCAACCAGAAAAGCTATNNSACCTGGTATCAACAGAAA |
| 105 | L2 Primer 1 for h5C9AM CDRW L1 L2 H2 library | 257 | CCGAAGCTTCTGATTTATNNSGCATCTACCCTCGAAAGC |
| | L2 Primer 2 for h5C9AM CDRW L1 L2 H2 library | 258 | CTGATTTATTGGGCATCTNNSCTCGAAAGCGGAGTCCCT |
| | L2 Primer 3 for h5C9AM CDRW L1 L2 H2 library | 259 | GATTTATTGGGCATCTACCCTCNNSAGCGGAGTCCCTTCTCGC |
| | H2 Primer 1 for h5C9AM CDRW L1 L2 H2 library | 260 | GGCCTGGAATGGGTTGCANNSATTAACATGTATACCGGC |
| | H2 Primer 2 for h5C9AM CDRW L1 L2 H2 library | 261 | GAATGGGTTGCATGGATTNNSATGTATACCGGCGAACCG |
| | H2 Primer 3 for h5C9AM_CDRW_L1_L2 H2 library | 262 | GAATGGGTTGCATGGATTAACNNSTATACCGGCGAACCGACC |
| | H2 Primer 4 for h5C9AM CDRW L1 L2 H2 library | 263 | GTTGCATGGATTAACATGNNSACCGGCGAACCGACCTAT |
| | H2 Primer 5 for h5C9AM CDRW L1 L2 H2 library | 264 | GCATGGATTAACATGTATNNSGGCGAACCGACCTATGCC |
| | H2 Primer 6 for h5C9AM CDRW L1 L2 H2 library | 265 | GATTAACATGTATACCGGCNNSCCGACCTATGCCGATGAC |
| | H2 Primer 7 for h5C9AM CDRW L1 L2 H2 library | 266 | GATTAACATGTATACCGGCGAANNSACCTATGCCGATGACTTC |
| | H2 Primer 8 for h5C9AM CDRW L1 L2 H2 library | 267 | CATGTATACCGGCGAACCGNNSTATGCCGATGACTTCAAG |
| 106 | Kunkel primer 1 for linker mutation | 268 | RGCVGCRGCRGC |
| | Kunkel primer 2 for linker mutation | 269 | RGCRGCVGCRGCRGC |
| | Kunkel primer 3 for linker mutation | 270 | RGCRGCRGCVGCRGCRGC |
| | Kunkel primer 4 for linker mutation | 271 | RGCRGCRGCVGCRGCRGCRGCVGCRGCRGCRGCVGCRGCRGCRGC |
| | Kunkel primer 5 for linker mutation | 272 | RGCRGCRGCRGCVGCRGCRGCRGCVGCRGCRGCRGCVGCRGCRGCRGC |
| | Kunkel primer 6 for linker mutation | 273 | RGCRGCRGCRGCVGCRGCRGCRGCVGCRGCRGCRGCVGCRGCRGCRGCRGC |
| 107 | General formula for CLDN 18.2 VL-CDR1 | 274 | KSSQSLLNX$_1$GNX$_2$KSYLT (X$_1$ is S, T, Y, F, or W; X$_2$ is Q, N, W, F, Y, I, M, or V) |
| | General formula for CLDN 18.2 VL-CDR2 | 275 | WASTLX$_3$S (X$_3$ is any amino acid residue) |

TABLE 1-continued

| Ab # | Ori ID | SEQ ID | SEQUENCE |
|---|---|---|---|
| | General formula for CLDN 18.2 VL-CDR3 | 276 | QNAYX$_4$FPFT (X$_4$ is S, T, F, Y, or W) |
| | General formula for CLDN 18.2 VH-CDR2 | 277 | WINMYTGX$_5$X$_6$X$_7$YADDFKG (X$_5$ is E, D, K, H, or R; X$_6$ is P, K, R, H, T, or S; and X$_7$ is S, T, V, I, or L) |
| | General formula for CLDN 18.2 VH-CDR3 | 278 | LYX$_8$GNSLDY (X$_8$ is N, Q, K, R, or H) |
| Ob-12A4 | Chain 1 | 279 | DIQMTQSPSSLSASVGDRVTITCKSSQSLLNSGNQKSYL TWYQQKPGKAPKLLIYWASTLESGVPSRFSGSGSGTDYT LTISSLQPEDFATYYCQNAYFPFTFGQGTKVEIKSGGG GQVQLVQSGAEVKKPGSSVKVSCKTSGDTFSTYAISWVR QAPGQGLEWMGGIIPIFGKAHYAQKFQGRVTITADESTS TAYMELSSLRSEDTAVYFCARKFHFVSGSPFGMDVWGQG TTVTVSSGGGGSEPKSSDKTHTCPPCPAPELLGGPSVFL FPPKPKDTLMISRTPEVTCVVVDVSHEDPEVKFNWYVDG VEVHNAKTKPREEQYNSTYRVVSVLTVLHQDWLNGKEYK CKVSNKALPAPIEKTISKAKGQPREPQVYTLPPCREEMT KNQVSLWCLVKGFYPSDIAVEWESNGQPENNYKTTPPVL DSDGSFFLYSKLTVDKSRWQQGNVFSCSVMHEALHNHYT QKSLSLSPGK |
| | Chain 2 | 280 | EIVLTQSPATLSLSPGERATLSCRASQSVSSYLAWYQQK PGQAPRLLIYDASNRATGIPARFSGSGSGTDFTLTISSL EPEDFAVYYCQQRSNWPTFGQGTKVEIKSGGGGEVQLVE SGGGLVQPGGSLRLSCAVSGYTFSMNWVRQAPGKGLEWV AWINMYTGEPTYADDFKGRFTISRDDSKNTLYLQMNSLR AEDTAVYYCARLYNGNSLDYWGQGTLVTVSSGGGGSEPK SSDKTHTCPPCPAPELLGGPSVFLFPPKPKDTLMISRTP EVTCVVVDVSHEDPEVKFNWYVDGVEVHNAKTKPREEQY NSTYRVVSVLTVLHQDWLNGKEYKCKVSNKALPAPIEKT ISKAKGQPREPQVCTLPPSREEMTKNQVSLSCAVKGFYP SDIAVEWESNGQPENNYKTTPPVLDSDGSFFLVSKLTVD KSRWQQGNVFSCSVMHEALHNRFTQKSLSLSPGK |
| | CLDN-VL | 13 | DIQMTQSPSSLSASVGDRVTITCKSSQSLLNSGNQKSYL TWYQQKPGKAPKLLIYWASTLESGVPSRFSGSGSGTDYT LTISSLQPEDFATYYCQNAYFPFTFGQGTKVEIK |
| | CLDN-VL CDR1 | 6 | KSSQSLLNSGNQKSYLT |
| | CLDN-VL CDR2 | 12 | WASTLES |
| | CLDN-VL CDR3 | 14 | QNAYFPFT |
| | CLDN-VH | 56 | EVQLVESGGGLVQPGGSLRLSCAVSGYTFSMNWVRQAPG KGLEWVAWINMYTGEPTYADDFKGRFTISRDDSKNTLYL QMNSLRAEDTAVYYCARLYNGNSLDYWGQGTLVTVSS |
| | CLDN-VH CDR1 | 10 | GYTFSMN |
| | CLDN-VH CDR2 | 57 | WINMYTGEPTYADDFKG |
| | CLDN-VH CDR3 | 4 | LYNGNSLDY |
| | PDL1-VL | 281 | EIVLTQSPATLSLSPGERATLSCRASQSVSSYLAWYQQK PGQAPRLLIYDASNRATGIPARFSGSGSGTDFTLTISSL EPEDFAVYYCQQRSNWPTFGQGTKVEIK |
| | PDL1-VL CDR1 | 282 | RASQSVSSYLA |
| | PDL1-VL CDR2 | 283 | DASNRAT |
| | PDL1-VL CDR3 | 284 | QQRSNWPT |
| | PDL1-VH | 285 | QVQLVQSGAEVKKPGSSVKVSCKTSGDTFSTYAISWVRQ APGQGLEWMGGIIPIFGKAHYAQKFQGRVTITADESTST AYMELSSLRSEDTAVYFCARKFHFVSGSPFGMDVWGQGT TVTVSS |
| | PDL1-VH CDR1 | 286 | GDTFSTYAIS |
| | PDL1-VH CDR2 | 287 | GIIPIFGKAHYAQKFQG |
| | PDL1-VH CDR3 | 288 | KFHFVSGSPFGMDV |
| | L1 and L3 | 121 | SGGGG |
| | L2 and L4 | 164 | GGGGS |
| | Fc-chain A | 208 | EPKSSDKTHTCPPCPAPELLGGPSVFLFPPKPKDTLMIS RTPEVTCVVVDVSHEDPEVKFNWYVDGVEVHNAKTKPRE EQYNSTYRVVSVLTVLHQDWLNGKEYKCKVSNKALPAPI EKTISKAKGQPREPQVYTLPPCREEMTKNQVSLWCLVKG FYPSDIAVEWESNGQPENNYKTTPPVLDSDGSFFLYSKL TVDKSRWQQGNVFSCSVMHEALHNHYTQKSLSLSPGK |
| | Fc-chain B | 209 | EPKSSDKTHTCPPCPAPELLGGPSVFLFPPKPKDTLMIS RTPEVTCVVVDVSHEDPEVKFNWYVDGVEVHNAKTKPRE EQYNSTYRVVSVLTVLHQDWLNGKEYKCKVSNKALPAPI EKTISKAKGQPREPQVCTLPPSREEMTKNQVSLSCAVKG FYPSDIAVEWESNGQPENNYKTTPPVLDSDGSFFLVSKL TVDKSRWQQGNVFSCSVMHEALHNRFTQKSLSLSPGK |

TABLE 1-continued

| Ab # | Ori ID | SEQ ID | SEQUENCE |
|---|---|---|---|
| Ob-12A4-bad | Chain 1 | 289 | DIQMTQSPSSLSASVGDRVTITCKSSQSLLNSGNQKSYL TWYQQKPGKAPKLLIYWASTLESGVPSRFSGSGSGTDYT LTISSLQPEDFATYYCQNAYFFPFTFGQGTKVEIKSGGG GQVQLVQSGAEVKKPGSSVKVSCKTSGDTFSTYAISWVR QAPGQGLEWMGGIIPLEGKAHYAQKFQGRVTITADESTS TAYMELSSLRSEDTAVYFCARKFHFVRGSPFGMDVWGQG TTVTVSSGGGGSEPKSSDKTHTCPPCPAPELLGGPSVFL FPPKPKDTLMISRTPEVTCVVVDVSHEDPEVKFNWYVDG VEVHNAKTKPREEQYNSTYRVVSVLTVLHQDWLNGKEYK CKVSNKALPAPIEKTISKAKGQPREPQVYTLPPCREEMT KNQVSLWCLVKGFYPSDIAVEWESNGQPENNYKTTPPVL DSDGSFFLYSKLTVDKSRWQQGNVFSCSVMHEALHNHYT QKSLSLSPGK |
| | Chain 2 | 290 | EIVLTQSPATLSLSPGERATLSCRASQSVSSYLAWYQQK PGQAPRLLIYDASNRAPGIPARFSGSGSGTDFTLTISSL EPEDFAVYYCQQRSNWPTFGQGTKVEIKSGGGGEVQLVE SGGGLVQPGGSLRLSCAVSGYTFSMNWVRQAPGKGLEWV AWINMYTGEPTYADDFKGRFTISRDDSKNTLYLQMNSLR AEDTAVYYCARLYNGNSLDYWGQGTLVTVSSGGGGSEPK SSDKTHTCPPCPAPELLGGPSVFLFPPKPKDTLMISRTP EVTCVVVDVSHEDPEVKFNWYVDGVEVHNAKTKPREEQY NSTYRVVSVLTVLHQDWLNGKEYKCKVSNKALPAPIEKT ISKAKGQPREPQVCTLPPSREEMTKNQVSLSCAVKGFYP SDIAVEWESNGQPENNYKTTPPVLDSDGSFELVSKLTVD KSRWQQGNVFSCSVMHEALHNRFTQKSLSLSPGK |
| | CLDN-VL | 13 | DIQMTQSPSSLSASVGDRVTITCKSSQSLLNSGNQKSYL TWYQQKPGKAPKLLIYWASTLESGVPSRFSGSGSGTDYT LTISSLQPEDFATYYCQNAYFFPFTFGQGTKVEIK |
| | CLDN-VL CDR1 | 6 | KSSQSLLNSGNQKSYLT |
| | CLDN-VL CDR2 | 12 | WASTLES |
| | CLDN-VL CDR3 | 14 | QNAYFFPFT |
| | CLDN-VH | 56 | EVQLVESGGGLVQPGGSLRLSCAVSGYTFSMNWVRQAPG KGLEWVAWINMYTGEPTYADDFKGRFTISRDDSKNTLYL QMNSLRAEDTAVYYCARLYNGNSLDYWGQGTLVTVSS |
| | CLDN-VH CDR1 | 10 | GYTFSMN |
| | CLDN-VH CDR2 | 57 | WINNYTGEPTYADDFKG |
| | CLDN-VH CDR3 | 4 | LYNGNSLDY |
| | PDL1-VL | 291 | EIVLTQSPATLSLSPGERATLSCRASQSVSSYLAWYQQK PGQAPRLLIYDASNRAPGIPARFSGSGSGTDFTLTISSL EPEDFAVYYCQQRSNWPTFGQGTKVEIK |
| | PDL1-VL CDR1 | 282 | RASQSVSSYLA |
| | PDL1-VL CDR2 | 292 | DASNRAP |
| | PDL1-VL CDR3 | 284 | QQRSNWPT |
| | PDL1-VH | 293 | QVQLVQSGAEVKKPGSSVKVSCKTSGDTFSTYAISWVRQ APGQGLEWMGGIIPLFGKAHYAQKFQGRVTITADESTST AYMELSSLRSEDTAVYFCARKFHFVRGSPFGMDVWGQGT TVTVSS |
| | PDL1-VH CDP1 | 286 | GDTFSTYAIS |
| | PDL1-VH CDR2 | 294 | GIIPLEGKAHYAQKFQG |
| | PDL1-VH CDR3 | 295 | KFHPVRGSPFGMDV |
| | L1 and L3 | 121 | 85555 |
| | L2 and L4 | 164 | GGGGS |
| | Fc-chain A | 208 | EPKSSDKTHTCPPCPAPELLGGPSVELPPKPKDTLMIS RTPEVTCVVVDVSHEDPEVKFNWYVDGVEVHNAKTKPRE EQYNSTYRVVSVLTVLHQDWLNGKEYKCKVSNKALPAPI EKTISKAKGQPREPQVYTLPPCREEMTKNQVSLWQLVKG FYPSDIAVEWESNGQPENNYKTTPPVLDSDGSFFLVSKL TVDKSRWQQGNVESCSVMHEALHNHYTQKSLSLSPGK |
| | Fc-chain B | 209 | EPKSSDKTHTCPPCPAPELLGGPSVFLFPPKPKDTLKIS RTPEVTCVVVDVSHEDPEVKFNWYVDGVEVHNAKTKPRE EQYNSTYRVVSVLTVLHQDWLNGKEYKCKVSNKALPAPI EKTISKAKGQPREPQVCTLPPSREEMTKNQVSLSCAVKG FYPSDIAVEWESNGQPENNYKTTPPVLDSDGSFFLVSKL TVDKSRWQQGNVFSCSVMHEALHNRFTQKSLSLSPGK |

TABLE 2

Sequence: Anti-PDL1 12A4 Antibodies

| | | Sequence | SEQ ID NO |
|---|---|---|---|
| VH CDR1 | | GDTFSTYAIS | 286 |
| VH CDR2 | | GIIPX₁FGKAH (X₁ is I or L) | 296 |
| | | GIIPIFGKAHYAQKFQG | 287 |
| | | GIIPLFGKAHYAQKFQG | 294 |
| VH CDR3 | | KFX₁FVX₂GSPFGMDV (X₁ is H or R; X₂ is S or R) | 297 |
| | | KFHFVSGSPFGMDV | 288 |
| | | KFHFVRGSPFGMDV | 295 |
| | | KFRFVSGSPFGMDV | 298 |
| VL CDR1 | | RASQSVSSYX₁X₂ (X₁ is L or M; X₂ is A, S, or E) | 299 |
| | | RASQSVSSYLA | 282 |
| | | RASQSVSSYLS | 300 |
| | | RASQSVSSYMA | 301 |
| | | RASQSVSSYLE | 302 |
| VL CDR2 | | DASNRAX₁ (X₁ is T, P, M, or E) | 303 |
| | | DASNRAT | 283 |
| | | DASNRAP | 292 |
| | | DASNRAM | 304 |
| | | DASNRAE | 305 |
| VL CDR3 | | QQRX₁NWPT (X₁ is S or A) | 306 |
| | | QQRSNWPT | 284 |
| | | QQRANWPT | 307 |
| 12A4 | VH | QVQLVQSGAEVKKPGSSVKVSCKTSGDTFSTYAISWVRQAPGQGLEWMGGIIPIFGKAHYAQKFQGRVTITADESTSTAYMELSSLRSEDTAVYFCARKFHFVSGSPFGMDVWGQGTT VTVSS | 285 |
| | VL | EIVLTQSPATLSLSPGERATLSCRASQSVSSYLAWYQQKPGQAPRLLIYDASNRATGIPARFSGSGSGTDFTLTISSLEPEDFAVYYCQQRSNWPTFGQGTKVEIK | 281 |
| 12A4a | VH | QVQLVQSGAEVKKPGSSVKVSCKTSGDTFSTYAISWVRQAPGQGLEWMGGIIPIFGKAHYAQKFQGRVTITADESTSTAYMELSSLRSEDTAVYFCARKFHFVSGSPFGMDVWGQGTTVTVSS | 308 |
| | VL | EIVLTQSPATLSLSPGERATLSCRASQSVSSYLAWYQQKPGQAPRLLIYDASNRAPGIPARFSGSGSGTDFTLTISSLEPEDFAVYYCQQRSNWPTFGQGTKVEIK | 309 |
| 12A4b | VH | QVQLVQSGAEVKKPGSSVKVSCKTSGDTFSTYAISWVRQAPGQGLEWMGGIIPIFGKAHYAQKFQGRVTITADESTSTAYMELSSLRSEDTAVYFCARKFHFVRGSPFGMDVWGQGTTVTVSS | 310 |
| | VL | EIVLTQSPATLSLSPGERATLSCRASQSVSSYLAWYQQKPGQAPRLLIYDASNRATGIPARFSGSGSGTDFTLTISSLEPEDFAVYYCQQRSNWPTFGQGTKVEIK | 311 |
| 12A4c | VH | QVQLVQSGAEVKKPGSSVKVSCKTSGDTFSTYAISWVRQAPGQGLEWMGGIIPIFGKAHYAQKFQGRVTITADESTSTAYMELSSLRSEDTAVYFCARKFRFVSGSPFGMDVWGQGTTVTVSS | 312 |
| | VL | EIVLTQSPATLSLSPGERATLSCRASQSVSSYLAWYQQKPGQAPRLLIYDASNRATGIPARFSGSGSGTDFTLTISSLEPEDFAVYYCQQRSNWPTFGQGTKVEIK | 313 |
| 12A4d | VH | QVQLVQSGAEVKKPGSSVKVSCKTSGDTFSTYAISWVRQAPGQGLEWMGGIIPLFGKAHYAQKFQGRVTITADESTSTAYMELSSLRSEDTAVYFCARKFHFVSGSPFGMDVWGQGTTVTVSS | 314 |
| | VL | EIVLTQSPATLSLSPGERATLSCRASQSVSSYLAWYQQKPGQAPRLLIYDASNRATGIPARFSGSGSGTDFTLTISSLEPEDFAVYYCQQRSNWPTFGQGTKVEIK | 315 |
| 12A4e | VH | QVQLVQSGAEVKKPGSSVKVSCKTSGDTFSTYAISWVRQAPGQGLEWMGGIIPIFGKAHYAQKFQGRVTITADESTSTAYMELSSLRSEDTAVYFCARKFHFVSGSPFGMDVWGQGTTVTVSS | 316 |
| | VL | EIVLTQSPATLSLSPGERATLSCRASQSVSSYLAWYQQKPGQAPRLLIYDASNRATGIPARFSGSGSGTDFTLTISSLEPEDFAVYYCQQRANWPTFGQGTKVEIK | 317 |
| 12A4f | VH | QVQLVQSGAEVKKPGSSVKVSCKTSGDTFSTYAISWVRQAPGQGLEWMGGIIPIFGKAHYAQKFQGRVTITADESTSTAYMELSSLRSEDTAVYFCARKFHFVSGSPFGMDVWGQGTTVTVSS | 318 |
| | VL | EIVLTQSPATLSLSPGERATLSCRASQSVSSYLAWYQQKPGQAPRLLIYDASNRAMGIPARFSGSGSGTDFTLTISSLEPEDFAVYYCQQRSNWPTFGQGTKVEIK | 319 |
| 12A4g | VH | QVQLVQSGAEVKKPGSSVKVSCKTSGDTFSTYAISWVRQAPGQGLEWMGGIIPIFGKAHYAQKFQGRVTITADESTSTAYMELSSLRSEDTAVYFCARKFHFVSGSPFGMDVWGQGTTVTVSS | 320 |
| | VL | EIVLTQSPATLSLSPGERATLSCRASQSVSSYLSWYQQKPGQAPRLLIYDASNRAPGIPARFSGSGSGTDFTLTISSLEPEDFAVYYCQQRSNWPTFGQGTKVEIK | 321 |

TABLE 2-continued

Sequence: Anti-PDL1 12A4 Antibodies

| | | Sequence | SEQ ID NO |
|---|---|---|---|
| 12A4h | VH | QVQLVQSGAEVKKPGSSVKVSCKTSGDTFSTYAISWVRQAPGQGLEWMGGIIPIFGKAHYAQKFQGRVTITADESTSTAYMELSSLRSEDTAVYFCARKFHFVSGSPFGMDVWGQGTTVTVSS | 322 |
| | VL | EIVLTQSPATLSLSPGERATLSCRASQSVSSYMAWYQQKPGQAPRLLIYDASNRAEGIPARFSGSGSGTDFTLTISSLEPEDFAVYYCQQRANWPTFGQGTKVEIK | 323 |
| 12A4i | VH | QVQLVQSGAEVKKPGSSVKVSCKTSGDTFSTYAISWVRQAPGQGLEWMGGIIPIFGKAHYAQKFQGRVTITADESTSTAYMELSSLRSEDTAVYFCARKFHFVSGSPFGMDVWGQGTTVTVSS | 324 |
| | VL | EIVLTQSPATLSLSPGERATLSCRASQSVSSYLEWYQQKPGQAPRLLIYDASNRATGIPARFSGSGSGTDFTLTISSLEPEDFAVYYCQQRSNWPTFGQGTKVEIK | 325 |
| 12A4ad | VH | QVQLVQSGAEVKKPGSSVKVSCKTSGDTFSTYAISWVRQAPGQGLEWMGGIIPLFGKAHYAQKFQGRVTITADESTSTAYMELSSLRSEDTAVYFCARKFHFVSGSPFGMDVWGQGTTVTVSS | 326 |
| | VL | EIVLTQSPATLSLSPGERATLSCRASQSVSSYLAWYQQKPGQAPRLLIYDASNRAPGIPARFSGSGSGTDFTLTISSLEPEDFAVYYCQQRSNWPTFGQGTKVEIK | 327 |
| 12A4ba | VH | QVQLVQSGAEVKKPGSSVKVSCKTSGDTFSTYAISWVRQAPGQGLEWMGGIIPIFGKAHYAQKFQGRVTITADESTSTAYMELSSLRSEDTAVYFCARKFHFVRGSPFGMDVWGQGTTVTVSS | 328 |
| | VL | EIVLTQSPATLSLSPGERATLSCRASQSVSSYLAWYQQKPGQAPRLLIYDASNRAPGIPARFSGSGSGTDFTLTISSLEPEDFAVYYCQQRSNWPTFGQGTKVEIK | 329 |
| 12A4bd | VH | QVQLVQSGAEVKKPGSSVKVSCKTSGDTFSTYAISWVRQAPGQGLEWMGGIIPLFGKAHYAQKFQGRVTITADESTSTAYMELSSLRSEDTAVYFCARKFHFVRGSPFGMDVWGQGTTVTVSS | 330 |
| | VL | EIVLTQSPATLSLSPGERATLSCRASQSVSSYLAWYQQKPGQAPRLLIYDASNRATGIPARFSGSGSGTDFTLTISSLEPEDFAVYYCQQRSNWPTFGQGTKVEIK | 331 |
| 12A4bad | VH | QVQLVQSGAEVKKPGSSVKVSCKTSGDTFSTYAISWVRQAPGQGLEWMGGIIPLFGKAHYAQKFQGRVTITADESTSTAYMELSSLRSEDTAVYFCARKFHFVRGSPFGMDVWGQGTTVTVSS | 293 |
| | VL | EIVLTQSPATLSLSPGERATLSCRASQSVSSYLAWYQQKPGQAPRLLIYDASNRAPGIPARFSGSGSGTDFTLTISSLEPEDFAVYYCQQRSNWPTFGQGTKVEIK | 291 |

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A bispecific antibody, comprising a first antigen-binding moiety that binds human claudin 18.2, and a second antigen-binding moiety that binds human PD-L1, wherein the first antigen-binding moiety comprises:
   (a) a first heavy chain variable domain ($V_H$), which comprises the same heavy chain complementarity-determining regions (CDRs) as a reference anti-human claudin 18.2 antibody; and
   (b) a first light chain variable domain ($V_L$), which comprises the same light chain CDRs as the reference anti-human claudin 18.2 antibody; and
   wherein the reference anti-human claudin 18.2 antibody has a heavy chain and a light chain comprising the following amino acid sequences, respectively:
   (1) SEQ ID NOs: 15 and 16,
   (2) SEQ ID NOs: 20 and 16,
   (3) SEQ ID NOs: 26 and 27,
   (4) SEQ ID NOs: 33 and 34,
   (5) SEQ ID NOs: 37 and 38,
   (6) SEQ ID NOs: 42 and 43,
   (7) SEQ ID NOs: 48 and 49,
   (8) SEQ ID NOs: 54 and 55,
   (9) SEQ ID NOs: 58 and 16,
   (10) SEQ ID NOs: 60 and 61,
   (11) SEQ ID NOs: 63 and 64,
   (12) SEQ ID NOs: 67 and 68,
   (13) SEQ ID NOs: 70 and 71,
   (14) SEQ ID NOs: 73 and 74,
   (15) SEQ ID NOs: 76 and 77,
   (16) SEQ ID NOs: 79 and 61,
   (17) SEQ ID NOs: 81 and 64,
   (18) SEQ ID NOs: 83 and 68,
   (19) SEQ ID NOs: 85 and 71,
   (20) SEQ ID NOs: 86 and 74,
   (21) SEQ ID NOs: 87 and 77,
   (22) SEQ ID NOs: 88 and 55,
   (23) SEQ ID NOs: 89 and 43,
   (24) SEQ ID NOs: 91 and 92,
   (25) SEQ ID NOs: 94 and 95, or
   (26) SEQ TD NOs: 96 and 95.

2. The bispecific antibody of claim 1, wherein the second antigen-binding moiety that binds human PD-L1 comprises:
   (a) a second $V_H$, which comprises the same heavy chain complementarity-determining regions (CDRs) as a reference anti-human PD-L1 antibody; and
   (b) a second light chain variable domain ($V_L$), which comprises the same light chain CDRs as the reference anti-human PD-L1 antibody; and
   wherein the reference anti-human PD-L1 antibody is selected from the group consisting of durvalumab, atezolizumab, avelumab, and an 12A4 antibody, wherein the 12A4 antibody has a heavy chain and a light chain comprising the following amino acid sequences, respectively:
   (1) SEQ ID NOs: 285 and 281,
   (2) SEQ ID NOs: 308 and 309,
   (3) SEQ ID NOs: 310 and 311,
   (4) SEQ ID NOs: 312 and 313,
   (5) SEQ ID NOs: 314 and 315,
   (6) SEQ ID NOs: 316 and 317,
   (7) SEQ ID NOs: 318 and 319,
   (8) SEQ ID NOs: 320 and 321,
   (9) SEQ ID NOs: 322 and 323,
   (10) SEQ ID NOs: 324 and 325,
   (11) SEQ ID NOs: 326 and 327,
   (12) SEQ ID NOs: 328 and 329,
   (13) SEQ ID NOs: 330 and 331, or
   (14) SEQ ID NOs: 293 and 291.

3. The bispecific antibody of claim 2, wherein the first $V_H$ is the same as the $V_H$ chain of the reference anti-human claudin 18.2 antibody, and/or wherein the first $V_L$ is the same as the $V_L$ of the reference anti-human claudin 18.2 antibody; or wherein the second $V_H$ is the same as the $V_H$ chain of the reference anti-human PD-L1 antibody, and/or wherein the second $V_L$ is the same as the $V_L$ of the reference anti-human PD-L1 antibody.

4. The bispecific antibody of claim 2, wherein the first antigen-binding moiety and the second antigen-binding moiety are located on a single polypeptide.

5. The bispecific antibody of claim 4, wherein the single polypeptide comprises, from N-terminus to C-terminus:
   (i) a first variable region fragment, which is the first $V_H$, the first $V_L$, the second $V_H$, or the second $V_L$;
   (ii) a first peptide linker (L1)
   (iii) a second variable region fragment, which is the first $V_H$, the first $V_L$, the second $V_H$, or the second $V_L$;
   (iv) a second peptide linker (L2);
   (v) a third variable region fragment, which is which is the first $V_H$, the first $V_L$, the second $V_H$, or the second $V_L$;

(vi) a third peptide linker (L3); and
(vii) a fourth variable region fragment, which is which is the first $V_H$, the first $V_L$, the second $V_H$, or the second $V_L$;
wherein the first variable region fragment, the second variable region fragment, the third variable region fragment, and the fourth variable region fragment collectively comprises all of the first $V_H$, the first $V_L$, the second $V_H$, and the second $V_L$.

6. The bispecific antibody of claim 5, wherein at least one of the L1, L2, and L3 peptide linkers is a G/S rich peptide linker.

7. The bispecific antibody of claim 6,
wherein L1 comprises the motif of $X_1X_2X_3X_4X_5X_6$, in which:
$X_1$ represents Glycine (G), Serine (S), or absent;
$X_2$ represents Glycine (G), Serine (S), or absent;
$X_3$ represents Glycine (G), or Serine (S);
$X_4$ represents Glycine (G), Arginine (R), or Serine (S);
$X_5$ represents Glycine (G), or Serine (S); and
$X_6$ represents Glycine (G), or Serine (S);
wherein $L_2$ comprises the motif of $X_1X_2X_3X_4X_5X_6X_7X_8X_9X_{10}X_{11}X_{12}X_{13}X_{14}X_{15}X_{16}X_{17}X_{18}X_{19}X_{20}$, in which:
$X_1$ represents Glycine (G), or Serine (S);
$X_2$ represents Glycine (G), or Serine (S);
$X_3$ represents Glycine (G), or Serine (S);
$X_4$ represents Glycine (G), Serine (S), or Arginine (R);
$X_5$ represents Glycine (G), Serine (S), or Arginine (R);
$X_6$ represents Glycine (G), or Serine (S);
$X_7$ represents Glycine (G), or Serine (S);
$X_8$ represents Glycine (G) or absent;
$X_9$ represents Glycine (G) or absent;
$X_{10}$ represents Glycine (G) or absent;
$X_{11}$ represents Glycine (G), or Serine (S), or absent;
$X_{12}$ represents Glycine (G), Serine (S), Arginine (R), or absent;
$X_{13}$ represents Glycine (G), Serine (S), or Arginine (R);
$X_{14}$ represents Glycine (G), or Serine (S);
$X_{15}$ represents Glycine (G), or Serine (S);
$X_{16}$ represents Glycine (G), Serine (S), or Arginine (R);
$X_{17}$ represents Glycine (G), Serine (S), Asparagine (N), or Arginine (R);
$X_{18}$ represents Glycine (G), or Serine (S);
$X_{19}$ represents Glycine (G), or Serine (S); and
$X_{20}$ represents Glycine (G), or Serine (S); or
wherein $L_3$ comprises the motif of $X_1X_2X_3X_4X_5X_6$, in which
$X_1$ represents Glycine (G), Serine (S), or absent;
$X_2$ represents Glycine (G), Serine (S), or absent;
$X_3$ represents Glycine (G), or Serine (S);
$X_4$ represents Glycine (G), Arginine (R), or Serine (S);
$X_5$ represents Glycine (G), or Serine (S); and
$X_6$ represents Glycine (G), or Serine (S).

8. The bispecific antibody of claim 7,
wherein in $L_1$, $X_1$ represents absent, $X_2$ represents absent, $X_3$ represents G, $X_4$ represents G, $X_5$ represents G, and/or $X_6$ represents G;
wherein in $L_2$, each of $X_1$-$X_{20}$ independently, represents G; or
wherein in $L_3$; $X_1$ represents G; $X_2$ represents S; $X_3$ represents G; $X_4$ represents G; $X_5$ represents G; and $X_6$ represents G.

9. The bispecific antibody of claim 5, wherein the $L_1$-$L_3$ peptide linkers comprise the following amino acid sequences, respectively:
SEQ ID NOs: 121, 122, and 121;
SEQ ID NOs: 121, 123, and 121;
SEQ ID NOs: 124, 125, and 126;
SEQ ID NOs: 121, 127, and 121;
SEQ ID NOs: 121, 128, and 129;
SEQ ID NOs: 121, 130, and 121;
SEQ ID NOs: 131, 132, and 133;
SEQ ID NOs: 134, 135, and 126;
SEQ ID NOs: 134, 136, and 137;
SEQ ID NOs: 134, 138, and 139;
SEQ ID NOs: 140, 122, and 141;
SEQ ID NOs: 124, 142, and 143;
SEQ ID NOs: 124, 144, and 143;
SEQ ID NOs: 145, 146, and 147;
SEQ ID NOs: 145, 148, and 149;
SEQ ID NOs: 150, 125, and 151;
SEQ ID NOs: 152, 153, and 154;
SEQ ID NOs: 155, 156, and 133;
SEQ ID NOs: 157, 158, and 121;
SEQ ID NOs: 159, 160, and 161; or
SEQ ID NOs: 141, 162, and 163.

10. The bispecific antibody of claim 4, wherein a disulfide bond is formed between a variable region of the first antigen-binding moiety and a variable region in the second antigen-binding moiety, wherein:
(a) the first $V_L$ or the second $V_L$ contains C at position 43 (C43) and the first $V_H$ or the second $V_H$ contains C at position 105 (C105) corresponding to the Kabat numbering; and wherein the disulfide bond is formed between C43 in the first $V_L$ and C105 in the first $V_H$, or between C43 in the second $V_L$ and C105 in the second $V_H$;
(b) the first $V_L$ or the second $V_L$ contains C at position 100 (C100) and the first $V_H$ or the second $V_H$ contains C at position 44 (C44) corresponding to the Kabat numbering; and wherein the disulfide bond is formed between C100 in the first $V_L$ and C44 in the first $V_H$, or between C100 in the second $V_L$ and C44 in the second $V_H$;
(c) the first $V_H$ contains C at position 3 (C3) or position 9 (C9) and the second $V_H$ contains C at position 42 (C42) or position 112 (C112) corresponding to the Kabat numbering, or vice versa, and wherein the disulfide bond is formed between C3 and C42, or C9 and C112;
(d) the first $V_L$ contains C at position 43 (C43) and the first $V_H$ contains C at position 105 (C105) corresponding to the Kabat numbering; and wherein the disulfide bond is formed between C43 and C105;
(e) the second $V_L$ contains C at position 43 (C43) and the second $V_H$ contains C at position 105 (C105) corresponding to the Kabat numbering; and wherein the disulfide bond is formed between C43 and C105;
(f) the second $V_H$ contains C at position 3 (C3) and the first $V_H$ contains C at position 42 (C42) corresponding to the Kabat numbering; and wherein the a disulfide bond is formed between C3 and C42;
(g) the second $V_H$ contains C at position 9 (C9) and the first $V_H$ contains C at position 112 (C112) corresponding to the Kabat numbering; and wherein the disulfide bond is formed between C9 and C112;
(h) the second $V_H$ contains C at position 44 (C44) and the second $V_L$ contains C at position 100 (C100) corresponding to the Kabat numbering; and wherein the disulfide bond is formed between C44 and C100;

(i) the first V$_H$ contains C at position 44 (C44) and the first V$_L$ contains C at position 100 (C100) corresponding to the Kabat numbering; and wherein the disulfide bond is formed between C44 and C100;

(j) the second V$_H$ contains C at positon 105 (C105) and the second V$_L$ contains C at position 43 (C43) corresponding to the Kabat numbering; and wherein the disulfide bond is formed between C105 and C43; or (k) the first V$_H$ contains C at position 105 (C105) and the first V$_L$ contains C at position 43 (C43) corresponding to the Kabat numbering; and wherein the disulfide bond is formed between C105 and C43.

11. The bispecific antibody of claim 4, wherein the second V$_L$ of the second antigen-binding moiety that binds human PD-L1 comprises the amino acid sequence of: EIVLTQSPGTLSLSPGER ATLSCRASQRVSSSYLAWYQQKPGQX$_1$PRLLIY DASSRATGIPDR FSGSGSGTDFTLTISR LEPEDFAVYYCQQYGSLPWTFGX$_2$GTKVEIK (SEQ ID NO 171), in which X$_1$ represents Alanine (A), or Cysteine (C); and X$_2$ represents Glutamine (Q), or Cysteine (C); or wherein the second V$_H$ of the second antigen-binding moiety that binds human PD-L1 comprises the amino acid sequence of: EVX$_1$LVESGX$_2$GLVQPG GSLRLSCAASGFTFSRYWMSWVRQAPGKX$_3$ LEWVANIKQDGSEK YYVDSVKGRFTISRD-NAKNSLYLQMNSLRAEDTAVYYCAREGG WFGELAFDYWGX$_4$GTL VTVSS (SEQ ID NO 170), in which X$_1$ represents Glutamine (Q), or Cysteine (C); X$_2$ represents Glycine (G), or Cysteine (C); X$_3$ represents amino acid residues Glycine (G), or Cysteine (C); and X$_4$ represents Glutamine (Q), or Cysteine (C).

12. The bispecific antibody of claim 11, wherein in the second V$_L$, X$_1$ is A and/or X$_2$ is Q; or wherein in the second V$_H$, X$_1$ is Q, X$_2$ is G, X$_3$ is G, and/or X$_4$ is Q.

13. The bispecific antibody of claim 4, wherein the single polypeptide further comprises an Fc fragment of an immunoglobulin at the C-terminus and optionally a fourth peptide linker (L4) connecting the Fc fragment to the rest of the single polypeptide.

14. The bispecific antibody of claim 4, wherein the polypeptide comprises an amino acid sequence selected from the group consisting of SEQ ID NOs: 172, 173, 174, 175, 176, 177, 178, 179, 180, 181, 182, 183, 184, 185, 186, 187, 188, 189, 190, 191, 192, 193, 194, 195, 196, 197, 198, 199, 200, and 201.

15. The bispecific antibody of claim 2, wherein the bispecific antibody comprises a first polypeptide and a second polypeptide, each of which comprises the first V$_H$ or the first V$_L$ of the first antigen-binding moiety and the second V$_L$ or the second V$_H$ of the second antigen-binding moiety, respectively.

16. The bispecific antibody of claim 15, wherein:

(a) the first polypeptide comprises, from N-terminus to C-terminus, the first V$_L$, a first peptide linker (L1), the second V$_H$, and optionally a second peptide linker (L2); and (b) the second polypeptide comprises, from N-terminus to C-terminus, the second V$_L$, a third peptide linker (L3), and the first V$_H$, and optionally a fourth peptide linker (L4).

17. The bispecific antibody of claim 16, wherein:

(a) the first polypeptide comprises, from N-terminus to C-terminus, the first V$_H$, a first peptide linker (L1), the second V$_L$, and optionally a second peptide linker (L2); and (b) the second polypeptide comprises, from N-terminus to C-terminus, the second V$_H$, a third peptide linker (L3), the first V$_L$, and optionally a fourth peptide linker (L4).

18. The bispecific antibody of claim 16, wherein the first polypeptide further comprises a first C-terminal fragment, and wherein the second polypeptide further comprises a second C-terminal fragment, and wherein the first C-terminal fragment and the second C-terminal fragment form a dimer.

19. The bispecific antibody of claim 18, wherein the first C-terminal fragment is a first Fc fragment of a first IgG molecule and the second C-terminal fragment is a second Fc fragment of a second IgG molecule, and wherein the first Fc fragment and the second Fc fragment form an IgG Fc region.

20. The bispecific antibody of claim 19, wherein the first Fc fragment comprising a first CH2 domain and a first CH3 domain, and the second Fc fragment comprises a second CH2 domain and a second CH3 domain, wherein either the first CH2 and the second CH2 domains each comprise an amino acid modification relative to a wild-type counterpart to form a knob and a hole, or the first CH3 and the second CH3 domains each comprise an amino acid modification relative to a wild-type counterpart to form a knob and a hole.

21. The bispecific antibody of claim 16, wherein the L$_1$-L$_4$ peptide linkers comprise the following amino acid sequences, respectively: SEQ ID NOs: 121, 164, 121 and 164.

22. The bispecific antibody of claim 15, wherein the first polypeptide and the second polypeptide comprise the following amino acid sequences, respectively:

SEQ ID NOs: 202 and 203;
SEQ ID NOs: 204 and 205;
SEQ ID NOs: 206 and 207;
SEQ ID NOs: 279 and 280; or
SEQ ID NOs: 289 and 290.

23. A pharmaceutical composition, comprising (i) the bispecific antibody of claim 1, and (ii) a pharmaceutically acceptable carrier.

24. A pharmaceutical composition, comprising (i) a nucleic acid or nucleic acid set comprising a nucleic acid sequence(s) encoding the bispecific antibody of claim 1, and (ii) a pharmaceutically acceptable carrier.

25. A bispecific antibody, comprising a first antigen-binding moiety that binds human claudin 18.2, and a second antigen-binding moiety that binds human PD-L1, wherein the first antigen-binding moiety and the second antigen-binding moiety are located on a single polypeptide, wherein the first antigen-binding moiety that binds human claudin 18.2 comprises a first heavy chain variable region (V$_H$) and a first light chain variable region (V$_L$), and wherein:

the first V$_L$ comprises the amino acid sequence of:

(i) DIQMTQSPSSLSASVGDRVTITCKSSQSLL NX$_1$GNQKSYLTWYQQKPGKX$_2$PK LLIYWA STLX$_3$SGVPSRFSGSGSGTDYTLTISSLQPEDF ATYYCQNAYFFPFTFGX$_4$GTKVEIK (SEQ ID NO 167), in which X$_1$ represents Serine (S), or Tryptophan (W); X$_2$ represents Alanine (A), or Cysteine (C); X$_3$ represents Glutamic acid (E), or Glutamine (Q); and X$_4$ represents Glutamine (Q), or Cysteine (C); or (ii) DIQMTQSPSSLSASVGDRVTITCKSSQSLL NSGNQKSYLTWYQQKPGKX$_1$PKL LIY-WASTLESGVPSRFSGSGSGTDYTLTISSLQPED-FATYYCQNAYFFPFTFX$_2$ (SEQ ID NO: 169, in which X$_1$ represents Alanine (A), or Cysteine (C); X$_2$ represents Glutamine (Q), or Cysteine (C); and the first V$_H$ comprises the amino acid sequence of:

(i) EVQLVESGGGLVQPGGSLRLSCAVSGYTF SMNWVRQAPX$_1$KX$_2$LEWVAWIN MYTGEX$_3$ TYADDFKGRFTISRDDSKNTLYLQMNSLRA EDTAVYYCARLYNGNSLDYWGX$_4$GTLVTVX$_5$S (SEQ ID NO 166), in which X$_1$ represents Glycine (G), or Cysteine (C); X$_2$ represents Glycine (G), or Cysteine (C); X$_3$ represents Proline (P) or Arginine (R); X$_4$ represents Glutamine (Q), or Cysteine (C); and X$_5$ represents Serine (S), or Cysteine (C); or (ii) EVQLVESGGGLVQPGGSLRLSCAVSGYT FSMNWVRQAPX$_1$KX$_2$LEWVAWIN MYTGE PTYADDFKGRFTISRDDSKNTLYLQMNSLR AEDTAVYYCARLYNGNSLDYWGX$_3$GTLV TVX$_4$S (SEQ ID NO 168), in which X$_1$ represents amino acid residues Glycine (G), or Cysteine (C); X$_2$ represents amino acid residues Glysine (G), or Cysteine (C), X$_3$ represents amino acid residues Glutamine (Q), or Cysteine (C); and X$_4$ represents amino acid residues Serine (S), or Cysteine (C).

26. The bispecific antibody of claim 25,
wherein in the first V$_L$, X$_1$ is S, X$_2$ is A, X$_3$ is E, and/or X$_4$ is Q; or
wherein in (i) of the first V$_H$, X$_1$ represents G; X$_2$ represents G; X$_3$ represents P; X$_4$ represents Q; and/or X$_5$ represents S.

27. An isolated nucleic acid or nucleic acid set, comprising a nucleotide sequence(s) encoding the bispecific antibody set forth in claim 1.

28. A host cell or host cell set, comprising a vector or vector set that comprises the nucleic acid or nucleic acid set of claim 27.

29. A method for preparing an antibody or bispecific antibody, comprising: culturing the host cell or host cell set of claim 28 under conditions allowing for expression of the antibody or bispecific antibody, and harvesting the antibody or bispecific antibody thus produced.

30. A method of inhibiting cells expressing human CLDN 18.2, comprising contacting administering an effective amount of the pharmaceutical composition of claim 23 to a subject in need thereof.

* * * * *